US012606872B2

(12) United States Patent
Noguer et al.

(10) Patent No.: US 12,606,872 B2
(45) Date of Patent: Apr. 21, 2026

(54) METHODS FOR STRATIFICATION AND EARLY DETECTION OF ADVANCED ADENOMA AND/OR COLORECTAL CANCER USING DNA METHYLATION MARKERS

(71) Applicant: Universal Diagnostics, S.A., Seville (ES)

(72) Inventors: Pol Canal Noguer, Seville (ES); Juan Carlos Higareda Almaraz, Ljubljana (SI); Francesco Mattia Mancuso, Seville (ES); Kristi Kruusmaa, Ljubljana (SI); Alejandro Requena Bermejo, Seville (ES); Marko Chersicola, Ljubljana (SI); Pablo Pérez Martínez, Seville (ES); Pablo Antonio Camino Faillace, Seville (ES); Primož Knap, Ljubljana (SI); Vivian Erklavec Zajec, Ljubljana (SI); Špela Zavodnik, Ljubljana (SI); Carme Nolla Colomer, Seville (ES); Fernando Trincado Alonso, Seville (ES)

(73) Assignee: Universal Diagnostics, S.A., Seville (ES)

( * ) Notice: Subject to any disclaimer, the term of this patent is extended or adjusted under 35 U.S.C. 154(b) by 597 days.

(21) Appl. No.: 18/096,337

(22) Filed: Jan. 12, 2023

(65) Prior Publication Data

US 2024/0158862 A1 May 16, 2024

Related U.S. Application Data

(60) Provisional application No. 63/425,882, filed on Nov. 16, 2022.

(51) Int. Cl.
*C12Q 1/6886* (2018.01)

(52) U.S. Cl.
CPC ...... *C12Q 1/6886* (2013.01); *C12Q 2600/112* (2013.01); *C12Q 2600/154* (2013.01)

(58) Field of Classification Search
CPC .................. C12Q 1/6886; C12Q 2600/154
See application file for complete search history.

(56) References Cited

U.S. PATENT DOCUMENTS

| | | | |
|---|---|---|---|
| 6,265,171 B1 | 7/2001 | Herman et al. |
| 6,605,432 B1 | 8/2003 | Huang |
| 6,812,339 B1 | 11/2004 | Venter et al. |
| 7,144,701 B2 | 12/2006 | Huang |
| 7,745,391 B2 | 6/2010 | Mintz et al. |
| 7,807,358 B1 | 10/2010 | Huang |
| 8,048,634 B2 | 11/2011 | Lai |
| 9,745,622 B2 | 8/2017 | An et al. |
| 9,850,523 B1 | 12/2017 | Chudova et al. |
| 10,006,925 B2 | 6/2018 | Bitenc et al. |
| 10,301,680 B2 | 5/2019 | Ahlquist et al. |
| 10,392,666 B2 | 8/2019 | Lo et al. |
| 10,428,388 B2 | 10/2019 | An et al. |
| 11,001,898 B2 | 5/2021 | Bitenc et al. |
| 11,118,228 B2 | 9/2021 | Allawi et al. |
| 11,345,967 B2 | 5/2022 | Morris |
| 11,396,679 B2 | 7/2022 | Bitenc et al. |
| 11,530,453 B2 | 12/2022 | Bitenc et al. |
| 11,728,007 B2 | 8/2023 | Ghosh |
| 11,773,453 B2 | 10/2023 | Talasaz |
| 11,827,942 B2 | 11/2023 | Mortimer et al. |
| 11,869,661 B2 | 1/2024 | Maher |
| 11,879,158 B2 | 1/2024 | Talasaz |
| 11,898,199 B2 | 2/2024 | Bitenc et al. |
| 11,929,148 B2 | 3/2024 | Filippova et al. |
| 2007/0237813 A1 | 10/2007 | Misawa et al. |
| 2007/0298506 A1 | 12/2007 | Ordway et al. |
| 2010/0167940 A1 | 7/2010 | Feinberg |
| 2010/0240549 A1 | 9/2010 | Brown |
| 2010/0298158 A1 | 11/2010 | DePinho et al. |
| 2011/0318738 A1 | 12/2011 | Jones et al. |
| 2012/0289581 A1 | 11/2012 | Chang et al. |
| 2013/0012410 A1 | 1/2013 | Zou et al. |
| 2013/0085681 A1 | 4/2013 | Deciu et al. |
| 2013/0189684 A1 | 7/2013 | Ehrich et al. |

(Continued)

FOREIGN PATENT DOCUMENTS

| | | |
|---|---|---|
| CA | 3236697 A1 | 5/2023 |
| EP | 2481813 A1 | 8/2012 |

(Continued)

OTHER PUBLICATIONS

Moser et al., "Targeted bisulfite sequencing: A novel tool for the assessment of DNA methylation with high sensitivity and increased coverage," Psychoneuroendocrinology, vol. 120, pp. 1-8. (Year: 2020).*
Su et al., "FGF14 is a Functional Tumor Suppressor Through Inhibiting PI3K/ AKT/MTOR Pathway in Colorectal Cancer," Gut, vol. 68, A15. (Year: 2019).*
Wu et al., "A novel cell-free DNA methylation-based model improves the early detection of colorectal cancer," Molecular Oncology, vol. 15, pp. 2702-2714. (Year: 2021).*
Chiou et al., "Methylation-based enrichment facilitates low-cost, noninvasive genomic scale sequencing of populations from feces," Scientific Reports, vol. 8, pp. 1-10. (Year: 2018).*
GENECARDS, GAD2 Gene—Glutamate Decarboxylase 2, 31 pages, (2023).

(Continued)

*Primary Examiner* — Young J Kim
(74) *Attorney, Agent, or Firm* — Choate, Hall & Stewart LLP; William R. Haulbrook; Samuel R. Polio

(57) ABSTRACT

The present disclosure provides for, among other things, methods and systems for detecting, diagnosing, predicting, monitoring, screening for, staging, and/or providing survival prognosis for advanced adenoma and/or colorectal cancer using DNA methylation markers. For example, described herein are DNA methylation markers that enable categorization and prognosis evaluation of advanced adenoma (AA) and/or colorectal cancer (CRC) patients with high accuracy from human biospecimens.

11 Claims, 6 Drawing Sheets

Specification includes a Sequence Listing.

(56) References Cited

U.S. PATENT DOCUMENTS

| | | |
|---|---|---|
| 2013/0288247 A1 | 10/2013 | Mori et al. |
| 2014/0128283 A1 | 5/2014 | Feinberg et al. |
| 2015/0011403 A1 | 1/2015 | Lo et al. |
| 2015/0072866 A1 | 3/2015 | Weisburg et al. |
| 2015/0152505 A1 | 6/2015 | Lapointe et al. |
| 2016/0333416 A1 | 11/2016 | Babiarz et al. |
| 2016/0355885 A1 | 12/2016 | Weinhausel et al. |
| 2017/0016048 A1 | 1/2017 | Blauwkamp et al. |
| 2017/0101674 A1 | 4/2017 | So et al. |
| 2017/0298439 A1 | 10/2017 | Ahlquist et al. |
| 2017/0335401 A1 | 11/2017 | Allawi et al. |
| 2017/0356051 A1 | 12/2017 | Ishioka et al. |
| 2017/0369948 A1 | 12/2017 | Markowitz et al. |
| 2018/0051338 A1 | 2/2018 | West et al. |
| 2018/0119137 A1 | 5/2018 | Matsuguchi et al. |
| 2018/0148777 A1 | 5/2018 | Kirkizlar et al. |
| 2018/0245157 A1 | 8/2018 | Allawi et al. |
| 2018/0251859 A1 | 9/2018 | Ahlquist et al. |
| 2018/0258498 A1 | 9/2018 | Ahlquist et al. |
| 2018/0305765 A1 | 10/2018 | Feber et al. |
| 2018/0363063 A1 | 12/2018 | Guerrero-Preston et al. |
| 2019/0025308 A1 | 1/2019 | Cummings et al. |
| 2019/0032149 A1 | 1/2019 | Van Engeland et al. |
| 2019/0085406 A1 | 3/2019 | Mortimer et al. |
| 2019/0112645 A1 | 4/2019 | Woodhouse et al. |
| 2019/0161805 A1 | 5/2019 | Ahlquist et al. |
| 2019/0161806 A1 | 5/2019 | Ahlquist et al. |
| 2019/0256921 A1 | 8/2019 | Mueller et al. |
| 2019/0256924 A1 | 8/2019 | Vogelstein et al. |
| 2019/0352721 A1 | 11/2019 | Kusunoki et al. |
| 2020/0017916 A1 | 1/2020 | Ren |
| 2020/0131582 A1 | 4/2020 | Zhou et al. |
| 2020/0157640 A1 | 5/2020 | Letourneur et al. |
| 2020/0340062 A1 | 10/2020 | Salhia |
| 2020/0377954 A1 | 12/2020 | Bitenc et al. |
| 2020/0377959 A1 | 12/2020 | Bitenc et al. |
| 2021/0017605 A1 | 1/2021 | Jaimovich et al. |
| 2021/0139948 A1 | 5/2021 | Bitenc et al. |
| 2021/0230707 A1 | 7/2021 | Bitenc et al. |
| 2021/0277487 A1 | 9/2021 | Bitenc et al. |
| 2021/0324477 A1 | 10/2021 | Xiang et al. |
| 2021/0332440 A1 | 10/2021 | Kruusmaa et al. |
| 2021/0355542 A1 | 11/2021 | Bitenc et al. |
| 2021/0404010 A1 | 12/2021 | Bitenc et al. |
| 2021/0404011 A1 | 12/2021 | Bitenc et al. |
| 2022/0106644 A1 | 4/2022 | Taylor et al. |
| 2022/0136058 A1 | 5/2022 | Allawi et al. |
| 2022/0186323 A1 | 6/2022 | Mortimer et al. |
| 2022/0228221 A1 | 7/2022 | Curtis |
| 2022/0389521 A1 | 12/2022 | Bitenc et al. |
| 2022/0403471 A1 | 12/2022 | Morris et al. |
| 2022/0403473 A1 | 12/2022 | Lewin et al. |
| 2022/0411878 A1 | 12/2022 | Kruusmaa |
| 2023/0028856 A1 | 1/2023 | Ahlquist et al. |
| 2023/0090925 A1 | 3/2023 | Liu |
| 2023/0175058 A1 | 6/2023 | Delubac et al. |
| 2023/0178181 A1 | 6/2023 | Mahajan et al. |
| 2023/0183815 A1 | 6/2023 | Bitenc et al. |
| 2023/0193395 A1 | 6/2023 | Liu et al. |
| 2023/0203473 A1 | 6/2023 | Diniz De Carvalho et al. |
| 2023/0220492 A1 | 7/2023 | St. John et al. |
| 2023/0242995 A1 | 8/2023 | Van Engeland et al. |
| 2023/0323446 A1 | 10/2023 | Ariazi et al. |
| 2024/0060143 A1 | 2/2024 | Yip et al. |
| 2024/0084397 A1 | 3/2024 | Mahajan et al. |
| 2024/0279746 A1 | 8/2024 | Bitenc et al. |

FOREIGN PATENT DOCUMENTS

| | | | | |
|---|---|---|---|---|
| EP | 2497834 | A2 | 9/2012 | |
| EP | 2886659 | A1 | 6/2015 | |
| EP | 2899275 | A1 | 7/2015 | |
| EP | 2977467 | A2 | 1/2016 | |
| EP | 4022093 | A1 | 7/2022 | |
| WO | WO-02/081749 | A2 | 10/2002 | |
| WO | WO-2005/001142 | A2 | 1/2005 | |
| WO | WO-2007/149269 | A2 | 12/2007 | |
| WO | WO-2010/118559 | A1 | 10/2010 | |
| WO | WO-2012/034170 | A1 | 3/2012 | |
| WO | WO-2012/047899 | A2 | 4/2012 | |
| WO | WO-2012/104642 | A1 | 8/2012 | |
| WO | WO-2012/154979 | A2 | 11/2012 | |
| WO | WO-2012/167145 | A2 | 12/2012 | |
| WO | WO-2012/170715 | A1 | 12/2012 | |
| WO | WO-2013/057581 | A2 | 4/2013 | |
| WO | WO-2013/097868 | A1 | 7/2013 | |
| WO | WO-2014/032227 | A1 | 3/2014 | |
| WO | WO-2014/062218 | A1 | 4/2014 | |
| WO | WO-2015/116837 | A1 | 8/2015 | |
| WO | WO-2015/153283 | A1 | 10/2015 | |
| WO | WO-2015/153284 | A1 | 10/2015 | |
| WO | WO-2015/159292 | A2 | 10/2015 | |
| WO | WO-2016/011021 | A1 | 1/2016 | |
| WO | WO-2016/060278 | A1 | 4/2016 | |
| WO | WO-2016/109782 | A2 | 7/2016 | |
| WO | WO-2017/012592 | A1 | 1/2017 | |
| WO | WO-2017/043497 | A1 | 3/2017 | |
| WO | WO-2017/048932 | A1 | 3/2017 | |
| WO | WO-2017/192221 | A1 | 11/2017 | |
| WO | WO-2017/201606 | A1 | 11/2017 | |
| WO | WO-2017/212428 | A1 | 12/2017 | |
| WO | WO-2018/087129 | A1 | 5/2018 | |
| WO | WO-2018/119452 | A2 | 6/2018 | |
| WO | WO-2018/140781 | A1 | 8/2018 | |
| WO | WO-2018/195211 | A1 | 10/2018 | |
| WO | WO-2018/209361 | A2 | 11/2018 | |
| WO | WO-2019/068082 | A1 | 4/2019 | |
| WO | WO-2019/175876 | A2 | 9/2019 | |
| WO | WO-2020/069350 | A1 | 4/2020 | |
| WO | WO-2020/163410 | A1 | 8/2020 | |
| WO | WO-2020/232109 | A1 | 11/2020 | |
| WO | WO-2020/239895 | A2 | 12/2020 | |
| WO | WO-2020/239896 | A1 | 12/2020 | |
| WO | WO-2021/016441 | A1 | 1/2021 | |
| WO | WO-2021/041726 | A1 | 3/2021 | |
| WO | WO-2021094017 | A1 * | 5/2021 | ............ C12Q 1/686 |
| WO | WO-2021/202351 | A1 | 10/2021 | |
| WO | WO-2021/209161 | A1 | 10/2021 | |
| WO | WO-2021/216477 | A1 | 10/2021 | |
| WO | WO-2021/228418 | A1 | 11/2021 | |
| WO | WO-2022/002423 | A1 | 1/2022 | |
| WO | WO-2022/002424 | | 1/2022 | |
| WO | WO-2022/003572 | A1 | 1/2022 | |
| WO | WO-2022/238559 | A1 | 11/2022 | |
| WO | WO-2022/238560 | A1 | 11/2022 | |
| WO | WO-2023/023123 | A1 | 2/2023 | |
| WO | WO-2023/083308 | A1 | 5/2023 | |

OTHER PUBLICATIONS

GENECARDS, MYO3A Gene—Myosin IIIA, 29 pages, (2023).

UCSC Genome Browser 3, CpG Island Info, Band 10p12.1, 2 pages, (2022).

UCSC Genome Browser 4, CpG Island Info, Band 20q13.31, 2 pages, (2022).

Aberle, D.R., et al., Reduced lung-cancer mortality with low-dose computed tomographic screening, New England Journal of Medicine, 365(5):395-409, (2011).

Adalsteinsson, V.A. et al., Scalable whole-exome sequencing of cell-free DNA reveals high concordance with metastatic tumors, Nat. Commun., 8(1):1324, (2017).

Adler, A. et al., Improving compliance to colorectal cancer screening using blood and stool based tests in patients refusing screening colonoscopy in Germany, BMC Gastroenterology, 14:183, (2014).

Adusumalli, S. et al., Methodological aspects of whole-genome bisulfite sequencing analysis, Briefings in Bioinformatics, 16(3):369-379, (2014).

Andersson, I., et al., Mammographic screening and mortality from breast cancer: the Malmö mammographic screening trial, British Medical Journal, 297(6654): 943-8, (1988).

Bacolod, M. D. et al., Application of Multiplex Bisulfite PCR-Ligase Detection Reaction-Real-Time Quantitative PCR Assay in

(56)          References Cited

OTHER PUBLICATIONS

Interrogating Bioinformatically Identified, Blood-Based Methylation Markers for Colorectal Cancer, The Journal of Molecular Diagnostics, 22(7):886-900, (2020).

Beikircher, G. et al., Multiplexed and Sensitive DNA Methylation Testing Using Methylation-Sensitive Restriction Enzymes "MSRE-qPCR", DNA Methylation Protocols, Methods in Molecular Biology 1708:Ch21:407-424, (2018).

Blesa, J. R. et al., NRF-1 is the major transcription factor regulating the expression of the human TOMM34 gene, Biochemistry and Cell Biology, 86(1):46-56, (2008).

Bray, F. et al., Global Cancer Statistics 2018: GLOBOCAN Estimates of Incidence and Mortality Worldwide for 36 Cancers in 185 Countries, CA Cancer J Clin., 68:394-424, (2018).

Breast Cancer Screening (PDQ®)-Health Professional Version, <https://www.cancer.gov/types/breast/hp/breast-screening-pdq#section/all>. Retrieved on Jul. 17, 2020.

Calderwood, A. H. et al., Colon adenoma features and their impact on risk of future advanced adenomas and colorectal cancer, World Journal of Gastrointestinal Oncology, 8(12):826-834, (2016).

Campan, M. et al., MethyLight and Digital MethyLight, DNA Methylation Protocols, Methods in Molecular Biology, 1708:CH25:497-513, (2018).

Chang, C. P.-Y. et al., Elevated cell-free serum DNA detected in patients with myocardial infarction, Clinica Chimica Acta 327:95-101, (2003).

Chen, J. et. al., DNA methylation biomakers in stool for early screening of colorectal cancer, Journal of Cancer,10(21):5264-5271, (2019).

Chen, J.J., et. al., DNA methylation assay for colorectal carcinoma, Cancer Biology & Medicine, 14(1):42-49, (2017).

Chen, Y. et al., Tissue-independent and tissue-specific patterns of DNA methylation alteration in cancer, Epigenetics & Chromatin, 9:10, (2016).

Chiu, R. W. K. et al., Noninvasive prenatal diagnosis of fetal chromosomal aneuploidy by massively parallel genomic sequencing of DNA in maternal plasma, PNAS, 105(51):20458-20463, (2008).

Demissie, K., et al., Empirical comparison of the results of randomized controlled trials and case-control studies in evaluating the effectiveness of screening mammography, J. Clin. Epidemiol., 51(2):81-91, (1998).

DOE Joint Genome Institute, AC012313, (2003).

DOE Joint Genome Institute, AC024563, (2002).

Esteller, M., CpG island hypermethylation and tumor suppressor genes: a booming present, a brighter future, Oncogene, 21:5427-5440, (2002).

Exner, R. et al., Potential of DNA methylation in rectal cancer as diagnostic and prognostic biomarkers, Br. J. Cancer, 113(7):1035-1045 (2015).

Fackler, M. J. and Sukumar, S., Quantitation of DNA Methylation by Quantitative Multiplex Methylation-Specific PCR (QM-MSP) Assay, DNA Methylation Protocols, Methods in Molecular Biology, 1708:CH24:473-496, (2018).

Fan, C.H.. et al., Noninvasive diagnosis of fetal aneuploidy by shotgun sequencing DNA from maternal blood, Proceedings of The National Academy of Sciences, 105(42):16266-16271 (2008).

Frommer, M. et al., A genomic sequencing protocol that yields a positive display of 5-methylcytosine residues in individual DNA strands, Proc. Natl. Acad. Sci. USA, 89:1827-1831, (1992).

Galanopoulos, M., et. al., Abnormal DNA methylation as a cell-free circulating DNA biomarker for colorectal cancer detection: A review of literature, World Journal of Gastrointestinal Oncology, 9(4):142-152, (2017).

Galeazzi, M. et al., Dosage and characterization of circulating DNA: present usage and possible applications in systemic autoimmune disorders, Autoimmunity Reviews, 2:50-55, (2003).

Gasc, C. et al., Survey and Summary: Sequence capture by hybridization to explore modern and ancient genomic diversity in model and nonmodel organisms, Nucleic Acids Research, 44(10):4504-4518, (2016).

Genecards, ALKAL1 Gene—ALK and LTK Ligand 1, 18 pages, (2022).

Gibson, J.A. and Odze, R.D., Pathology of premalignant colorectal neoplasia, Dig. Endosc., 28(3):312-323 (2016).

Gonzalgo, M. L. and Liang, G., Methylation-sensitive single-nucleotide primer extension (Ms-SNuPE) for quantitative measurement of DNA methylation, Nature Protocols, 2(8):1931-1936, (2007).

Heidary, M. et al., The dynamic range of circulating tumor DNA in metastatic breast cancer, Breast Cancer Res., 16(4):421, (2014).

Hemmasi, G., et al., Prevalence of colorectal adenoma in an average-risk population aged 40-50 versus 50-60 years, European Journal of Cancer Prevention (ECP), pp. 1-5, (2014).

Herman, J. G. et al., Methylation-specific PCR: A novel PCR assay for methylation status of CpG islands, Proc. Natl. Acad. Sci. USA, 93:9821-9826, (1996).

Hussmann, D. and Hansen, L. L., Methylation-Sensitive High Resolution Melting (MS-HRM), DNA Methylation Protocols, Methods in Molecular Biology, 1708:CH28:551-571, (2018).

Imperiale, T. F. et al., Multitarget Stool DNA Testing for Colorectal-Cancer Screening, Correspondence to the Editor, The New England Journal of Medicine, doi:10.1056/NEJMc1405215, 371(2):184-188, (2014).

Imperiale, T. F. et al., Multitarget Stool DNA Testing for Colorectal-Cancer Screening, The New England Journal of Medicine, 370(14):1287-1297, (2014).

Ivanov, M. et al., In-solution hybrid capture of bisulfite-converted DNA for targeted bisulfite sequencing of 174 ADME genes, Nucleic Acids Research, 46(6):e72, 9 pages, (2013).

Karsenti, D. et al., Adenoma and advanced neoplasia detection rates increase from 45 years of age, World Journal of Gastroenterology, 25(4): 447-456 (2019).

Kirkizlar, E. et al., Detection of Clonal and Subclonal Copy-Number Variants in Cell-Free DNA from Patients with Breast Cancer Using a Massively Multiplexed PCR Methodology, Transl. Oncol., 8(5):407-416, (2015).

Kok-Sin, T., et. al., Identification of diagnostic markers in colorectal cancer via integrative epigenomics and genomics data, Oncology Reports, 34:22-32, (2015).

Kordowski, F., et al., Aberrant DNA methylation of ADAMTS16 in colorectal and other epithelial cancers, BMC Cancer, 18(1):4, (2018).

Krueger, F. and Andrews, S.R., Bismark: a flexible aligner and methylation caller for Bisulfite-Seq applications, Bioinformatics, 27(11):1571-2, (2011).

Kruusmaa, K. et. al., MSRE-qPCR for analysis of gene specific methylation can be accurately used for detection and validation of colorectal cancer-specific patterns, 4Bio Summit (Jan. 1, 2018). <www.universaldx.com/wp-content/uploads/2017/05/4Bio-poster-November-2018.pdf>. Retrieved on Aug. 19, 2020.

Kukita, Y. et al., High-fidelity target sequencing of individual molecules identified using barcode sequences: de novo detection and absolute quantitation of mutations in plasma cell-free DNA from cancer patients, DNA Res., 22(4):269-277, (2015).

Kutsenko, A., et. al., NotI flanking sequences: a tool for gene discovery and verification of the human genome, Nucleic Acids Research, 30(14):3163-3170, (2002).

Laird, P. W., Applications of Next-Generation Sequencing: Principles and challenges of genomewide DNA methylation analysis, Nature Review Genetics, 11:191-203, (2010).

Lam, K. et al., DNA methylation based biomakers in colorectal cancer: A systematic review, Elsevier Science BV, Biochimica et Biophysica Acta 1866:106-1202 (2016).

Leary, R.J. et al., Detection of chromosomal alterations in the circulation of cancer patients with whole-genome sequencing, Sci. Transl. Med., 4(162):162ra154, (2012).

Leon, S. A. et al., Free DNA in the Serum of Cancer Patients and the Effect of Therapy, Cancer Research, 37:646-650, (1977).

(56) References Cited

OTHER PUBLICATIONS

Li, H. et. al., Identification of novel DNA methylation markers in colorectal cancer using MIRA-based microarrays, Oncology Reports, 28(1):99-104, (2012).

Lianidou, E., Detection and relevance of epigenetic markers on ctDNA: recent advances and future outlook, Mol. Oncol., 15(6):1683-1700, (2021).

Liles, E. G. et al., Uptake of a colorectal cancer screening blood test is higher than of a fecal test offered in clinic: A randomized trial, Cancer Treatment and Research Communications, 10:27-31, (2017).

Liu, W-B et al., TMEM196 acts as a novel functional tumour suppressor inactivated by DNA methylation and is a potential prognostic biomarker in lung cancer, Oncotarget, 6(25):21225-21239, (2015).

Liu, Y. et al., Methylation-sensitive enrichment of minor DNA alleles using a double-strand DNA-specific nuclease, Nucleic Acids Research, 45(6):e39, 11 pages, (2017).

Lowe, T., et. al., A Computer program for selection of oligonucleotide primers for polymerase chain reactions, Nucleic Acids Research. 18(7):1757-1761, (1990).

Margolin, G. et al., Robust Detection of DNA Hypermethylation of ZNF154 as a Pan-Cancer Locus with in Silico Modeling for Blood-Based Diagnostic Development, The Journal of Molecular Diagnostics, 18(2):283-298, (2016).

Masser, D. R. et al., Targeted DNA Methylation Analysis by Next-generation Sequencing, Journal of Visualized Experiments, 96:e52488, 11 pages, (2015).

Melnikov, A. A., et. al., MSRE-PCR for analysis of gene-specific DNA methylation, Nucleic Acids Research, 33(10): e93-e93, (2015).

Meyer, D. et al., Package 'e1071', Misc Functions of the Department of Statistics, Probability Theory Group (Formerly: E1071), TU Wien, HTTPS://cran.r-project.org/web/packages/e1071/index.html, 63 pages, (2019).

Michels, K.B., The promises and challenges of epigenetic epidemiology, Exp. Gerontol., 45(4):297-301, (2010).

Mitchell, S. M. et al., A panel of genes methylated with high frequency in colorectal cancer, BMC Cancer, Biomed Central, London, GB, 14(1):54, 15 pages, (2014).

Nakamura, A. et al., Relationship between sodium excretion and pioglitazone-induced edema, Journal of Diabetes Investigation, 1(5):208-211, (2010).

Navarro, M. et al., Colorectal cancer population screening programs worldwide in 2016: An Update, World J Gastroenterol, 23(20):3632-3642, (2017).

O'Connell B., and Crockett S., The clinical impact of serrated colorectal polyps, Clinical Epidemiology, 9: 113-125 (2017).

Oh, T. et al., Genome-Wide Identification and Validation of a Novel Methylation Biomarker, SDC2, for Blood-Based Detection of Colorectal Cancer, The Journal of Molecular Diagnostics, 15(4):498-507, (2013).

Perakis, S. et al., Advances in Circulating Tumor DNA Analysis, Adv. Clin. Chem., 80:73-153, (2017).

Petko, Z. et al., Aberrantly methylated CDKN2A, MGMT, and MLH1 in colon polyps and in fecal DNA from patients with colorectal polyps, Clin. Cancer Res., 11(3):1203-1209 (2005).

Potter, N. T. et al., Validation of a Real-Time PCR-Based Qualitative Assay for the Detection of Methylated SEPT9 DNA in Human Plasma, Clinical Chemistry, 60(9):1183-1191, (2014).

Pulverer, W. et al., The stem cell signature of CHH/CHG methylation is not present in 271 cancer associated 5'UTR gene regions, Biochimie, 94(11):2345-2352 (2012).

QIAamp® Circulating Nucleic Acid Handbook, For concentration and purification of free-circulating DNA, RNA, miRNA, and viral nucleic acids from human plasma, serum, urine, or other cell-free body fluids, Oct. 2019.

QIAamp® MinElute® ccfDNA Handbook, For concentration and purification of circulation cell-free DNA from plasma or serum, Jan. 2020.

Rahib, L., et. al., Projecting cancer incidence and deaths to 2030: the unexpected burden of thyroid, liver, and pancreas cancers in the United States, Cancer Research, 74(11):2913-21, (2014).

Schwarzenbach, H. et al., Cell-free nucleic acids as biomarkers in cancer patients, Nature Reviews Cancer, 11:426-437, (2011).

Shaukat, A. et al., Long-Term Mortality after Screening for Colorectal Cancer, The New England Journal of Medicine, 369(12):1106-1114, (2013).

Singh, K. E. et al., Colorectal Cancer Incidence Among Young Adults in California, Journal of Adolescent and Young Adult Oncology, 3(4):176-184, (2014).

Snyder, M.W. et al., Cell-free DNA Comprises an In vivo Nucleosome footprint that informs its Tissues-Of-Origin, Cell, 164: pp. 57-68, (2016).

Swarup, V. and Rajeswari, M.R., Circulating (cell-free) nucleic acids—A promising, non-invasive tool for early detection of several human diseases, FEBS Letters 581:795-799, (2007).

The Cancer Genome Atlas Program, <https://www.cancer.gov/about-nci/organization/ccg/research/structural-genomics/toga>. Retrieved on Jul. 17, 2020.

UCSC Genome Browser 1, CpG Island Info, Band 9p21.3, 2 pages, (2020).

UCSC Genome Browser 2, CpG Island Info, Band 8q11.23, 2 pages, (2020).

Vainio, H., et al., IARC Handbooks of Cancer Prevention Programme Head: Harri Vainio. vol. 7: Breast Cancer Screening, pp. 1-236, (2002).

Van Der Vlugt, M. et al., Adherence to colorectal cancer screening: four rounds of faecal immunochemical test-based screening, British Journal of Cancer, 116(1):44-49, (2017).

Wan, M. et al., Identification of Smoking-Associated Differentially Methylated Regions Using Reduced Representation Bisulfite Sequencing and Cell type-Specific Enhancer Activation and Gene Expression, Environ. Health Perspect., 126(4):047015 (2018).

Wittenberger, T. et al., DNA methylation markers for early detection of women's cancer: promise and challenges, Epigenomics, 6(3):311-327, (2014).

Yan, H., et al., Identifying CpG sites with different differential methylation frequencies in colorectal cancer tissues based on individualized differential methylation analysis, Oncotarget, 29(8): 47356-47364, (2017).

Yang, Y., et. al., Identification of regulatory role of DNA methylation in colon cancer gene expression via systematic bioinformatics analysis, Medicine, 96(47):1-7, (2017).

Zhang, S. et al., CRISPR/Cas9-mediated knockout of NSD1 suppresses the hepatocellular carcinoma development via the NSD1/H3/Wnt10b signaling pathway, Journal of Experimental and Clinical Cancer Research, 38(1):467, (2019).

Zhou, X. et al., Identification of epigenetic modulators in human breast cancer by integrated analysis of DNA methylation and RNA-Seq data, Epigenetics, 13(5):473-489, (2018).

Estecio, M.R.H. et al., High-throughput methylation profiling by MCA coupled to CpG island microarray, Genome Res., 17(10):1529-1536 (2007).

Mori, Y. et al., Novel candidate colorectal cancer biomarkers identified by methylation microarray-based scanning, Endocr. Relat. Cancer, 18(4):465-478 (2011).

Bedin, C. et al., Diagnostic and prognostic role of cell-free DNA testing for colorectal cancer patients, Int. J. Cancer, 140(8):1888-1898 (2017).

International Search Report for PCT/EP2023/081968, 7 pages, (mailed Apr. 10, 2024).

Jacob, S.T. and Motiwala, T., Epigenetic regulation of protein tyrosine phosphatases: potential molecular targets for cancer therapy, Cancer Gene Ther., 12(8):665-672 (2005).

Khamas, A. et al., Genome-wide screening for methylation-silenced genes in colorectal cancer, Int. J. Oncol., 41(2):490-496 (2012).

Written Opinion for PCT/EP2023/081968, 12 pages, (mailed Apr. 10, 2024).

Ebbert, M.T.W. et al., Evaluating the necessity of PCR duplicate removal from next-generation sequencing data and a comparison of approaches, BMC Bioinformatics, 17(Suppl 7):239 (2016).

(56)                    References Cited

OTHER PUBLICATIONS

Fadda, A. et al., Colorectal cancer early methylation alterations affect the crosstalk between cell and surrounding environment, tracing a biomarker signature specific for this tumor, Int. J. Cancer, 143(4):907-920, Supplementary Materials and Methods included, (2018).

Illumina, CpG Loci Identification Technical Note, 2 pages, (2010).

Illumina, HumanMethylation450 manifest file (extract), 6 pages, (2008).

Illumina, TruSeq DNA Methylation Kit Reference Guide, 40 pages, (2016).

Illumina, TruSeq DNA Methylation Library Preparation Guide, 20 pages, (2014).

Kruusmaa, K. et al., Development and clinical performance of an accurate cell-free DNA (cfDNA) methylation assay for early detection of colorectal cancer, Poster, 3 pages, (2020).

Naumov, V.A. et al., Genome-scale analysis of DNA methylation in colorectal cancer using Infinium HumanMethylation450 BeadChips, Epigenetics, 8(9):921-934 (2013).

Olova, N.N. and Andrews, S., Whole Genome Methylation Sequencing via Enzymatic Conversion (EM-seq): Protocol, Data Processing, and Analysis, bioRxiv preprint, 23 pages, (2023).

UCSC Genome Browser on Human (GRCh38/hg38), chr4:143,540,989-143,735,008, 1 page, (2013).

UCSC Genome Browser on Human (GRCh38/hg38), chr4:143,699,944-143,701,144, 1 page, (2013).

UCSC Genome Browser, ZNF132, ADAMTS2 (exons 1 and 2), LONRF2 (exon 1), ZNF542 (exons 1 and 2), ZNF492 (exon 1), 2 pages, (2024).

Wood, L.D. et al., The genomic landscapes of human breast and colorectal cancers, Science, 318(5853):1108-1113 (2007).

* cited by examiner

| Characteristics | Controls (n=550) | cNEG (n=155) | BEN (n=337) | NAA (n=58) | AA (n=149) | CRC (n=298) |
|---|---|---|---|---|---|---|
| Age (years, mean (IQR)) | 60 (55-65) | 60 (55-65) | 60 (54-64) | 61 (55-67) | 62 (56-67) | 66 (59-73) |
| Prediction outcome per sub-group | p = 0.31 | p = 0.37 | p = 0.50 | p = 0.62 | p = 0.57 | p = 0.80 |
| Gender (n (%)) | | | | | | |
| Male | 274 (49.8%) | 76 (51%) | 159 (52.8%) | 39 (67.2%) | 93 (62.4%) | 155 (52%) |
| Female | 276 (50.2%) | 79 (49%) | 178 (47.2%) | 19 (32.8%) | 56 (37.6%) | 143 (48%) |
| Prediction outcome per sub-group | p = 0.64 | p = 1 | p = 0.70 | p = 0.56 | p = 0.57 | p = 1 |
| Body mass index (kg/m2, mean (IQR)) | 27 (24-29) | 26 (24-29) | 27 (24-30) | 28 (24-30) | 28 (24-31) | 27 (24-30) |
| Prediction outcome per sub-group | p = 0.55 | p = 1 | p = 0.31 | p = 0.62 | p = 0.80 | p = 1 |
| Study country | | | | | | |
| Germany | 82 | 39 | 42 | 1 | 2 | 4 |
| Spain | 342 | 93 | 212 | 37 | 107 | 154 |
| Ukraine | 42 | 16 | 26 | . | 8 | 132 |
| United States | 84 | 7 | 57 | 20 | 32 | 8 |
| Prediction outcome per sub-group | p = 0.31 | p = 0.37 | p = 0.70 | p = 0.55 | p = 0.55 | p = 0.56 |
| Lesion location | | | | | | |
| Distal colon | | | | | 75 | 118 |
| Proximal colon | | | | | 54 | 118 |

FROM FIG. 5A

| | | |
|---|---|---|
| Rectal | 20 | 62 |
| Prediction outcome per sub-group | $p = 0.62$ | $p = 0.55$ |

Histology

| | |
|---|---|
| Tubular | 82 |
| Tubulovillous | 51 |
| Serrated | 13 |
| Carcinoma in situ | 3 |
| Prediction outcome per sub-group | $p = 0.55$ |

Dysplasia grade

| | |
|---|---|
| High | 63 |
| Low | 86 |
| Significance testing | $p = 0.78$ |

Stage

| | |
|---|---|
| Stage I | 56 |
| Stage II | 114 |
| Stage III | 96 |
| Stage IV | 32 |
| Prediction outcome per sub-group | $p = 0.55$ |

Total sample number = 997

FIG. 5B

METHODS FOR STRATIFICATION AND EARLY DETECTION OF ADVANCED ADENOMA AND/OR COLORECTAL CANCER USING DNA METHYLATION MARKERS

CROSS REFERENCE TO RELATED APPLICATIONS

This application claims priority to and benefit of U.S. Provisional Application No. 63/425,882, filed Nov. 16, 2022, the contents of which are hereby incorporated herein by reference in its entirety.

SEQUENCE LISTING

The instant application contains a Sequence Listing which has been submitted electronically in XML format and is hereby incorporated by reference in its entirety. Said XML copy, created on May 19, 2023, is named 2011722-0117_SL.xml and is 133,969 bytes in size.

TECHNICAL FIELD

This invention relates generally to methods and systems for detecting, diagnosing, predicting, monitoring, screening for, staging, and/or providing survival prognosis for advanced adenoma and/or colorectal cancer.

BACKGROUND

Disease detection is an important component of prevention of disease progression, diagnosis, and treatment. For example, early detection of colorectal cancer (CRC) has been shown to improve outcomes of those suffering from CRC through early treatment of CRC. However, despite the availability of current tools to screen for and diagnose CRC and other cancers, millions of individuals still die annually from diseases, such as CRC, which are treatable through early intervention and detection. Current tools to screen for and diagnose diseases are insufficient.

Deoxyribonucleic acid (DNA) methylation (DNAme) is an important epigenetic marker in diverse species. DNA methylation in vertebrates is characterized by the addition of a methyl or hydroxymethyl group to the C5 position of cytosine, which occurs mainly in the context of CG dinucleotides. DNA changes in methylation states is a mechanism for inactivation of cancer-associated genes, including tumor suppressor genes, in CRC and in other human cancers. FIG. 1 shows a simplified example of how DNA methylation changes gene activation in cancer cells compared to normal cells.

DNA methylation impacts numerous cellular processes including, for example, cellular differentiation. Dysregulation of methylation, therefore, can lead to disease, including cancer. Accumulated changes in DNA methylation (e.g., hypermethylation or hypomethylation), especially when the changes are located in crucial genes, can result in cancerous cells. These changes in methylation status, if detected, can be used to predict susceptibility of a subject to developing cancer, as well as the development or presence of cancer.

There is a need for new and more efficient markers that can be used in a non-invasive and high adherence yielding CRC screening context.

SUMMARY

The present disclosure provides, among other things, methods and systems for detecting, diagnosing, predicting, monitoring, screening for, staging, and/or providing survival prognosis for advanced adenoma and/or colorectal cancer using DNA methylation markers and further investigating the fragment sizes of cell-free DNA particles carrying methylation signals. For example, described herein are DNA methylation markers that in combination with fragment size values enable categorization and prognosis evaluation of advanced adenoma (AA) and/or colorectal cancer (CRC) patients with high accuracy from human biospecimens.

In certain embodiments, the markers or maker panels made up of the specified markers provide advanced adenoma and/or colorectal cancer screening at high specificity at early or premalignant stage, minimizing the negative and false positive cases when interrogated in samples taken from a subject. The methylation markers specified herein demonstrate high accuracy AA and CRC stratification of patients whose anonymized data was obtained from The Cancer Genome Atlas (TCGA) database.

Without wishing to be bound to a particular theory, acquired methylation events in promoter regions of tumor suppressor genes are thought to silence expression, whereas demethylation events at the promoter regions of oncogenes are thought to activate these genes, thus contributing to oncogenesis. DNA methylation is believed to be a more chemically and biologically stable process for use in diagnostic tools than RNA or protein expression. Furthermore, methylation events are thought to be highly tissue specific, making these markers more broadly informative and sensitive than individual DNA mutations and providing high specificity. Aberrant methylation patterns of CpG islands located in the promoter regions of tumor suppressor genes is an important mechanism for gene inactivation. DNA methylation affects readability of the DNA sequence wrapped around nucleosomes, linking methylation analysis to cfDNA fragment size parameters.

In experiments conducted while developing the biomarker panel described herein, markers were identified first from tissue whole genome bisulfite sequencing (WGBS) data and then verified in several plasma verification studies.

Resulting regions shown in Table 1 were further analyzed, using comparisons of gene expression and the methylation state of DNA markers from 455 patient data obtained with Illumina 450k methylation microarrays, said data collected by the TCGA consortium.

TABLE 1

| List of 82 genomic regions found to have significantly altered methylation pattern in CRC patients. | | | | |
|---|---|---|---|---|
| Region ID | Length of region | promoters | 1to5kb | 5UTRs |
| (SEQ ID NO.: 1) 12:15322092-15323246 | 1155 | PTPRO | | PTPRO |
| (SEQ ID NO.: 2) 7:35185896-35187104 | 1209 | DPY19L2P1 | DPY19L2P1 | |

TABLE 1-continued

List of 82 genomic regions found to have significantly altered methylation pattern in CRC patients.

| | | | | |
|---|---|---|---|---|
| (SEQ ID NO.: 3) 13:102392801-102392992 | 192 | FGF14 | | |
| (SEQ ID NO.: 4) 1:114152968-114153628 | 661 | SYT6 | SYT6 | SYT6 |
| (SEQ ID NO.: 5) 1:98053750-98054230 | 481 | | MIR137HG | |
| (SEQ ID NO.: 6) 10:101134320-101134800 | 481 | | TLX1NB | |
| (SEQ ID NO.: 7) 10:99329142-99330642 | 1501 | | | CNNM1 |
| (SEQ ID NO.: 8) 11:104163784-104164216 | 433 | PDGFD | | PDGFD |
| (SEQ ID NO.: 9) 11:7251463-7252363 | 901 | SYT9 | | SYT9 |
| (SEQ ID NO.: 10) 11:8080764-8081056 | 293 | TUB | AC116456.2 | |
| (SEQ ID NO.: 11) 12:104457176-104457696 | 521 | | | CHST11 |
| (SEQ ID NO.: 12) 12:132887749-132888077 | 329 | CHFR, AC127070.1 | CHFR | |
| (SEQ ID NO.: 13) 12:63150784-63151598 | 815 | AVPR1A, AC135584.1 | AVPR1A | AVPR1A |
| (SEQ ID NO.: 14) 13:101916754-101917294 | 541 | FGF14 | | |
| (SEQ ID NO.: 15) 14:70188798-70189399 | 602 | SLC8A3 | | SLC8A3 |
| (SEQ ID NO.: 16) 17:35448276-35448579 | 304 | SLFN13 | SLFN13 | SLFN13 |
| (SEQ ID NO.: 17) 17:46819204-46819444 | 241 | WNT3 | | |
| (SEQ ID NO.: 18) 18:28177326-28177787 | 462 | CDH2 | | CDH2 |
| (SEQ ID NO.: 19) 19:31351575-31351815 | 241 | | TSHZ3 | |
| (SEQ ID NO.: 20) 19:36916030-36916584 | 555 | ZNF568, ZNF829 | | ZNF568, ZNF829 |
| (SEQ ID NO.: 21) 19:53254573-53254933 | 361 | ZNF677 | ZNF677, VN1R2 | ZNF677 |
| (SEQ ID NO.: 22) 2:100321258-100322771 | 1514 | LONRF2 | | LONRF2 |
| (SEQ ID NO.: 23) 2:136765857-136766361 | 505 | | | |
| (SEQ ID NO.: 24) 2:181456539-181457919 | 1381 | ITGA4 | ITGA4 | ITGA4 |
| (SEQ ID NO.: 25) 2:181457952-181458372 | 421 | ITGA4 | | |
| (SEQ ID NO.: 26) 2:29115036-29115576 | 541 | CLIP4 | CLIP4 | CLIP4 |
| (SEQ ID NO.: 27) 2:29115806-29116764 | 959 | | CLIP4 | |
| (SEQ ID NO.: 28) 2:29920045-29921364 | 1320 | | ALK | ALK |
| (SEQ ID NO.: 29) 2:31136905-31138399 | 1495 | GALNT14 | | GALNT14 |
| (SEQ ID NO.: 30) 2:95025841-95026142 | 302 | | | |
| (SEQ ID NO.: 31) 20:21509396-21510116 | 721 | | NKX2-2-AS1 | |
| (SEQ ID NO.: 32) 20:23048312-23051297 | 2986 | THBD | THBD | THBD |
| (SEQ ID NO.: 33) 20:43188844-43189744 | 901 | PTPRT, AL021395.1 | AL021395.1 | PTPRT |
| (SEQ ID NO.: 34) 20:61252479-61254380 | 1902 | | | CDH4 |
| (SEQ ID NO.: 35) 21:33071167-33071887 | 721 | AP000282.1, OLIG1 | | |
| (SEQ ID NO.: 36) 22:48576292-48577132 | 841 | TAFA5 | | TAFA5 |
| (SEQ ID NO.: 37) 3:134795824-134796604 | 781 | EPHB1 | | EPHB1 |
| (SEQ ID NO.: 38) 3:141051399-141052239 | 841 | SPSB4 | | SPSB4 |
| (SEQ ID NO.: 39) 3:143119740-143121239 | 1500 | AC018450.1 | CHST2 | CHST2 |
| (SEQ ID NO.: 40) 3:192409037-192410302 | 1266 | FGF12 | FGF12 | FGF12 |

TABLE 1-continued

List of 82 genomic regions found to have significantly
altered methylation pattern in CRC patients.

| | | | | |
|---|---|---|---|---|
| (SEQ ID NO.: 41)<br>3:38039219-38039410 | 192 | | | |
| (SEQ ID NO.: 42)<br>3:96813876-96814374 | 499 | EPHA6 | | |
| (SEQ ID NO.: 43)<br>4:143699944-143701144 | 1201 | FREM3,<br>AC107223.1 | | |
| (SEQ ID NO.: 44)<br>4:183904790-183906478 | 1689 | STOX2 | | STOX2 |
| (SEQ ID NO.: 45)<br>4:20252431-20252893 | 463 | SLIT2 | SLIT2 | |
| (SEQ ID NO.: 46)<br>4:81030777-81031022 | 246 | BMP3 | | BMP3 |
| (SEQ ID NO.: 47)<br>5:179343982-179344854 | 873 | | | |
| (SEQ ID NO.: 48)<br>5:180353618-180354114 | 497 | GFPT2 | GFPT2 | |
| (SEQ ID NO.: 49)<br>5:32711664-32712564 | 901 | NPR3 | | NPR3 |
| (SEQ ID NO.: 50)<br>6:123803544-123804226 | 683 | NKAIN2 | | NKAIN2 |
| (SEQ ID NO.: 51)<br>6:163413181-163413961 | 781 | QKI,<br>CAHM | QKI | |
| (SEQ ID NO.: 52)<br>6:31815355-31815955 | 601 | HSPA1A,<br>HSPA1L | | HSPA1A |
| (SEQ ID NO.: 53)<br>6:391674-392694 | 1021 | IRF4 | IRF4 | IRF4 |
| (SEQ ID NO.: 54)<br>6:72621373-72622257 | 885 | KCNQ5,<br>FO393414.3 | | KCNQ5 |
| (SEQ ID NO.: 55)<br>6:72622261-72623373 | 1113 | FO393414.3 | FO393414.3 | |
| (SEQ ID NO.: 56)<br>7:103989079-103989646 | 568 | RELN | | RELN |
| (SEQ ID NO.: 57)<br>7:141073222-141073810 | 589 | TMEM178B | TMEM178B | |
| (SEQ ID NO.: 58)<br>7:141074279-141074546 | 268 | TMEM178B | | TMEM178B |
| (SEQ ID NO.: 59)<br>7:151409258-151410098 | 841 | WDR86,<br>WDR86-AS1 | WDR86-AS1 | WDR86 |
| (SEQ ID NO.: 60)<br>7:153886164-153886404 | 241 | DPP6 | | |
| (SEQ ID NO.: 61)<br>7:157336370-157336577 | 208 | DNAJB6 | DNAJB6 | DNAJB6 |
| (SEQ ID NO.: 62)<br>7:159144190-159144938 | 749 | VIPR2 | | VIPR2 |
| (SEQ ID NO.: 63)<br>7:19117486-19118112 | 627 | TWIST1 | AC003986.3,<br>TWIST1 | TWIST1 |
| (SEQ ID NO.: 64)<br>7:28409622-28410342 | 721 | | CREB5 | CREB5 |
| (SEQ ID NO.: 65)<br>7:37448742-37448854 | 113 | | | ELMO1 |
| (SEQ ID NO.: 66)<br>7:38630658-38631461 | 804 | AMPH | | AMPH |
| (SEQ ID NO.: 67)<br>7:43112316-43113632 | 1317 | HECW1 | HECW1-IT1,<br>HECW1 | HECW1 |
| (SEQ ID NO.: 68)<br>7:50304073-50304411 | 339 | IKZF1 | IKZF1 | IKZF1 |
| (SEQ ID NO.: 69)<br>7:50304762-50304947 | 186 | IKZF1 | IKZF1 | IKZF1 |
| (SEQ ID NO.: 70)<br>7:93889427-93891122 | 1696 | TFPI2,<br>AC002076.1 | AC002076.1 | TFPI2 |
| (SEQ ID NO.: 71)<br>8:142451692-142452592 | 901 | | | |
| (SEQ ID NO.: 72)<br>8:66961046-66962606 | 1561 | TCF24 | | TCF24 |
| (SEQ ID NO.: 73)<br>8:68330607-68331757 | 1151 | C8orf34,<br>C8orf34-AS1 | | C8orf34 |
| (SEQ ID NO.: 74)<br>8:71843436-71844516 | 1081 | MSC,<br>MSC-AS1 | MSC | MSC |
| (SEQ ID NO.: 75)<br>8:96145538-96145718 | 181 | | AP003465.2 | |
| (SEQ ID NO.: 76)<br>8:96160146-96160866 | 721 | GDF6 | | GDF6 |
| (SEQ ID NO.: 77)<br>8:96494109-96494705 | 597 | | | SDC2 |
| (SEQ ID NO.: 78)<br>8:96494903-96495378 | 476 | | | |

TABLE 1-continued

List of 82 genomic regions found to have significantly
altered methylation pattern in CRC patients.

| | |
|---|---|
| (SEQ ID NO.: 79) | 378 |
| 8:96495148-96495525 | |
| (SEQ ID NO.: 80) | 301 |
| 8:98951212-98951512 | |
| (SEQ ID NO.: 81) | 361 |
| 8:98951542-98951902 | |
| (SEQ ID NO.: 82) | 332 |
| 9:134407349-134407680 | |

| Region ID | exons | introns |
|---|---|---|
| 12:15322092-15323246 | PTPRO | PTPRO, RERG |
| 7:35185896-35187104 | DPY19L2P1 | |
| 13:102392801-102392992 | | |
| 1:114152968-114153628 | SYT6 | SYT6 |
| 1:98053750-98054230 | AC104453.1 | AC104453.1 |
| 10:101134320-101134800 | TLX1 | TLX1 |
| 10:99329142-99330642 | CNNM1 | |
| 11:104163784-104164216 | PDGFD | PDGFD |
| 11:7251463-7252363 | SYT9 | SYT9 |
| 11:8080764-8081056 | | TUB |
| 12:104457176-104457696 | CHST11 | CHST11 |
| 12:132887749-132888077 | AC127070.1 | AC127070.1, CHFR |
| 12:63150784-63151598 | AVPR1A, AC135584.1 | AC135584.1 |
| 13:101916754-101917294 | | FGF14 |
| 14:70188798-70189399 | SLC8A3 | AL160191.1 |
| 17:35448276-35448579 | SLFN13 | SLFN13 |
| 17:46819204-46819444 | | WNT3 |
| 18:28177326-28177787 | CDH2 | |
| 19:31351575-31351815 | | AC025809.1 |
| 19:36916030-36916584 | ZNF568, ZNF829 | |
| 19:53254573-53254933 | ZNF677 | ZNF677 |
| 2:100321258-100322771 | LONRF2 | LONRF2 |
| 2:136765857-136766361 | | THSD7B |
| 2:181456539-181457919 | ITGA4 | ITGA4 |
| 2:181457952-181458372 | ITGA4 | ITGA4 |
| 2:29115036-29115576 | CLIP4 | CLIP4 |
| 2:29115806-29116764 | | CLIP4 |
| 2:29920045-29921364 | | |
| 2:31136905-31138399 | GALNT14 | GALNT14 |
| 2:95025841-95026142 | MAL | MAL, AC103563.7 |
| 20:21509396-21510116 | | |
| 20:23048312-23051297 | THBD | |
| 20:43188844-43189744 | PTPRT | PTPRT |
| 20:61252479-61254380 | CDH4 | CDH4 |
| 21:33071167-33071887 | OLIG1 | OLIG1 |
| 22:48576292-48577132 | TAFA5 | TAFA5 |
| 3:134795824-134796604 | EPHB1 | EPHB1 |
| 3:141051399-141052239 | SPSB4 | SPSB4 |
| 3:143119740-143121239 | CHST2 | |
| 3:192409037-192410302 | FGF12 | FGF12 |
| 3:38039219-38039410 | DLEC1 | |
| 3:96813876-96814374 | | |
| 4:143699944-143701144 | FREM3, AC107223.1 | AC107223.1 |
| 4:183904790-183906478 | STOX2 | STOX2 |
| 4:20252431-20252893 | | |
| 4:81030777-81031022 | BMP3 | |
| 5:179343982-179344854 | ADAMTS2 | ADAMTS2 |
| 5:180353618-180354114 | | |
| 5:32711664-32712564 | NPR3 | NPR3 |
| 6:123803544-123804226 | NKAIN2 | |
| 6:163413181-163413961 | CAHM | |
| 6:31815355-31815955 | HSPA1A | HSPA1A |
| 6:391674-392694 | IRF4 | IRF4 |
| 6:72621373-72622257 | KCNQ5, FO393414.3 | |
| 6:72622261-72623373 | KCNQ5 | KCNQ5 |
| 7:103989079-103989646 | RELN | RELN |
| 7:141073222-141073810 | | |
| 7:141074279-141074546 | TMEM178B | |
| 7:151409258-151410098 | WDR86, WDR86-AS1 | WDR86, WDR86-AS1 |
| 7:153886164-153886404 | | |
| 7:157336370-157336577 | DNAJB6 | |
| 7:159144190-159144938 | VIPR2 | VIPR2 |
| 7:19117486-19118112 | TWIST1 | |
| 7:28409622-28410342 | CREB5 | CREB5 |
| 7:37448742-37448854 | ELMO1 | ELMO1 |
| 7:38630658-38631461 | AMPH | AMPH |

TABLE 1-continued

List of 82 genomic regions found to have significantly
altered methylation pattern in CRC patients.

| | | |
|---|---|---|
| 7:43112316-43113632 | HECW1, AC005537.1 | HECW1, AC005537.1 |
| 7:50304073-50304411 | IKZF1 | IKZF1 |
| 7:50304762-50304947 | IKZF1 | IKZF1 |
| 7:93889427-93891122 | TFPI2, AC002076.1 | TFPI2, AC002076.1, GNGT1 |
| 8:142451692-142452592 | | ADGRB1 |
| 8:66961046-66962606 | TCF24 | TCF24 |
| 8:68330607-68331757 | C8orf34, C8orf34-AS1 | C8orf34, C8orf34-AS1 |
| 8:71843436-71844516 | MSC, MSC-AS1 | MSC, MSC-AS1 |
| 8:96145538-96145718 | | GDF6 |
| 8:96160146-96160866 | GDF6 | GDF6 |
| 8:96494109-96494705 | SDC2 | SDC2 |
| 8:96494903-96495378 | | SDC2 |
| 8:96495148-96495525 | | SDC2 |
| 8:98951212-98951512 | | OSR2 |
| 8:98951542-98951902 | OSR2 | OSR2 |
| 9:134407349-134407680 | | RXRA |

The candidate markers provide the possibility to stratify cellular differences on the origin of the tumor and predict patient prognosis and clinical outcome. As such, the analysis provides specific markers or marker combinations for purposes of AA and/or CRC stratification and/or tumor origin identification. As a result, improved accuracy of patient diagnosis, prognosis, clinical outcome and survival prediction may be achieved Furthermore, in certain embodiments, the marker panel is a combination of 1600 or fewer genomic regions, or, in some embodiments, the marker is one region. In some embodiments the marker(s) is/are in a high-density promoter region. In certain embodiments, the markers and/or panels of markers including methylations as well as mutations.

In one aspect, the invention is directed to a method of identifying (e.g., sub-categorizing, stratifying, detecting, diagnosing, predicting, monitoring, screening for, staging, and/or providing survival prognosis for) a condition in a human subject, the method comprising: determining a methylation status for each of one or more (e.g., at least 3, at least 5, at least 10, at least 15, at least 20, at least 25, at least 30, at least 35, at least 40, at least 45, at least 50, at least 55, at least 60, at least 65, at least 70, at least 75, at least 80, or at least 82) markers identified in deoxyribonucleic acid (DNA) fragments (DNA fragments) from a sample obtained from the subject; and identifying (e.g., sub-categorizing, stratifying, detecting, diagnosing, predicting, monitoring, screening for, staging, and/or providing survival prognosis for) the condition in the subject based at least in part on the determined methylation status of each of the one or more markers identified in the DNA fragments, wherein each of the one or more markers is a methylation locus comprising at least a single differentially methylated region (DMR) or a portion of a DMR selected from the 82 DMRs listed in Table 1 (i.e., SEQ ID NOs. 1 to 82) (e.g., each said portion comprising at least one (1) CpG and/or each said methylation locus having a length equal to or less than 302 bp).

In certain embodiments, the identifying step comprises identifying the condition in the subject based at least in part on (i) the determined methylation status of each of the one or more markers identified in the DNA fragments and (ii) a determined size of each of the DNA fragments in which the one or more markers are identified.

In certain embodiments, the identifying step comprises identifying the condition in the subject based at least in part on (i) the determined methylation status of each of the one or more markers identified in the DNA fragments and (ii) a determined size and start/end nucleotide sequence of each of the DNA fragments in which the one or more markers are identified.

In certain embodiments, the condition is colorectal cancer (CRC).

In certain embodiments, the condition is advanced adenoma (AA).

In certain embodiments, the method identifies whether the subject has either colorectal cancer (CRC) or advanced adenoma (AA) as an undifferentiated diagnosis (i.e., the method identifies that the subject has either CRC or AA, but the method does not specify which of the two diagnoses the subject has).

In certain embodiments, the method identifies whether the subject has either colorectal cancer (CRC) or advanced adenoma (AA) as a differentiated diagnosis (i.e., the method identifies that the subject has either CRC or AA, and the method also specifies which of the two diagnoses the subject has).

In certain embodiments, the sample is a member selected from the group consisting of a tissue sample, a blood sample, a stool sample, and a blood product sample.

In certain embodiments, the sample comprises DNA that is isolated from blood or plasma of the human subject.

In certain embodiments, the DNA is cell-free DNA (cfDNA) of the human subject.

In certain embodiments, the method comprises determining the methylation status of each of the one or more markers using next generation sequencing (NGS).

In certain embodiments, the method comprises using one or more capture baits that enrich for a target region to capture one or more corresponding methylation locus/loci.

In certain embodiments, each methylation locus is equal to or less than 302 bp in length.

In certain embodiments, the method comprises: converting unmethylated cytosines of a plurality of DNA fragments in a sample into uracils to generate a plurality of converted DNA fragments, wherein the plurality of DNA fragments were obtained from a biological sample; and sequencing the plurality of converted DNA fragments to generate a plurality of sequence reads, wherein each sequence read corresponds to a converted DNA fragment.

In certain embodiments, the plurality of DNA fragments (in total) comprise at least 1 ng, at least 5 ng, at least 10 ng, or at least 20 ng of DNA.

In certain embodiments, the plurality of DNA fragments consist of or consist essentially of DNA fragments each of which has a length in a range from 10 bp to 800 bp (e.g., from about 50 bp to about 250 bp; from about 250 bp to about 480 bp; from about 480 bp to about 800 bp; from about 125 bp to about 200 bp; or from about 140 bp to about 160 bp (e.g., for cfDNA))(e.g., from about 50 bp to about 150 bp, from about 150 bp to about 350 bp; or from about 200 bp to about 300 bp (e.g., for sheared DNA)).

In certain embodiments, the plurality of DNA fragments consist of or consist essentially of DNA fragments each of which has a length in a range from 1000 bp to 200,000 bp [e.g., an average length of about 10,000 bp (e.g., for genomic DNA, e.g., from a sample comprising tissue or buffy coat)].

In certain embodiments, each of the plurality of sequence reads is at least 50 bp, at least 100 bp, at least 150 bp, at least 200 bp, at least 300 bp, or more.

Definitions

In this application, the use of "or" means "and/or" unless stated otherwise. The articles "a" and "an" are used herein to refer to one or to more than one (i.e., to at least one) of the grammatical object of the article. By way of example, "an element" refers to one element or more than one element. As used in this application, the term "comprise" and variations of the term, such as "comprising" and "comprises," are not intended to exclude other additives, components, integers or steps. As used in this application, the terms "about" and "approximately" are used as equivalents. Any numerals used in this application with or without about/approximately are meant to cover any normal fluctuations appreciated by one of ordinary skill in the relevant art. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Administration: As used herein, the term "administration" typically refers to the administration of a composition to a subject or system, for example to achieve delivery of an agent that is, is included in, or is otherwise delivered by, the composition. Administration to an animal subject (e.g., to a human) may be by any appropriate route. For example, in some embodiments, administration may be bronchial (including by bronchial instillation), buccal, enteral, interdermal, intra-arterial, intradermal, intragastric, intramedullary, intramuscular, intranasal, intraperitoneal, intrathecal, intravenous, intraventricular, within a specific organ (e. g. intrahepatic), mucosal, nasal, oral, rectal, subcutaneous, sublingual, topical, tracheal (including by intratracheal instillation), transdermal, vaginal and vitreal. In some embodiments, administration may involve intermittent dosing. In some embodiments, administration may involve continuous dosing (e.g., perfusion) for at least a selected period of time. As is known in the art, antibody therapy is commonly administered parenterally (e.g., by intravenous or subcutaneous injection).

Advanced Adenoma: As used herein, the term "advanced adenoma" refers to cells that exhibit first indications of relatively abnormal, uncontrolled, and/or autonomous growth but are not yet classified as cancerous alterations. In the context of colon tissue, "advanced adenoma" refers to neoplastic growth that shows signs of high grade dysplasia, and/or size that is >=10 mm, and/or villious histological type, and/or serrated histological type with any type of dysplasia.

Agent: As used herein, the term "agent" refers to an entity (e.g., for example, a small molecule, peptide, polypeptide, nucleic acid, lipid, polysaccharide, complex, combination, mixture, system, or phenomenon such as heat, electric current, electric field, magnetic force, magnetic field, etc.).

Amelioration: As used herein, the term "amelioration" refers to the prevention, reduction, palliation, or improvement of a state of a subject. Amelioration includes, but does not require, complete recovery or complete prevention of a disease, disorder or condition.

Amplicon or amplicon molecule: As used herein, the term "amplicon" or "amplicon molecule" refers to a nucleic acid molecule generated by transcription from a template nucleic acid molecule, or a nucleic acid molecule having a sequence complementary thereto, or a double-stranded nucleic acid including any such nucleic acid molecule. Transcription can be initiated from a primer.

Amplification: As used herein, the term "amplification" refers to the use of a template nucleic acid molecule in combination with various reagents to generate further nucleic acid molecules from the template nucleic acid molecule, which further nucleic acid molecules may be identical to or similar to (e.g., at least 70% identical, e.g., at least 75%, 80%, 85%, 90%, 91%, 92%, 93%, 94%, 95%, 96%, 97%, 98%, 99%, or 100% identical to) a segment of the template nucleic acid molecule and/or a sequence complementary thereto. Amplification generally refers to the production of multiple copies of a specific nucleic acid portion, typically starting from a small amount of the polynucleotide. It is to be differentiated from non-specific template replication (e.g., replication that is template-dependent but not dependent on a specific template). Template specificity is frequently described in terms of "target" specificity. Target sequences are "targets" in the sense that they are sought to be sorted out from other nucleic acid. Amplification techniques, like, but not limited to, polymerase-chain reaction (PCR), have been designed primarily for this sorting out.

Amplification reaction mixture: As used herein, the terms "amplification reaction mixture" or "amplification reaction" refer to a template nucleic acid molecule together with reagents sufficient for amplification of the template nucleic acid molecule.

Biological pathway: As used herein, the term "biological pathway" refers to a set of interactions or changes in a cell that leads to production of a specific product or a change in cell fate. Each pathway in combination with other pathways or separately can cause a particular molecule production, switch gene activity or lead the cell to a particular position, etc. Herein, these set of interactions are used to demonstrate the relationship between the aberrant methylated regions and its biological function, determining its clinical and diagnostic values.

Biological Sample: As used herein, the term "biological sample" generally refers to a sample obtained or derived from a biological source (e.g., a tissue or organism or cell culture) of interest, as described herein. In some embodiments, a source of interest comprises an organism, such as an animal or human. In some embodiments, a biological sample is or comprises biological tissue or fluid. In some embodiments, a biological sample may be or comprise bone marrow; blood; blood cells; ascites; tissue or fine needle biopsy samples; cell-containing body fluids; free floating nucleic acids; sputum; saliva; urine; cerebrospinal fluid, peritoneal fluid; pleural fluid; feces; lymph; gynecological fluids; skin swabs; vaginal swabs; oral swabs; nasal swabs; washings or lavages such as a ductal lavages or broncheoalveolar lavages; aspirates; scrapings; bone marrow specimens; tissue biopsy specimens; surgical specimens; feces, other body fluids, secretions, and/or excretions; and/or cells therefrom, etc. In some embodiments, a biological sample is or comprises cells obtained from an individual. In some embodiments, obtained cells are or include cells from an individual from whom the sample is obtained. In some embodiments, a sample is a "primary sample" obtained directly from a source of interest by any appropriate means. For example, in some embodiments, a primary biological sample is obtained by methods selected from the group consisting of biopsy (e.g., fine needle aspiration or tissue biopsy), surgery, collection of body fluid (e.g., blood, lymph, feces etc.), etc. In some embodiments, as will be clear from context, the term "sample" refers to a preparation that is obtained by processing (e.g., by removing one or more components of and/or by adding one or more agents to) a primary sample. For example, filtering using a semi-permeable membrane. Such a "processed sample" may comprise, for example nucleic acids or proteins extracted from a sample or obtained by subjecting a primary sample to techniques such as amplification or reverse transcription of mRNA, isolation and/or purification of certain components, etc.

Biomarker: As used herein, the term "biomarker," consistent with its use in the art, refers to a to an entity whose presence, level, or form, correlates with a particular biological event or state of interest, so that it is considered to be a "marker" of that event or state. Those of skill in the art will appreciate, for instance, in the context of a DNA biomarker, that a biomarker can be or include a locus (such as one or more methylation loci) and/or the status of a locus (e.g., the status of one or more methylation loci). To give but a few examples of biomarkers, in some embodiments, e.g., as set forth herein, a biomarker can be or include a marker for a particular disease, disorder or condition, or can be a marker for qualitative of quantitative probability that a particular disease, disorder or condition can develop, occur, or reoccur, e.g., in a subject. In some embodiments, e.g., as set forth herein, a biomarker can be or include a marker for a particular therapeutic outcome, or qualitative of quantitative probability thereof. Thus, in various embodiments, e.g., as set forth herein, a biomarker can be predictive, prognostic, and/or diagnostic, of the relevant biological event or state of interest. A biomarker can be an entity of any chemical class. For example, in some embodiments, e.g., as set forth herein, a biomarker can be or include a nucleic acid, a polypeptide, a lipid, a carbohydrate, a small molecule, an inorganic agent (e.g., a metal or ion), or a combination thereof. In some embodiments, e.g., as set forth herein, a biomarker is a cell surface marker. In some embodiments, e.g., as set forth herein, a biomarker is intracellular. In some embodiments, e.g., as set forth herein, a biomarker is found outside of cells (e.g., is secreted or is otherwise generated or present outside of cells, e.g., in a body fluid such as blood, urine, tears, saliva, cerebrospinal fluid, and the like). In some embodiments, e.g., as set forth herein, a biomarker is methylation status of a methylation locus. In some instances, e.g., as set forth herein, a biomarker may be referred to as a "marker."

To give but one example of a biomarker, in some embodiments e.g., as set forth herein, the term refers to expression of a product encoded by a gene, expression of which is characteristic of a particular tumor, tumor subclass, stage of tumor, etc. Alternatively or additionally, in some embodiments, e.g., as set forth herein, presence or level of a particular marker can correlate with activity (or activity level) of a particular signaling pathway, for example, of a signaling pathway the activity of which is characteristic of a particular class of tumors.

Those of skill in the art will appreciate that a biomarker may be individually determinative of a particular biological event or state of interest, or may represent or contribute to a determination of the statistical probability of a particular biological event or state of interest. Those of skill in the art will appreciate that markers may differ in their specificity and/or sensitivity as related to a particular biological event or state of interest.

Biomolecule: As used herein, "biomolecule" refers to bioactive, diagnostic, and prophylactic molecules. Biomolecules that can be used in the present invention include, but are not limited to, synthetic, recombinant or isolated peptides and proteins such as antibodies and antigens, receptor ligands, enzymes, and adhesion peptides; nucleotides and polynucleic acids such as DNA and antisense nucleic acid molecule; activated sugars and polysaccharides; bacteria; viruses; and chemical drugs such as antibiotics, anti-inflammatories, and antifungal agents.

Bisulfite reagent: As used herein, the term "bisulfite reagent" refers to a reagent comprising bisulfite, disulfite, hydrogen sulfite, or combinations thereof to distinguish between methylated and unmethylated cytidines, e.g., in CpG dinucleotide sequences.

Blood component: As used herein, the term "blood component" refers to any component of whole blood, including red blood cells, white blood cells, plasma, platelets, endothelial cells, mesothelial cells, epithelial cells, and cell-free DNA. Blood components also include the components of plasma, including proteins, metabolites, lipids, nucleic acids, and carbohydrates, and any other cells that can be present in blood, e.g., due to pregnancy, organ transplant, infection, injury, or disease.

Cancer: As used herein, the terms "cancer," "malignancy," "neoplasm," "tumor," and "carcinoma," are used interchangeably to refer to a disease, disorder, or condition in which cells exhibit or exhibited relatively abnormal, uncontrolled, and/or autonomous growth, so that they display or displayed an abnormally elevated proliferation rate and/or aberrant growth phenotype. In some embodiments, e.g., as set forth herein, a cancer can include one or more tumors. In some embodiments e.g., as set forth herein, a cancer can be or include cells that are precancerous (e.g., benign), malignant, pre-metastatic, metastatic, and/or non-metastatic. In some embodiments e.g., as set forth herein, a cancer can be or include a solid tumor. In some embodiments e.g., as set forth herein, a cancer can be or include a hematologic tumor. In general, examples of different types of cancers known in the art include, for example, colorectal cancer, hematopoietic cancers including leukemias, lymphomas (Hodgkin's and non-Hodgkin's), myelomas and myeloproliferative disorders; sarcomas, melanomas, adenomas, carcinomas of solid tissue, squamous cell carcinomas of the mouth, throat, larynx, and lung, liver cancer, genitourinary cancers such as prostate, cervical, bladder, uterine, and endometrial cancer and renal cell carcinomas, bone cancer, colorectal cancer, skin cancer, cutaneous or intraocular melanoma, cancer of the endocrine system, cancer of the thyroid gland, cancer of the parathyroid gland, head and neck cancers, breast cancer, gastro-intestinal cancers and nervous system cancers, benign lesions such as papillomas, and the like.

Chemotherapeutic agent: As used herein, the term "chemotherapeutic agent," consistent with its use in the art, refers to one or more agents known, or having characteristics known to, treat or contribute to the treatment of cancer. In particular, chemotherapeutic agents include pro-apoptotic, cytostatic, and/or cytotoxic agents. In some embodiments e.g., as set forth herein, a chemotherapeutic agent can be or include alkylating agents, anthracyclines, cytoskeletal disruptors (e.g., microtubule targeting moieties such as taxanes, maytansine, and analogs thereof, of), epothilones, histone deacetylase inhibitors HDACs), topoisomerase inhibitors (e.g., inhibitors of topoisomerase I and/or topoisomerase II), kinase inhibitors, nucleotide analogs or nucleotide precursor analogs, peptide antibiotics, platinum-based agents, retinoids, vinca alkaloids, and/or analogs that share a relevant anti-proliferative activity. In some particular embodiments e.g., as set forth herein, a chemotherapeutic agent can be or include of Actinomycin, All-trans retinoic acid, an Auiristatin, Azacitidine, Azathioprine, Bleomycin, Bortezomib, Carboplatin, Capecitabine, Cisplatin, Chlorambucil, Cyclophosphamide, Curcumin, Cytarabine, Daunorubicin, Docetaxel, Doxifluridine, Doxorubicin, Epirubicin, Epothilone, Etoposide, Fluorouracil, Gemcitabine, Hydroxyurea, Idarubicin, Imatinib, Irinotecan, Maytansine and/or analogs thereof (e.g., DM1) Mechlorethamine, Mercaptopurine, Methotrexate, Mitoxantrone, a Maytansinoid, Oxaliplatin, Paclitaxel, Pemetrexed, Teniposide, Tioguanine, Topotecan, Valrubicin, Vinblastine, Vincristine, Vindesine, Vinorelbine, or a combination thereof. In some embodiments e.g., as set forth herein, a chemotherapeutic agent can be utilized in the context of an antibody-drug conjugate. In some embodiments e.g., as set forth herein, a chemotherapeutic agent is one found in an antibody-drug conjugate selected from the group consisting of: hLL1-doxorubicin, hRS7-SN-38, hMN-14-SN-38, hLL2-SN-38, hA20-SN-38, hPAM4-SN-38, hLL1-SN-38, hRS7-Pro-2-P-Dox, hMN-14-Pro-2-P-Dox, hLL2-Pro-2-P-Dox, hA20-Pro-2-P-Dox, hPAM4-Pro-2-P-Dox, hLL1-Pro-2-P-Dox, P4/D10-doxorubicin, gemtuzumab ozogamicin, brentuximab vedotin, trastuzumab emtansine, inotuzumab ozogamicin, glembatumomab vedotin, SAR3419, SAR566658, BIIB015, BT062, SGN-75, SGN-CD19A, AMG-172, AMG-595, BAY-94-9343, ASG-SME, ASG-22ME, ASG-16M8F, MDX-1203, MLN-0264, anti-PSMA ADC, RG-7450, RG-7458, RG-7593, RG-7596, RG-7598, RG-7599, RG-7600, RG-7636, ABT-414, IMGN-853, IMGN-529, vorsetuzumab mafodotin, and lorvotuzumab mertansine. In some embodiments e.g., as set forth herein, a chemotherapeutic agent can be or comprise of farnesyl-thiosalicylic acid (FTS), 4-(4-Chloro-2-methylphenoxy)-N-hydroxybutanamide (CMH), estradiol (E2), tetramethoxystilbene (TMS), 6-tocatrienol, salinomycin, or curcumin.

Combination therapy: As used herein, the term "combination therapy" refers to administration to a subject of to two or more agents or regimens such that the two or more agents or regimens together treat a disease, condition, or disorder of the subject. In some embodiments, e.g., as set forth herein, the two or more therapeutic agents or regimens can be administered simultaneously, sequentially, or in overlapping dosing regimens. Those of skill in the art will appreciate that combination therapy includes but does not require that the two agents or regimens be administered together in a single composition, nor at the same time.

Comparable: As used herein, the term "comparable" refers to members within sets of two or more conditions, circumstances, agents, entities, populations, etc., that may not be identical to one another but that are sufficiently similar to permit comparison there between, such that one of skill in the art will appreciate that conclusions can reasonably be drawn based on differences or similarities observed. In some embodiments, e.g., as sort forth herein, comparable sets of conditions, circumstances, agents, entities, populations, etc. are typically characterized by a plurality of substantially identical features and zero, one, or a plurality of differing features. Those of ordinary skill in the art will understand, in context, what degree of identity is required to render members of a set comparable. For example, those of ordinary skill in the art will appreciate that members of sets of conditions, circumstances, agents, entities, populations, etc., are comparable to one another when characterized by a sufficient number and type of substantially identical features to warrant a reasonable conclusion that differences observed can be attributed in whole or part to non-identical features thereof.

Corresponding to: As used herein, the term "corresponding to" refers to a relationship between two or more entities. For example, the term "corresponding to" may be used to designate the position/identity of a structural element in a compound or composition relative to another compound or composition (e.g., to an appropriate reference compound or composition). For example, in some embodiments, a monomeric residue in a polymer (e.g., a nucleic acid residue in a polynucleotide) may be identified as "corresponding to" a residue in an appropriate reference polymer. Those of ordinary skill in the art readily appreciate how to identify "corresponding" nucleic acids. For example, those skilled in the art will be aware of various sequence alignment strategies, including software programs such as, for example, BLAST, CS-BLAST, CUSASW++, DIAMOND, FASTA, GGSEARCH/GLSEARCH, Genoogle, HMMER, HHpred/HHsearch, IDF, Infernal, KLAST, USEARCH, parasail, PSI-BLAST, PSI-Search, ScalaBLAST, Sequilab, SAM, SSEARCH, SWAPHI, SWAPHI-LS, SWIMM, or SWIPE that can be utilized, for example, to identify "corresponding" residues in nucleic acids in accordance with the present disclosure. Those of skill in the art will also appreciate that, in some instances, the term "corresponding to" may be used to describe an event or entity that shares a relevant similarity with another event or entity (e.g., an appropriate reference event or entity). To give but one example, a fragment of DNA in a sample from a subject may be described as "corresponding to" a gene in order to indicate, in some embodiments, that it shows a particular degree of sequence identity or homology, or shares a particular characteristic sequence element.

Detectable moiety: The term "detectable moiety" as used herein refers to any element, molecule, functional group, compound, fragment, or other moiety that is detectable. In some embodiments, e.g., as sort forth herein, a detectable moiety is provided or utilized alone. In some embodiments, e.g., as sort forth herein, a detectable moiety is provided and/or utilized in association with (e.g., joined to) another agent. Examples of detectable moieties include, but are not limited to, various ligands, radionuclides (e.g., $^{3}$H, $^{14}$C, $^{18}$F, $^{19}$F, $^{32}$P, $^{35}$S, $^{135}$I, $^{125}$I, $^{123}$I, $^{64}$Cu, $^{187}$Re, $^{111}$In, $^{90}$Y, $^{99m}$Tc, $^{177}$Lu, $^{89}$Zr etc.), fluorescent dyes, chemiluminescent agents, bioluminescent agents, spectrally resolvable inorganic fluorescent semiconductors nanocrystals (i.e., quantum dots), metal nanoparticles, nanoclusters, paramagnetic metal ions, enzymes, colorimetric labels, biotin, dioxigenin, haptens, and proteins for which antisera or monoclonal antibodies are available.

Diagnosis: As used herein, the term "Diagnosis" refers to determining whether, and/or the qualitative of quantitative probability that, a subject has or will develop a disease, disorder, condition, or state. For example, in diagnosis of cancer, diagnosis can include a determination regarding the risk, type, stage, malignancy, or other classification of a cancer. In some instances, e.g., as sort forth herein, a diagnosis can be or include a determination relating to prognosis and/or likely response to one or more general or particular therapeutic agents or regimens.

Diagnostic information: As used herein, the term "diagnostic information" or "information for use in diagnosis" refers to information useful in determining whether a patient has a disease, disorder or condition and/or in classifying a disease, disorder or condition into a phenotypic category or any category having significance with regard to prognosis of a disease, disorder or condition, or likely response to treatment (either treatment in general or any particular treatment) of a disease, disorder or condition. Similarly, "diagnosis" refers to providing any type of diagnostic information, including, but not limited to, whether a subject is likely to have or develop a disease, disorder or condition, state, staging or characteristic of a disease, disorder or condition as manifested in the subject, information related to the nature or classification of a tumor, information related to prognosis and/or information useful in selecting an appropriate treatment. Selection of treatment may include the choice of a particular therapeutic agent or other treatment modality such as surgery, radiation, etc., a choice about whether to withhold or deliver therapy, a choice relating to dosing regimen (e.g., frequency or level of one or more doses of a particular therapeutic agent or combination of therapeutic agents), etc. Diagnostic information can include, without limitation, biomarker status information.

Differentially methylated: As used herein, the term "differentially methylated" describes a methylation site for which the methylation status differs between a first condition and a second condition. A methylation site that is differentially methylated can be referred to as a differentially methylated site. In some instances, e.g., as sort forth herein, a DMR is defined by the amplicon produced by amplification using oligonucleotide primers, e.g., a pair of oligonucleotide primers selected for amplification of the DMR or for amplification of a DNA region of interest present in the amplicon. In some instances, e.g., as sort forth herein, a DMR is defined as a DNA region amplified by a pair of oligonucleotide primers, including the region having the sequence of, or a sequence complementary to, the oligonucleotide primers. In some instances, e.g., as sort forth herein, a DMR is defined as a DNA region amplified by a pair of oligonucleotide primers, excluding the region having the sequence of, or a sequence complementary to, the oligonucleotide primers. As used herein, a specifically provided DMR can be unambiguously identified by the name of an associated gene followed by three digits of a starting position, such that, for example, a DMR starting at position 100785927 of ZAN can be identified as ZAN '927. As used herein, a specifically provided DMR can be unambiguously identified by the chromosome number followed by the starting and ending positions of a DMR.

Differentially methylated region: As used herein, the term "differentially methylated region" (DMR) refers to a DNA region that includes one or more differentially methylated sites. A DMR that includes a greater number or frequency of methylated sites under a selected condition of interest, such as a cancerous state, can be referred to as a hypermethylated DMR. A DMR that includes a smaller number or frequency of methylated sites under a selected condition of interest, such as a cancerous state, can be referred to as a hypomethylated DMR. A DMR that is a methylation biomarker for colorectal cancer can be referred to as a colorectal cancer DMR. A DMR that is a methylation biomarker for advanced adenoma can be referred to as an advanced adenoma DMR. In some instances, e.g., as set forth herein, a DMR can be a single nucleotide, which single nucleotide is a methylation site. In some instances, e.g., as set forth herein, a DMR has a length of at least 10, at least 15, at least 20, at least 30, at least 50, or at least 75 base pairs. In some instances, e.g., as set forth herein, a DMR has a length of equal to or less than 5,000 bp, 4,000 bp, 3,000 bp, 2,000 bp, 1,000 bp, 950 bp, 900 bp, 850 bp, 800 bp, 750 bp, 700 bp, 650 bp, 600 bp, 550 bp, 500 bp, 450 bp, 400 bp, 350 bp, 300 bp, 250 bp, 200 bp, 150 bp, 100 bp, 50 bp, 40 bp, 30 bp, 20 bp, or 10 bp (e.g., where methylation status is determined using quantitative polymerase chain reaction (qPCR), e.g., methylation sensitive restriction enzyme quantitative polymerase chain reaction (MSRE-qPCR)) (e.g., where methylation status is determined using a next generation sequencing technique, e.g., targeted next generation sequencing). In some instances, e.g., as set forth herein, a DMR that is a methylation biomarker for advanced adenoma may also be useful in identification of colorectal cancer and vice versa.

DNA region: As used herein, "DNA region" refers to any contiguous portion of a larger DNA molecule. Those of skill in the art will be familiar with techniques for determining whether a first DNA region and a second DNA region correspond, based, e.g., on sequence similarity (e.g., sequence identity or homology) of the first and second DNA regions and/or context (e.g., the sequence identity or homology of nucleic acids upstream and/or downstream of the first and second DNA regions).

Except as otherwise specified herein, sequences found in or relating to humans (e.g., that hybridize to human DNA) are found in, based on, and/or derived from the example representative human genome sequence commonly referred to, and known to those of skill in the art, as *Homo sapiens* (human) genome assembly GRCh38, hg38, and/or Genome Reference Consortium Human Build 38. Those of skill in the art will further appreciate that DNA regions of hg38 can be referred to by a known system including identification of particular nucleotide positions or ranges thereof in accordance with assigned numbering.

Dosing regimen: As used herein, the term "dosing regimen" can refer to a set of one or more same or different unit doses administered to a subject, typically including a plurality of unit doses administration of each of which is separated from administration of the others by a period of time. In various embodiments, e.g., as set forth herein, one or more or all unit doses of a dosing regimen may be the same or can vary (e.g., increase over time, decrease over time, or be adjusted in accordance with the subject and/or with a medical practitioner's determination). In various embodiments, e.g., as set forth herein, one or more or all of the periods of time between each dose may be the same or can vary (e.g., increase over time, decrease over time, or be adjusted in accordance with the subject and/or with a medical practitioner's determination). In some embodiments, e.g., as set forth herein, a given therapeutic agent has a recommended dosing regimen, which can involve one or more doses. Typically, at least one recommended dosing regimen of a marketed drug is known to those of skill in the art. In some embodiments, e.g., as set forth herein, a dosing regimen is correlated with a desired or beneficial outcome when administered across a relevant population (i.e., is a therapeutic dosing regimen).

Downstream: As used herein, the term "downstream" means that a first DNA region is closer, relative to a second DNA region, to the C-terminus of a nucleic acid that includes the first DNA region and the second DNA region.

Early stage: As used herein, the term "early stage" refers to a localized stage where cancer has not yet spread to nearby lymph nodes (NO) or to distant sites (M0). For example, pathologically it would be cancer stages from stage 0 to stage II C.

Gene: As used herein, the term "gene" refers to a single DNA region, e.g., in a chromosome, that includes a coding sequence that encodes a product (e.g., an RNA product and/or a polypeptide product), together with all, some, or none of the DNA sequences that contribute to regulation of the expression of coding sequence. In some embodiments, e.g., as set forth herein, a gene includes one or more non-coding sequences. In some particular embodiments, e.g., as set forth herein, a gene includes exonic and intronic sequences. In some embodiments, e.g., as set forth herein, a gene includes one or more regulatory elements that, for example, can control or impact one or more aspects of gene expression (e.g., cell-type-specific expression, inducible expression, etc.). In some embodiments, e.g., as set forth herein, a gene includes a promoter. In some embodiments, e.g., as set forth herein, a gene includes one or both of a (i) DNA nucleotides extending a predetermined number of nucleotides upstream of the coding sequence and (ii) DNA nucleotides extending a predetermined number of nucleotides downstream of the coding sequence. In various embodiments, e.g., as set forth herein, the predetermined number of nucleotides can be 500 bp, 1 kb, 2 kb, 3 kb, 4 kb, 5 kb, 10 kb, 20 kb, 30 kb, 40 kb, 50 kb, 75 kb, or 100 kb.

Gene ontology: The term "gene ontology" (GO) refers to a set of concepts to describe the function of gene products in organisms. It represents computational aspects of biological systems. GO has independent categories, herein are used two: biological process and molecular function, in each category gene products in different biological system concepts are analyzed. These concepts are used to demonstrate the relationship between the aberrant methylated regions and its biological function, determining its clinical and diagnostic values.

Homology: As used herein, the term "homology" refers to the overall relatedness between polymeric molecules, e.g., between nucleic acid molecules (e.g., DNA molecules and/or RNA molecules) and/or between polypeptide molecules. Those of skill in the art will appreciate that homology can be defined, e.g., by a percent identity or by a percent homology (sequence similarity). In some embodiments, e.g., as set forth herein, polymeric molecules are considered to be "homologous" to one another if their sequences are at least 25%, 30%, 35%, 40%, 45%, 50%, 55%, 60%, 65%, 70%, 75%, 80%, 85%, 90%, 95%, or 99% identical. In some embodiments, e.g., as set forth herein, polymeric molecules are considered to be "homologous" to one another if their sequences are at least 25%, 30%, 35%, 40%, 45%, 50%, 55%, 60%, 65%, 70%, 75%, 80%, 85%, 90%, 95%, or 99% similar.

Hybridize: As used herein, "hybridize" refers to the association of a first nucleic acid with a second nucleic acid to form a double-stranded structure, which association occurs through complementary pairing of nucleotides. Those of skill in the art will recognize that complementary sequences, among others, can hybridize. In various embodiments, e.g., as set forth herein, hybridization can occur, for example, between nucleotide sequences having at least 70% complementarity, e.g., at least 75%, 80%, 85%, 90%, 91%, 92%, 93%, 94%, 95%, 96%, 97%, 98%, 99%, or 100% complementarity. Those of skill in the art will further appreciate that whether hybridization of a first nucleic acid and a second nucleic acid does or does not occur can dependence upon various reaction conditions. Conditions under which hybridization can occur are known in the art.

Hypomethylation: As used herein, the term "hypomethylation" refers to the state of a methylation locus having at least one fewer methylated nucleotides in a state of interest as compared to a reference state (e.g., at least one fewer methylated nucleotides in colorectal cancer than in a healthy control).

Hypermethylation: As used herein, the term "hypermethylation" refers to the state of a methylation locus having at least one more methylated nucleotide in a state of interest as compared to a reference state (e.g., at least one more methylated nucleotide in colorectal cancer than in a healthy control).

Identity, identical: As used herein, the terms "identity" and "identical" refers to the overall relatedness between polymeric molecules, e.g., between nucleic acid molecules (e.g., DNA molecules and/or RNA molecules) and/or between polypeptide molecules. Methods for the calculation of a percent identity as between two provided sequences are known in the art. Calculation of the percent identity of two nucleic acid or polypeptide sequences, for example, can be performed by aligning the two sequences (or the complement of one or both sequences) for optimal comparison purposes (e.g., gaps can be introduced in one or both of a first and a second sequences for optimal alignment and non-identical sequences can be disregarded for comparison purposes). The nucleotides or amino acids at corresponding positions are then compared. When a position in the first sequence is occupied by the same residue (e.g., nucleotide or amino acid) as the corresponding position in the second sequence, then the molecules are identical at that position. The percent identity between the two sequences is a function of the number of identical positions shared by the sequences and, optionally, taking into account the number of gaps and the length of each gap, which may need to be introduced for optimal alignment of the two sequences. The comparison of sequences and determination of percent identity between two sequences can be accomplished using a computational algorithm, such as BLAST (basic local alignment search tool).

"Improved," "increased," or "reduced": As used herein, these terms, or grammatically comparable comparative terms, indicate values that are relative to a comparable reference measurement. For example, in some embodiments, e.g., as set forth herein, an assessed value achieved with an agent of interest may be "improved" relative to that obtained with a comparable reference agent or with no agent. Alternatively or additionally, in some embodiments, e.g., as set forth herein, an assessed value in a subject or system of interest may be "improved" relative to that obtained in the same subject or system under different conditions or at a different point in time (e.g., prior to or after an event such as administration of an agent of interest), or in a different, comparable subject (e.g., in a comparable subject or system that differs from the subject or system of interest in presence of one or more indicators of a particular disease, disorder or condition of interest, or in prior exposure to a condition or agent, etc.). In some embodiments, e.g., as set forth herein, comparative terms refer to statistically relevant differences (e.g., differences of a prevalence and/or magnitude sufficient to achieve statistical relevance). Those of skill in the art will be aware, or will readily be able to determine, in a given context, a degree and/or prevalence of difference that is required or sufficient to achieve such statistical significance.

Kaplan-Meier estimate or product limit estimate refers to the statistical test with which the occurrence probability of an event at a certain time point can be measured. The probability at a certain time will be multiplied by previous possibilities to gain the results, herein is used to estimate the survival function from lifetime data.

Locus of a nucleic acid refers to a subregion of a nucleic acid, e.g., a CpG island, single nucleotide, a gene on a chromosome, etc.

Marker: A marker, as used herein, refers to an entity or moiety whose presence or level is a characteristic of a particular state or event. In some embodiments, presence or level of a particular marker may be characteristic of presence or stage of a disease, disorder, or condition. To give but one example, in some embodiments, the term refers to a gene expression product that is characteristic of a particular tumor, tumor subclass, stage of tumor, etc. Alternatively, or additionally, in some embodiments, a presence or level of a particular marker correlates with activity (or activity level) of a particular signaling pathway, for example that may be characteristic of a particular class of tumors. The statistical significance of the presence or absence of a marker may vary depending upon the particular marker. In some embodiments, detection of a marker is highly specific in that it reflects a high probability that the tumor is of a particular subclass. Such specificity may come at the cost of sensitivity (i.e., a negative result may occur even if the tumor is a tumor that would be expected to express the marker).

Conversely, markers with a high degree of sensitivity may be less specific that those with lower sensitivity. According to the present invention a useful marker need not distinguish tumors of a particular subclass with 100% accuracy. A marker may be a metabolite, lipid, fatty acid, and/or poly-unsaturated fatty acid. In certain embodiments, the term marker may refer to a ratio of two entities (e.g., moieties).

Methylation: As used herein, the term "methylation" includes methylation at any of (i) C5 position of cytosine; (ii) N4 position of cytosine; and (iii) the N6 position of adenine. Methylation also includes (iv) other types of nucleotide methylation. A nucleotide that is methylated can be referred to as a "methylated nucleotide" or "methylated nucleotide base." Accordingly, a "methylated nucleotide" or a "methylated nucleotide base" refers to the presence of a methyl moiety on a nucleotide base, where the methyl moiety is not present in a recognized typical nucleotide base. In certain embodiments, e.g., as set forth herein, methylation specifically refers to methylation of cytosine residues. In some instances, methylation specifically refers to methylation of cytosine residues present in CpG sites.

Methylation assay: As used herein, the term "methylation assay" refers to any technique that can be used to determine the methylation status of a methylation locus. For example, a methylation assay may refer to a technique for determining the methylation state of one or more CpG dinucleotide sequences within a sequence of a nucleic acid.

Methylation biomarker: As used herein, the term "methylation biomarker" refers to a biomarker that is or includes at least one methylation locus and/or the methylation status of at least one methylation locus, e.g., a hypermethylated locus. In particular, a methylation biomarker is a biomarker characterized by a change between a first state and a second state (e.g., between a cancerous state and a non-cancerous state) in methylation status of one or more nucleic acid loci.

Methylation locus: As used herein, the term "methylation locus" refers to a DNA region that includes at least one differentially methylated region. A methylation locus that includes a greater number or frequency of methylated sites under a selected condition of interest, such as a cancerous state, can be referred to as a hypermethylated locus. A methylation locus that includes a smaller number or frequency of methylated sites under a selected condition of interest, such as a cancerous state, can be referred to as a hypomethylated locus. In some instances, e.g., as set forth herein, a methylation locus has a length of at least 10, at least 15, at least 20, at least 30, at least 50, or at least 75 base pairs. In some instances, e.g., as set forth herein, a methylation locus has a length of less than 5000 bp, 4,000 bp, 3,000 bp, 2,000 bp, 1,000 bp, 950 bp, 900 bp, 850 bp, 800 bp, 750 bp, 700 bp, 650 bp, 600 bp, 550 bp, 500 bp, 450 bp, 400 bp, 350 bp, 300 bp, 250 bp, 200 bp, 150 bp, 100 bp, 50 bp, 40 bp, 30 bp, 20 bp, or 10 bp (e.g., where methylation status is determined using quantitative polymerase chain reaction (qPCR), e.g., methylation sensitive restriction enzyme quantitative polymerase chain reaction (MSRE-qPCR)).

Methylation site: As used herein, a methylation site refers to a nucleotide or nucleotide position that is methylated in at least one condition. In its methylated state, a methylation site can be referred to as a methylated site.

The terms "methylation-specific restriction enzyme" or "methylation-sensitive restriction enzyme" refers to an enzyme that selectively digests a nucleic acid dependent on the methylation state of its recognition site.

Methylation status: As used herein, "methylation status," "methylation state," or "methylation profile" refer to the number, frequency, or pattern of methylation at methylation sites within a methylation locus. Accordingly, a change in methylation status between a first state and a second state can be or include an increase in the number, frequency, or pattern of methylated sites, or can be or include a decrease in the number, frequency, or pattern of methylated sites. In various instances, a change in methylation status in a change in methylation value.

Methylation value: As used herein, the term "methylation value" refers to a numerical representation of a methylation status, e.g., in the form of number that represents the frequency or ratio of methylation of a methylation locus. In some instances, e.g., as set forth herein, a methylation value can be generated by a method that includes quantifying the amount of intact nucleic acid present in a sample following restriction digestion of the sample with a methylation dependent restriction enzyme. In some instances, e.g., as set forth herein, a methylation value can be generated by a method that includes comparing amplification profiles after bisulfite reaction of a sample. In some instances, e.g., as set forth herein, a methylation value can be generated by comparing sequences of bisulfite-treated and untreated nucleic acids. In some instances, e.g., as set forth herein, a methylation value is, includes, or is based on a quantitative PCR result.

The methylation state of a particular nucleic acid sequence (e.g., a gene marker or DNA region as described herein) can indicate the methylation state of every base in the sequence or can indicate the methylation state of a subset of the bases (e.g., of one or more cytosines) within the sequence, or can indicate information regarding regional methylation density within the sequence with or without providing precise information of the locations within the sequence the methylation occurs.

The terms "methylation state", "methylation profile", and "methylation status" also refer to the relative concentration, absolute concentration, or pattern of methylated C or unmethylated C throughout any particular region of a nucleic acid in a biological sample. For example, if the cytosine (C) residue(s) within a nucleic acid sequence are methylated it may be referred to as "hypermethylated" or having "increased methylation", whereas if the cytosine (C) residue(s) within a DNA sequence are not methylated it may be referred to as "hypomethylated" or having "decreased methylation". Likewise, if the cytosine (C) residue(s) within a nucleic acid sequence are methylated as compared to another nucleic acid sequence (e.g., from a different region or from a different individual, etc.) that sequence is considered hypermethylated or having increased methylation compared to the other nucleic acid sequence. Alternatively, if the cytosine (C) residue(s) within a DNA sequence are not methylated as compared to another nucleic acid sequence (e.g., from a different region or from a different individual, etc.) that sequence is considered hypomethylated or having decreased methylation compared to the other nucleic acid sequence.

Sequences are said to be "differentially methylated" or as having a "difference in methylation" or having a "different methylation state" when they differ in the extent (e.g., one has increased or decreased methylation relative to the other), frequency, or pattern of methylation. The term "differential methylation" can refer to a difference in the level or pattern of nucleic acid methylation in a cancer positive sample as compared with the level or pattern of nucleic acid methylation in a cancer negative sample.

Mutation: As used herein, the term "mutation" refers to a genetic variation in a biomolecule (e.g., a nucleic acid or a protein) as compared to a reference biomolecule. For example, a mutation in a nucleic acid may, in some embodiments, comprise a nucleobase substitution, a deletion of one or more nucleobases, an insertion of one or more nucleobases, an inversion of two or more nucleobases, or a truncation, as compared to a reference nucleic acid molecule. Similarly, a mutation in a protein may comprise an amino acid substitution, insertion, inversion, or truncation, as compared to a reference polypeptide. Additional mutations, e.g., fusions and indels, are known to those of skill in the art. In some embodiments, a mutation comprises a genetic variant that is associated with a loss of function of a gene product. A loss of function may be a complete abolishment of function, e.g., an abolishment of the enzymatic activity of an enzyme, or a partial loss of function, e.g., a diminished enzymatic activity of an enzyme. In some embodiments, a mutant comprises a genetic variant that is associated with a gain of function, e.g., with a negative or undesirable alteration in a characteristic or activity in a gene product. In some embodiments, a mutant is characterized by a reduction or loss in a desirable level or activity as compared to a reference; in some embodiments, a mutant is characterized by an increase or gain of an undesirable level or activity as compared to a reference. In some embodiments, the reference biomolecule is a wild-type biomolecule.

Nucleic acid: As used herein, in its broadest sense, the term "nucleic acid" refers to any compound and/or substance that is or can be incorporated into an oligonucleotide chain. In some embodiments e.g., as set forth herein, a nucleic acid is a compound and/or substance that is or can be incorporated into an oligonucleotide chain via a phosphodiester linkage. As will be clear from context, in some embodiments e.g., as set forth herein, the term nucleic acid refers to an individual nucleic acid residue (e.g., a nucleotide and/or nucleoside), and in some embodiments e.g., as set forth herein refers to an polynucleotide chain comprising a plurality of individual nucleic acid residues. A nucleic acid can be or include DNA, RNA, or a combinations thereof. A nucleic acid can include natural nucleic acid residues, nucleic acid analogs, and/or synthetic residues. In some embodiments e.g., as set forth herein, a nucleic acid includes natural nucleotides (e.g., adenosine, thymidine, guanosine, cytidine, uridine, deoxyadenosine, deoxythymidine, deoxyguanosine, and deoxycytidine). In some embodiments e.g., as set forth herein, a nucleic acid is or includes of one or more nucleotide analogs (e.g., 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, 0(6)-methylguanine, 2-thiocytidine, methylated bases, intercalated bases, and combinations thereof).

In some embodiments e.g., as set forth herein, a nucleic acid has a nucleotide sequence that encodes a functional gene product such as an RNA or protein. In some embodiments e.g., as set forth herein, a nucleic acid includes one or more introns. In some embodiments e.g., as set forth herein, a nucleic acid includes one or more genes. In some embodiments e.g., as set forth herein, nucleic acids are prepared by one or more of isolation from a natural source, enzymatic synthesis by polymerization based on a complementary template (in vivo or in vitro), reproduction in a recombinant cell or system, and chemical synthesis.

In some embodiments e.g., as set forth herein, a nucleic acid analog differs from a nucleic acid in that it does not utilize a phosphodiester backbone. For example, in some embodiments e.g., as set forth herein, a nucleic acid can include one or more peptide nucleic acids, which are known in the art and have peptide bonds instead of phosphodiester bonds in the backbone. Alternatively or additionally, in some embodiments e.g., as set forth herein, a nucleic acid has one or more phosphorothioate and/or 5'-N-phosphoramidite linkages rather than phosphodiester bonds. In some embodiments e.g., as set forth herein, a nucleic acid comprises one or more modified sugars (e.g., 2'-fluororibose, ribose, 2'-deoxyribose, arabinose, and hexose) as compared with those in natural nucleic acids.

In some embodiments, e.g., as set forth herein, a nucleic acid is or includes at least 3, 4, 5, 6, 7, 8, 9, 10, 15, 20, 25, 30, 35, 40, 45, 50, 55, 60, 65, 70, 75, 80, 85, 90, 95, 100, 1 10, 120, 130, 140, 150, 160, 170, 180, 190, 20, 225, 250, 275, 300, 325, 350, 375, 400, 425, 450, 475, 500, 600, 700, 800, 900, 1000, 1500, 2000, 2500, 3000, 3500, 4000, 4500, 5000 or more residues. In some embodiments, e.g., as set forth herein, a nucleic acid is partly or wholly single stranded, or partly or wholly double stranded.

Nucleic acid detection assay: As used herein, the term "nucleic acid detection assay" refers to any method of determining the nucleotide composition of a nucleic acid of interest. Nucleic acid detection assays include but are not limited to, DNA sequencing methods (e.g., next generation sequencing methods), polymerase chain reaction-based methods, probe hybridization methods, ligase chain reaction, etc.

Nucleotide: As used herein, the term "nucleotide" refers to a structural component, or building block, of polynucleotides, e.g., of DNA and/or RNA polymers. A nucleotide includes of a base (e.g., adenine, thymine, uracil, guanine, or cytosine) and a molecule of sugar and at least one phosphate group. As used herein, a nucleotide can be a methylated nucleotide or an un-methylated nucleotide. Those of skill in the art will appreciate that nucleic acid terminology, such as, as examples, "locus" or "nucleotide" can refer to both a locus or nucleotide of a single nucleic acid molecule and/or to the cumulative population of loci or nucleotides within a plurality of nucleic acids (e.g., a plurality of nucleic acids in a sample and/or representative of a subject) that are representative of the locus or nucleotide (e.g., having the same identical nucleic acid sequence and/or nucleic acid sequence context, or having a substantially identical nucleic acid sequence and/or nucleic acid context).

Oligonucleotide primer: As used herein, the term oligonucleotide primer, or primer, refers to a nucleic acid molecule used, capable of being used, or for use in, generating amplicons from a template nucleic acid molecule. Under transcription-permissive conditions (e.g., in the presence of nucleotides and a DNA polymerase, and at a suitable temperature and pH), an oligonucleotide primer can provide a point of initiation of transcription from a template to which the oligonucleotide primer hybridizes. Typically, an oligonucleotide primer is a single-stranded nucleic acid between 5 and 200 nucleotides in length. Those of skill in the art will appreciate that optimal primer length for generating amplicons from a template nucleic acid molecule can vary with conditions including temperature parameters, primer composition, and transcription or amplification method. A pair of oligonucleotide primers, as used herein, refers to a set of two oligonucleotide primers that are respectively complementary to a first strand and a second strand of a template double-stranded nucleic acid molecule. First and second members of a pair of oligonucleotide primers may be referred to as a "forward" oligonucleotide primer and a "reverse" oligonucleotide primer, respectively, with respect to a template nucleic acid strand, in that the forward oligonucleotide primer is capable of hybridizing with a nucleic acid strand complementary to the template nucleic acid strand, the reverse oligonucleotide primer is capable of hybridizing with the template nucleic acid strand, and the position of the forward oligonucleotide primer with respect to the template nucleic acid strand is 5' of the position of the reverse oligonucleotide primer sequence with respect to the template nucleic acid strand. It will be understood by those of skill in the art that the identification of a first and second oligonucleotide primer as forward and reverse oligonucleotide primers, respectively, is arbitrary inasmuch as these identifiers depend upon whether a given nucleic acid strand or its complement is utilized as a template nucleic acid molecule.

Overlapping: The term "overlapping" is used herein in reference to two regions of DNA, each of which contains a sub-sequence that is substantially identical to a sub-sequence of the same length in the other region (e.g., the two regions of DNA have a common sub-sequence). "Substantially identical" means that the two identically-long sub-sequences differ by fewer than a given number of base pairs. In certain instances, e.g., as set forth herein, each sub-sequence has a length of at least 20 base pairs that differ by fewer than 4, 3, 2, or 1 base pairs from each other (e.g., the two sub-sequences having at least 80%, at least 85%, at least 90%, at least 95% similarity, at least 97% similarity, at least 98% similarity, at least 99% similarity, or at least 99.5% similarity). In certain instances, e.g., as set forth herein, each sub-sequence has a length of at least 24 base pairs that differ by fewer than 5, 4, 3, 2, or 1 base pairs (e.g., the two sub-sequences having at least 80%, at least 85%, at least 90%, at least 95% similarity, at least 97% similarity, at least 98% similarity, at least 99% similarity, or at least 99.5% similarity). In certain instances, e.g., as set forth herein, each sub-sequence has a length of at least 50 base pairs that differ by fewer than 10, 9, 8, 7, 6, 5, 4, 3, 2, or 1 base pairs (e.g., the two sub-sequences having at least 80%, at least 85%, at least 90%, at least 95% similarity, at least 97% similarity, at least 98% similarity, at least 99% similarity, or at least 99.5% similarity). In certain instances, e.g., as set forth herein, each sub-sequence has a length of at least 100 base pairs that differ by fewer than 20, 15, 10, 9, 8, 7, 6, 5, 4, 3, 2, or 1 base pairs (e.g., the two sub-sequences having at least 80%, at least 85%, at least 90%, at least 95% similarity, at least 97% similarity, at least 98% similarity, at least 99% similarity, or at least 99.5% similarity). In certain instances, e.g., as set forth herein, each sub-sequence has a length of at least 200 base pairs that differ by fewer than 40, 30, 20, 15, 10, 9, 8, 7, 6, 5, 4, 3, 2, or 1 base pairs (e.g., the two sub-sequences having at least 80%, at least 85%, at least 90%, at least 95% similarity, at least 97% similarity, at least 98% similarity, at least 99% similarity, or at least 99.5% similarity). In certain instances, e.g., as set forth herein, each sub-sequence has a length of at least 250 base pairs that differ by fewer than 50, 40, 30, 20, 15, 10, 9, 8, 7, 6, 5, 4, 3, 2, or 1 base pairs (e.g., the two sub-sequences having at least 80%, at least 85%, at least 90%, at least 95% similarity, at least 97% similarity, at least 98% similarity, at least 99% similarity, or at least 99.5% similarity). In certain instances, e.g., as set forth herein, each sub-sequence has a length of at least 300 base pairs that differ by fewer than 60, 50, 40, 30, 20, 15, 10, 9, 8, 7, 6, 5, 4, 3, 2, or 1 base pairs (e.g., the two sub-sequences having at least 80%, at least 85%, at least 90%, at least 95% similarity, at least 97% similarity, at least 98% similarity, at least 99% similarity, or at least 99.5% similarity). In certain instances, e.g., as set forth herein, each sub-sequence has a length of at least 500 base pairs that differ by fewer than 100, 60, 50, 40, 30, 20, 15, 10, 9, 8, 7, 6, 5, 4, 3, 2, or 1 base pairs (e.g., the two sub-sequences having at least 80%, at least 85%, at least 90%, at least 95% similarity, at least 97% similarity, at least 98% similarity, at least 99% similarity, or at least 99.5% similarity). In certain instances, e.g., as set forth herein, each sub-sequence has a length of at least 1000 base pairs that differ by fewer than 200, 100, 60, 50, 40, 30, 20, 15, 10, 9, 8, 7, 6, 5, 4, 3, 2, or 1 base pairs (e.g., the two sub-sequences having at least 80%, at least 85%, at least 90%, at least 95% similarity, at least 97% similarity, at least 98% similarity, at least 99% similarity, or at least 99.5% similarity). In certain instances, e.g., as set forth herein, the subsequence of a first region of the two regions of DNA may comprise the entirety of the second region of the two regions of DNA (or vice versa) (e.g., the common sub-sequence may contain the whole of either or both regions). In certain embodiments, where a methylation locus has a sequence that comprises at "least a portion of" a DMR sequence listed herein (e.g., at least 20%, at least 30%, at least 40%, at least 50%, at least 60%, at least 70%, at least 80%, or at least 90% of the DMR sequence), the overlapping portion of the methylation locus has at least 95% similarity, at least 98% similarity, or at least 99% similarity with the overlapping portion of the DMR sequence (e.g., if the overlapping portion is 100 bp, the portion of the methylation locus that overlaps with the portion of the DMR differs by no more than 1 bp, no more than 2 bp, or no more than 5 bp). In certain embodiments, where a methylation locus has a sequence that comprises "at least a portion of" a DMR sequence listed herein, this means the methylation locus has a subsequence in common with the DMR sequence that has a consecutive series of bases that covers at least 20%, at least 30%, at least 40%, at least 50%, at least 60%, at least 70%, at least 80%, or at least 90% of the DMR sequence, e.g., wherein the subsequence in common differs by no more than 1 bp, no more than 2 bp, or no more than 5 bp). In certain embodiments, where a methylation locus has a sequence that comprises "at least a portion of" a DMR sequence listed herein, this means the methylation locus contains at least a portion of (e.g., at least 20%, at least 30%, at least 40%, at least 50%, at least 60%, at least 70%, at least 80%, or at least 90% of) the CpG dinucleotides corresponding to the CpG dinucleotides within the DMR sequence.

Pharmaceutical composition: As used herein, the term "pharmaceutical composition" refers to a composition in which an active agent is formulated together with one or more pharmaceutically acceptable carriers. In some embodiments, e.g., as set forth herein, the active agent is present in a unit dose amount appropriate for administration to a subject, e.g., in a therapeutic regimen that shows a statistically significant probability of achieving a predetermined therapeutic effect when administered to a relevant population. In some embodiments, e.g., as set forth herein, a pharmaceutical composition can be formulated for administration in a particular form (e.g., in a solid form or a liquid form), and/or can be specifically adapted for, for example: oral administration (for example, as a drenche (aqueous or non-aqueous solutions or suspensions), tablet, capsule, bolus, powder, granule, paste, etc., which can be formulated specifically for example for buccal, sublingual, or systemic absorption); parenteral administration (for example, by subcutaneous, intramuscular, intravenous or epidural injection as, for example, a sterile solution or suspension, or sustained-release formulation, etc.); topical application (for example, as a cream, ointment, patch or spray applied for example to skin, lungs, or oral cavity); intravaginal or intrarectal administration (for example, as a pessary, suppository, cream, or foam); ocular administration; nasal or pulmonary administration, etc.

Pharmaceutically acceptable: As used herein, the term "pharmaceutically acceptable," as applied to one or more, or all, component(s) for formulation of a composition as disclosed herein, means that each component must be compatible with the other ingredients of the composition and not deleterious to the recipient thereof.

Pharmaceutically acceptable carrier: As used herein, the term "pharmaceutically acceptable carrier" refers to a pharmaceutically-acceptable material, composition, or vehicle, such as a liquid or solid filler, diluent, excipient, or solvent encapsulating material, that facilitates formulation and/or modifies bioavailability of an agent, e.g., a pharmaceutical agent. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations.

Polyposis syndromes: The terms "polyposis" and "polyposis syndrome", as used herein, refer to hereditary conditions that include, but are not limited to, familial adenomatous polyposis (FAP), hereditary nonpolyposis colorectal cancer (HNPCC)/Lynch syndrome, Gardner syndrome, Turcot syndrome, MUTYH polyposis, Peutz-Jeghers syndrome, Cowden disease, familial juvenile polyposis, and hyperplastic polyposis. In certain embodiments, polyposis includes serrated polyposis syndrome. Serrated polyposis is classified by a subject having 5 or more serrated polyps proximal to the sigmoid colon with two or more at least 10 mm in size, having a serrated polyp proximal to the sigmoid colon in the context of a family history of serrated polyposis, and/or having 20 or more serrated polyps throughout the colon.

Portion when used in reference to a gene refers to fragments of that gene. The fragments may range in size from a few nucleotides to the entire gene sequence minus one nucleotide. Thus, "a nucleotide comprising at least a portion of a gene" may comprise fragments of the gene or the entire gene.

Prevent or prevention: The terms "prevent" and "prevention," as used herein in connection with the occurrence of a disease, disorder, or condition, refers to reducing the risk of developing the disease, disorder, or condition; delaying onset of the disease, disorder, or condition; delaying onset of one or more characteristics or symptoms of the disease, disorder, or condition; and/or to reducing the frequency and/or severity of one or more characteristics or symptoms of the disease, disorder, or condition. Prevention can refer to prevention in a particular subject or to a statistical impact on a population of subjects. Prevention can be considered complete when onset of a disease, disorder, or condition has been delayed for a predefined period of time.

Probe: As used herein, the terms "probe", "capture probe", or "bait" refer to a single- or double-stranded nucleic acid molecule that is capable of hybridizing with a complementary target and, in certain embodiments, includes a detectable moiety. In certain embodiments, e.g., as set forth herein, a probe is a restriction digest product or is a synthetically produced nucleic acid, e.g., a nucleic acid produced by recombination or amplification. In some instances, e.g., as set forth herein, a probe is a capture probe useful in detection, identification, and/or isolation of a target sequence, such as a gene sequence. In various instances, e.g., as set forth herein, a detectable moiety of probe can be, e.g., an enzyme (e.g., ELISA, as well as enzyme-based histochemical assays), fluorescent moiety, radioactive moiety, or moiety associated with a luminescence signal.

Prognosis: As used herein, the term "prognosis" refers to determining the qualitative of quantitative probability of at least one possible future outcome or event. As used herein, a prognosis can be a determination of the likely course of a disease, disorder, or condition such as cancer in a subject, a determination regarding the life expectancy of a subject, or a determination regarding response to therapy, e.g., to a particular therapy.

Prognostic information: As used herein, the terms "prognostic information" and "predictive information" are used to refer to any information that may be used to indicate any aspect of the course of a disease or condition either in the absence or presence of treatment. Such information may include, but is not limited to, the average life expectancy of a patient, the likelihood that a patient will survive for a given amount of time (e.g., 6 months, 1 year, 5 years, etc.), the likelihood that a patient will be cured of a disease, the likelihood that a patient's disease will respond to a particular therapy (wherein response may be defined in any of a variety of ways). Prognostic and predictive information are included within the broad category of diagnostic information. Prognostic information can include, without limitation, biomarker status information.

Promoter: As used herein, a "promoter" can refer to a DNA regulatory region that directly or indirectly (e.g., through promoter-bound proteins or substances) associates with an RNA polymerase and participates in initiation of transcription of a coding sequence.

Ratio: As used herein, the term "ratio" refers to a calculable relationship used to compare amounts of two species that indicates the relative amounts of the species. The species may be markers, such as metabolites and/or lipids (e.g., fatty acids), for example. A ratio may be a direct proportion or inverse proportion (e.g., a first amount divided by a second amount, or the second amount divided by the first amount, respectively). A ratio may be weighted and/or normalized (either the numerator, the denominator, or both). The two amounts may be physical quantities or arbitrary values that correspond to physical quantities. For example, a ratio may be calculated from two intensity amounts (i.e., in arbitrary units) in two species (e.g., markers) measured by a mass spectrometry technique.

Reference: As used herein describes a standard or control relative to which a comparison is performed. For example, in some embodiments, e.g., as set forth herein, an agent, subject, animal, individual, population, sample, sequence, or value of interest is compared with a reference or control agent, subject, animal, individual, population, sample, sequence, or value. In some embodiments, e.g., as set forth herein, a reference or characteristic thereof is tested and/or determined substantially simultaneously with the testing or determination of the characteristic in a sample of interest. In some embodiments, e.g., as set forth herein, a reference is a historical reference, optionally embodied in a tangible medium. Typically, as would be understood by those of skill in the art, a reference is determined or characterized under comparable conditions or circumstances to those under assessment, e.g., with regard to a sample. Those skilled in the art will appreciate when sufficient similarities are present to justify reliance on and/or comparison to a particular possible reference or control.

Risk: As used herein with respect to a disease, disorder, or condition, the term "risk" refers to the qualitative of quantitative probability (whether expressed as a percentage or otherwise) that a particular individual will develop the disease, disorder, or condition. In some embodiments, e.g., as set forth herein, risk is expressed as a percentage. In some embodiments, e.g., as set forth herein, a risk is a qualitative of quantitative probability that is equal to or greater than 0, 1, 2, 3, 4, 5, 6, 7, 8, 9, 10, 20, 30, 40, 50, 60, 70, 80, 90, or 100%. In some embodiments, e.g., as set forth herein, risk is expressed as a qualitative or quantitative level of risk relative to a reference risk or level or the risk of the same outcome attributed to a reference. In some embodiments, e.g., as set forth herein, relative risk is increased or decreased in comparison to the reference sample by a factor of 1.1, 1.2, 1.3, 1.4, 1.5, 1.6, 1.7, 1.8, 1.9, 2, 3, 4, 5, 6, 7, 8, 9, 10, or more.

Sample: As used herein, the term "sample" typically refers to an aliquot of material obtained or derived from a source of interest. In some embodiments, e.g., as set forth herein, a source of interest is a biological or environmental source. In some embodiments, e.g., as set forth herein, a sample is a "primary sample" obtained directly from a source of interest. In some embodiments, e.g., as set forth herein, as will be clear from context, the term "sample" refers to a preparation that is obtained by processing of a primary sample (e.g., by removing one or more components of and/or by adding one or more agents to a primary sample). Such a "processed sample" can include, for example cells, nucleic acids, or proteins extracted from a sample or obtained by subjecting a primary sample to techniques such as amplification or reverse transcription of nucleic acids, isolation and/or purification of certain components, etc.

In certain instances, e.g., as set forth herein, a processed sample can be a DNA sample that has been amplified (e.g., pre-amplified). Thus, in various instances, e.g., as set forth herein, an identified sample can refer to a primary form of the sample or to a processed form of the sample. In some instances, e.g., as set forth herein, a sample that is enzyme-digested DNA can refer to primary enzyme-digested DNA (the immediate product of enzyme digestion) or a further processed sample such as enzyme-digested DNA that has been subject to an amplification step (e.g., an intermediate amplification step, e.g., pre-amplification) and/or to a filtering step, purification step, or step that modifies the sample to facilitate a further step, e.g., in a process of determining methylation status (e.g., methylation status of a primary sample of DNA and/or of DNA as it existed in its original source context).

Screening: As used herein, the term "screening" refers to any method, technique, process, or undertaking intended to generate diagnostic information and/or prognostic information. Accordingly, those of skill in the art will appreciate that the term screening encompasses method, technique, process, or undertaking that determines whether an individual has, is likely to have or develop, or is at risk of having or developing a disease, disorder, or condition, e.g., colorectal cancer, advanced adenoma.

Specificity: As used herein, the "specificity" of a biomarker refers to the percentage of samples that are characterized by absence of the event or state of interest for which measurement of the biomarker accurately indicates absence of the event or state of interest (true negative rate). In various embodiments, e.g., as set forth herein, characterization of the negative samples is independent of the biomarker, and can be achieved by any relevant measure, e.g., any relevant measure known to those of skill in the art. Thus, specificity reflects the probability that the biomarker would detect the absence of the event or state of interest when measured in a sample not characterized that event or state of interest. In particular embodiments in which the event or state of interest is colorectal cancer, e.g., as set forth herein, specificity refers to the probability that a biomarker would detect the absence of colorectal cancer in a subject lacking colorectal cancer. Lack of colorectal cancer can be determined, e.g., by histology.

Sensitivity: As used herein, the "sensitivity" of a biomarker refers to the percentage of samples that are characterized by the presence of the event or state of interest for which measurement of the biomarker accurately indicates presence of the event or state of interest (true positive rate). In various embodiments, e.g., as set forth herein, characterization of the positive samples is independent of the biomarker, and can be achieved by any relevant measure, e.g., any relevant measure known to those of skill in the art. Thus, sensitivity reflects the probability that a biomarker would detect the presence of the event or state of interest when measured in a sample characterized by presence of that event or state of interest. In particular embodiments in which the event or state of interest is colorectal cancer, e.g., as set forth herein, sensitivity refers to the probability that a biomarker would detect the presence of colorectal cancer in a subject that has colorectal cancer. Presence of colorectal cancer can be determined, e.g., by histology.

Single Nucleotide Polymorphism (SNP): As used herein, the term "single nucleotide polymorphism" or "SNP" refers to a particular base position in the genome where alternative bases are known to distinguish one allele from another. In some embodiments, one or a few SNPs and/or CNPs is/are sufficient to distinguish complex genetic variants from one another so that, for analytical purposes, one or a set of SNPs and/or CNPs may be considered to be characteristic of a particular variant, trait, cell type, individual, species, etc., or set thereof. In some embodiments, one or a set of SNPs and/or CNPs may be considered to define a particular variant, trait, cell type, individual, species, etc., or set thereof.

Solid Tumor: As used herein, the term "solid tumor" refers to an abnormal mass of tissue including cancer cells. In various embodiments, e.g., as set forth herein, a solid tumor is or includes an abnormal mass of tissue that does not contain cysts or liquid areas. In some embodiments, e.g., as set forth herein, a solid tumor can be benign; in some embodiments, a solid tumor can be malignant. Examples of solid tumors include carcinomas, lymphomas, and sarcomas. In some embodiments, e.g., as set forth herein, solid tumors can be or include adrenal, bile duct, bladder, bone, brain, breast, cervix, colon, endometrium, esophagum, eye, gall bladder, gastrointestinal tract, kidney, larynx, liver, lung, nasal cavity, nasopharynx, oral cavity, ovary, penis, pituitary, prostate, retina, salivary gland, skin, small intestine, stomach, testis, thymus, thyroid, uterine, vaginal, and/or vulval tumors.

Stage of cancer: As used herein, the term "stage of cancer" refers to a qualitative or quantitative assessment of the level of advancement of a cancer. In some embodiments, e.g., as set forth herein, criteria used to determine the stage of a cancer can include, but are not limited to, one or more of where the cancer is located in a body, tumor size, whether the cancer has spread to lymph nodes, whether the cancer has spread to one or more different parts of the body, etc. In some embodiments, e.g., as set forth herein, cancer can be staged using the so-called TNM System, according to which T refers to the size and extent of the main tumor, usually called the primary tumor; N refers to the number of nearby lymph nodes that have cancer; and M refers to whether the cancer has metastasized. In some embodiments, e.g., as set forth herein, a cancer can be referred to as Stage 0 (abnormal cells are present but have not spread to nearby tissue, also called carcinoma in situ, or CIS; CIS is not cancer, but it can become cancer), Stage I-III (cancer is present; the higher the number, the larger the tumor and the more it has spread into nearby tissues), or Stage IV (the cancer has spread to distant parts of the body). In some embodiments, e.g., as set forth herein, a cancer can be assigned to a stage selected from the group consisting of: in situ (abnormal cells are present but have not spread to nearby tissue); localized (cancer is limited to the place where it started, with no sign that it has spread); regional (cancer has spread to nearby lymph nodes, tissues, or organs): distant (cancer has spread to distant parts of the body); and unknown (there is not enough information to identify cancer stage).

Stratification: Herein, "stratification" refers to any analytical process in which the patients will be classified in separate groups. The groups can share some similar features or characteristics that make them unique as a group. Stratification can be used for any of the study features that will help for the purpose of CRC diagnostic prediction, early detection, monitoring, treatment guidance and survival prognosis.

Survival: Herein, "survival" refers to the time duration the patient has lived since the start of a disease (e.g., cancer) or start of a treatment. This is a term with which can be described how effective a novel approach (including, prognosis, screening, diagnosis, treatment, and monitoring, etc.) is in face of disease progression.

Susceptible to: An individual who is "susceptible to" a disease, disorder, or condition is at risk for developing the disease, disorder, or condition. In some embodiments, e.g., as set forth herein, an individual who is susceptible to a disease, disorder, or condition does not display any symptoms of the disease, disorder, or condition. In some embodiments, e.g., as set forth herein, an individual who is susceptible to a disease, disorder, or condition has not been diagnosed with the disease, disorder, and/or condition. In some embodiments, e.g., as set forth herein, an individual who is susceptible to a disease, disorder, or condition is an individual who has been exposed to conditions associated with, or presents a biomarker status (e.g., a methylation status) associated with, development of the disease, disorder, or condition. In some embodiments, e.g., as set forth herein, a risk of developing a disease, disorder, and/or condition is a population-based risk (e.g., family members of individuals suffering from the disease, disorder, or condition).

Subject: As used herein, the term "subject" refers to an organism, typically a mammal (e.g., a human). In some embodiments, e.g., as set forth herein, a subject is suffering from a disease, disorder or condition. In some embodiments, e.g., as set forth herein, a subject is susceptible to a disease, disorder, or condition. In some embodiments, e.g., as set forth herein, a subject displays one or more symptoms or characteristics of a disease, disorder or condition. In some embodiments, e.g., as set forth herein, a subject is not suffering from a disease, disorder or condition. In some embodiments, e.g., as set forth herein, a subject does not display any symptom or characteristic of a disease, disorder, or condition. In some embodiments, e.g., as set forth herein, a subject is someone with one or more features characteristic of susceptibility to or risk of a disease, disorder, or condition. In some embodiments, e.g., as set forth herein, a subject is a patient. In some embodiments, e.g., as set forth herein, a subject is an individual to whom diagnosis has been performed and/or to whom therapy has been administered. In some instances, e.g., as set forth herein, a human subject can be interchangeably referred to as an "individual."

Therapeutic agent: As used herein, the term "therapeutic agent" refers to any agent that elicits a desired pharmacological effect when administered to a subject. In some embodiments, e.g., as set forth herein, an agent is considered to be a therapeutic agent if it demonstrates a statistically significant effect across an appropriate population. In some embodiments, e.g., as set forth herein, the appropriate population can be a population of model organisms or a human population. In some embodiments, e.g., as set forth herein, an appropriate population can be defined by various criteria, such as a certain age group, gender, genetic background, preexisting clinical conditions, etc. In some embodiments, e.g., as set forth herein, a therapeutic agent is a substance that can be used for treatment of a disease, disorder, or condition. In some embodiments, e.g., as set forth herein, a therapeutic agent is an agent that has been or is required to be approved by a government agency before it can be marketed for administration to humans. In some embodiments, e.g., as set forth herein, a therapeutic agent is an agent for which a medical prescription is required for administration to humans.

Therapeutically effective amount: As used herein, the term "therapeutically effective amount" refers to an amount that produces a desired effect for which it is administered. In some embodiments, e.g., as set forth herein, the term refers to an amount that is sufficient, when administered to a population suffering from or susceptible to a disease, disorder, or condition, in accordance with a therapeutic dosing regimen, to treat the disease, disorder, or condition. Those of ordinary skill in the art will appreciate that the term therapeutically effective amount does not in fact require successful treatment be achieved in a particular individual. Rather, a therapeutically effective amount can be an amount that provides a particular desired pharmacological response in a significant number of subjects when administered to individuals in need of such treatment. In some embodiments, e.g., as set forth herein, reference to a therapeutically effective amount can be a reference to an amount as measured in one or more specific tissues (e.g., a tissue affected by the disease, disorder or condition) or fluids (e.g., blood, saliva, serum, sweat, tears, urine, etc.). Those of ordinary skill in the art will appreciate that, in some embodiments, a therapeutically effective amount of a particular agent can be formulated and/or administered in a single dose. In some embodiments, e.g., as set forth herein, a therapeutically effective agent can be formulated and/or administered in a plurality of doses, for example, as part of a multi-dose dosing regimen.

Treatment: As used herein, the term "treatment" (also "treat" or "treating") refers to administration of a therapy that partially or completely alleviates, ameliorates, relieves, inhibits, delays onset of, reduces severity of, and/or reduces incidence of one or more symptoms, features, and/or causes of a particular disease, disorder, or condition, or is administered for the purpose of achieving any such result. In some embodiments, e.g., as set forth herein, such treatment can be of a subject who does not exhibit signs of the relevant disease, disorder, or condition and/or of a subject who exhibits only early signs of the disease, disorder, or condition. Alternatively or additionally, such treatment can be of a subject who exhibits one or more established signs of the relevant disease, disorder and/or condition. In some embodiments, e.g., as set forth herein, treatment can be of a subject who has been diagnosed as suffering from the relevant disease, disorder, and/or condition. In some embodiments, e.g., as set forth herein, treatment can be of a subject known to have one or more susceptibility factors that are statistically correlated with increased risk of development of the relevant disease, disorder, or condition. In various examples, treatment is of a cancer.

Upstream: As used herein, the term "upstream" means a first DNA region is closer, relative to a second DNA region, to the N-terminus of a nucleic acid that includes the first DNA region and the second DNA region.

Unit dose: As used herein, the term "unit dose" refers to an amount administered as a single dose and/or in a physically discrete unit of a pharmaceutical composition. In many embodiments, e.g., as set forth herein, a unit dose contains a predetermined quantity of an active agent. In some embodiments, e.g., as set forth herein, a unit dose contains an entire single dose of the agent. In some embodiments, e.g., as set forth herein, more than one unit dose is administered to achieve a total single dose. In some embodiments, e.g., as set forth herein, administration of multiple unit doses is required, or expected to be required, in order to achieve an intended effect. A unit dose can be, for example, a volume of liquid (e.g., an acceptable carrier) containing a predetermined quantity of one or more therapeutic moieties, a predetermined amount of one or more therapeutic moieties in solid form, a sustained release formulation or drug delivery device containing a predetermined amount of one or more therapeutic moieties, etc. It will be appreciated that a unit dose can be present in a formulation that includes any of a variety of components in addition to the therapeutic agent(s). For example, acceptable carriers (e.g., pharmaceutically acceptable carriers), diluents, stabilizers, buffers, preservatives, etc., can be included. It will be appreciated by those skilled in the art, in many embodiments, e.g., as set forth herein, a total appropriate daily dosage of a particular therapeutic agent can comprise a portion, or a plurality, of unit doses, and can be decided, for example, by a medical practitioner within the scope of sound medical judgment. In some embodiments, e.g., as set forth herein, the specific effective dose level for any particular subject or organism can depend upon a variety of factors including the disorder being treated and the severity of the disorder; activity of specific active compound employed; specific composition employed; age, body weight, general health, sex and diet of the subject; time of administration, and rate of excretion of the specific active compound employed; duration of the treatment; drugs and/or additional therapies used in combination or coincidental with specific compound(s) employed, and like factors well known in the medical arts.

Unmethylated: As used herein, the terms "unmethylated" and "non-methylated" are used interchangeably and mean that an identified DNA region includes no methylated nucleotides.

Variant: As used herein, the term "variant" refers to an entity that shows significant structural identity with a reference entity but differs structurally from the reference entity in the presence, absence, or level of one or more chemical moieties as compared with the reference entity. In some embodiments, e.g., as set forth herein, a variant also differs functionally from its reference entity. In general, whether a particular entity is properly considered to be a "variant" of a reference entity is based on its degree of structural identity with the reference entity. A variant can be a molecule comparable, but not identical to, a reference. For example, a variant nucleic acid can differ from a reference nucleic acid at one or more differences in nucleotide sequence. In some embodiments, e.g., as set forth herein, a variant nucleic acid shows an overall sequence identity with a reference nucleic acid that is at least 85%, 86%, 87%, 88%, 89%, 90%, 91%, 92%, 93%, 94%, 95%, 96%, 97%, or 99%. In many embodiments, e.g., as set forth herein, a nucleic acid of interest is considered to be a "variant" of a reference nucleic acid if the nucleic acid of interest has a sequence that is identical to that of the reference but for a small number of sequence alterations at particular positions. In some embodiments, e.g., as set forth herein, a variant has 10, 9, 8, 7, 6, 5, 4, 3, 2, or 1 substituted residues as compared with a reference. In some embodiments, e.g., as set forth herein, a variant has not more than 5, 4, 3, 2, or 1 residue additions, substitutions, or deletions as compared with the reference. In various embodiments, e.g., as set forth herein, the number of additions, substitutions, or deletions is fewer than about 25, about 20, about 19, about 18, about 17, about 16, about 15, about 14, about 13, about 10, about 9, about 8, about 7, about 6, and commonly are fewer than about 5, about 4, about 3, or about 2 residues.

BRIEF DESCRIPTION OF THE DRAWINGS

The foregoing and other objects, aspects, features, and advantages of the present disclosure will become more apparent and better understood by referring to the following description taken in conjunction with the accompanying drawings, in which:

FIGS. 5A and 5B are schematics depicting a breakdown of data for the samples used in Example #4 presented herein, according to an illustrative embodiment.

DETAILED DESCRIPTION

Figure 1:
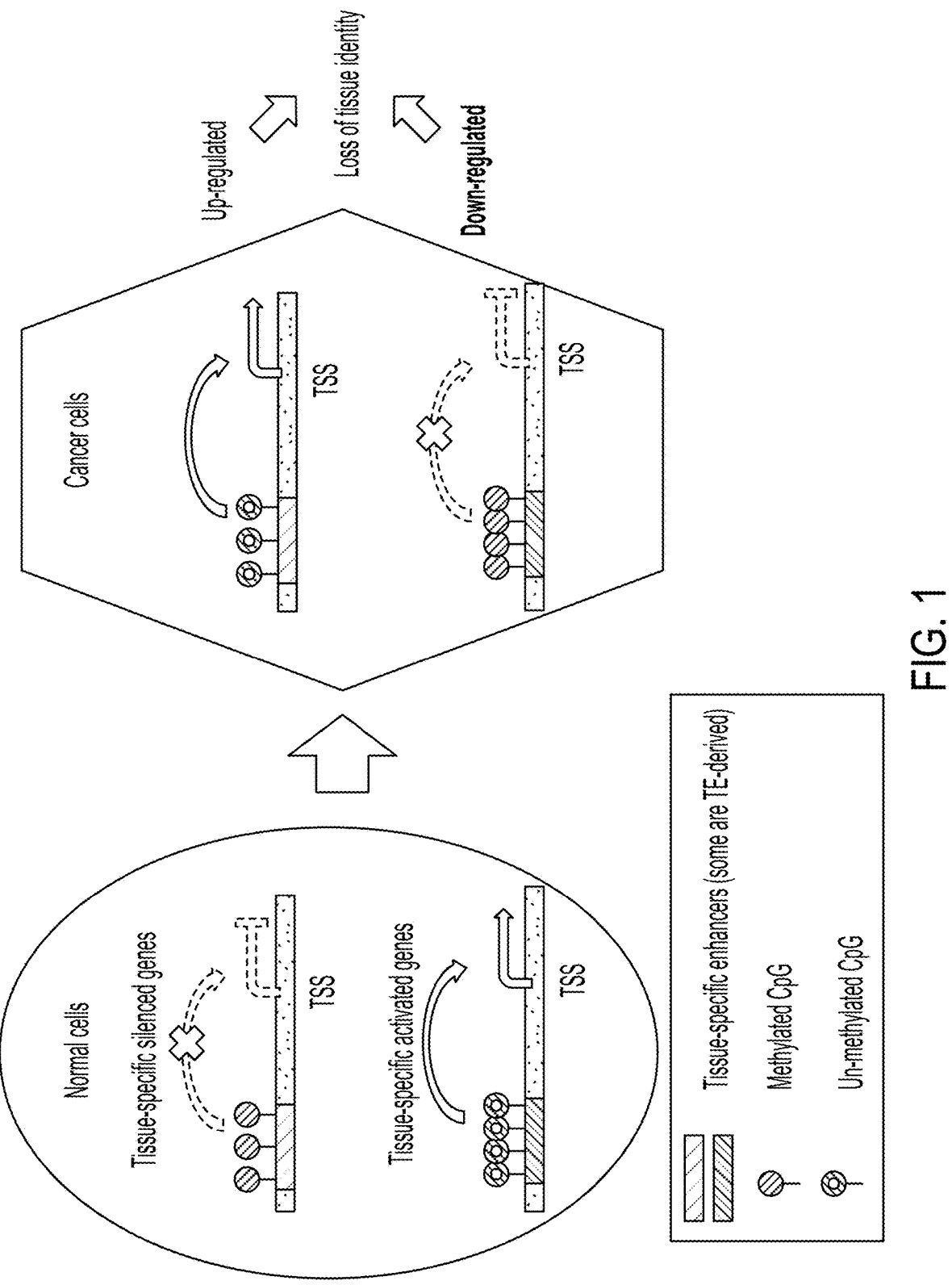
FIG. 1 is a schematic diagram illustrating DNA methylation in normal cells vs. cancer cells.

It is contemplated that systems, architectures, devices, methods, and processes of the claimed invention encompass variations and adaptations developed using information from the embodiments described herein. Adaptation and/or modification of the systems, architectures, devices, methods, and processes described herein may be performed, as contemplated by this description.

Throughout the description, where articles, devices, systems, and architectures are described as having, including, or comprising specific components, or where processes and methods are described as having, including, or comprising specific steps, it is contemplated that, additionally, there are articles, devices, systems, and architectures of the present invention that consist essentially of, or consist of, the recited components, and that there are processes and methods according to the present invention that consist essentially of, or consist of, the recited processing steps.

It should be understood that the order of steps or order for performing certain action is immaterial so long as the invention remains operable. Moreover, two or more steps or actions may be conducted simultaneously.

The mention herein of any publication, for example, in the Background section, is not an admission that the publication serves as prior art with respect to any of the claims presented herein. The Background section is presented for purposes of clarity and is not meant as a description of prior art with respect to any claim.

Documents are incorporated herein by reference as noted. Furthermore, documents whose citations are presented herein are incorporated herein by reference in their entireties, whether or not specifically noted. Where there is any discrepancy in the meaning of a particular term, the meaning provided in the Definition section above is controlling.

Headers are provided for the convenience of the reader—the presence and/or placement of a header is not intended to limit the scope of the subject matter described herein.

DNA methylation has been previously shown to have diagnostic and predictive potential for colorectal cancer (CRC). Methylation changes can also be used for patient stratification and monitoring. Patient stratification can improve treatment outcomes by providing clinician better ways of sub-categorizing CRC patients.

Cell-free DNA (cfDNA) found in the bloodstream is primarily a byproduct of cell death, with short fragment size, mostly corresponding to an average length of mononucleosome size. Circulating fetal DNA has been shown to be shorter than maternal DNA in plasma, and these size differences have been used to improve sensitivity of noninvasive prenatal diagnosis. Similar findings have been noted in cancer patients, with tumor-derived DNA fragments (ctDNA) being shorter than the non-tumor cell-derived fraction.

Differences in fragment lengths of circulating DNA combined with methylation signals could be exploited to enhance sensitivity for detecting the presence of ctDNA and for noninvasive genomic analysis of cancer.

Synopsis of Experiments Performed

The aim of these experiments was to evaluate putative methylation markers in the context of early cancer development and diagnostics as well as further investigate the biological significance of these regions.

Biomarker discovery was performed via whole genome bisulfite sequencing (WGBS) of 88 CRC, 48 advanced adenoma (AA) and corresponding adjacent normal tissue (NAT) samples. A short-list of significantly hypermethylated regions (DMRs) was correlated to transcriptomics data from 512 CRC patients in The Cancer Genome Atlas (TCGA) cohort. Pathway enrichment for biological pathway analysis of the DMRs was done by using Kyoto Encyclopedia of Genes and Genomes (KEGG) pathway database. Survival analysis was performed using Kaplan-Meier method on sub-groups of patients divided by the methylation status of individual markers. Finally, individual marker significance of selected regions was evaluated by analyzing 26 plasma samples from early stage (stage I-IIA) CRC samples and 42 colonoscopy verified controls (CNT) with targeted methylation sequencing assay.

4167 putative marker regions were identified from biomarker discovery with WGBS. Differential signal could be observed both between AA and NAT and CRC and NAT, while several of these regions were differentially methylated also between AA and CRC samples, indicating biological signal change with adenoma progression to cancer. 84 hypermethylated DMRs from several verification studies were further evaluated against transcriptome data from TCGA, where overlap for 69 genes was found. 19 of these genes showed a significant down-regulation (p<0.05), indicating a link between hypermethylation and gene expression. 2 genes showed significant up-regulation (p<0.05), which could indicate other epigenic processes to be in place. KEGG pathway analysis revealed that the top pathways involved were axonal guidance, ephrin receptor signaling, epithelial-mesenchymal transition and FGF signaling, which all play significant role in the context of cancer development and progression. Kaplan-Meier analysis showed significant correlation to patients 5-year survival prediction linked to 3 genes: FGF14 (p=0.025, HR=1.75), DPY19L2P1 (p=0.012, HR=1.86), PTPRO (p=0.046, HR=1.63). Targeted sequencing analysis on plasma samples of patients with early stage (I-IIA) colorectal cancer and age and gender matching colonoscopy-verified controls, showed high individual marker accuracy with AUC=0.78 for FGF14, AUC=0.81 for DPY19L2P1 and AUC=0.73 for PTPRO.

Methylation markers have distinct signals in early development of CRC, with high individual accuracy for separating early-stage cancers from matching controls. These regions have an impact on gene expression and can be linked to relevant biological pathways. Extending early detection potential of the markers to further prognostics and stratification can lead to better outcomes and improved survival of patients.

Methylation Assays

Methylation state of the specified markers can be assessed with different technological approaches and as such, is not restricted to any specific method by which a gene's methylation state is measured. For example, methylation state can be measured by a genome sequencing method where whole genome is scanned on base-pair resolution. Another method can involve analyzing changes in methylation patterns with a PCR-based process that involves digestion of DNA with methylation-sensitive restriction enzymes prior to PCR amplification.

In the context of MSRE-qPCR, the amount of total DNA is determined by directly measuring the portion of extracted DNA with real-time or digital PCR in its native form. Then, part of the DNA is digested with restriction enzymes that degrades unmethylated DNA, leaving only methylated strands intact. Resulting methylated sequences are then determined using once again either a real-time PCR or digital PCR.

Real-time PCR-based methods comprise generating a standard curve for the unmethylated target by using external standards. The standard curve is constructed from at least two points and relates the real-time Ct value for undigested and digested DNA to known quantitative standards. Next, the test sample Ct values are determined for the digested and undigested populations and the genomic equivalents of DNA are calculated from the standard curves produced. Ct values of undigested and digested DNA are evaluated to establish markers that were truly digested and thus producing a Ct values of 45 and markers that failed to be amplified from the samples and can be considered as failed values. Filtered and corrected values from digested DNA can then be compared directly between different condition groups to establish the relative differences in methylation levels between the groups. Additionally, delta-difference between the Ct values of undigested and digested DNA can be used for the same purpose.

Digital PCR based methods involve distributing a reaction across a 96- or 384-well plate or higher in a microfluidic device, such that the mean initial template DNA concentration is less than one molecule per reaction compartment. Amplification of methylated DNA molecules occurs in a small minority of PCR wells, and therefore represents a digital readout of the original number of template molecules in each sample.

In addition, other techniques that utilize bisulfite treatment of DNA as a starting point for methylation analysis can be used. These include methylation-specific PCR (MSP) (Herman et al. (1992) Proc. Natl. Acad. 20 Sci. USA 93: 9821-9826), Methylation Specific Nuclease assisted Minor-allele Enrichment (MS-NaME)-PCR (Liu Y et al. Nucleic Acids Res. 2017 Apr. 7; 45(6):e39.), Methylation-Sensitive High-Resolution Melting (MS-HRM) PCR (Hussmann D, Hansen L L. Methods Mol Biol. 2018; 1708:551-571.), the texts of which are incorporated herein by reference in their entireties.

For evaluating a methylation state, the methylation state is often expressed as the fraction or percentage of individual strands of DNA that is methylated at a particular site (e.g., at a single nucleotide, at a particular region or locus, at a longer sequence of interest, e.g., up to a −50-bp, 100-bp, 150-bp, 200-bp, 500-bp, 1000-bp subsequence of a DNA or longer) relative to the total population of DNA in the sample comprising that particular site.

Neoplasia of a biological sample can also be indicated when a methylation ratio of one or more DNA methylation markers relative to a level of bisulfite-treated DNA copy number of a reference gene is different, wherein the one or more DNA methylation markers comprises a base in a differentially methylated region (DMR). The methylation ratio includes the ratio of the methylation level of the DNA methylation marker and the level of a region in a reference gene determined by the same means used for the determination of the methylation level of the biomarker. Usually, the methylation ratio is represented by the ratio of the methylation level of the DNA methylation marker and the level of a region in a reference gene determined by the same means used for the determination of the methylation level of the DNA methylation marker.

The methylation ratio can be the ratio of the methylation level of a DNA methylation marker and the level of a region of a reference gene, both of which are quantitatively measured using real-time polymerase chain reaction (PCR) or by droplet digital PCR (ddPCR) method. For example, the methylation level of a DNA methylation marker from a sample of a subject can be quantitatively measured using a pair of primers and an oligonucleotide probe, where one primer, both primers, the oligonucleotide probe, or both primers and the oligonucleotide probe are capable of distinguishing between and selectively amplifying of methylated and unmethylated nucleic acid, e.g., after the nucleic acid has been modified by a modifying agent, e.g., digesting the unmethylated DNA with methylation specific enzymes or using bisulfite for converting unmethylated cytosine to a converted nucleic acid.

Biomarker Discovery

The purpose of this Example is to identify differentially methylated regions (DMRs) in DNA of colorectal cancer and colonic adenoma samples (e.g., samples from subjects having advanced adenoma). Identification of DMRs was performed by comparing DNA of subjects having colorectal cancer and/or colonic adenomas with matching control samples. This comparison allowed for development of methods that would elucidate colorectal cancer and advanced adenoma related methylation patterns from cell-free (cfDNA).

Whole genome bisulfite sequencing (WGBS) was used to identify differences in methylation status in samples of genomic DNA (gDNA) and cfDNA obtained from a variety of sources. gDNA was obtained from tissue samples with different histological backgrounds (e.g., colorectal cancer, colonic adenoma, lung cancer, breast cancer, colorectal cancer, gastric cancer, and matching controls) and buffy coat samples.

Genomic DNA (gDNA) from tissue and buffy coat samples was extracted using a DNeasy Blood & Tissue kit (Qiagen) according to a manufacturer's protocol. Extracted gDNA was then further processed in order to fragment it. For example, gDNA was fragmented into segments having lengths of about 400 bp with a Covaris 5220 ultra-sonicator.

cfDNA from plasma samples was extracted using QlAamp Circulating Nucleic Acid kit (Qiagen) according to the manufacturer's protocol.

The extracted and fragmented gDNA (genomic DNA) and cfDNA was bisulfite-converted with EZ DNA Methylation-Lightning kit (ZymoResearch). Sequencing libraries were prepared from the bisulfite converted DNA fragments by using Accel-NGS Methyl-seq DNA library kit (Swift Biosciences). The converted DNA fragments were sequenced with average depth of 37.5× with NovaSeq6000 (Illumina) equipment, using paired-end sequencing. For this experiment, paired-end sequencing was conducted such that 150 bp of each end of a converted DNA fragment was covered (e.g., 2×150). The sequenced reads were aligned to a bisulfite-converted human genome (Ensembl 91 assembly) using Bisulfite Read Mapper with Bowtie 2. The following steps were used to align sequenced reads to a bisulfite-converted human genome:

1. Evaluation of the sequencing quality
2. Alignment to a reference genome (hG38)
3. Deduplication and cleaning from adapter dimers
4. Methylation calling (e.g., identification of methylated nucleic acids)

Differentially methylated region analysis was done by comparing beta (β) values of individual CpGs of the colon cancer and/or colonic adenoma tissue samples to a matching control tissue. The β-value reflects methylation level of CpG reads in a sample. A β value of 0 indicates no methylated reads were found at a specific CpG location, while a β value of 1 indicates that all reads were fully methylated. Individual CpG methylation value scores were combined into regions of having a minimum of 3 CpGs within 50 bp distance of one another. The q-value of the region, which is the p-value corrected with a between-group label permutation test, was evaluated in order to select for regions of DNA from subjects with colorectal cancer and/or colonic adenoma which were significantly differently methylated from the same region in DNA obtained from a control subject. A q-value<0.05 was considered to show high statistical significance of a differentially methylated region (DMR). Significant regions were further evaluated to determine if there was a significant methylation signal compared to tissue samples with non-colorectal cancer origin, control tissue samples of non-colorectal origin, buffy coat samples, and cfDNA from healthy individuals.

In total, 4167 DMRs were initially identified as being significant for colorectal cancer and/or advanced adenoma. These DMRs include regions that are more indicative of colorectal cancer, DMRs that are more indicative of different histological subtypes of colonic adenomas, and regions that are indicative of both colorectal cancer and advanced adenoma.

Further cancer signal analysis was done using on the selected target regions from whole genome sequencing data using a read-wise signal scoring method. Thresholds were calculated in tissue-control paired samples to allow maximum separation between cancer and control reads. The calculated scores were applied to each read obtained from plasma cfDNA of subjects.

Example #1: Feature Evaluation Against Transcriptome Data

A feature evaluation study was undertaken by evaluating data from The Cancer Genome Atlas (TCGA) Research Network (http://cancergenome.nih.gov/) for CRC (TCGA-COAD, TCGA-READ) and normal tissue.

A short-list of 82 (Table 1) hypermethylated DMRs from the initial list of 4167 DMRs were verified in several plasma cfDNA studies and selected to be further evaluated against transcriptome data from TCGA. The study included several steps, where initially DMR regions were matched against 450K Illumina methylation array data available in TCGA, to identify regions present in TCGA data.

The comparison was performed on supervised mode, assigning two groups to be contrasted as healthy tissue and tumor tissue. Fisher's exact test and Benjamini-Hochberg multiple hypothesis correction was used to compare frequency of each motif flanking the positive CpG probes to a background defined by all distal probes on the array. Those CpGs that passed the minimum threshold (significant methylation difference 0.2, p value 0.05), were considered as causing functional change.

Second, it was attempted to identify methylation patterns that potentially are linked to clonal evolution in a particular tumor type. In order to archive this, KEGG pathway analysis was carried out to capture the biological processes related to regulatory networks, morphogenesis, development and cell differentiation.

Results

Overlap of 69 genes with 409 individual CpG counts was identified. The methylation signal of these 69 genes was then correlated to gene expression levels through an Enhancer Linking by Methylation/Expression Relationships algorithm to relate the methylation levels to gene expression, which could indicate functional changes happening due to methylation level changes.

19 genes (22 regions) (Table 2) in total showed a significant down-regulation (p<0.05), indicating a link between hypermethylation and gene expression. 2 genes (2 regions) (Table 3) showed significant up-regulation (p<0.05), which could indicate other epigenic processes to be in place.

TABLE 2

List of 22 genomic regions (19 genes) found to have significant down-regulation in CRC patients.

| |
| --- |
| 1:114152968-114153628 (SEQ ID NO.: 4) |
| 11:7251463-7252363 (SEQ ID NO.: 9) |
| 11:8080764-8081056 (SEQ ID NO.: 10) |
| 12:15322092-15323246 (SEQ ID NO.: 1) |
| 2:100321258-100322771 (SEQ ID NO.: 22) |
| 2:29115036-29115576 (SEQ ID NO.: 26) |
| 2:29115806-29116764 (SEQ ID NO.: 27) |
| 2:29920045-29921364 (SEQ ID NO.: 28) |
| 3:96813876-96814374 (SEQ ID NO.: 42) |
| 4:183904790-183906478 (SEQ ID NO.: 44) |
| 4:20252431-20252893 (SEQ ID NO.: 45) |
| 4:81030777-81031022 (SEQ ID NO.: 46) |
| 6:391674-392694 (SEQ ID NO.: 53) |
| 6:72621373-72622257 (SEQ ID NO.: 54) |
| 6:72622261-72623373 (SEQ ID NO.: 55) |
| 7:103989079-103989646 (SEQ ID NO.: 56) |
| 7:141073222-141073810 (SEQ ID NO.: 57) |
| 7:141074279-141074546 (SEQ ID NO.: 58) |
| 7:153886164-153886404 (SEQ ID NO.: 60) |
| 7:159144190-159144938 (SEQ ID NO.: 62) |
| 7:19117486-19118112 (SEQ ID NO.: 63) |
| 7:35185896-35187104 (SEQ ID NO.: 2) |

TABLE 3

List of 2 genomic regions (2 genes) found to have significant up-regulation in CRC patients.

| |
| --- |
| 7:93889427-93891122 (SEQ ID NO.: 70) |
| 8:66961046-66962606 (SEQ ID NO.: 72) |

Figure 2:
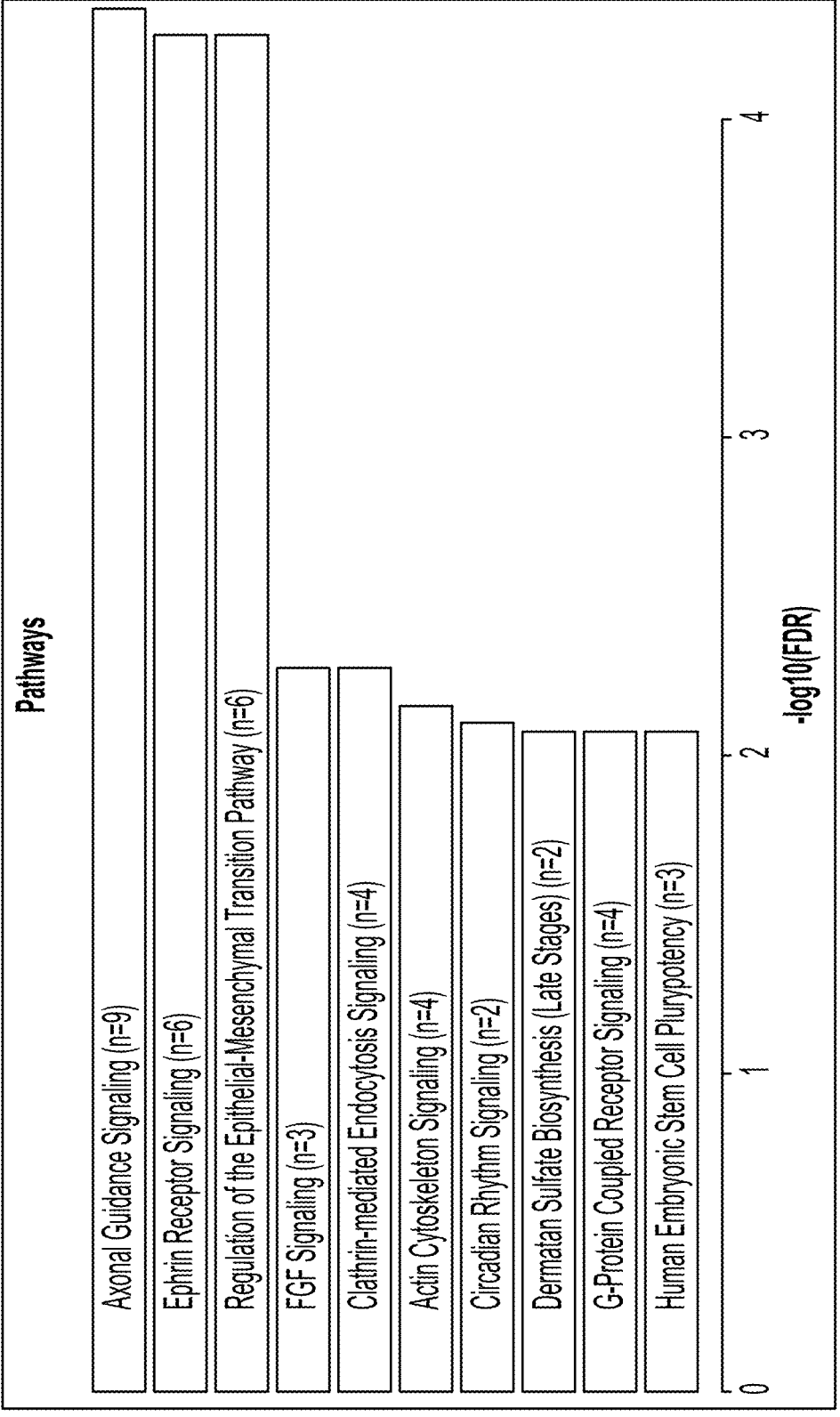
FIG. 2 is a bar-plot demonstrating the biological pathways marker regions belong to according to Kyoto Encyclopedia of Genes and Genomes (KEGG) pathway database.

COAD/READ KEGG pathway analysis (see FIG. 2) revealed that the top pathways involved were axonal guidance, ephrin receptor signaling, epithelial-mesenchymal transition and FGF signaling, which all play significant role in the context of cancer development and progression.

Example #2: Feature Evaluation for Patient Stratification and 5-Survival Prediction Third, in order to assess the 5-year survival function, each marker was evaluated using a Kaplan-Meier analysis on methylation high (>20% methylated reads) and methylation low (<20% methylated reads) patient groups. A total of 142 patients were assigned to high methylation group and a total of 142 patients were assigned to low methylation group. Groups were balanced in terms of age, gender, cancer stage and location.

Figure 3:
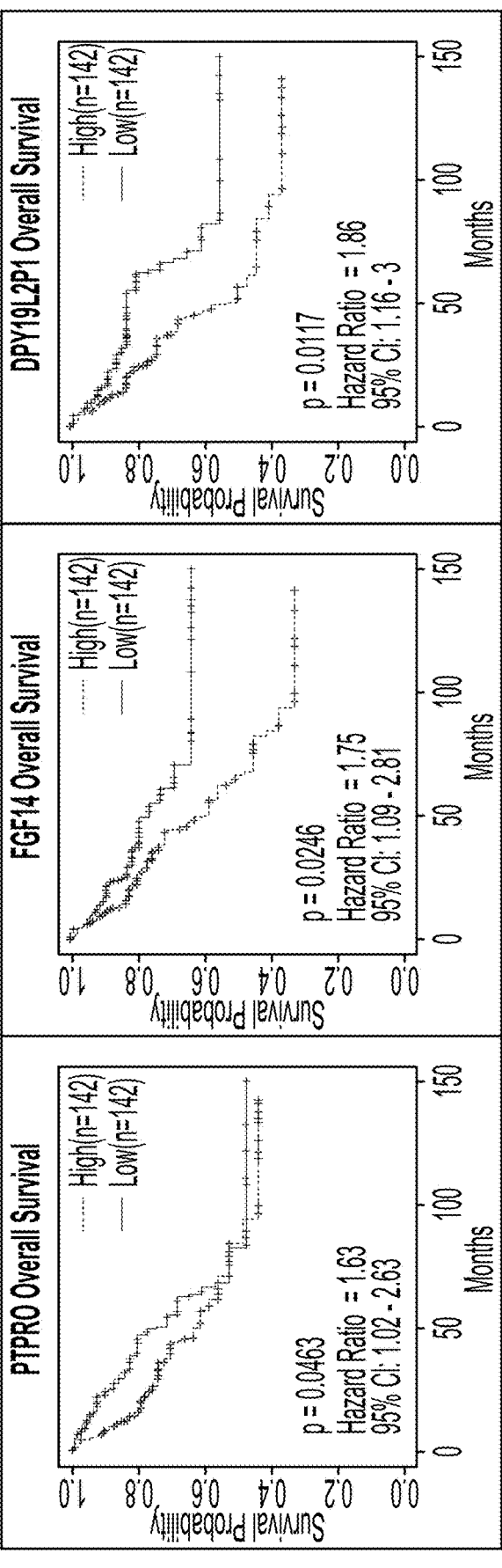
FIG. 3 are graphs demonstrating a Kaplan-Meier analysis on hierarchical clustered divided patient groups from TCGA-COAD/READ, according to an illustrative embodiment.

Results 5-year survival prediction significantly linked to 3 genes (Table 4): FGF14 (p=0.025, HR=1.75), DPY19L2P1 (p=0.012, HR=1.86), PTPRO (p=0.046, HR=1.63), where HR=hazards ratio (FIG. 3).

TABLE 4

List of 3 genomic regions (3 genes) for which five-year survival prediction in CRC patients is significantly linked

| Region ID | 5-year survival p-value | 5-year survival HR | Early detection AUC |
|---|---|---|---|
| (SEQ ID NO.: 2) 7:35185896-35187104 | 0.012 | 1.86 | 81% |
| (SEQ ID NO.: 3) 13:102392801-102392992 | 0.025 | 1.75 | 71% |
| (SEQ ID NO.: 1) 12:15322092-15323246 | 0.046 | 1.63 | 73% |

Example #3: Feature Evaluation for Early Stage Detection

Fourth, targeted hybrid-capture based methylation sequencing analysis on cfDNA extracted from plasma samples of patients with early stage (I-IIA) colorectal cancer (26 patients) and age and gender matching colonoscopy-verified controls (43 patients) was performed to check the individual marker performance of the survival stratification linked markers (Table 4) for early-stage cancer detection.

Results for Examples Above

Targeted hybrid-capture based methylation sequencing analysis on plasma samples of patients with early stage (I-IIA) colorectal cancer and age and gender matching colonoscopy-verified controls, showed high individual marker accuracy with AUC=78% for FGF14, AUC=81% for DPY19L2P1 and AUC=73% for PTPRO (FIG. 3).

Example #4: Large Multi-Cohort Study Shows Accurate Detection of Early-Stage Colorectal Cancer and Advanced Adenoma Patients Using Cell-Free DNA Methylation and Fragmentation Signals This study utilized cell-free DNA (cfDNA) methylation, fragmentation characteristics of selected cancer-related biomarker regions, tumor-derived signal deduction and a machine learning algorithm to refine a blood test for the early detection of CRC and advanced adenomas (AA). The aim of the study was to assess the diagnostic accuracy of the test for CRC.

This was a prospective, international (Spain, Ukraine, Germany and USA [part of NCT04792684 study] population), observational cohort study. Plasma samples from 997 patients were collected either prior to a scheduled screening colonoscopy or prior to colonic surgery for primary CRC. cfDNA samples from 170 early stage (I-II), 128 late-stage (III-IV) CRC patients (mean age 66 [44-84], female 48%, distal cancers 60%), 149 AA patients (63 high grade dysplasia; 84 low grade, >1 cm) and 550 age, gender and country of origin matched colonoscopy-checked controls were included. 155 of the control patients had a negative colonoscopy finding (cNEG), 337 had benign findings of diverticulosis, hemorrhoids, previously undiagnosed gastrointestinal diseases and/or hyperplastic polyps (BEN), 58 had non-advanced adenomas (NAA). Samples were analyzed utilizing hybrid-capture based sequencing methodology. A panel of targeted biomarkers was previously identified through tissue- and plasma-based discovery and verification workflow. Individual cfDNA fragments belonging to each biomarker region were scored for cancer-specific methylation and fragmentation signals. Finally, calculated scores were used in prediction model building and testing for establishing panel accuracy.

Per-region and per-DNA fragment scores were calculated comparing methylation patterns of cancerous and normal adjacent tissue samples and then applied to plasma cfDNA. For each region in cfDNA, fragment sizes were also calculated per sample and used as inputs in a machine learning algorithm, which was a standard random forest-based classifier.

The prediction model, utilizing a panel of 82 methylation and fragmentation scores originating from biomarkers belonging to relevant cancer development and progression related pathways, such as axonal guidance, ephrin receptor signaling, epithelial-mesenchymal transition and FGF signaling, correctly classified 93% (276/298) of CRC patients and 54% (81/149) AA patients. The 82-member panel of genomic regions shown in Table 1 (SEQ ID Nos. 1-81) was used. Sensitivity per cancer stage ranged from 85% (48/56) for stage I, 94% (107/114) stage II, 94% (90/96) stage III and 97% (31/32) stage IV. Fragmentation signals contributed most to early-stage cancers (I-II), while methylation signals were more significant for late stage (III-IV) detection. High grade dysplasia AA sensitivity was 52% (33/63), while low grade>1 cm AA sensitivity was 57% (48/84). Specificity of the model was 92% (504/550), with 83% (48/58) NAA, 93% (312/337) BEN and 93% (144/155) cNEG patients correctly identified. Lesion location, gender, age, BMI and country of origin were not significantly (p>0.05) correlated to prediction outcome. Differential methylation signals can be identified early on in cancer and even pre-cancer level, with markers belonging to different biological pathways that play significant role in the context of cancer development and progression.

For more detailed biological relevance, a couple of examples can be seen as follows: DPY19L2P1 enables glycosyltransferase activity. Alterations in glycosyltransferase levels and glycosylation patterns have been linked to tumorigenesis and metastasis. FGF14 functions as a tumor suppressor through inhibiting PI3K/AKT/mTOR Pathway. PTPRO has been shown to have prognostic power and function as tumor suppressor in human lung squamous cell carcinoma.

From this study, it is found that the use of methylation and fragmentation characteristics of cancer-related cfDNA regions, combined with a machine-learning algorithm, is highly accurate for early-stage (I-II) CRCs (91% sensitivity) and AA (54% sensitivity) at 92% specificity.

Figure 4:
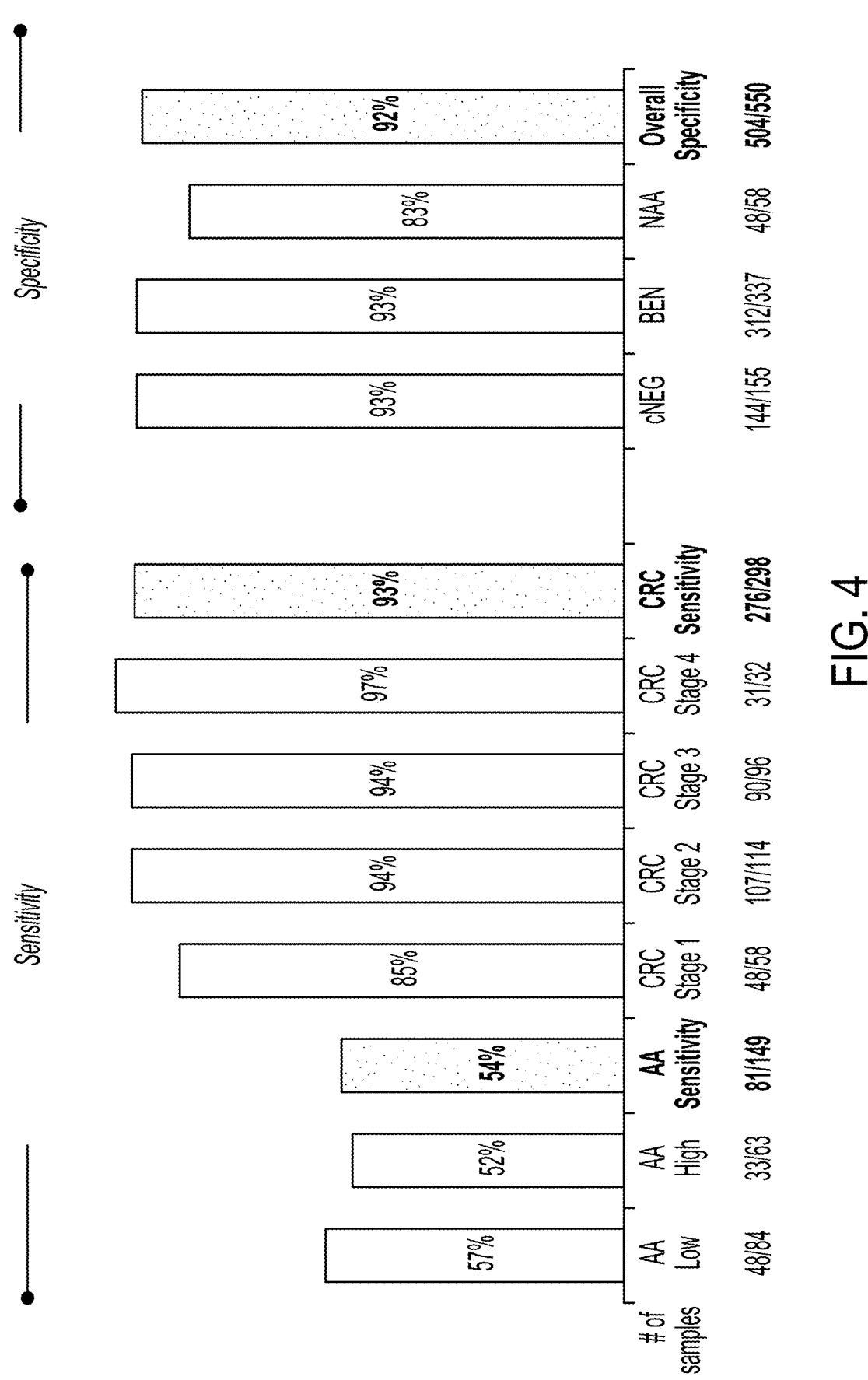
FIG. 4 are graphs showing sensitivity and specificity values for prediction outcomes (advanced adenoma and colorectal cancer) using an 82-member panel (the genomic regions in Table 1, Seq. ID Nos. #1-82), per Example #4 presented herein, according to an illustrative embodiment.

FIG. 4 are graphs showing sensitivity and specificity values for prediction outcomes (advanced adenoma and colorectal cancer) using the 82-member panel (the genomic regions in Table 1, Seq. ID Nos. #1-82). "AA Low" indicates low-advanced adenomas with low grade dysplasia, >=1 cm. "AA High" indicates advanced adenomas with high grade dysplasia. "CRC" indicates colorectal cancer. "cNEG" represents patients with no colonoscopy findings. "BEN" indicates patients with benign colonoscopy findings such as:

diverticulosis, hemorrhoids, previously undiagnosed gastro-intestinal diseases, inflammatory and/or hyperplastic polyps. "NAA" indicates non-advanced adenomas.

FIGS. 5A and 5B are schematics depicting a breakdown of data for the samples used in Example #4. "CRC" indicates colorectal cancer. "cNEG" represents patients with no colonoscopy findings. "BEN" indicates patients with benign colonoscopy findings such as: diverticulosis, hemorrhoids, previously undiagnosed gastrointestinal diseases, inflammatory and/or hyperplastic polyps. "NAA" indicates non-advanced adenomas. "AA" indicates advanced adenomas. "CRC" indicates colorectal cancer. For the prediction outcome per sub-group, the p-value analysis was done with Benjamini Hochberg with false discovery rate (fdr) adjustment for evaluating prediction outcome differences per demographic sub-groups of different age ranges, BMI ranges, gender, study country, lesion location, advanced adenoma histology, advanced adenoma dysplasia, and cancer stage, with p>0.05 indicating no significant outcome difference between sub-groups.

Methods for Assaying Methylation State of Selected Markers

Target nucleic acid can be isolated from a sample through different approaches, for example, via a direct gene capture by, for example, isolating target nucleic acid from a sample through, for example, removal of assay inhibiting agents to produce a clarified sample, capture of a target nucleic acid (if present) from the clarified sample with a capture reagent to form a capture complex, isolating the capture complex from the clarified sample, and recovering the target nucleic acid (if present) from the capture complex in a nucleic acid solution.

Fragments of the isolated DNA are amplified using sets of primer oligonucleotides and an amplification enzyme. The amplification of several DNA segments can be carried out simultaneously in one and the same reaction vessel. The amplification may be carried out using a polymerase chain reaction (PCR). Amplicons are typically 100 to 2000 base pairs in length.

DNA amplification can then be followed by further treatment of the DNA with methylation-specific enzymes and measuring the methylation status with qPCR or ddPCR. MSRE-qPCR is a method for analyzing a nucleic acid for the presence of 5-methylcytosine based upon methylation specific restriction enzyme method described by Beikircher, et al. Methods Mol Biol. 2018; 1708:407-424 or variations. Restriction enzymes have been used for investigating DNA methylation patterns. Generally, methylation-sensitive restriction enzymes (MSREs), which contain CpG motifs in their recognition site are used. Since the activity of these enzymes is blocked by 5-methylcytosine, then only unmethylated sites are digested while methylated regions remain unaffected. Thus, upon successful digestion followed by PCR amplification, only methylated DNA should result in a detectable PCR product.

Design of MSRE-qPCR assays is usually less complicated than the design of bisulfite-based assays, as "native" DNA is targeted with only conditions that primers must cover target regions presenting at least one MSRE-cut-site, but more cut-sites give a better outcome. CpG-rich regions, which are mostly also candidate regions for methylation differences, are good targets for MSRE-qPCR assay design, as they typically contain a large number of suitable MSRE cut-sites. The use of more than one MSRE, in particular restriction enzymes AciI, Hin6I, HpyCH4IV, and HpaII usually provide a very good coverage of CpG-rich sequences. The availability of sample is often a limiting factor, especially in the context of analyzing cell-free DNA, but this can be overcome by using preamplification upon MSRE digestion. Methylation-specific restriction enzyme approach can also be combined with digital PCR.

Methylation markers may be also detected by use of methylation-specific primer oligonucleotides. This technique (MSP) has been described in U.S. Pat. No. 6,265,171 to Herman, the text of which is incorporated herein by reference in its entirety. The use of methylation status specific primers for the amplification of bisulfite treated DNA allows the differentiation between methylated and unmethylated nucleic acids. MSP primer pairs contain at least one primer that hybridizes to a bisulfite treated CpG dinucleotide. Therefore, the sequence of said primers comprises at least one CpG dinucleotide. MSP primers specific for non-methylated DNA contain a "T" at the position of the C position in the CpG.

Another method for analyzing a nucleic acid for the presence of 5-methylcytosine is based upon the bisulfite method described by Frommer, et al. for the detection of 5-methylcytosines in DNA (Frommer et al. Proc Natl Acad Sci USA. 1992 Mar. 1; 89(5):1827-31) or variations thereafter.

The bisulfite method of mapping 5-methylcytosines is based on the observation that cytosine, but not 5-methylcytosine, reacts with hydrogen sulfite ion (also known as bisulfite). Therefore, DNA that has been treated with bisulfite retains only methylated cytosines. Various methylation assay procedures can be used in conjunction with bisulfite treatment according to the present technology. These assays allow for determination of the methylation state of one or a many of CpG dinucleotides (e.g., CpG islands) within a nucleic acid sequence. Such assays involve, among other techniques, sequencing of bisulfite-treated nucleic acid, PCR (for sequence-specific amplification), Methylation-Specific PCR, Methylation Specific Nuclease-assisted Minor-allele Enrichment PCR, Methylation-Specific Restriction Enzyme qPCR, Methylation-Sensitive High-Resolution Melting.

Targeted sequencing-based protocols entail PCR amplification of target regions of interest from bisulfite-converted genomic DNA, followed by DNA sequencing library preparation using techniques such as standard Illumina protocols or transposase-based Nextera XT technology. Next-generation sequencing (NGS) techniques offer single base resolution reading of CpG methylation levels.

Additionally, assays such as "MethyLight™" (a fluorescence-based real-time PCR technique) (Campan M et al. Methods Mol Biol. 2018; 1708:497-513.) can be used for evaluation of the methylation status. MethyLight is a quantitative, fluorescence-based, real-time PCR method to sensitively detect and quantify DNA methylation of candidate regions of the genome. MethyLight is uniquely suited for detecting low-frequency methylated DNA regions against a high background of unmethylated DNA, as it combines methylation-specific priming with methylation-specific fluorescent probing (Campan M et al. Methods Mol Biol. 2018; 1708:497-513.). Additionally, MethyLight can be combined with Digital PCR, for the highly sensitive detection of individual methylated molecules, with use in disease detection and screening (Campan M et al. Methods Mol Biol. 2018; 1708:497-513.).

MSP (methylation-specific PCR) allows for assessing the methylation status of virtually any group of CpG sites within a CpG island, independent of the use of methylation-sensitive restriction enzymes (Herman et al. Proc. Natl. Acad. Sci. USA 93:9821-9826, 1996). MSP allows for highly sensitive detection (detection level of 0.1% of the alleles, with full specificity) of locus-specific DNA methylation, using PCR amplification of bisulfite-converted DNA. The bisulfite-modified DNA is PCR amplified using specific primers sets, one that binds specifically to the methylated sequence and other that only binds to the unmethylated sequence. MSP results can then be obtained using gel electrophoresis, not requiring further restriction or sequencing analysis.

The Quantitative Multiplex Methylation-Specific PCR (QM-MSP) is another method for sensitive quantification of DNA methylation by using methylation specific primers (Fackler M J, Sukumar S. Methods Mol Biol. 2018; 1708: 473-496). QM-MSP is a two-step PCR approach, where in the first step, one pair of gene-specific primers (forward and reverse) amplifies the methylated and unmethylated copies of the same gene simultaneously and in multiplex, in one PCR reaction. This methylation-independent amplification step produces amplicons of up to $10^9$ copies per μL after 36 cycles of PCR. In the second step, the amplicons of the first reaction are quantified with a standard curve using real-time PCR and two independent fluorophores to detect methylated/unmethylated DNA of each gene in the same well (e.g., 6FAM and VIC). One methylated copy is detectable in 100,000 reference gene copies.

Methylation-Sensitive High-Resolution Melting (MS-HRM) (Hussmann D, Hansen L L. Methods Mol Biol. 2018; 1708:551-571.). Methylation-Sensitive High-Resolution Melting (MS-HRM) is an in-tube, PCR-based method to detect methylation levels at specific loci of interest. A unique primer design facilitates a high sensitivity of the assays enabling detection of down to 0.1-1% methylated alleles in an unmethylated background.

Primers for MS-HRM assays are designed to be complementary to the methylated allele, and a specific annealing temperature enables these primers to anneal both to the methylated and the unmethylated alleles thereby increasing the sensitivity of the assays. Bisulfite treatment of the DNA prior to performing MS-HRM ensures a different base composition between methylated and unmethylated DNA, which is used to separate the resulting amplicons by high resolution melting.

MS-NaME (Methylation Specific Nuclease-assisted Minor-allele Enrichment) reaction (Liu Y et al. Nucleic Acids Res. 2017 Apr. 7; 45(6):e39.) can be used alone or in combination with one or more of these methods. Minor-allele Enrichment (MS-NaME) employs a double-strand-specific DNA nuclease (DSN) to remove excess DNA with normal methylation patterns. The technique utilizes oligo-nucleotide probes that direct DSN activity to multiple targets in bisulfite-treated DNA, simultaneously. Oligonucleotide probes targeting unmethylated sequences generate local double stranded regions resulting to digestion of unmethylated targets and leaving methylated targets intact; and vice versa. Subsequent amplification of the targeted regions results in enrichment of the targeted methylated or unmethylated minority-epigenetic-alleles.

Ms-SNuPE™ (Methylation-sensitive Single Nucleotide Primer Extension) reactions (Gonzalgo M L & Liang G, Nat Protoc. 2007; 2(8):1931-6.), Strand-specific PCR can be performed to generate a DNA template for quantitative methylation analysis using Ms-SNuPE. SNuPE is then performed with oligonucleotide(s) designed to hybridize immediately upstream of the CpG site(s) being interrogated. Reaction products are electrophoresed on polyacrylamide gels for visualization and quantitation by phosphor-image analysis.

The fragments obtained via amplification can also carry directly or indirectly detectable labels such as fluorescent labels, radionuclides, or detachable molecule fragments having a typical mass that can be detected in a mass spectrometer. The detection may be carried out and visualized by means of, e.g., matrix assisted laser desorption/ionization mass spectrometry (MALDI) or using electron spray mass spectrometry (ESI).

Colorectal Cancer

In certain embodiments, methods and compositions of the present disclosure are useful for detecting, diagnosing, predicting, monitoring, screening for, staging, and/or providing survival prognosis for colorectal cancer.

Colorectal cancers include colorectal cancers at any of the various possible stages known in the art, including, e.g., Stages 0, Stage I, Stage II, Stage III, and Stage IV colorectal cancers. Colorectal cancers include all stages of the Tumor/Node/Metastasis (TNM) staging system. With respect to colorectal cancer, T can refer to whether the tumor is confined to the top layers of colorectal duct cells or has not invaded deeper tissues; N can refer to whether the tumor has spread to lymph nodes, and if so how many lymph nodes and where they are located; and M can refer to whether the cancer has spread to other parts of the body, and if so which parts and to what extent. Particular stages of T, N, and M are known in the art. T stages can include TX, T0, Tis, T1, T2, T3, T4; N stages can include NX, N0, N1, N2; M stages can include M0, M1.

In certain instances, the present disclosure includes screening of early stage colorectal cancer. Early stage colorectal cancers can include, e.g., colorectal cancers localized within a subject, e.g., in that they have not yet spread to lymph nodes of the subject, e.g., lymph nodes near to the cancer (stage NO), and have not spread to distant sites (stage M0). Early stage cancers include colorectal cancers corresponding to, e.g., Stages 0 to II.

Methods and compositions of the present disclosure are useful for stratifying of colorectal cancer in all of its forms and stages, including without limitation those named herein or otherwise known in the art, as well as all subsets thereof. Accordingly, the person of skill in art will appreciate that all references to colorectal cancer provided here include, without limitation, colorectal cancer in all of its forms and stages, including without limitation those named herein or otherwise known in the art, as well as all subsets thereof.

Subjects and Samples

A sample analyzed using methods and compositions provided herein can be any biological sample and/or any sample including nucleic acids. In various particular embodiments, a sample analyzed using methods and compositions provided herein can be a sample from a mammal. In various particular embodiments, a sample analyzed using methods and compositions provided herein can be a sample from a human subject. In various particular embodiments, a sample analyzed using methods and compositions provided herein can be a sample form a mouse, rat, pig, horse, chicken, or cow.

In various instances, a human subject is a subject diagnosed or seeking diagnosis as having, diagnosed as or seeking diagnosis as at risk of having, and/or diagnosed as or seeking diagnosis as at immediate risk of having, colorectal cancer. In various instances, a human subject is a subjected identified as a subject in need of screening for colorectal cancer. In certain instances, a human subject is a subject identified as in need of colorectal cancer screening by a medical practitioner. In various instances, a human subject is identified as in need of colorectal cancer screening due to age, e.g., due to an age equal to or greater than 40 years, e.g., an age equal to or greater than 49, 45, 50, 55, 60, 65, 70, 75, 80, 85, or 90 years, though in some instances a subject 18 years old or older may be identified as at risk and/or in need of screening for colorectal cancer. In various instances, a human subject is identified as being high risk and/or in need of screening for colorectal cancer based on, without limitation, familial history, prior diagnoses, and/or an evaluation by a medical practitioner. In various instances, a human subject is a subject not diagnosed as having, not at risk of having, not at immediate risk of having, not diagnosed as having, and/or not seeking diagnosis for a cancer such as colorectal cancer.

A sample from a subject, e.g., a human or other mammalian subject, can be a sample of, e.g., blood, blood component (e.g., plasma, buffy coat), cfDNA (cell free DNA), ctDNA (circulating tumor DNA), stool, or tissue. In some particular embodiments, a sample is an excretion or bodily fluid of a subject (e.g., stool, blood, plasma, lymph, or urine of a subject) or a tissue sample. A sample from a subject can be a cell or tissue sample, e.g., a cell or tissue sample that is of a cancer or includes cancer cells, e.g., of a tumor or of a metastatic tissue. In various embodiments, a sample from a subject, e.g., a human or other mammalian subject, can be obtained by biopsy or surgery.

In various particular embodiments, a sample is a sample of cell-free DNA (cfDNA). cfDNA is typically found in biological fluids (e.g., plasma, serum, or urine) in short, double-stranded fragments. The concentration of cfDNA is typically low, but can significantly increase under particular conditions, including without limitation pregnancy, autoimmune disorder, myocardial infraction, and cancer. Circulating tumor DNA (ctDNA) is the component of circulating DNA specifically derived from cancer cells. ctDNA can be present in human fluids. For example in some instances, ctDNA can be found bound to and/or associated with leukocytes and erythrocytes. In some instances, ctDNA can be found not bound to and/or associated with leukocytes and erythrocytes. Various tests for detection of tumor-derived cfDNA are based on detection of genetic or epigenetic modifications that are characteristic of cancer (e.g., of a relevant cancer). Genetic or epigenetic modifications characteristic of cancer can include, without limitation, oncogenic or cancer-associated mutations in tumor-suppressor genes, activated oncogenes, hypermethylation, and/or chromosomal disorders. Detection of genetic or epigenetic modifications characteristic of cancer or pre-cancer can confirm that detected cfDNA is ctDNA.

cfDNA and ctDNA provide a real-time or nearly real-time metric of the methylation status of a source tissue. cfDNA and ctDNA have a half-life in blood of about 2 hours, such that a sample taken at a given time provides a relatively timely reflection of the status of a source tissue.

Various methods of isolating nucleic acids from a sample (e.g., of isolating cfDNA from blood or plasma) are known in the art. Nucleic acids can be isolated, e.g., without limitation, standard DNA purification techniques, by direct gene capture (e.g., by clarification of a sample to remove assay-inhibiting agents and capturing a target nucleic acid, if present, from the clarified sample with a capture agent to produce a capture complex, and isolating the capture complex to recover the target nucleic acid).

In certain embodiments, a sample may have a required minimum amount of DNA (e.g., cfDNA, gDNA) (e.g., DNA fragments) for later determining a methylation status. For example, in certain embodiments, a sample may be required to have at least 5 ng, at least 10 ng, at least 20 ng (or more) DNA.

Methods of Measuring Methylation Status

Methylation status can be measured by a variety of methods known in the art and/or by methods provided in this specification. Those of skill in the art will appreciate that a method for measuring methylation status can generally be applied to samples from any source and of any kind, and will further be aware of processing steps available to modify a sample into a form suitable for measurement by a given methodology.

In certain embodiments, the processing steps involve fragmenting or shearing DNA of the sample. For example, genomic DNA (e.g., gDNA) obtained from a cell, tissue, or other source may require fragmentation prior to sequencing. In certain embodiments, DNA may be fragmented prior to measurement of methylation status using a physical method (e.g., using an ultra-sonicator, a nebulizer technique, hydrodynamic shearing, etc.). In certain embodiments, DNA may be fragmented using an enzymatic method (e.g., using an endonuclease or a transposase). Certain samples, e.g., cfDNA samples, may not require fragmentation. cfDNA fragments are about 200 bp in length and may be appropriate for certain methods provided herein. DNA fragments of about 100-1000 bp in length are suitable for analysis in certain NGS techniques described herein including, for example, Illumina® based techniques. Certain technologies may require DNA fragments of about 100-1000 bp range. In contrast, DNA fragments of about 10 kb or longer are suitable for long read sequencing technologies.

Methods of measuring methylation status include, without limitation, methods including whole genome bisulfite sequencing, targeted bisulfite sequencing, targeted enzymatic methylation sequencing, methylation-status-specific polymerase chain reaction (PCR), methods including mass spectrometry, methylation arrays, methods including methylation-specific nucleases, methods including mass-based separation, methods including target-specific capture (e.g., hybrid capture), and methods including methylation-specific oligonucleotide primers. Certain particular assays for methylation utilize a bisulfite reagent (e.g., hydrogen sulfite ions) or enzymatic conversion reagents (e.g., Tet methylcytosine dioxygenase 2).

Bisulfite reagents can include, among other things, bisulfite, disulfite, hydrogen sulfite, sodium metabisulphite, or combinations thereof, which reagents can be useful in distinguishing methylated and unmethylated nucleic acids. Bisulfite interacts differently with cytosine and 5-methylcytosine. In typical bisulfite-based methods, contacting of DNA (e.g., single stranded DNA, double stranded DNA) with bisulfite deaminates (e.g., converts) unmethylated cytosine to uracil, while methylated cytosine remains unaffected. Methylated cytosines, but not unmethylated cytosines, are selectively retained. Thus, in a bisulfite processed sample, uracil residues stand in place of, and thus provide an identifying signal for, unmethylated cytosine residues, while remaining (methylated) cytosine residues thus provide an identifying signal for methylated cytosine residues. Bisulfite processed samples can be analyzed, e.g., by next generation sequencing (NGS) or other methods disclosed herein.

In some embodiments, bisulfite processed samples may be treated using a bisulfite ratio of bisulfite to DNA that is at least. In certain embodiments, the bisulfite processed sample comprises single stranded DNA fragments or double stranded DNA fragments.

In some embodiments, bisulfite treatment includes subjecting DNA fragments (e.g., double stranded DNA) to one or more denaturation-conversion cycles in order to convert unmethylated cytosines to uracils in the DNA fragments. Denaturation converts double stranded DNA fragments in the sample to single stranded DNA fragments. Conversion changes the unmethylated cytosines of the single stranded DNA into uracils. In some embodiments, only one denaturation-conversion cycle are performed. In some embodiments, two, three, four, five, six, seven, eight, nine, ten, fifteen, twenty, or more denaturation-conversion cycles are performed. In some embodiments, the temperature of the denaturation step is performed at a temperature of about 80-100° C. (e.g., about 90-97° C., e.g., about 96° C.). In some embodiments, the denaturation step is performed for less than 10 minutes (e.g., less than 5 minutes, less than 5 minutes, less than 2 minutes, or less). In certain embodiments, the conversion step is performed for less than 2.5 hr (e.g., less than 2 hr, less than 1 hr, less than 30 minutes, less than 15 minutes, or less). In certain embodiments, the conversion step is performed at a temperature of 55 to 65° C. In certain embodiments, the converted DNA fragments may be stored at a temperature of about 4° C. after performing the denaturation-conversion cycle(s). In some embodiments, bisulfite treatment may be applied prior to library preparation. In some embodiments, bisfulfite treatment may be applied after library preparation.

Enzymatic conversion reagents can include Tet methyl-cytosine dioxygenase 2 (TET2). TET2 oxidizes 5-methyl-cytosine and thus protects it from the consecutive deamination by APOBEC. APOBEC deaminates unmethylated cytosine to uracil, while oxidized 5-methylcytosine remains unaffected. Thus, in a TET2 processed sample, uracil residues stand in place of, and thus provide an identifying signal for, unmethylated cytosine residues, while remaining (methylated) cytosine residues thus provide an identifying signal for methylated cytosine residues. TET2 processed samples can be analyzed, e.g., by next generation sequencing (NGS). In certain embodiments, APOBEC refers to a member (or plurality of members) of the Apolipoprotein B mRNA Editing Catalytic Polypeptide-like (APOBEC) family. In certain embodiments, APOBEC may refer to APOBEC-1, APOBEC-2, APOBEC-3A, APOBEC-3B, APOBEC-3C, APOBEC-3D, APOBEC-3E, APOBEC-3F, APOBEC-3G. APOBEC-3H, APOBEC-4, and/or Activation-induced (cytidine) deaminase (AID).

Methods of measuring methylation status can include, without limitation, massively parallel sequencing (e.g., next-generation sequencing) to determine methylation state, e.g., sequencing by-synthesis, real-time (e.g., single-molecule) sequencing, bead emulsion sequencing, nanopore sequencing, or other sequencing techniques known in the art. In some embodiments, a method of measuring methylation status can include whole-genome sequencing, e.g., measuring whole genome methylation status from bisulfite or enzymatically treated material with base-pair resolution.

In some embodiments, a method of measuring methylation status includes reduced representation bisulfite sequencing e.g., utilizing use of restriction enzymes to measure methylation status of high CpG content regions from bisulfite or enzymatically treated material with base-pair resolution.

In some embodiments, a method of measuring methylation status can include targeted sequencing e.g., measuring methylation status of pre-selected genomic location from bisulfite or enzymatically treated material with base-pair resolution.

In some embodiments, the pre-selection (capture) (e.g., enrichment) of regions of interest (e.g., DMRs) can be done by complementary in vitro synthesized oligonucleotide sequences (e.g., capture baits/probes). Capture probes (e.g., oligonucleotide capture probes, oligonucleotide capture baits) are useful in targeted sequencing (e.g., NGS) techniques to enrich for particular regions of interest in an oligonucleotide (e.g., DNA) sequence. For example, enrichment of target regions is useful when sequences of particular pre-determined regions of DNA are sequenced. In certain embodiments, capture probes are about 10 to 1000 bp long (e.g., about 10 to about 200 bp long) (e.g., about 120 bp long). In certain embodiments, one or more capture probes are targeted to capture a region of interest (e.g., a genomic marker) corresponding to one or more methylation loci (e.g., methylation loci comprising at least a portion of one or more DMRs). In certain embodiments, capture probes are targeted to methylation loci that are hypomethylated or hypermethylated. For example, a capture probe may be targeted to a particular methylation loci. However, if fragments of DNA corresponding to a methylation loci are converted (e.g., bisulfite or enzymatic converted) prior to enrichment using a capture probe, the sequence of the converted DNA fragments will change as described herein due to particular cytosine residues being unmethylated. Therefore, targeting an unconverted DNA region may result in some mismatches if cytosines are hypomethylated. Though capture probe-target sequence hybridization may tolerate some mismatches, a second probe may be required to enrich for DNA regions which are hypomethylated.

In certain embodiments, capture probes are evaluated (e.g., prior to sequencing) for their ability to target multiple regions of the genome of interest. For example, when designing a capture probe to target a particular region of interest (e.g., a DMR), the ability for a capture probe to target multiple regions of the genome may be considered. As discussed herein, mismatches in pairing (e.g., non-Watson-Crick pairing) allow for capture probes to hybridize to other, unintended regions of a genome. In addition, a particular target sequence may be repeated elsewhere in a genome. Repeat sequences are common for sequences that are highly repetitive. In certain embodiments, capture probes are designed such that they only target a few similar regions of the genome. In certain embodiments, capture probes may hybridize to 500 or fewer, 100 or fewer, 50 or fewer, 10 or fewer, 5 or fewer similar regions in a genome. In certain embodiments, a similar region to the target of region of interest is calculated using a 24 bp window moving around a genome and matching the region of the window to a reference sequence according to sequence order similarity. Other size windows and/or techniques may be used.

For example, hybrid-capture of one or more DNA fragments (e.g., ctDNA, fragmented gDNA) may be performed using capture probes targeted to predetermined regions of interested of a genome. In certain embodiments, capture probes target at least 2 (e.g., at least 3, 4, 5, 6, 7, 8, 9, 10, 11, 12, 13, 14, 15, 16, 17, 18, 19, 20, 21, 22, 23, 24, 25, 50, 75, 100, 150, or more) predetermined regions of interest (e.g., genomic markers, e.g., DMRs). In certain embodiments, the capture probes overlap. In certain embodiments, the overlapping probes overlap at least 10%, at least 20%, at least 30%, at least 40%, at least 50%, at least 60% or more.

In certain embodiments, the capture probes are nucleic acid probes (e.g., DNA probes, RNA probes). In some embodiments, a method may also include identifying mutated regions (e.g., individual nucleotide bases) using targeted sequencing e.g., determining the presence of a mutation in one or more pre-selected genomic locations (e.g., a genomic marker, e.g., a mutation marker). In certain embodiments, mutations may also be identified from bisulfite or enzymatically treated DNA with base-pair resolution.

In some embodiments, a method for measuring methylation status can include Illumina Methylation Assays e.g., measuring over 850,000 methylation sites quantitatively across a genome at single-nucleotide resolution.

Various methylation assay procedures can be used in conjunction with bisulfite treatment to determine methylation status of a target sequence such as a DMR. Such assays can include, among others, Methylation-Specific Restriction Enzyme qPCR, sequencing of bisulfite-treated nucleic acid, PCR (e.g., with sequence-specific amplification), Methylation Specific Nuclease-assisted Minor-allele Enrichment PCR, and Methylation-Sensitive High Resolution Melting. In some embodiments, DMRs are amplified from converted (e.g., bisulfite or enzyme converted) DNA fragments for library preparation.

In some embodiments, a sequencing library may be prepared using converted (e.g., bisulfite or enzyme converted) oligonucleotide fragments (e.g., cfDNA, gDNA fragments, synthetic nucleotide sequences, etc.) according to, e.g., an Illumina protocol, an Accel-NGS® Methyl-Seq DNA Library Kit (Swift Bioscience) protocol, a transpose-based Nextera XT protocol, or the like. In some embodiments, the oligonucleotide fragments are DNA fragments which have been converted (e.g., bisulfite or enzyme converted). In certain embodiments, DNA fragments used in preparation of a sequencing library may be single stranded DNA fragments or double stranded DNA fragments. In certain embodiments, a library may be prepared by attaching adapters to DNA fragments. Adapters contain short (e.g., about 100 to about 1000 bp) sequences (e.g., oligonucleotide sequences) that allow oligonucleotide fragments of a library (e.g., a DNA library) to bind to and generate clusters on a flow cell used in, for example, next generation sequencing (NGS). Adapters may be ligated to library fragments prior to NGS. In certain embodiments, a ligase enzyme covalently links the adapter and library fragments. In certain embodiments, adapters are attached to either one or both of the 5' and 3' ends of converted DNA fragments. In certain embodiments, the attaching step is performed such that at least 40%, at least 50%, at least 60%, at least 70% of the converted DNA fragments are attached to adapter. In certain embodiments, the attaching step is performed such that at least 40%, at least 50%, at least 60%, at least 70% of the converted DNA fragments have an adapter attached at both the 5' and 3' ends In certain embodiments, adapters used herein contain a sequence of oligonucleotides that aid in sample identification. For example, in certain embodiments, adapters include a sample index. A sample index is a short sequence (e.g., about 8 to about 10 bases) of nucleic acids (e.g., DNA, RNA) that serve as sample identifiers and allow for, among other things, multiplexing and/or pooling of multiple samples in a single sequencing run and/or on a flow cell (e.g., used in a NGS technique). In certain embodiments, an adapter at a 5' end, a 3' end, or both of a converted single stranded DNA fragment includes a sample index. In certain embodiments, an adapter sequence may include a molecular barcode. A molecular barcode may serve as a unique molecular identifier to identify a target molecule during, for example, DNA sequencing. In certain embodiments, DNA barcodes may be randomly generated. In certain embodiments, DNA barcodes may be predetermined or predesigned. In certain embodiments, the DNA barcodes are different on each DNA fragment. In certain embodiments, the DNA barcodes may be the same for two single stranded DNA fragments that are not complementary to one another (e.g., in a Watson-Crick pair with each other) in the biological sample. In certain embodiments, DNA fragments may be amplified (e.g., using PCR) after ligation of adapters to DNA fragments. In certain embodiments, at least 40% (e.g., at least at least 50%, at least 60%, at least 70%) of the converted DNA fragments have an adapter attached at both the 5' and 3' ends.

In certain embodiments, high-throughput and/or next-generation sequencing (NGS) techniques are used to achieve base-pair level resolution of an oligonucleotide (e.g., a DNA) sequence, permitting analysis of methylation status and/or identification of mutations. For example, in certain embodiments, NGS may include single-end or paired-end sequencing. In single-end sequencing, a technique reads a sequenced fragment in one direction—from one end of a fragment to the opposite end of the fragment. In certain embodiments, this produces a single DNA sequence that then may be aligned to a reference sequence. In paired-end sequencing, a sequenced fragment is read in a first direction from one end of the fragment to the opposite end of the fragment. The sequenced fragment may be read until a specified read length is reached. Then, the sequenced fragment is read in a second direction, which is opposite to the first direction. In certain embodiments, having multiple read pairs may help to improve read alignment and/or identify mutations (e.g., insertions, deletions, inversion, etc.) that may not be detected by single-end reading.

Another method, that can be used for methylation detection includes PCR amplification with methylation-specific oligonucleotide primers (MSP methods), e.g., as applied to bisulfite-treated sample (see, e.g., Herman 1992 Proc. Natl. Acad. Sci. USA 93: 9821-9826, which is herein incorporated by reference with respect to methods of determining methylation status). Use of methylation-status-specific oligonucleotide primers for amplification of bisulfite-treated DNA allows differentiation between methylated and unmethylated nucleic acids. Oligonucleotide primer pairs for use in MSP methods include at least one oligonucleotide primer capable of hybridizing with sequence that includes a methylation site, e.g., a CpG site. An oligonucleotide primer that includes a T residue at a position complementary to a cytosine residue will selectively hybridize to templates in which the cytosine was unmethylated prior to bisulfite treatment, while an oligonucleotide primer that includes a G residue at a position complementary to a cytosine residue will selectively hybridize to templates in which the cytosine was methylated cytosine prior to bisulfite treatment. MSP results can be obtained with or without sequencing amplicons, e.g., using gel electrophoresis. MSP (methylation-specific PCR) allows for highly sensitive detection (detection level of 0.1% of the alleles, with full specificity) of locus-specific DNA methylation, using PCR amplification of bisulfite-converted DNA.

Another method that can be used to determine methylation status after bisulfite treatment of a sample is Methylation-Sensitive High Resolution Melting (MS-HRM) PCR (see, e.g., Hussmann 2018 Methods Mol Biol. 1708:551-571, which is herein incorporated by reference with respect to methods of determining methylation status). MS-HRM is an in-tube, PCR-based method to detect methylation levels at specific loci of interest based on hybridization melting. Bisulfite treatment of the DNA prior to performing MS-HRM ensures a different base composition between methylated and unmethylated DNA, which is used to separate the resulting amplicons by high resolution melting. A unique primer design facilitates a high sensitivity of the assays enabling detection of down to 0.1-1% methylated alleles in an unmethylated background. Oligonucleotide primers for MS-HRM assays are designed to be complementary to the methylated allele, and a specific annealing temperature enables these primers to anneal both to the methylated and the unmethylated alleles thereby increasing the sensitivity of the assays.

Another method that can be used to determine methylation status after bisulfite treatment of a sample is Quantitative Multiplex Methylation-Specific PCR (QM-MSP). QM-MSP uses methylation specific primers for sensitive quantification of DNA methylation (see, e.g., Fackler 2018 Methods Mol Biol. 1708:473-496, which is herein incorporated by reference with respect to methods of determining methylation status). QM-MSP is a two-step PCR approach, where in the first step, one pair of gene-specific primers (forward and reverse) amplifies the methylated and unmethylated copies of the same gene simultaneously and in multiplex, in one PCR reaction. This methylation-independent amplification step produces amplicons of up to $10^9$ copies per μL after 36 cycles of PCR. In the second step, the amplicons of the first reaction are quantified with a standard curve using real-time PCR and two independent fluorophores to detect methylated/unmethylated DNA of each gene in the same well (e.g., 6FAM and VIC). One methylated copy is detectable in 100,000 reference gene copies.

Another method that can be used to determine methylation status after bisulfite treatment of a sample is Methylation Specific Nuclease-assisted Minor-allele Enrichment (MS-NaME) (see, e.g., Liu 2017 Nucleic Acids Res. 45(6): e39, which is herein incorporated by reference with respect to methods of determining methylation status). Ms-NaME is based on selective hybridization of probes to target sequences in the presence of DNA nuclease specific to double-stranded (ds) DNA (DSN), such that hybridization results in regions of double-stranded DNA that are subsequently digested by the DSN. Thus, oligonucleotide probes targeting unmethylated sequences generate local double stranded regions resulting to digestion of unmethylated targets; oligonucleotide probes capable of hybridizing to methylated sequences generate local double-stranded regions that result in digestion of methylated targets, leaving methylated targets intact. Moreover, oligonucleotide probes can direct DSN activity to multiple targets in bisulfite-treated DNA, simultaneously. Subsequent amplification can enrich non-digested sequences. Ms-NaME can be used, either independently or in combination with other techniques provided herein.

Another method that can be used to determine methylation status after bisulfite treatment of a sample is Methylation-sensitive Single Nucleotide Primer Extension (Ms-SNuPE™) (see, e.g., Gonzalgo 2007 Nat Protoc. 2(8):1931-6, which is herein incorporated by reference with respect to methods of determining methylation status). In Ms-SNuPE, strand-specific PCR is performed to generate a DNA template for quantitative methylation analysis using Ms-SNuPE. SNuPE is then performed with oligonucleotide(s) designed to hybridize immediately upstream of the CpG site(s) being interrogated. Reaction products can be electrophoresed on polyacrylamide gels for visualization and quantitation by phosphor-image analysis. Amplicons can also carry a directly or indirectly detectable labels such as a fluorescent label, radionuclide, or a detachable molecule fragment or other entity having a mass that can be distinguished by mass spectrometry. Detection may be carried out and/or visualized by means of, e.g., matrix assisted laser desorption/ionization mass spectrometry (MALDI) or using electron spray mass spectrometry (ESI).

Certain methods that can be used to determine methylation status after bisulfite treatment of a sample utilize a first oligonucleotide primer, a second oligonucleotide primer, and an oligonucleotide probe in an amplification-based method. For instance, the oligonucleotide primers and probe can be used in a method of real-time polymerase chain reaction (PCR) or droplet digital PCR (ddPCR). In various instances, the first oligonucleotide primer, the second oligonucleotide primer, and/or the oligonucleotide probe selectively hybridize methylated DNA and/or unmethylated DNA, such that amplification or probe signal indicate methylation status of a sample.

Other bisulfite-based methods for detecting methylation status (e.g., the presence of level of 5-methylcytosine) are disclosed, e.g., in Frommer (1992 Proc Natl Acad Sci USA. 1; 89(5):1827-31, which is herein incorporated by reference with respect to methods of determining methylation status).

In certain MSRE-qPCR embodiments, the amount of total DNA is measured in an aliquot of sample in native (e.g., undigested) form using, e.g., real-time PCR or digital PCR.

Various amplification technologies can be used alone or in conjunction with other techniques described herein for detection of methylation status. Those of skill in the art, having reviewed the present specification, will understand how to combine various amplification technologies known in the art and/or described herein together with various other technologies for methylation status determination known in the art and/or provided herein. Amplification technologies include, without limitation, PCR, e.g., quantitative PCR (qPCR), real-time PCR, and/or digital PCR. Those of skill in the art will appreciate that polymerase amplification can multiplex amplification of multiple targets in a single reaction. PCR amplicons are typically 100 to 2000 base pairs in length. In various instances, an amplification technology is sufficient to determine methylations status.

Digital PCR (dPCR) based methods involve dividing and distributing a sample across wells of a plate with 96-, 384-, or more wells, or in individual emulsion droplets (ddPCR) e.g., using a microfluidic device, such that some wells include one or more copies of template and others include no copies of template. Thus, the average number of template molecules per well is less than one prior to amplification. The number of wells in which amplification of template occurs provides a measure of template concentration. If the sample has been contacted with MSRE, the number of wells in which amplification of template occurs provides a measure of the concentration of methylated template.

In various embodiments a fluorescence-based real-time PCR assay, such as MethyLight™, can be used to measure methylation status (see, e.g., Campan 2018 Methods Mol Biol. 1708:497-513, which is herein incorporated by reference with respect to methods of determining methylation status). MethyLight is a quantitative, fluorescence-based, real-time PCR method to sensitively detect and quantify DNA methylation of candidate regions of the genome. MethyLight is uniquely suited for detecting low-frequency methylated DNA regions against a high background of unmethylated DNA, as it combines methylation-specific priming with methylation-specific fluorescent probing. Additionally, MethyLight can be combined with Digital PCR, for the highly sensitive detection of individual methylated molecules, with use in disease detection and screening.

Real-time PCR-based methods for use in determining methylation status typically include a step of generating a standard curve for unmethylated DNA based on analysis of external standards. A standard curve can be constructed from at least two points and can permit comparison of a real-time Ct value for digested DNA and/or a real-time Ct value for undigested DNA to known quantitative standards. In particular instances, sample Ct values can be determined for MSRE-digested and/or undigested samples or sample aliquots, and the genomic equivalents of DNA can be calculated from the standard curve. Ct values of MSRE-digested and undigested DNA can be evaluated to identify amplicons digested (e.g., efficiently digested; e.g., yielding a Ct value of 45). Amplicons not amplified under either digested or undigested conditions can also be identified. Corrected Ct values for amplicons of interest can then be directly compared across conditions to establish relative differences in methylation status between conditions. Alternatively or additionally, delta-difference between the Ct values of digested and undigested DNA can be used to establish relative differences in methylation status between conditions.

In certain particular embodiments, targeted bisulfite sequencing (e.g., using hybrid capture) among other techniques, can be used to determine the methylation status of a methylation biomarker for a disease and/or condition. For example, a colorectal neoplasm (e.g., advanced adenoma and/or colorectal cancer) methylation biomarker that is or includes a single methylation locus. In certain particular embodiments, targeted bisulfite sequencing, among other techniques, can be used to determine the methylation status of a methylation biomarker that is or includes two or more methylation loci.

Those of skill in the art will appreciate that in embodiments in which a plurality of methylation loci (e.g., a plurality of DMRs) are analyzed for methylation status in a method of screening for colorectal cancer provided herein, methylation status of each methylation locus can be measured or represented in any of a variety of forms, and the methylation statuses of a plurality of methylation loci (preferably each measured and/or represented in a same, similar, or comparable manner) be together or cumulatively analyzed or represented in any of a variety of forms. In various embodiments, methylation status of each methylation locus can be measured as methylation portion. In various embodiments, methylation status of each methylation locus can be represented as the percentage value of methylated reads from total sequencing reads compared against reference sample. In various embodiments, methylation status of each methylation locus can be represented as a qualitative comparison to a reference, e.g., by identification of each methylation locus as hypermethylated or hypomethylated.

In some embodiments in which a single methylation locus is analyzed, hypermethylation of the single methylation locus constitutes a diagnosis that a subject is suffering from or possibly suffering from a condition (e.g., cancer) (e.g., advanced adenoma, colorectal cancer), while absence of hypermethylation of the single methylation locus constitutes a diagnosis that the subject is likely not suffering from a condition. In some embodiments, hypermethylation of a single methylation locus (e.g., a single DMR) of a plurality of analyzed methylation loci constitutes a diagnosis that a subject is suffering from or possibly suffering from the condition, while the absence of hypermethylation at any methylation locus of a plurality of analyzed methylation loci constitutes a diagnosis that a subject is likely not suffering from the condition. In some embodiments, hypermethylation of a determined percentage (e.g., a predetermined percentage) of methylation loci (e.g., at least 10% (e.g., at least 10%, at least 20%, at least 30%, at least 40%, at least 50%, at least 60%, at least 70%, at least 80%, at least 90%, or 100%)) of a plurality of analyzed methylation loci constitutes a diagnosis that a subject is suffering from or possibly suffering from the condition, while the absence of hypermethylation of a determined percentage (e.g., a predetermined percentage) of methylation loci (e.g., at least 10% (e.g., at least 10%, at least 20%, at least 30%, at least 40%, at least 50%, at least 60%, at least 70%, at least 80%, at least 90%, or 100%)) of a plurality of analyzed methylation loci constitutes a diagnosis that a subject is not likely suffering from the condition. In some embodiments, hypermethylation of a determined number (e.g., a predetermined number) of methylation loci (e.g., at least 1, 2, 3, 4, 5, 6, 7, 8, 9, 10, 11, 12, 13, 14, 15, 16, 17, 18, 19, 20, 21, 22, 23, 24, 25, 26, 50, 100, 150, or more DMRs) of a plurality of analyzed methylation loci (e.g. 2, 3, 4, 5, 6, 7, 8, 9, 10, 11, 12, 13, 14, 15, 16, 17, 18, 19, 20, 21, 22, 23, 24, 25, 26, 50, 100, 150, or more DMRs) constitutes a diagnosis that a subject is suffering from or possibly suffering from the condition, while the absence of hypermethylation of a determined number (e.g., a predetermined number) of methylation loci (e.g., at least 1, 2, 3, 4, 5, 6, 7, 8, 9, 10, 11, 12, 13, 14, 15, 16, 17, 18, 19, 20, 21, 22, 23, 24, 25, 26, 50, 100, 150, or more DMRs) of a plurality of analyzed methylation loci (e.g., 2, 3, 4, 5, 6, 7, 8, 9, 10, 11, 12, 13, 14, 15, 16, 17, 18, 19, 20, 21, 22, 23, 24, 25, 26, 50, 100, 150, or more DMRs) constitutes a diagnosis that a subject is not likely suffering from the condition.

In some embodiments, methylation status of a plurality of methylation loci (e.g., a plurality of DMRs) is measured qualitatively or quantitatively and the measurement for each of the plurality of methylation loci are combined to provide a diagnosis. In some embodiments, the quantitatively measured methylation status of each of a plurality of methylation loci is individually weighted, and weighted values are combined to provide a single value that can be comparative to a reference in order to provide a diagnosis.

In some embodiments, methylation status may include determination of methylated and/or unmethylated reads mapped to a genomic region (e.g., a DMR). For example, when using particular sequencing technologies as disclosed herein (e.g., NGS, whole genome bisulfite sequencing, etc.), sequence reads are produced. A sequence read is an inferred sequence of base pairs (e.g., a probabilistic sequence) corresponding to all or part of a sequenced oligonucleotide (e.g., DNA) fragment (e.g., cfDNA fragments, gDNA fragments). In certain embodiments, sequence reads may be mapped (e.g., aligned) to a particular region of interest using a reference sequence (e.g., a bisulfite converted reference sequence) in order to determine if there are any alterations or variations in a read. Alterations may include methylation and/or mutations. A region of interest may include one or more genomic markers including a methylation marker (e.g., a DMR), a mutation marker, or other marker as disclosed herein.

For example, in the case of bisulfite or enzymatically treated DNA fragments, treatment converts unmethylated cytosines to uracils, while methylated cytosines are not converted to uracils. Accordingly, a sequence read produced for a DNA fragment that has methylated cytosines will be different from a sequence read produced for the same DNA fragment that does not have methylated cytosine. Methylation at sites where a cytosine nucleotide is followed by a guanine nucleotide (e.g., CpG sites) may be of particular interest.

Quality Control Protocol

In certain embodiments, quality control steps may be implemented. Quality control steps are used to determine whether or not particular steps or processes were conducted within particular parameters. In certain embodiments, quality control steps may be used to determine the validity of results of a given analysis. In addition or alternatively, quality control steps may be used to determine sequenced data quality. For example, quality control steps may be used to determine read coverage of one or more regions of DNA. Quantitative metrics for quality control include, but are not limited to AT dropout rate, GC dropout rate, bisulfite conversion rate (e.g., bisulfite conversion efficiency), and the like. Failure to meet a threshold quality control condition (e.g., a minimum conversion rate, a maximum CG dropout rate, etc.) may indicate, for example, that one or more of the conversion steps were not performed within appropriate parameters.

For example, in the methods described herein, various steps of a conversion protocol may be optimized to decrease AT and/or GC dropout rate. As is understood by those of skill in the art, AT and GC dropout metrics indicate the degree of inadequate coverage of a particular target region based on its AT or GC content. In certain embodiments, samples having a low GC dropout rate is useful in identifying which samples were processed appropriately. For example, a GC dropout rate found to be less than 10%, less than 9%, less than 8%, less than 7%, less than 6%, less than 5%, less than 4%, or less may be useful in identifying appropriately processed samples.

In certain embodiments, a quality control step may involve determining an on and/or off-target ratio. Sequence reads that align to a region of interest (e.g., a DMR) are considered to be on-target, while sequence reads that do not align to the region of interest (e.g., a DMR) are considered to be off-target. In certain embodiments, the on-target ratio is represented as a percentage of on-target bases to the total number of aligned bases. In certain embodiments, the on-target ratio is represented as a percentage of on-target and near-target bases to the total number of aligned bases. Near-target bases may be a base within a certain number of bases (e.g., within 500 bp, within 200 bp, within 100 bp) of the target region. In certain embodiments, the on-target ratio is at least 10%, least 20%, least 30%, least 40%, least 50%, least 60%, least 70%, at least 80%, at least 90%, at least 95%, at least 99% or more for a sequencing experiment to pass quality control. In certain embodiments, the off-target ratio is represented as a percentage of off-target bases to the total number of aligned bases. In certain embodiments, an off-target ratio is less than 95%, less than 90%, less than 85%, less than 80%, less than 70%, less than 60%, less than 50%, less than 40%, less than 30%, less than 20%, less than 10%, less than 1% for a sequencing experiment to pass quality control.

In certain embodiments, a quality control step may include determining quality scores for mapped sequence reads. A quality score is a value which quantifies a probability that a sequence read is incorrectly mapped. For example, when mapping short or repetitive sequences, it is possible that a sequence will be mapped to multiple places in a reference genome. The quality score considers the best alignment of the sequence read to the reference genome as compared to other possible alignments of the sequence read to the reference genome. In certain embodiments, the quality score is a Mapping Quality (MAPQ) score. The MAPQ is the negative, log-scaled probability that a read is misaligned. A high score indicates a high confidence that a read is aligned correctly, while a low score indicates a low confidence that a read is aligned correctly. In certain embodiments, the MAPQ score may be calculated using the following equation:

$$\text{MAPQ score} = -10 \log_{10} \Pr\{\text{mapping position is wrong}\}.$$

In certain embodiments, the MAPQ score is rounded to the nearest integer. In certain embodiments Pr is a probability that the sequence read is incorrectly mapped as obtained from an alignment (e.g., mapping) tool. In certain embodiments, the scaling factor is 1 (instead of 10), or another number.

Artificial Spike-In Control

Control nucleic acid (e.g., DNA) molecules (e.g., "spike-in controls") may be used to evaluate or estimate conversion efficiency of unmethylated and methylated cytosines to uracils. Control nucleic acid molecules may be used in sequencing methods involving conversion (e.g., bisulfite or enzymatic conversion) of DNA samples.

When DNA is subjected to conversion (e.g., bisulfite or enzymatic conversion) as described herein, conversion may be incomplete. That is, some number of unmethylated cytosines may not be converted to uracils. If the conversion is not complete such that unmethylated cytosines are not mostly converted, the unconverted unmethylated cytosines may be identified as methylated when the DNA sequenced. Accordingly, in order to determine whether or not bisulfite conversion is complete, a control DNA molecule may be subjected to conversion along with DNA fragments from a sample. In certain embodiments, sequencing the converted control DNA molecules (e.g., using an NGS technique as described herein) generates a plurality of control sequence reads. Control sequence reads may be used to determine conversion rates of unmethylated and/or methylated cytosines to uracils.

Prior techniques did not recognize that controls (e.g., a control DNA molecule) were useful to include in each sample. Rather, they presumed that conversion efficiencies remained relatively consistent between samples for a given run. However, it is found that the conversion rate of unmethylated cytosines to uracils in DNA fragments may vary significantly from one sample to another. For example, conversion efficiency may range from 10% to 110% within a single batch of processed samples. Note, there can be overconversion such that conversion efficiency can be greater than 100%, e.g., the conversion efficiency is 110% when 10% of the methylated cytosine gets converted. In certain embodiments, the conversion efficiency ranges from 30% to 110%. In other embodiments, the conversion efficiency ranges from 50% to 100%.

In certain embodiments, a control DNA molecule may be added to a sample after fragmentation and before conversion using e.g., bisulfite or enzymatic reagents. In certain embodiments, a plurality (e.g., two, three, four or more) control DNA sequences may be added to DNA fragments of a sample. A control DNA molecule may be a known sequence. For example, the sequence, number of methylated bases, and number of unmethylated bases of the control sequence had been determined prior to addition of the control DNA molecule to the sample. In certain embodiments, a control sequence may be a DNA sequence which is produced in vitro to contain artificially methylated or unmethylated nucleotides (e.g., methylated cytosines). In certain embodiments, a control sequence may be a DNA sequence which is produced to contain completely unmethylated DNA nucleotides.

A high conversion efficiency of the spike-in control sequence may be used to infer the conversion efficiency of a DNA fragments undergoing the same conversion process as a spike-in control. For example, deamination of at least at least 98% of unmethylated cytosines in the unmethylated spike-in control DNA sequence indicates that conversion efficiency is high and that a sample may pass a quality control assessment. In certain embodiments, at least 90%, at least 95%, at least 96%, at least 97%, at least 98%, at least 99% of unmethylated cytosines of a plurality of DNA fragments of a control DNA sequence are converted into uracils. A high conversion efficiency is important as it is ideal for all (or nearly all) of the unmethylated cytosines to be converted to uracils when subjecting DNA to bisulfite or enzymatic treatments. As described above, unconverted, unmethylated cytosines may serve as a source of noise in the data.

In addition, conversion of methylated cytosines to uracils is undesirable when DNA is treated using a conversion process. Conversion of methylated cytosines of a spike-in control is indicative that methylated cytosines have been converted to uracils in a DNA sample subjected to the same treatment as the methylated spike-in control. Methylated cytosines in a methylated spike-in control should not convert to uracils. For the same reasons as described above, methylated cytosines being converted to uracils may result in misidentification of purportedly unmethylated cytosines during methylation analysis. In certain embodiments, at most 5%, at most 4%, at most 3%, at most 2% or at most 1% of methylated cytosines of a plurality of DNA fragments of a control DNA sequence are converted into uracils. For example, deamination of at most 2% of methylated cytosines in a methylated spike-in control DNA sequence indicates that conversion efficiency is high and that a sample may pass a quality control assessment.

Applications

Methods and compositions of the present disclosure can be used in any of a variety of applications. For example, methods and compositions of the present disclosure can be used to screen, or aid in screening for a condition (e.g., colorectal cancer). In various instances, screening using methods and compositions of the present disclosure can detect any stage of colorectal cancer, including without limitation early-stage colorectal cancer. In some embodiments, screening using methods and compositions of the present disclosure is applied to individuals 40 years of age or older, e.g., 40, 45, 50, 55, 60, 65, 70, 75, 80, 85, or 90 years or older. In particular, individuals 40 years of age or older are of interest for colorectal cancer screening. In some embodiments, screening using methods and compositions of the present disclosure is applied to individuals 18 years of age or older, e.g., 18, 20, 25, 30, 35, 40, 45, 50, 55, 60, 65, 70, 75, 80, 85, or 90 years or older. In some embodiments, screening using methods and compositions of the present disclosure is applied to individuals 18 to 40 years of age. In various embodiments, screening using methods and compositions of the present disclosure is applied to individuals experiencing abdominal pain or discomfort, e.g., experiencing undiagnosed or incompletely diagnosed abdominal pain or discomfort. In various embodiments, screening using methods and compositions of the present disclosure is applied to individuals experiencing no symptoms likely to be associated with a cancer. Thus, in certain embodiments, screening using methods and compositions of the present disclosure is fully or partially preventative or prophylactic, at least with respect to later or non-early stages of cancer.

In various embodiments, cancer screening using methods and compositions of the present disclosure can be applied to an asymptomatic human subject. In particular, a subject can be referred to as "asymptomatic" if the subject does not report, and/or demonstrate by non-invasively observable indicia (e.g., without one, several, or all of device-based probing, tissue sample analysis, bodily fluid analysis, surgery, or cancer screening), sufficient characteristics of the condition to support a medically reasonable suspicion that the subject is likely suffering from the condition.

Those of skill in the art will appreciate that regular, preventative, and/or prophylactic screening for colorectal cancer improves diagnosis. Generally, and particularly in embodiments in which screening in accordance with the present disclosure is carried out annually, and/or in which a subject is asymptomatic at time of screening, methods and compositions of the present invention are especially likely to detect early stage colorectal cancer.

In various embodiments, colorectal cancer screening in accordance with the present disclosure is performed once for a given subject or multiple times for a given subject. In various embodiments, colorectal cancer screening in accordance with the present disclosure is performed on a regular basis, e.g., every six months, annually, every two years, every three years, every four years, every five years, or every ten years.

In various embodiments, screening using methods and compositions disclosed herein will provide a diagnosis of a condition (e.g., a class of colorectal cancer). Colorectal cancer sub-categorization on a molecular level could help with better pre-treatment stratification of the patients and could help to direct the treatment regiments, which in return could lead to better outcomes. This has been shown to be the case for other cancer types such as breast cancer. Traditionally, molecular subtyping has been done on whole-genome sequencing and copy number variation identification, based on patterns of chromosomal structural variation with potential clinical utility. DNA methylation gives another layer for sub-categorization to the patients by providing cell-of-origin type of signature, that could identify different cellular origin of the cancer. In other instances, screening for colorectal neoplasms using methods and compositions disclosed herein will be indicative of having one or more conditions, but not definitive for diagnosis of a particular condition. For example, screening may be used to classify a subject as having one or more conditions or combination of conditions including, but not limited to, advanced adenoma and/or colorectal cancer. In various instances, screening using methods and compositions of the present disclosure can be followed by a further diagnosis-confirmatory assay, which further assay can confirm, support, undermine, or reject a diagnosis resulting from prior screening, e.g., screening in accordance with the present disclosure.

In various embodiments, screening in accordance with methods and compositions of the present disclosure reduces colorectal cancer mortality, e.g., by early colorectal cancer diagnosis. Data supports that colorectal cancer screening reduces colorectal cancer mortality, which effect persisted for over 30 years (see, e.g., Shaukat 2013 N Engl J Med. 369(12):1106-14). Moreover, colorectal cancer is particularly difficult to treat at least in part because colorectal cancer, absent timely screening, may not be detected until cancer is past early stages. For at least this reason, treatment of colorectal cancer is often unsuccessful. To maximize population-wide improvement of colorectal cancer outcomes, utilization of screening in accordance with the present disclosure can be paired with, e.g., recruitment of eligible subjects to ensure widespread screening.

In various embodiments, screening of colorectal neoplasms including one or more methods and/or compositions disclosed herein is followed by treatment of colorectal cancer, e.g., treatment of early stage colorectal cancer. In various embodiments, treatment of colorectal cancer, e.g., early stage colorectal cancer, includes administration of a therapeutic regimen including one or more of surgery, radiation therapy, and chemotherapy. In various embodiments, treatment of colorectal cancer, e.g., early stage colorectal cancer, includes administration of a therapeutic regimen including one or more of treatments provided herein for treatment of stage 0 colorectal cancer, stage I colorectal cancer, and/or stage II colorectal cancer.

In various embodiments, treatment of colorectal cancer includes treatment of early stage colorectal cancer, e.g., stage 0 colorectal cancer or stage I colorectal cancer, by one or more of surgical removal of cancerous tissue e.g., by local excision (e.g., by colonoscope), partial colectomy, or complete colectomy.

In various embodiments, treatment of colorectal cancer includes treatment of early stage colorectal cancer, e.g., stage II colorectal cancer, by one or more of surgical removal of cancerous tissue (e.g., by local excision (e.g., by colonoscope), partial colectomy, or complete colectomy), surgery to remove lymph nodes near to identified colorectal cancer tissue, and chemotherapy (e.g., administration of one or more of 5-FU and leucovorin, oxaliplatin, or capecitabine).

In various embodiments, treatment of colorectal cancer includes treatment of stage III colorectal cancer, by one or more of surgical removal of cancerous tissue (e.g., by local excision (e.g., by colonoscopy-based excision), partial colectomy, or complete colectomy), surgical removal of lymph nodes near to identified colorectal cancer tissue, chemotherapy (e.g., administration of one or more of 5-FU, leucovorin, oxaliplatin, capecitabine, e.g., in a combination of (i) 5-FU and leucovorin, (ii) 5-FU, leucovorin, and oxaliplatin (e.g., FOLFOX), or (iii) capecitabine and oxaliplatin (e.g., CAPEOX)), and radiation therapy.

In various embodiments, treatment of colorectal cancer includes treatment of stage IV colorectal cancer, by one or more of surgical removal of cancerous tissue (e.g., by local excision (e.g., by colonoscope), partial colectomy, or complete colectomy), surgical removal of lymph nodes near to identified colorectal cancer tissue, surgical removal of metastases, chemotherapy (e.g., administration of one or more of 5-FU, leucovorin, oxaliplatin, capecitabine, irinotecan, VEGF-targeted therapeutic agent (e.g., bevacizumab, ziv-aflibercept, or ramucirumab), EGFR-targeted therapeutic agent (e.g., cetuximab or panitumumab), Regorafenib, trifluridine, and tipiracil, e.g., in a combination of or including (i) 5-FU and leucovorin, (ii) 5-FU, leucovorin, and oxaliplatin (e.g., FOLFOX), (iii) capecitabine and oxaliplatin (e.g., CAPEOX), (iv) leucovorin, 5-FU, oxaliplatin, and irinotecan (FOLFOXIRI), and (v) trifluridine and tipiracil (Lonsurf)), radiation therapy, hepatic artery infusion (e.g., if cancer has metastasized to liver), ablation of tumors, embolization of tumors, colon stent, colorectomy, colostomy (e.g., diverting colostomy), and immunotherapy (e.g., pembrolizumab).

Those of skill in the art that treatments of colorectal cancer provided herein can be utilized, e.g., as determined by a medical practitioner, alone or in any combination, in any order, regimen, and/or therapeutic program. Those of skill in the art will further appreciate that advanced treatment options may be appropriate for earlier stage cancers in subjects previously having suffered a cancer or colorectal cancer, e.g., subjects diagnosed as having a recurrent colorectal cancer.

In some embodiments, methods and compositions for colorectal neoplasm screening provided herein can inform treatment and/or payment (e.g., reimbursement for or reduction of cost of medical care, such as screening or treatment) decisions and/or actions, e.g., by individuals, healthcare facilities, healthcare practitioners, health insurance providers, governmental bodies, or other parties interested in healthcare cost.

In some embodiments, methods and compositions for colorectal neoplasm screening provided herein can inform decision making relating to whether health insurance providers reimburse a healthcare cost payer or recipient (or not), e.g., for (1) screening itself (e.g., reimbursement for screening otherwise unavailable, available only for periodic/regular screening, or available only for temporally- and/or incidentally-motivated screening); and/or for (2) treatment, including initiating, maintaining, and/or altering therapy, e.g., based on screening results. For example, in some embodiments, methods and compositions for colorectal neoplasm screening provided herein are used as the basis for, to contribute to, or support a determination as to whether a reimbursement or cost reduction will be provided to a healthcare cost payer or recipient. In some instances, a party seeking reimbursement or cost reduction can provide results of a screen conducted in accordance with the present specification together with a request for such reimbursement or cost reduction of a healthcare cost. In some instances, a party making a determination as to whether or not to provide a reimbursement or cost reduction of a healthcare cost will reach a determination based in whole or in part upon receipt and/or review of results of a screen conducted in accordance with the present specification.

For the avoidance of any doubt, those of skill in the art will appreciate from the present disclosure that methods and compositions for colorectal cancer diagnosis of the present specification are at least for in vitro use. Accordingly, all aspects and embodiments of the present disclosure can be performed and/or used at least in vitro.

Kits

The present disclosure includes, among other things, kits including one or more compositions for use in screening as provided herein, optionally in combination with instructions for use thereof in screening (e.g., screening for colorectal cancer and/or other diseases or conditions associated with an aberrant methylation status, e.g., neurodegenerative diseases, gastrointestinal disorders, and the like). In various embodiments, a kit for screening a diseases or conditions associated with an aberrant methylation status can include one or more oligonucleotide probes (e.g., one or more biotinylated oligonucleotide probes). In certain embodiments, the kit for screening optionally includes one or more bisulfite conversion reagents as disclosed herein. In certain embodiments, the kit for screening optionally includes one or more enzymatic conversion reagents as disclosed herein. In certain embodiments, the kit for screening may include one or more adapters as described herein. In certain embodiments, the kit may include one or more reagents used in library preparation. In certain embodiments, the kit may include software (e.g., for analyzing methylation status of DMRs).

Elements of different implementations described herein may be combined to form other implementations not specifically set forth above. Elements may be left out of the processes, computer programs, databases, etc. described herein without adversely affecting their operation. In addition, the logic flows depicted in the figures do not require the particular order shown, or sequential order, to achieve desirable results. Various separate elements may be combined into one or more individual elements to perform the functions described herein.

Throughout the description, where apparatus and systems are described as having, including, or comprising specific components, or where processes and methods are described as having, including, or comprising specific steps, it is contemplated that, additionally, there are apparatus, and systems of the present invention that consist essentially of, or consist of, the recited components, and that there are processes and methods according to the present invention that consist essentially of, or consist of, the recited processing steps.

It should be understood that the order of steps or order for performing certain action is immaterial so long as the invention remains operable. Moreover, two or more steps or actions may be conducted simultaneously.

While the invention has been particularly shown and described with reference to specific preferred embodiments, it should be understood by those skilled in the art that various changes in form and detail may be made therein without departing from the spirit and scope of the invention as defined by the appended claims.

OTHER EMBODIMENTS

While we have described a number of embodiments, it is apparent that our basic disclosure and examples may provide other embodiments that utilize or are encompassed by the compositions and methods described herein. Therefore, it will be appreciated that the scope of is to be defined by that which may be understood from the disclosure and the appended claims rather than by the specific embodiments that have been represented by way of example.

All references cited herein are hereby incorporated by reference.

---

SEQUENCES

```
12:15322092-15323246 (SEQ ID NO.: 1)
TCTACAGTCACAACTACCCAACTGTTATTGATCCTTTATAACTGCAATTGAGT
ACAGATGTAGGAAGATTGAGAGGGAACTGGGATCTGGCGCCTGGATTGCTCAAGAG
AGGTCAGGGAAACCCCTCAGAACTCCTGAGACCCAGAGATTGAGGGAGGGGTTGAG
GCGGAGTCTGCAATGGGGGCTGTCCAGCAGTAGCAAGCAGCGGGCCGATCCTGGTG
GAGGGTTGGGAGGCTGCTGTCATTTTATGGGTCGGCAGCCAGAGTGAGAGTGTCCCT
GCTGCCAGAGGACTACGGCGGGCTGGGCGCGGGGTCCCCGCCTCTCGCTCACCACA
CAGACCCCGCGCCTCCTCTGGCAGCCGCGGTGGTGGCGGCGGCAGAGCCTCGCCCA
CTCCAATCCCCACCCTCTCCATCCTTAGTCATTAAAGAACAGCAGCGCCTGGCACGT
TCTTGGAGGACCCCGGGCGCAGAGGAGGAAAGGGAGCAGGCGCAGGGGGACTGGA
AAGGCAGCATGCGCTCGCCAGGAGCAACCTCGGCGCCCAGGGTCTGAGGCTGCAGC
CCCAGTTCGCCATTGTGAGCCGCCGCCGGGGGAGTCCGCTAGCGCAGCCGTGCCCCC
GAGTCCCCGTCCGCGCAGCGATGGGGCACCTGCCCACGGGGATACACGGCGCCCGC
CGCCTCCTGCCTCTGCTCTGGCTCTTTGTGCTGTTCAAGGTAGGGGAGCTCCTCCACC
CCTTTTTCCCAGCGGTCCGGGCGGCAGCCGCGCTCCGGCGCCCTCGCTCTGCCGTTG
GGAGCGGCGCGCCCCAGGGCACGATGGCCCAGCCGCGGGAAGCGCCTGCCGTGCAG
CCTGGGCGCACGCTTTGTTGTCCTCGCGTGTGCGTGTTCCTGGTGGTCTTGAGAGGTA
GGGGGGGGGGGGAAGAATAAGGGAAGTTTGCTCCCTCCGGCTTTCGCCCTTTGTGCT
CTTTTATCGCTGCTGAAATCCACATCAAAGGTGGGCTTGTTGGATCGTGCTTTCTCAG
GCAAAATGAGGTCACTTTCTTTTCTGGTTTCCACTGCACCCCAACGCTGCTTAACCTT
TCCGCCCTCCCTCGCACAGAATGCTTTGTCTTAATTTTCCTTACTGCTGGAATTATAC
ACTGGAGAGTGGAGGGGGACTGAG

7:35185896-35187104 (SEQ ID NO.: 2)
CTCCTGGCGCCCCCTGGCAGTTTCCCGCCGCCTAGGGCCGACTTTTCCACCTC
CAGCTCCCGGGCGGGGGAGGCCCCGTACGGCCGCTTAGACGGGCTGGGGCGGGAAG
ATTGCAGCGGCTTTGGGTTTACTCCTTGTTTCTTCATAATCCCTAGTGGAGCTGGGTC
AATTTCAGGCACAGCCCATCCGAGTCAGGCGAGGTCCAGAAAGGCCTGACTCGCCT
GGCAGCCTCAACGGACTTGTCCCCGCAGCCGTTGACTAGCCGTTGACGAGCGGACCT
CCCGGTCGTCATGGCGACTGTGAAATGTAGGGTGGAGCGCATGCGTTCGAAGCCATT
CGCGCGGGCAGTCCCTGCGTGTCCCCCTGCGTGTCCCCCCACGTGCTCCCCAGCGCG
CGCAGCACCCCGCCTCTGCGCTTCCCCGAGCGTGCAGCTTCCGGTGAGGGCAGCCCC
ACGCACAGCCCCCAACACCCTCCCCAGCGCCTGCAGCCTTCGGTGCGCGCAGTCCCC
AAGCCCACATGCGCAGTTCTCACCTTGCGCGCAGCCCCACGTACAGCCCCCAACACG
CTCCCAGCCCCACTGGCGCAGAACCCATCACCGCTTGCCCTTCACGCGCTTCATTGG
GAGTGCAGCTCCCACCCCGAGCGCGCAGCTCCACGCAGCCTCTCCACACTCTCCCCA
GCGCTTGCAGCACCCCCCAGTGCGCACAGCTCTGCCAGTAGCTTCCCGGCGCGCCGC
CCCTGCACCGCTTCGGGCCATAACCTTGCTGGCGACTAAGTCTGAAGAACTTCCTGT
GGTTTCATTCTTTTCTTCAGGTTTAGTCTTAGCTCTGACATTTTAACCAAAAGGTTAC
ACGTTAATTAACGAGGTATTAAAGGGGAAGATCTCAGCTGAAAGAAATGACTGTAG
GAAGTGTGTCAGGGAAGCCAACGGAACCGCTGGCCCGCCGGTGGTGCGCCCGGCAT
TAGGAAAGTCTCTACGATCGCTGAGGTATCGGGCAGTCAGTGCCCGTTGCCAACGCG
GAGGGAACGGGCGGAGACTGCGGGCAACACGTGGCAGAGCCGGCGTGAGTCCGGT
GGGTCTGATCCCAGAGCCTCAGGTTGACGCCACTTCCTTGGCACGGAACAGCGTTTA
CTGAATCTTAGAGCAAAATGCTTTTCCAATGAGGTTCCTCAGAAGTCATCGGCCCTA
GGAGCGGTGTGCTCAAGCGC

13:102392801-102392992 (SEQ ID NO.: 3)
GGACCGCTCACCACTGCTCACTGCTCTTCCTCCCTGGTCTTTCCACCTTCAACC
TTGCCCAACCCAGAGCTGTTTTCCACGCTGTAGTCATAATGGTTGTCTAAAGGGTAG
ATATGATCATGACACAGAAGAGAGCTCACGATCTGTGCCTCACTACCTTGCAACCCC
ACTCACTACCTGCCACTCCCTAGA
```

-continued

---
SEQUENCES
---

1:114152968-114153628 (SEQ ID NO.: 4)
GTGGGGGAAGGACGCCGCAACACCCTCATACCCTCCCCCACCCCGCCCCCTG
TCCCCCGCCCCCCAGCGGAGACGCGGAAAACCACTCGCAGCCGGAGAGACACCCGG
ACACAAAGACCTCGTGCCAGCCGCAGACCCAAGTTTCTCCCGGAGAGACTGGGGGT
CCGCCCGCGTTCACCGCGAGAACACACAAACGGACGGACAGACCGACGCACGGACC
CGGGGACCTCGACACTCGCTAGGAGGCAAGCCCTATTCCTCAGCCGGGCGCCCCTC
GTCTCCCGCTCTCTCCATGGACCCCTCTCCTGGCAAATCGCCCGCAGAGCGAGCTTG
GAGATGCGAGGGAAACTGAAGCCCCAAGGGTGCCCCGTCCTGGGAGCCTGGCTGTC
TGCGGGGTCCCCCGCATTCCGCAGTAGTAATACAGGAGGGCCGGGGGCTTCTACCC
CAACCTCCGCTCCCCTTCGGGTCTCTCCTGGCTGTGCAAGCGATGGGCCAGAGGGCT
GGACGAGGCTGGCTCCCAATCCAGAATCCCGAGCTGGGGAGTTCTCTCTAGGTTCTG
GGGCTCCTGGGACCGGGGCTTTGGGGAAGGGAGATCGCAGGACGGATATCCAGGAA
GGGAGGGGGCCCTGGGTCTCCCGTTACCTGCGCCTGCCGCGCTGGG

1:98053750-98054230 (SEQ ID NO.: 5)
CCACCTTGGATTTCAGATCGAGGAAAGGAAGCCAAAGCAAAGGTGTGGTTAC
ACAGGACATCCATAGACAAATCGTTGCCTCTCTAAGTGGGCCTGAGCTTTGCGGCTC
CAGAAGCGCGAGGCGCGGTTGGTGCGGACGCGGGGGCGTGGGAGTCATCGCTCTCC
CCGCAGCCCTGGCCGAGCTCTCTGCTGTCCTCCCGAGTTTGGGCCAGAGACCACGGC
TCACTCCCTAACGCCCTCGCAAGGACGGCTGCCCGTCGGGCCAAGGGCGCCCCGGG
CTGGAGGCCGGAGCAAGACGGCCCCGCGGGACTCGGGAGCCTTGGTAAGGCGGAG
GCTCAGACCCCGTTCACGAAAACGCCTGGCTCCTCCAGGATTTGTCAGGTCTTAAGC
AGCTCCGAGAAGGCTCCGCTGGCTCTTGGGGAACCCCGCTGTGCGGCTCACCCCCGT
TTGTCTCTCTCAAGCTCTCGCCCTCCTCCCCTGG

10:101134320-101134800 (SEQ ID NO.: 6)
CAAAATGACCGATGCGCAGGTCAAAACCTGGTTCCAGAACCGGCGGACAAA
GTGGAGGTGAGCAAGCGGGGGGGGGCCGGCCGCCCGCGAGCGGCGCGGTCTCAGGC
AGCTCTCGGTTCATTGGCCTCTCGTGGGGCGCACATACTTTTTCCGCTCGCGGTTTCT
GATCCTTTCGGAGGAGCGAGCTCCCGCTAGGCTTGCGGGGAGCTGGAAGCAACCGA
GGCCGATAGCTGGGATGGGGCTGAAGAGCCCTGGCTCTGTTTTACCGGAGGCTTCAG
GGCTTTCTGGTTGGCACACTCTCTGCCGGTGTAGACGCGGCAGGTCTATTCCGCCGC
TTGGGCAAACAGGCGGGTTAGTGCACTCCACGCAGTCCAGGCTCCAGGGATCTGTG
AGTCCTGGGGAGCTTTTTGTTTGCGCAAACTCTTGCTTATGGAATCCTGCTCTGTCCT
GGAGACTGGATGCAGAACAGCCCGCACCTTGTT

10:99329142-99330642 (SEQ ID NO.: 7)
GCTGCATCTCAGATATACCGAAGTGTGTACCCGCTACGCACAGTGCGGTGAT
GCCTGGCCACCTCCAGCCTCCAGCGGGGACCTCCTGCCCAGGTGGAGTCTGAATGCC
CACCGCCACCAGCCCACGCGCGCAGTGGGCGTACACGTGGTGACCTGCCTGCGGCT
GGGTTCCCAGCTCCGGCTCCTCCTCCCTCCAGCTCTCGCTCGGCTTCCTGCAGTATCA
CGTGCAGCTGCGCTGGGTGCAGGATGGCGGCGGCCGCGGCGGCGGCAGCAGCGGTG
GGTGTCAGGCTCCGGGACTGCTGCAGCCGAGGCGCTGTGCTCCTGCTCTTCTTTTCC
CTGTCTCCTCGGCCCCCGGCCGCCGCCGCCTGGCTGCTGGGCCTGCGGCCCGAGGAC
ACTGCTGGAGGCCGCGTGTCCCTGGAGGGGGGGCACCCTGCGCGCCGCCGAAGGCAC
CAGCTTCCTCCTGCGTGTCTATTTCCAGCCAGGACCGCCGGCCACCGCCGCACCGGT
GCCCTCACCGACCCTCAACTCGGGGGAGAATGGCACCGGCGACTGGGCTCCGCGGC
TCGTGTTCATCGAGGAGCCCCCGGGCGGTGGCGGCGTGGCCCCCAGCGCGGTCCCC
ACTCGCCCCCCGGGACCGCAGCGCTGCAGGGAGCAGAGCGACTGGGCATCGGACGT
GGAAGTCCTGGGGCCCTTGCGTCCCGGGGGCGTGGCAGGCTCGGCCCTGGTCCAGG
TGCGAGTGCGGGAGCTGCGCAAGGGCGAAGCGGAGCGGGGCGGCGCGGGCGGTGG
CGGGAAGCTCTTTTCACTCTGCGCCTGGGATGGGCGCGCGTGGCACCACCACGGCGC
CGCCGGCGGCTTCCTGCTGCGCGTTCGCCCGCGGTTGTACGGCCCAGGCGGGGACCT
GCTGCCCCCTGCGTGGCTGCGGGCGCTCGGGGCGCTCCTGCTGCTAGCCTTGTCGGC
CCTGTTCAGCGGCCTGCGCCTGAGCCTGCTGTCGCTGGACCCGGTGGAGTTACGGGT
GCTGCGGAACAGCGGCTCGGCCGCCGAGCAGGAGCAGGCGCGCCGCGTGCAGGCC
GTTCGCGGCAGGGGGACCCATCTGCTCTGCACCCTACTCCTGGGCCAAGCCGGAGCC
AACGCGGCCCTGGCTGGCTGGCTGTACACCTCGCTGCCGCCGGGCTTCGGGGGCACC
GGGGAAGACTACAGCGAAGAGGGGATCCACTTCCCGTGGCTGCCGGCGCTCGTGTG
CACCGGCGCGGTATTCCTGGGCGCCGAAATCTGCCCCTACTCAGTGTGTTCGCGGCA
CGGGCTGGCCATCGCCTCGCACAGCGTGTGCCTGACCCGGCTTCTGATGGCAGCCGC
CTTCCCCGTGTGCTACCCGCTGGGCCGCCTGCTGGACTGGGCGCTGCGCCAGGAGAT
AAGCACCTTCTACACGCGGGAGAAGTTGCTGGAGACGTTGCGGGCCGCAGACCCCT
ACAGTGACCTGGTGAAGGAGGAGCTCAACATCATAC

11:104163784-104164216 (SEQ ID NO.: 8)
AAATAAAATGAGTCTCTTACCATCTCGCCTGAGGTTGGCGTTGCGCAAAGCTT
TGATGGATGCGCTCTGCGGGGTTGCAGAAGTGTCCCGACAGCTGCAAAAGTTTGCGC
AGATTAGAGTGTAGACAAAGATGAGCCGGTGCATTTGGGATCAGCGACTAGAGACA
GCGTCGCTCCAAGAAAAAGCCGGGTTCTGCTCCCGGGACCGACGCCGCGCCGCCCT
GCGCTCTCGCCGCCTGCGCTCGCCCTGCGCTGGCCCGGGTCGCTGTGCTAATCGCCG
AGCTCTCCCCAAACTTCCTGCATGCTGAACTTTCCGAGCGCGTGTGGGTGCCGCACT
TCCTTGTGGTGCTGAGCTGATAAATGGTGACGGGACAAACAACAGGTTGACGTTTGT
TTGTTCGCCCCCTCCGGTGGCCGGCAGCTGCAGCACAGGC

-continued

| SEQUENCES |
| --- |

```
11:7251463-7252363 (SEQ ID NO.: 9)
AATCTTGGACCCAAACCCTGCATTTGGGCATCTGACACCCATAGGCCCATGG
TTCAAACCCAGGCGGCTCTTTCCAAGTTCGAAGCAGGGACTCGGTTCTGCGCATCTG
GCGGGTGTGCCCAGATTGTAACCTTCGCACTAGGCATCCAAGAACGTGCTTTGGACA
CACTCGGCGGTGGGAGCGGGTGCTTGGTTTGCATCAGGGATGAGGGGTGGAGTAGC
GAAAGCGCCCGGAGCGCGCACTCACTCACACTCCCCAAGCCAGGGCGCGGCCGCTC
TGGGCGCGAGGTCCCAAGCCAAGTCTCGCGCTCGGCCAGGAGCCGGGGAGTACCCC
AGGTCCCCGGTCTGGGGCCGCCGCTATCCTACCCTGCGGCGCGCACTCCTGACCTGG
CCCCGCCCCCGGCGGCCGCGAGTAGCGGGCGGAGCGCAAGCAGAGAGGCGCTCTG
GGCTGTGCGGCACCGCCTCTCCTCGGTGTCTGGGGAGGGACGGAGGGACCGGGCGG
GAGAGAGAGAAAGCCTGACCGACCGGCTGGCGAAGAGCTGCATGCAACCGGTGGG
AGGCCGGGCCGGCTGGGTCTGGGGCTCGGGCTCAGGCTCGCACCGTTTCTCGGCAG
GTCCCTGGCGGTGAGCGCGGACGGCCCGGAGGCGGCGGCTCTGAGCTGGCAGGCGG
AGGGCTGTCTCCTGCGCCCGCCTGCCCGGCGCGGTCCGAGGATGCGGGGGGGCGAT
GCCCGGGGCCAGGGACGCGCTCTGTCACCAGGCGCTGCAGCTGCTGGCCGAGCTCT
GTGCCCGTGGGGCCCTGGAGCACGACAGCTGCCAGGATTTCATTTACCACCTGCGGG
ACCGTGCCAGACCCCGGCTCCGCGACCCAGGTGAGTGCCGCCACCGCCGCCTGGAG
GGACCT

11:8080764-8081056 (SEQ ID NO.: 10)
CGGGGGTGTGGGAACTCGGAGGTGGGGGTGAGGGAAGGCCAACCTCCACGC
TTCGGCCCGGAGGTTCCCCCGCCTCTTCCTGCACGACTGGATTCCTTCTCCATCCGCG
CCTCCGGCCCGGTCCCTGCCCCGCCAAATCCGCGCATCGGTTTCCCATCCCATAGCG
CAGATAGGTAGGGCAGGTACACAGGGAGGTGTTCGAATGATCCCCGTTTCACAGAA
GACGAAACTGAGGCTGGGAGGCCTGGGGACTGGCCCGGCTGCAGCGCCGCCGTTAG
CCGAAGGTGGGAGCC

12:104457176-104457696 (SEQ ID NO.: 11)
CGCGCAGCCAGCGGGTCCACGCATCTCAGCACTTCCAGACCAACTCCGGCAC
CTTCCACACCCCTGCCCGGGCTGGGGGCTCCGAGAGCGGCCGCGAAGCGACTCCGA
TCCTCCCTCTGAGCCTTGCTCAGCTCTGCCCCGCGCCTCCCGGGCTCCGGTCCGCGCG
GCGGGGTCCCTGCTCCTGCGCCCCGGGCGCGCTTCCCGGACACCCCGGTCCCCGCAG
CCAGGACAAAGCCATGAAGCCAGCGCTGCTGGAAGTGATGAGGATGAACAGAATCT
GCCGGATGGTGCTGGCCACTTGCTTGGGATCCTTTATCCTGGTCATCTTCTATTTCCA
AAGTATGTTGCACCCAGGTAGGGGGCGCGTTAGCGTGGTTTTGTTGGATATTTTCTT
CTCTCTCGCGCTCTAGCTCGCTCCGCCTGATTTCTGCCTCTTCCAACCCTACCTCTCC
GCCTTCGGCCTCTTCGGGGCTCCTGGCTGCCCAGAGCTCCTGGCTGCCCAGATCTAC
CCGGGTCACCGC

12:132887749-132888077 (SEQ ID NO.: 12)
TTTGATCCTGACCAGGCGACTTCGTCGCCTGCGGATCACGGAAGTGGCTGCG
GTCGGCGCCATGTTATGTTGGGGCAGAAGGGACGGGGAACTTCCGGATTGGAAGCC
CCAAGGATTCTGAGAGCCCCGCTAATCTGGGGATGACTCCTAGGAGTAGAAGACGG
TCCATCTTAGTTGTCACGAGGTAGTGCACGTGGGGACCCTTTCGGGTACAGTTGCAC
ACAGTGGATCACACAGATCCGAAGTCTGAGGCACAGGGCGCGGTCCGCGAGTGGGA
GCGGCTGCTTGTGGGCAGGGTGGACGCGGGGCCACGTCTTGGCCGGCGTTTT

12:63150784-63151598 (SEQ ID NO.: 13)
CATGGGCTGGAGTTGCCCGAGGGCCCCGCGTCGGGACCGGCGGAGAGACGC
ATGCTGTCCATGCAGCTCCTACTCGGCCCTCTTCGGAGCTCCAGCCCTCGCGGGCCG
CTCCCTCCCCGTCTCGGAGGACTTGGGCTCCTCGTCCGAAGCGCAGGGTCTTTGGCG
CGCTCGCAGCTTGCCGGGCTCTGCGATCCCTCCAGTGGGCGTCTCCCGGAGCAGCGT
CCCGCCTGCCCACTGAGCAGCTCTCAGCAGGGTGAGCTGGCCCCTCTCCCTGCTCTG
CCTTTTTTCAACTTCGGCGAGGTCGGGAAGGTGAGCTCCGAGCTTCCGGAAGCACTG
GGTTCCCAACTCAAGTATTTATGCGGTGCTTGTTTCCTTGGGACGCGCTCCCTCCCGC
CCTATTGCCGGAAGACTGCTGGTTGCCTACTCCCCGCTCCCTGGAGTTTTATTTTTTC
CTCTCCCTACGTCGGTGTTTGTCCTCTGCATCACTGTGGAGGGGGTGGAGCTGGGAG
ACTCGCAGATTCCTCCTCACAGTAGGTGGGATCGTGGCGCTTTCCCGCTTTTCCCTTC
CAAAAACTTGGACAACTGGACGAGTCATGCCTTTTCTGGGCTCGTAGCCGTTTCCAC
AAGCTTCCCTCACTAGCCTTCCTCGCTAGCCTCCTTAACCATGCATTTGACTTCAACA
GGCACGCTAAGCGCGGTACCTGGAAACCTCCAGTCCACGCACCGGCGTCCACGCAT
CTAGCTCCTGCACCTGAACCTGGCTCTCGACCTCACCTCCTCCAGTCCGGGTTTCTTC
CTTCTCACCGAGCTCACCC

13:101916754-101917294 (SEQ ID NO.: 14)
GAGGGGGTGCCAGGCGGGACTGGGGAGAGGGGAAGGGGGGCTCAGTCCTGA
CCGGGACCCATCGCCCTCTCCGCGGGGCGCGGGGCCAGGCGCGCAGATGCGCCCAG
GGCGCAGCCGGACGATCCCGGGAAGCCGGACGTCGTGGCCGCCGCCGCTTGGCCAC
GTCCGAGTGGAGAGCGGGACCGCGGCTGCGGGCGCTGCTGGTCACCGCTCGTCGCA
GGAACCCCGGCGGGGGTCGCCACCGCCACTCGCGCTGCCTTCTCGCCCTGCCCGGCT
CCCGGGCGGGAGGTAGAGCCGGCCGGCGGCTCCCCGGGCGCCGGCTGGAGGGCGG
GTCCCGGCAGGGTCTCTGCGCGTCCGTCGGTCCGGGTCGCGCTGGGCAGGACTCAGC
GCCGGGCTCCAGCTGCCCGCGGGCCGGTGCCGCCGCCGGCGCCGCCCGCTCTCGGCT
TCTGCCGGTGATTGTCAAGTGCTTTGGAAATCAGCATCTGGAGAGACCAATCTTCTC
CCCTGAGATCTCTAATCAAACGCTCCGTTCCCACCCCAC
```

-continued

SEQUENCES

```
14:70188798-70189399 (SEQ ID NO.: 15)
CGCGCCCTGGCGGCTCCGAGGGACCTGGGCTCGGGCTTGCGGTCGCGTCGCC
TGGGCTTTCCCTGGGCTGGGAGCGCGCCGGGTCTCCGCCTTGCACGCTGTCACCGCG
GGAGACGTCTCGGCCTCGCCGCGCGCAGAGGGGACGCGCGGAGAGGCTGGTTTCTG
GGCGAGCGGAGAGCTTTGCCCATTAAGCTGCCGGAAGAAGCCAAATCAAAAAGCCA
ATCTCCAAGCCTCCAAACGGAACGTCACCCTATCAGCTGGGGAGACAGCGCCGCACT
GACTGACAAGCCGCGCATATTTATCCTCGCGCGCGGAGGGGAGACTCTCAGAACGC
TCCTCGACCAGCAGCGAGGAAGTCGAGCCCGCATCCCGCATCCCGCATCCCGCATCC
AGAGCCCCCGAGGGACGAATTCAGATCCAACCCCTGCCCCGCGGCCACCCACCCTA
GTCGTTGGAGCCTGGCGCCCGCGCCTCCCGGCCGGCAGCACGTCAAAACGGCGGCG
CGTCCTGACCTGGATTCCGCCGAGTTGGGAGCTCCAGGCAGCAGGCGGGCGCGCGG
CACCGGCTTTCCCCTTGTCCTCAGGAGACGCTGCCTGCAATTCC

17:35448276-35448579 (SEQ ID NO.: 16)
CGCAACGGGGGAAGCCTCCAGGACGCACTTGGCTCTGCCTGTTTGTTCCGCC
CCCGCGGAAACCGCTGCTCGCTGGGCAGGGGCTTTCTGTTTTGCAGCCGGAACAGG
AACACAGATAGCCCGCCAAGCCGCCGGCGACACCTTCCAACCCCTTTAGCTCTCCGC
ACCGTCCCTCCCCACCGCCCCGCCTCCACCCGCGCCGCGATCAAGTCCTCATAGCCT
TTTAGGGAATTTGCTCAGCAAACTAGCCGAACCCCAAAGGCAGGGGAGAAGCACGC
AAATACCCCGACTCCACCGGCTGGCC

17:46819204-46819444 (SEQ ID NO.: 17)
TCCAGCCTCCCGAGTCCGCCCGCTCTCTGGCCTCTCGTCCTGGCCGCGGGAGG
TCACTTCCCGGGTGTCCGAGGAACGTGCGGAAAAGTCCGCGGAGGCTCGAAGGTCT
GGCTGCGGGCGGCGCCGGGGGACGGAGCCGAGTGTCATTTGAGTCTTTTGTCAGGG
ATCAGATCGGTATCGGGACCTCCTGCTGCCTTTGCATTTCCTGCAACTGACACCAGC
GGCCAGTCGCATTTCCTGC

18:28177326-28177787 (SEQ ID NO.: 18)
CGTGTGAGCGTCTGCGAGTGTGTGGAGGCGGCTGCTGTGGCAGCGCAGGCGG
CTCGGCTCCGGCCCGGAGCGCAGCGGAAGCCGCGAGGGATGCAGCGGCGGGGACCT
TGGCCGGTGGAGGATGTGGAGGTGGAAGTGGAGCGGATGGCGCTCCCCAAGAGCTC
CGCCACGCGGAGGTTTCGGGCTCGTGGTTTTGCTTCCTCCGGGTCCCCGCTCCAGGGC
CGCTCGGCGCGACGAAGACGCCGGGGACAGCGCCGCGGGGAGGGCGCTCCGGGTC
GTGCGTGCTGCACCCACAAAGAGCAGCAGTCCCGCCACTCCGCGCCTCCGCTGCGTG
GGGGCCGAGGGGCGCTTCTCGGCTCCTCTTTCCGGTCCCCGGCGAGTTGGGAGACTG
TTCTCCGGCCTCGGCCGCAAGGGGGTGAGGCGAGGGGCCGGCGCGGTCTCTCCCGC
CGCGGCTCCGTCCCGC

19:31351575-31351815 (SEQ ID NO.: 19)
CCGGGGAGACGCGGCCGTGGAGCGTGAAACGCTTCTTGCAAGCGAGGAAAC
GGTGAGTTGGCCGACACCGCCGGCGGCCTCACCATTCTGGTGGCCGCGCTGAGCTCC
TGTCGCCTGGAGGCGGGTTGCGCCGCACGGGGTCAGCTCCCGCCGGCTCCCAGCTCA
CCTTCGAAGCTCCCACTTAGGCGCGCCCGGTGCGGCGTGTGCACAGCGCGGGGCGC
CGCACACGGAAGCGTGTAGT

19:36916030-36916584 (SEQ ID NO.: 20)
CGCCAGGAGTGACGAAACGTTCGAATTCCTGCGAGAAAAGTGGCAGGCCAC
CAGGCCCTCTGGGAAATGTAGTCCAGAGCGGGACCCACGCCGATTCCTGTCAGCTCC
TCGCCTGGGCCCACCCGAAACGGCTGCTCCCTCAACTCTCAACATCCAGCCGAGCCT
CGGAGTTGCGGGTCGCCGTAGCGCTGCGCAATGGAGATGAGCCTCCCGGGGAACCC
GGCCCAAGCCTCACCCTCACACAGGAAAGCAGATGTGTTCTGGCCGGAAGTTGAGT
GGGGCCGCGGGGCCTGCTGGGAGGTGTTGTCCTCGGAAACGTCGCTGGCGCGGAGG
GATGGTTCGGCGCTTTAGGCGTCTGTCACAGACCTATCTGCGGGTCGCCTTCACCCA
GCATCTCAGAAACTGCGCGCGGGATGAACATTCGGGTGTTTCCGGCAGGTGACGCT
GCCGAGTCCCCGCAGCAGGGGGCGAGCAAGGGACTCGCGGTTGACGGGACACGGA
TCCTCTAAGGCCCAGAGTGTCCCGAGTAGCGGCAGTGGGGAGTGCTCAGGGTAC

19:53254573-53254933 (SEQ ID NO.: 21)
GGTGGGCGGTCGGTGTCCACACTGACCTAAAGCAAAAAGGTCGGGGCCAGTA
CCCACTTCAGAACGATTTTAATCCGAAATGGACGCAGATCTCTAGACCCTCTCGGAG
CGACGGGACTGGGAACGTCTTAGGGCCACGCCGCGAGAGGAATGAGCAGGTTCGGG
GTTTTAACCTACAGGGCGACCCCAAAACCCGACAGCGGAGCGTGGGAACCTGTGGC
CCGCGAGGCGCAGGCTTGAACCCGAAAGACGGAGACTCACCCGAGAGCGCCAGTA
GCCCCGCGAGATCCGCTTCCGGGTCGGCAGGAACCTGCGCGTACGCGAGTGCACTG
GGGCGGCGCAAGGGGCAAGGGCAGGGGCA

2:100321258-100322771 (SEQ ID NO.: 22)
CCACCTTTCACCTTCCCATCCTTAGGAAGCAAAGTGACCCCTAAGCCTAGACA
AAGCTCTCGAAAGCCCAAAGCCTCGGGCCCACCGGCCAGCTCCCCACCCCGCTGCT
GGGCCGGACAGGTGTAGGGGAGGCGGACCCGCCCCGCAGCCGACTCACCCAGCTCC
AGGGCCTGGTCGCACCTGAGCAGCGCGGCCTCCGGCTGCTGCTGGCGCTGCAGGCT
CCGCGCCTGGCCTGCCAGCCTGCGCAGCCGGCACTCGGCCGGGAAGCACTTCTCCA
GCAGGCCGCTCAGCACCACGTTCACGCGCCGCACCTGCGGCCGCGCGGGCCCTGGC
TCCACGCAGCGCTTGCAGACTGTGAGCCCGCAGGGCAGCGTCACCGGCTTATGCAG
CAGCCGCCGGCAGCGCGGGCAGCCGAGCAGGTCGCGGGGCGCGCGGGGCTCCGGG
GCCGGCCCTCCCTCGCCGGGCGCCTCGGGCTCGCCGCCCGGGTTCTCCGCGGACAGC
```

-continued

| SEQUENCES |
| --- |

```
GGCCGGTCGCGCAGGCCCACGGCGCGCACCAGGCCGCCCGCCAGCTCTTCCAGCTC
CTCCGGCCGCAGCGCCCCGAGCCGCGCGGCGCCGCGGAACGCGCCCAGGGCTTCGG
GGAGGCGGCCGGCGCGGGCCAGCGCGTCCCCCAGCCTCAGGCACAGGCCGCGGTCC
GGCTGCGCCAGCCCGGCTAGCATGGAGCGAAAGAGCTCGGCTGCCATCTCGTAGTC
GCCCGCGCGGAAGGCCTCGTCGCCCTCCTCTAAGCGCTGGGCGATCGGCTCCGCGCG
GTCGCAGCCAGGACACTGGGGCGGCGGCGGCGGCGGGACCGGCTCGGGGCTCATCA
CCGCGGGGCTGCGACGACGCGGGTCCGGAGCGAAGGCGCGGAGCAGGGAGGGATGC
GCTGCTGCTGGGAACTGGCCGGCGGGAGCGCGGTCTCAGCCCTCGCCAGCAGCCAC
GCGCGTCTGGGGGCGGCGCGCTGCGAGCGGCTGAGACCGCGGGCGGGGGCGGGCG
CCTGGCTTGGGCAGCGTCCTCAGCGCGGTGTGGGCGGCGAGCCCCGCAGGGCTGCA
ATCGTTCCGGGGTGGGGGCCGGGACAGGCACCGCGGGCGCAATCTGAGCCCCTGCC
CACGCGCAGCGGCCTCTCAGTCCCGCCGGCTTAGGTAACCCAGGTCGCTGCGGTAAC
GCAGTGACCGCGCTCCAGGTCCGCGTCTCTTGCGATGCTTCCCCCACTCGCCTGAGG
GCTCCTGCGCGACTGCGCGCGCGTCCTCTGCCTGCCGCCTCCCCGCAGAGGTGCCGG
GGCCCTGGGAGCAGGTGGCCTTGGCCGCGGGCTGCTGGCGCGCCGGCACCGCGGCA
CCTGCTCTTCCCCAGAGGCCTGGCCGCCCCCACAACCTGTGGCTCCGCTTAAGCAAG
AACCCAGGAAAAGTCACCAAACGCATCACGCATCTCTAGCTTCGACTTAGGAAATT
GTCCTAAATGACTGGGGAGGCTGAAGTGGGCACCCAGAGGCCCCGCCTCAGCGAGC
TT

2:136765857-136766361 (SEQ ID NO.: 23)
TGGAAGCGGATCTTCTCGGACGCCTCTGGCTTGGGGCTGCGGGAAGCGTGGG
CTGCCCGGGGCGCAGTGTGCGGAGACCCTCTAGGCGGGCGGGGACGCCCCACGCGG
CGACCTGAGCACCGACCTCATGCAACGGGACCGAACCTTGGGACCCGGGCAGCAGG
AGCTCTGTTCCCTTCACCTCCAGCTTGGTTTGAGGGATACTGATGAAGGAAACCGGG
GGTTTCCCGTCCTGCGCGGAGAGCCTCGGCGCCCAAAATCGAAAGGCCGGGAGTTG
TTCTGCAGGCTTTGCAAACAGGTTGACTGAGGGTTTCCTTTCCCGTAGCGCTGACTG
CGAAATCTGTGCATAGGCGTTCAGTGCCAGTGGAGGATAGCTGAGCAAGCCAAGAA
GTTTTGCAGCTTCCTCTGATTTATCGGTGGAGTGTCAGGAGGCTGTAGCAACAGTTT
ACATTTCCCCTGTCCCTGCGAGTGGCTAGGGGCAAGCTGGGCTCGGACGTGATATCC
T

2:181456539-181457919 (SEQ ID NO.: 24)
TTGCGTTGTGGGTCTCCGGCACATTTCAGAGGCTCATTAGGACCCTGACCCCA
CACTGGGGTTTACACCCCTAAAAGCAGGTGTGTCCCGTGGCAACTGAGTGGGTGCGT
GAAAAGGGGGGATCATCAATTACCAGCTGGAGCAATCCGAATCGGTTAAAGTGAAT
CAAGTCACAGTGCTTCCTTAACCCAACCTCTCTGTTGGGGTCAGCCACAGCCTAAAC
CGCCTGCCGTTCAGCCTGAGAGGCTGCTGCTAGCCTGCTCACGCATGCAGCCCGGGC
TGCAGAGGAAGTGTGGGGAGGAAGGAAGTGGGTATAGAAGGGTGCTGAGATGTGG
GTCTTGAAGAGAATAGCCATAACGTCTTTGTCACTAAAAATGTTCCCCAGGGGCCTTC
GGCGAGTCTTTTTGTTTGGTTTTTTGTTTTTAATCTGTGGCTCTTGATAATTTATCTAG
TGGTTGCCTACACCTGAAAAACAAGACACAGTGTTTAACTATCAACGAAAGAACTG
GACGGCTCCCCGCCGCAGTCCCACTCCCCGAGTTTGTGGCTGGCATTTGGGCCACGC
CGGGCTGGGCGGTCACAGCGAGGGGCGCGCAGTTTGGGGTCACACAGCTCCGCTTC
TAGGCCCCAACCACCGTTAAAAGGGGAAGCCCGTGCCCCATCAGGTCCGCTCTTGCT
GAGCCCAGAGCCATCCCGCGCTCTGCGGGCTGGGAGGCCCGGGCCAGGACGCGAGT
CCTGCGCAGCCGAGGTTCCCCAGCGCCCCCTGCAGCCGCGCGTAGGCAGAGACGGA
GCCCGGCCCTGCGCCTCCGCACCACGCCCGGGACCCCACCCAGCGGCCCGTACCCG
GAGAAGCAGCGCGAGCACCCGAAGCTCCCGGCTGGCGGCAGAAACGGGAGTGGG
GCCGGGCGAGTGCGCGGCATCCCAGGCCGGCCCGAACGCTCCGCCCGCGGTGGGCC
GACTTCCCCTCCTCTTCCCTCTCTCCTTCCTTTAGCCCGCTGGCGCCGGACACGCTGC
GCCTCATCTCTTGGGGCGTTCTTCCCCGTTGGCCAACCGTCGCATCCCGTGCAACTTT
GGGGTAGTGGCCGTTTAGTGTTGAATGTTCCCCACCGAGAGCGCATGGCTTGGGAAG
CGAGGCGCGAACCCGGCCCCCGAAGGGCCGCCGTCCGGGAGACGGTGATGCTGTTG
CTGTGCCTGGGGGTCCCGACCGGCCGCCCCTACAACGTGGACACTGAGAGCGCGCT
GCTTTACCAGGGCCCCCACAACACGCTGTTCGGCTACTCGGTCGTGCTGCACAGCCA
CGGGGCGAACCGATGGTGAGTAGAGTTGGACTGATGCGCCCTCAGCAGCTCAGAGC
GGCGTGAGAATGGCGCCCTAGGGATTC

2:181457952-181458372 (SEQ ID NO.: 25)
GAGGCAGGAGGGAAACGCTGCGAGAGCCAGCTCGCTGGAAATCTGCCAGGG
AAACTAACTTATCTTGGGGCGGCAGCGCCCCGGGTGCGTTATGGTGCAAGGTCTTGG
AGCTTCGAGTCGGGGGTGGTGGGCGGAGGAGGAGGTGGGGAAGCTGCCCTGCTGCG
GACTGCACATCTGTGGCGACAGGGAGCTCAGTGGGCAGCACAGCTCACGTCTGAGC
GCACGTGCACGTGTCTCGCTTTAGGCTCCTAGTGGGTGCGCCCACTGCCAACTGGCT
CGCCAACGCTTCAGTGATCAATCCCGGGGCGATTTACAGATGCAGGATCGGAAAGA
ATCCCGGCCAGACGTGCGAACAGCTCCAGCTGGGTGAGTTGGGTATGGGACCAGGA
GTTAGTGACCTCCCGACCCCCCATGTGGACCC

2:29115036-29115576 (SEQ ID NO.: 26)
TTGCTCAACGTGGGTGTAGCACGGATTAGGCCTTTTACAGCAAGCGCTGCCA
GCAGGGAACTGGTGGATGTACTCTTGACCACGCTCGGCTGGACTCTGGGGAGCCCA
AGACGGGTAAGACTAGGTCCCCGGCCCCAGCAGCTGGTGGGGGCGCCGCAGGTTAG
AGACGTGAGGCCGCGAGGCTGAGGGCTGTGAAGGCGGTGGGCACGCACGGCGTGC
CGGGGCCGCCTGGCTTCGCGGCGGGGGAGGTAACACTGCGACACCCCGCAGACGCT
GTCAGCCGGGGTCGCGCGCCCCGCGTGCGCCCGATCATCTGACTGCTGGGGAGTGCG
GGGGCGCGGGAGCCAGGCGAGCCAGCGCAGGCGCGCGCTGCCTCCTCCGTCCCCAC
```

-continued

---
SEQUENCES
---

```
CGAGTCCCCAGCGCGTGCGCGGGGCCGTGGCCGAGGCCTGCGCGCCGCCCGGCCGC
CTGCACTGCGCGCGCGCCCACCCCGCGTGGGAGGCAGCGGGAGGGGCCCGGAGAG
GTGTGGAGCGGCGCGGCGGGAGGCTCCGTGGGCGGCCACGGGA
```

2:29115806-29116764 (SEQ ID NO.: 27)
```
GCCCCGCGGCCGCCTCCCGTGGGCACCGGTGTCGCTGGCCGCGGGGAGGCCT
TCTCGGGGCGGAGCGGCCCACCCGGCGGGGATGGGGACTCCTCGTGGCGGCCGCTG
ACGGACGGCCCAACTTTAGGTTGAGGGGCGCGGGGTGTGCGGGACCCGGCGGCGGA
GCTGGGCTCTGGGCCACGACCGCCAGCCGCGGCTGCCCCGAGAGTCCCCGCACGCG
CAGTGGCTTTCCAACGCGGCCTCTTCCCATTTCTCACTTGACTCCCCTTGCGCATTAA
ATTGTCGAGAAACCTTTGGCCAGTGGGTCTTCAAAGCTAAACCAAATGGCTGTCCTT
GCAGTCCTTGGCTACCTGAGATCCCTTAATTCTGAACCATCCGCACCTGGGAGGGGA
AGTTGAAAGGAGCGCTGGAGCTGAGCCCGCATCCTTAAGGATCCCATTCACTGCTTA
TGATGGTAGAGCTTTGAATTAGATGTCAGGCTGTTCACGTCATCCAGACTCTGGTTTT
CAGCTCTGTGCTGAGACAGTGTTTTGATACGTATCAGAGGATGATGTTCCTATGGGA
CAATAACTTGCTGTATGTTCTGAGATACTAGACTGCGTTCATATTGTAGCACCATCAT
CGTATAAAACGGGCGCCTTTGAAAGGTTTCAGTAAACACCTTCCTCAGGAACATCCG
CCAGCACTTAAATTGTACTTCACTTTCACTTTGACGTTTGTTGTTTGTGAATCTTGTG
CACAATTTAAAGTGAGTCGTCTAAACAGCACAGGATCACGTGGTGCGGGGCATTGA
GCAACTGGGGAGGAAAGCAGAGACTTGAACCTGCTGGAGTCTAGTTGGTCTGCGTT
TTTATGTTGGAGAACCATCCTGGTTCCAGCTTATTTTGCTTTCGTAAATATGATGCAT
TTTTTAAATGCTTTCATTTGATACGGTCTATCTGGACTGTAAGATTGAGTCT
```

2:29920045-29921364 (SEQ ID NO.: 28)
```
GGACAGCCTTCCCTCTCTGCCCACTTCCGACGCCTTCTTCTCGGGCATCAGGC
GGATCCTCAGTCGCCCTTCGCCTTGGCGAATCCACCAACTGAACAGCTCGCTGAGAT
TGAACTGGAGCAGCCCCACAGCCGCCTCCCCGGGGGGCCCGACGCAACCCTCCAAG
ATCGCCTCCTCGCCCAGCTCCAGCACCAACTGCTTGGCACGCCGGAGCTTGCGCACG
GAGCCGCCCTTCAGCACCCTGGACAGCGTCCGGGCCTCTGCCGGGGCTGGTGAACC
GGCGGTCCAGGAGACCCCCGGCGCCGGCCCCAGCAACCTGAGCAGCGGGGCGCAGT
CCAGAGCTAGCGAGCCGCGGGCCTCGGGCCTGCCAGCCTTCAGCTCCGAGGAGGAT
GGTGGCAGCAGTAGGTCCCGGGCGTAGACACGGAAGAGCGAGGGCACCACGAAGT
CAACTGCCAGACTCTTCCTCTGCAGGCGCGAGTAGCTGAGTGGCTCCCGGGGCTGCA
GCGGCGGCCCCGCAGCTGGGGAGCCCGCGCGCTGGCCGGTCCCCATCCCGGAGCCC
ACAGCTGCCGTGGAAAGCAGCAGCGGCAGGAGCCACAGGAGCCCGATGGCTCCCAT
CCCGCCGGAGGAGGCCGTTTACACTGCTCTCCGGGCCCAGCCTCACCCTTCGCTCTC
CCCGAGATGGGAAGAGGCTCTGAACAGTCCTTGGTACCCAGCGGCTCCTTCCACCTG
ATCTCCAGAGGACTGTGCGTGCGCGCAAGTCTCTTGCTTTCCCCCAACTGCACGGAG
GCGAGCAGGAGTCTAAATGAAACAGACCTGGAAGCTCAGGGGCGAGTCCAGAGAC
ACTCAAGCACACTGGGCTCACTGGCTGGGACCTTGAGCCTCCCGCTCTCCGCGCCGA
GTGCCGCGCCCCGTCTGTAGCTCGCTGCGCTCGGTACAGAGGAACTACTATGGTTG
AAGGGAGGTGGCAGTTGGGTACCGTCCTCTCCTGCCCCCCCGCAGTCGGAGCTGGGG
TCTGTCCCCTCTCGGGGCAGCCTCCAATCTCTGCAACTTTTAAGGCTGAGAACGGCG
GCTCCCAGCTGCTGCACGCTGTCCTGGCCGCCTTTTGCGTTCCTTTTGGCTCCTCCAA
GCTCTTCTGCCCGGTCTGGGCGGGAACCGAGGGCGGAGGCTGCCGTCTTGCGCACCC
TCAAGCTATCTCTCCGCTGCGGGAAGGCTTCGGACTGTCTGCCTGCTGAACTTCTGG
GCGTGAATCCCAGCCCCCGCGCTGCGCAAGTTTGCAGCGTCCTTGCTCTCACCGGCG
CCTCGGCTCCTCAGAGTTCGCAG
```

2:31136905-31138399 (SEQ ID NO.: 29)
```
GAGACGCCACCTCCCGCCCACATCTTCCTGTTTTTCAGTCTCCCATTTCCGAC
CATAAGCTCCTCCAAGGCTTTTGCCCAGACCCCTAGACGACTGTTCTGGACCCAGTT
TATAAAGACTGCCTGGCTGGCCAGGAAATCCCCCAGAGGCCTCCTTCCGTGTCCCCG
GGCCAAATCTGTGAAGAGAAAACGGAAGGCTACCATGTCACGAAAAACTATGATCA
AATAAATTATTATGCCTTTTCTCCTATTGATCTGCCTTTTGTCAACTGATTTTCAGTGA
ACCTTCGGAGAGCCATGGGGAAGTTTTCCCTTTCCCCCTACAGGGCTCTGAATCTGA
AGGTAAGAGTGAGCCTATAGGGGGAACCTTCTGGCTCCCTCACAGGAACTGACTGA
GCAGGAGTTGGAAAAGCCACTTGGATTCCCATTTCCTCAACTCCCCGCCAATACCAA
GGCGTCTGTTTTTACAGGCTCTTTCGTGGTGTTCTGGGCACATTCAACTTCCAATGCA
GCTGAGAGGGTCGGGAACAGTTAGAGAACAGGGGTGGCAGCCGCCCGGGAGGCTG
CAAGGCGCTCGCCCGCAACGCACAGGCGCGCGCGGCGCACCCGGCCTCCGGCCTCC
CCAGGTCGGGCCTGGCAGCTGCGGGAAGGAGGTCAGCGCAGCCGCCCACACTTCGCC
CGGGCGCTGGCCCGACCCGACCGCCGGCGACTCTCTGGCAGCGCCCGGAGACCGCC
AGCCCCTGGGCCGCCCGTCCGCAGAGCCCCCTCCGCCCCGGGACCCTCGCGCGCAG
CTCAAGTTGGGGAGCCCCGCTCCGCAGGCGAGCGCGCGCCCACCACCCACACCCACT
GCCACTCATGCACACCGCGGGTCGGGAGATGCCCCCGAGCGTTTTAAAATCCAGAA
ACATCACATGGTAGCCACATCCGGCGGCTGTTACCTGCTCGCAGCACCCAGACCCTC
GCCCTGGTTTCCCGGGAGCCCGCAAACCCGGCACGCGGGCTGCGCGCCCTCCCGCA
AGCCACCGCTCAGCGCCAGCGCGCCGGCAAGCCGCCTACCTTAGGGGTCTGCACTTC
AGGTCCCGTCGGCACCTCCAACTTCCTCTTGGTTACCCAGAAGAACAGCAGCACCGT
GATCCAGAGCACCCGAAGACTGGCAGAACCAGCCGACGAGTCAGGCGCCGCCATGG
TCCCCTTTGCCGCTTCCTCTCCGCGGCGCTACGTCCCGGGGGCACCCCCCGGCGGTC
AGGGTTGGCGGGGCAGGAGTCCTGGCGAGCGCCTCGCTCTGGGGAGCTCTAGACCC
AGGATCCGGTTGGAGGGGCGGCAGGATCCTGCAAGGCGCCCTTCCCGCTTCGAAGA
GAAGCGAGCCTGGGTGGGGGGGTGCAGGGCGACCCGAAACGTGGCAGGGAAGGACC
GAGGGCAGCCAAGCTGGACGCCCGCTCCAGCGGGAGAAGCGCGGTGGCTGCCGAG
ATGTTCCCCACGCCGCCACCGCGGCTGCCGCC
```

SEQUENCES

2:95025841-95026142 (SEQ ID NO.: 30)
TCGGTCTTCACCACCTTGCCCGACTTGCTCTTCATCTTTGAGTTTGTGAGTGGC
TCCTGGCCGGGGAAGGGACGGGGTGGGCTGAGCCGTGCGCTCTCTCGGGCGCCCAG
CACAGCTGTCGGACGGGATCCGCTAGCTGCGCAGGTTCTGGGAGCATCGGGGCAGC
AGGCGCAGGGCGGGGACTAAGCCAGGGAAGTCCCCTCCCACCTCCGGTCCTTTGTG
CCCTTCTAGACCAACAGAATGAGGGGAACAGTCTACAGGACTATGGAGGAAAAACT
GGGTTCCCAACTGGGGTCAGATGT

20:21509396-21510116 (SEQ ID NO.: 31)
ACATAAGCCCCCAAACATTGCCAAGCTAGTGTGGAGAACAAAGGGAGACCTT
TTAGCATTTAGAAAAACTGCCCTTTCCCCGAGGATGAGCCCGGAGATGGGAAAGGA
CCTTTACTGGGGTATTAGAAAGACTTCCGAGCCCTCAATTATCCAGGGGCGGTGTGG
AACGCGGGAATAAAGTGTCATCGCGTCCCTGGGCTGCTGCGCAGAGTGCTATCGAC
GCACAGATTTGGTCGCACGGATAATCATGTTTGCTTTAGATATTGAATTAAACCTGA
TCATCAACTACAGGGAGCGAGAAAGTCAGCTGGGACCGCTCCTTTTGCCCGGCCTCC
TCACTGCCACCCAACCCCCCAGCCTTGATGGTGCAGCTTCGGAGAGAACAGAGATA
CAATTTCCAAATGCGCCGACGTTCAGTCCCTCAGCGTCTGCAGCACCCGCTGGGCTC
TGAGCTAGAGTCCCAAGTATTTTTAGAAACCCGCGAGATAGAGGAGAAAGGCTCAT
CCTCCAGTTGGCCAGGCTTCCTAAGACGCTCCCCCGCGTGGCCAAGTGTGCGCCAGC
ATCTGCCAAGGAGATCTTCCTCCAGCAACAAGGGTGGGACGGAATCCGTTCCCCGC
CGGAAAGATGGATGCGCCCTTCCCGGGCGTGCCCGGGGCTGTGTGCCCACTTCCCAT
CCGGGGAGCTCACCCCACCCCCAAACCTCTACTTCCTAGCAATCCAC

20:23048312-23051297 (SEQ ID NO.: 32)
GGAATGGGCGCGAAGCCCTCGGCGCAGACGCAGAGGTAGCTAGTTTGGTTCA
GGGGCTGGCACTGGTACTCGCAGTTGGCTCTGAAGCACGGGTCCACGGGCTCCACA
CACTCGCCGTCCACCAGGTCGTAGTTAGGGTAGCAGTGGCACTCGAAGCCACCCTGT
GTGTTGACACAGCGCTGCGGACACGGACTGGGCTCCAGTATGCAGTCATCCACGTCC
TCGCACCGGTGTTGGTCGGCCGCCAGCCGGTAGCCGGTCTCGCACATGCACGAGTA
GGAGCCCGGCTGGTCGGGGTTGGGAACGCAGAAGTGCTCGCAGAGGTCGTTGCAGG
ACTGCGTCGCGGATGCGGTGCAGGAGCGCCCGTCTGCCTGCAGGGCGGCGCCGGCT
GGGCACTGGCAGCGGGGAGCCCCAGGGATCGCATTGCACGCGTGCTCGCAGCCGCC
GTTCTCCACGCTGCAGTCCCAAGCGCCCGGCGCCTCCCTGGCCCAGTGCCCCTGGAC
CGCTCCGGGCGGCGCGGTGCACATTAGCTGTAAGCCGAGGGGAGCCACCGCGGCGG
AGCTGCCCACCGGCAGCGCCTGGAAGTCCGCTCCGCGGGCGCGCAACGGGGTGCCG
TAGGTGATCGAGACGGCGGCAGCCGCGGCGCCGGGCTCCACAGCCAGTGGCCTGCA
GGTGGCTGGGAAGTGGAACTCGCAGAGGAAGCCATCGGCCTTCACTTCGCACTGCT
GCTCCTCCCAGATCGGCTCGCTGGGCACAGTGGCCTCAGCAGCGGAGACAGCGACG
CACAACGGGCCGCAGAGGGGAGCCCCATTGAGGTCGAGCCGTGCCCACCTGCTATA
GCTGGTGTTGTTGTCTCCCGTAACCCACTGGAAGCCGCGCAGGGGCCCGAGGCGCTT
GGGGTCGCCGCAGCCGGGTGGCAGCTGCAGGCCGATCCAGAGGCGCCGGCGGCCAA
CGCCGCCGTCGCCGTTCAGTAGCAAGGAAATGACATCGGCAGCCACCGAGGAGCGC
ACTGTCATTAGGTGGCCCCGCAGTCCGTCGCAGATCTGACTGGCATTGAGGAAGGTC
GCGGGGCCCGGGTAGAGCGCGAAGCAGTCGTGCTCGACGCACTGGCTGCCACCCGG
CTGCGGCTCTGCGGGTGCGGGGAACCCCAGGCCGGCCAGGGCCAGCGCGCCAAGGA
CCAGGACCCCAAGCATGTTACCCAGGCGCGCCGCGTGCAGGCGCCGGGGAAAGCGC
GGGCACTGCGACAGGGCCGTGCCGGAGCAGAGGGGCACAGGACGCCGATGGCGAC
AGCCTCTCCTGTCCGTCCCAGCCCAGACACTTCTTGCCGCTGCGCGCAGCCCCTGCG
AGGCAGCCTCTGACATGCGGATCGGCCAGGGCTCGAGTTTATAAGTGCCCGGCCCTC
CCTCCCTGGACGTTCGGGAAAAGGAAGGAAGTGCCTGGTGGGAAGGGCTGATGCCG
CATACTCGGATTGCTGGGTTCTCTGGCCGCCCTTGCGCCCGCCCTCGCGCATGGGAT
CACCTCGCCGGGATGAGTAAACCCTGCCCTGGCGCAGGGAGGTTCTCGGGCGGGGC
CGACAGGGGCAGGCGCCAGGGAAGGCCAGCACCCCTGTAACAAGACGACTGTCCCC
GCCCACCACTCGGGCCCCCACGCGTGCAGCCCTCTTTCATCTCTTGGTCCTCCTTTCT
TTCTTTTTCATACATGTTACAGCCACTTCCAAGGAAAGCCTGGATTGCAAGAGCTCTG
GGAACCGGAGACTTCAGAGAAGAGGGCTTTGAATGGGGAGTGGGGGAGGTGGTGC
ACAGGACCTGCAAGACGCTGGGAGGGGTGATCGGCACCAAGGGCACTTTGGGAGGA
CCTGCCTAGGACGTGGACTTCCCCGAAGACAGGATCGCAAGGAGAGACAGCTGGAT
CCTGTCCGCGGCCAAGGTGCCTGGCTCAGGAAACCAGCGGAGCGCGCTTGGCCTCA
CAGGACAGTGGGTGTGGCTGGGGTGACGGGGCAGGGTGGGGAAGACTGGCCTAAC
ACCAGCGCCCTCTGCCCCATGGCTGGCCAGGGACCCGCGAGTCCCTGGACACGCAC
TGGCCAACGCCAGACCCCATCTCATCGGGTGGGGAAGTCGCGGGGACACTGTCAGG
GCGCCGAAGTCCGGACCCGGCTCAGAGGCGGTGGCAGGTGAATTGCTGCGGCGCCG
GGTAGGGGGGGGCGCGTGGGAGCGAGTCAGCCTGGCCAGTTTCGGCCCAGCTTCCG
AAGGATGGTGCTTCTTGCACCCCAACAGAGTGGCTGGCAACCCCCCAGGGGAGCGC
GCAGGATCCCAGCTGATCCCACCCGGGTCGGCTAAGGAGGTTTCCATTTCGTCCAGA
GTCCGAATTGATACCCACGTGCATAGAAACGCCACTTGCTCGGCAAAGGGCACTGA
AGAGCCACCGTCCTGTGGATGGGCAGGTGGGGGGGGGGCTGGAGGAGGACATGG
GAATCCGTCACTTTCGACCTCTTCCGGTGGTTCACTTACCGGGAATGCGGAAGAGTG
GGTCTCCCCCTCGGGTCGCCCCCATAATGGTGAGAGGCAAACTGTTTAAAAACACCC
TTGCCTCTCTCCTCTACTGTCCTCACAACGAGCGCCAGGGGGCGGCGCTGTCGAGCT
CTAAACAAAGCCAAGGAAGTTGGAGAAGTTTCGGGCTAAAAAGGGTTAAGGTGTAG
GAGCACAGAGTCCTCCTTCTGGGGTTGGAAGCTCCGTTCCCGGGCAGCTCAGCGTGG
ATTCCGCTGCGTTCACCTCTTGCCTCCAGGGCCCAGTAGATCCTGGGCTTTAAACAA
GAACAGAGAGTATGGCGTCTGCCACGTGCGACAGACACGCACCGGTGGGGTGGGCC
GGGCTGGACTGGACTGACCTGCAGTGACCAAACGGGTGGGGCGTGGACACTCTGAA

-continued

| SEQUENCES |
| --- |

AGTGAAAAAGGCAAGCACGACTGTCCCGCCGCACACTCCCCAGCGCCTTGGGGCAG
AGAGCCTCC

20:43188844-43189744 (SEQ ID NO.: 33)
TGCCTTTAGGAGCACGGCAGGCACCACCCCCCCGCCCCCGCTCCCCCTACTCT
GGGGAACTACCTCTGCTCACCGCCTTCCCGTGGCCAAACCCAAATATGAGTTCCCCG
AACTTTTCAGGAGCGGACGCGCTCACGGGTCAAATCCACTCCCCTCCAAGGGCCTTA
ACACGGGCGCCCAGCTACCTCGGAGAAAAGCCAGCGGGTAGGGCGGAGGTATTGCT
CTCGGTCATCAACGCAAACATCCCCTCGGGTGCCTACAGCGGCCTGCTTAGGGGAGC
AGCGTGTTCAGAGCAAATGGAGAGCTTCCTGTATCTCCGAGGAAAAAAGAAAAGCC
GCCGCCCCGGCAGCCTCGGCCTGCTGGGGACCTGTCCTCCCCACTAAAAGCGCGCGC
TGCCCGAGGAGCTGCCCGGGAGAGAACGCTCCACCCCGGGCGTCGGTGCCGCTCCT
CGTCTCGCCGCCCCAAACACTCAAGTGGCAGATTCCGACAAGTGGGAGGCAGCAAG
TGGAAATATTCGCAACAACCGCGGAAAGTTACTCCAGCCCGGGGGGGCCGGCAGGAA
ACTGAAGCGGGGAACTTCGCCAAACGCGGGCTGCCGAGGGACGCGAGGGGCCGGG
CTCGCTGGCCGGGGCGCGCGGGGACACTGCTTCCCGCGCCTGCAAGCTGAGACCCG
GGTTCCGGCCATGGGGACCCGCGCCCCCGCGAGCCCACACAACTTTCTCCTCCGAGG
GCCCCGCGGCTGGGGCCCGCGCGCATCCAGGAGGGAGCGGGGAGCCCAGGGGAG
CCGGGCGGGCGCACTCACCTGCGGCGCTCTGAGCCCGGGCGCCGGGCAGTGGCGGC
AGCTGCAGCCTCAGGAGCAGGCTGAGGGCGAGCGCGGCGAGGCTCGCCATCCGGGC
GGCGG

20:61252479-61254380 (SEQ ID NO.: 34)
TCCCGGTGCCGGGCACCGGGCGGGCGGCGGGGAAGATGACCGCGGGCGCCG
GCGTGCTCCTTCTGCTGCTCTCGCTCTCCGGCGCGCTCCGGGTAAGTTGCCGCCTCCC
GCCCCCGCCGTTCGGAAGCCCCGGGCAGCGGGAGGTCGTCCCCGGATCCCGCGGGG
CGCTCACACACCCGGCGGGGCTCTCCCGGGCTCCCCCGCCGCGCTCCCCGCTGCATC
CAGCCCGGCGCCCGCGCTCGGCGAAGCTGCCTGCGGTCGGCAGGAGCGGGAAGCCG
CCTGGGCAGCGGGGAGCGGCGGAGCAGGGTGGGAGTGGGGCTCGGTGGAGGACCC
GGGGAGCTCCGCCTGCACCGGACCCGCCGAGCCTCCCTCGAACGCCCAAAGCCCGT
AGCCGCTACCCGGAGCTCGGCTTGCCTGCATGGGGCAGGCTTCCACTGGCGGAGCC
GGCGCGCCCTCCATCGCCCGGGAGCCGCGCGCGCGGGAGTTGCCGAGCCCAGCCC
CGGCCGTGGCTGAAGGCGTGGGGCGCCCGGCGGCTGCGGGCCAGGGATCCGCGAGT
GCGGGGCGCCTGCCCGACCTCTCCTGCCCAAGGCCTGGGGGTCCGTCTAGCGGCGCC
GCTCAGTTCTGTGGGTGCCGGCAGGACCCGCGCTGCGGGTGGGCGGCGGGGTAGGA
CTGCGGGGCACTCTCACCCCCGAGCCCTCGGCGGGGCTGGAGCCTGCGTGTCCGGC
GGGGCCCCGGGGGCTGGGAGCTGGGCCGGGCTTGGGCCGGGAAGCCGGACGCCGG
GCGGGCGCGGCGCGGGAGGGCGCCCGGGAGGGCGAGCGGGTCTCCCGCTGCCTCT
GCAGAGCCCCGCGGGCCGGATTGCCAGCTTTGCTCTGCGCCTGGCGAGGTGCGCGG
CCCGCGGGGGCAGAGAGCGCGGCGGCTCCGGGGGCGCCCCTGGGCGGGAGGCGGAG
GGGCGGCGGGAGTTGCAGGAACCCCCTCTCGTGGCCGATCGGCCTCGCTGCCTTCTC
CCGGGCAGCGCTGTTGTAACCTCGGAAATAAACAAGTGCCAGCGGCGGGAGGCCCG
CTCCGAGGCCGCGGGCGCTGGGGGACGCGCTGGGCACACGCTTCGGGCGGGCGGA
AACTTTCCTGGGCGAGTTGAGCCTCCCACCGGGCTGCGGGTGCGATTTGGAGCTTCG
TGGCCGATGAAGAAAGCCGCGGTTTAGAGCTTTTCGTAAGGAATGACCCTGCGTCCC
GCTCTCCTCCCTCGGTGCTGGGGGTAGAGGGGCGCCCTCCGCGGTGCCGGCGTCGGG
AAGCCTGGAGCTCCGGGCTGGGGGCGGCCTCCGGAGTCGAAGCATGGGCGGGCGAC
GGCAGCGCGCGGAGCTGGAGGAGGCGGCGGGGGGGAGGCGCCACTGCCCGGTGCG
GGCTGCACCCGAGGCTTCCTGCGCTCGCCGGGGAGCCAAGCACCGCTGTGCTCCTGC
TCCTTCAGCGGGGCTGGCTTCCCGCTTGCACACACTGCCTCTCCCTCCACCACCTCCT
CCTGCCTGTCACGCCCCCTCCCAGAAGCTTGGTCGGAGGGCCCTGTCGTCCACCCCA
TCCTTCCCTGGCCCTGTGCCATGGGCTCTAGACTTCCCCACTGAGCAGGAAAGGCGA
GCGAGCTCCGGAGGACAGGAGGAGACCCCCTTTCCGGTCAGTTAGGGGAGCCGTCT
CCCTGCCTGGGCTGGAGATGGGGGGCTCCGAGGGTGAAAATGCGGGCTGAAGACTAG
AAGGTGGAAGCGCCCCCACTGCCTCCTCACCCCAGCCACCGGCAGCCTCCCGCAGA
GCTGCCTTCTTCGACCGGCTCCGGACCTAGTCCTAGAGAATCTTCTTCCTTTCTCTCC
TCTTTCTCCTCCCTCCCGGTGACCTGGAGAGGAGACAAGAAGCTGCCT

21:33071167-33071887 (SEQ ID NO.: 35)
GCATTTCGAACCTTCCAGTCCAGAGGAAGGGACTGTCGGGCACCCCCTTCCC
CGCCCCCACCCCTGGGACGTTAAAGTGACCAGAGCGGATGTTCGATGGCGCCTCGG
GGCAGTTTGGGGTTCTGGGTCGGTTCCAGCGGCTTTAGGCAGAAAGTGCTCGCTCTC
ACCCAGCACATCTCTCCTTGTCCCTGGAGTTGCGCGCTTCGCGGGGCCGATGTAG
AACTTAGGGCGCCTTGCCGTGGTTGGCGCGCCCCGGGTGCAGCGAGAGGCCATCCC
CGAGCGCTACCTCCCCGGAGCGGAGCACGCCGGCTCCCAGTACTAGGGGCTGCGCT
CGAGCAGTGGCGGGGCGGAGGGGTGGTTCTTTTCCTTCTCCTCCGCCAGAGGCCAC
GGGCGCCCTTGTTCCCGCCGGCCAGGTCCTATCAAAGGAGGCTGCCGGAACTCAAG
AGGCAGAAAAGACCAGTTAGGCGGTGCAGACGGTCTGGGACGTGGCAGACGGAC
GGACCCTCGGCGGACAGGTGGTCGGCGTCGGGGTGCGGTGGGTAGGGGCGAGGACA
ACGCAGGGTGCGCTGGGTTGGGACGTGGGTCCACTTTTGTAGACCAGCTGTTTGGAG
AGCTGTATTTAAGACTCGCTATCCAGTGTTTTGTCGCAGAGAGTTTTCGCTCTTAAA
TCCTGGGGGTTTCTTAGAAAGCAACTTAGAACTCGAGATTCACCTTTC

22:48576292-48577132 (SEQ ID NO.: 36)
TCCCCCCTGCCCAGAAAGACACAAATCGCCTCCCGGAGTGGCGCCTCCAGTC
GCGGCGGAGCGCGGCGTTGGCGGCGGATGGAGGGCGCGAGCGGGCGGCCGCGGAG
GCTGCACCCGGCGGGGCGCTGATGCGGCGCCTGGACCTTCGCTGCGCGACTTCGGG

| SEQUENCES |
| --- |

GGCGTCGGCCGAGTTGGGACTCCGCGATGCAGCTCCTGAAGGCGCTCTGGGCACTG
GCAGGGGCCGCGCTCTGCTGCTTCCTCGTCCTAGTGATCCACGCGCAGTTCCTCAAA
GAAGGTAATTGTCCCCGGGCGCGCGGACCGGTCCTCCGCGCTCTGCCCGGCTCGCGG
CGGCTCCGGCGCCCGACCCGGCTTCCAGCACGTTCCGCTGCCGCCGCGCTCGGCTGA
GGCTCGTGGAGCGCCACTGCGGGCCCGGAGCGGCCGGCGGCGCGACCCTACCAGGA
GCCCGACCCCCCGCGGATCTCGCTGCCCCGCGCCCATCGGGGCTCACCGGCAGGGC
GCGGGGTCGGGGCGCGCTGCGTTCTCGGTGCCTCTGGCGCCGCCCCGGATCCCCAGC
CCAAGCCGAGGCTGCCGTTCCCATCCCCTGCCCCACTGGGCTCGGTGGCAGCGGCGC
CCGCCCGCACGCCGCCGGGCCCTCGGTAGATGGCACCCAGCGCTCCACGGTGGCCGG
CCGGGCTGGGGGGGGAGCGGAGCTGGGACCCGCCAGGGTGGGCGCCGGGCTGGGA
CCCGCGGACGTCGGGAAACCGGCCTGCGCACCTGTTCCCCAGGGCCCAAGCCGCCT
TCCAGAGACCCATAGGTTTGGGAAGCAGGGGCTTGGTCACCGGGGTGCGCAGGTCC
CC

3:134795824-134796604 (SEQ ID NO.: 37)
GAGCCTCGGCCGCTGCCGAGCGCGGGGCTTGGGCGGCACCCACCAGAGCGCC
CCCGGCTGGCTCTTAGCGCCCGAAACTGGCTCGCGAGTCCCCCGGCTTCCTCGCCCC
GGCACTCCCTGGTAGCCTCGGTCTCCCGCAGCCCCCGCTCGGAGAGCTCGGAGCCCG
CTGCATTGCGGTGCATGCTCCTTAGCTCTGGGGCAGAGCCAGAGCTGGGCGTTGGGG
AGAAAGGGGTGCCTCTGGCCATCCGGCTCCTGGAGTACTGGCGCCCGTCTGCTCCCA
GGCACGGATACGCTTCTGAGCAGCCGCGCGCCACCTCCTTTTCTCCAGCTCGCAGTC
CACGGGCTAGTGGACTCTGCTTGGCGTGCAAGCACTGCGCGCGGGGGGCCGGAGAAG
CTCTGCCGTGGTATCCCGCAAGTGGCCGCCGAAGGAGAGGGGTGGAGTTCATTGGC
CGTACCCTTGGGGACCAGTCTGGTGGTCCGGGCGCCTGCGGGACTGCAGGTTTCCAG
GGTCAGTCGGGGAGAGGTGGAAACCCTTTTCGCCTCTTGAGCCTTGGAACAGGAGT
GGGCTGGGGTGAGTGGTCGGTCCTACCTAAAGTCTCCCAGCCTCTCCACCACCCCGG
AGAGGATACTCGGCGGCCGGGAGTCGTCGGGCAGCGTCACTCTCTGCCAGCTCAGA
CTTGGCGGTGCCTCCGGCTTGGTGGCTGGGAAAGCGCGCTCCAAAGACACCGTGCC
CGGCGCAGCGGGGAGCCTGGGCGCTCGGTAGCGCTCGCGAATCCCTGTGG

3:141051399-141052239 (SEQ ID NO.: 38)
CGGCGGCGGCGGAGGAGGGGGAGGCGGCGGCGGCTGCAGCATCCAGAGCTG
GCCGTGGCGGCCGGCGCGCCCCGCGCACAAAAGCACCCAGCCCCAGGGGAGGGCG
ATGAACACACCACATCCCGGGCCCGGGCCCCAGCTGCTGCTACCGCTGCGTGCGCTC
AGGGCGCTGGGGAAGACGCCCGGCGCGCCGGGGGGCCAGCGGCCGAGGCGCGGCCC
GTGCGCCCTGAGCGCGGGACTCGTCGCCCTCCGGGTCAGGCGCCAAGCTTCCAAGC
GGCTAGAGCGCGGGCCTTGGAGCGCCCCCAGGATCGCTTCAGTAAGGCGCTTCCCC
ACTCCAGGCCCGACCCCCGGCGCCTGAGCGCCAACTTCGCCAAGAACGCTCCTAACT
CCAGGCCATCCTGCAGCGCAGAGGGGGCGCTGCTGCCGGGCATCAGCCGTGAGGAC
GCGCCCTGGCCGTGCGGAGAGAGCCGGCATTTGCGGGTCACTCGGGCGCCCCTGA
GTGGGCGGCGGCGGCAGCAGACCCCTCTCCAGGGAGTCCAGGACCTGCCAGCGCTG
GGGATTCTTCCCGAACAGGCGCTTGCCCTCTCTTTTATGGTAAGTACTCTCCAGCTCC
TGGTGAGGGGCGCGCGGGGGCCGGGAGCCGAGATCCGGCTGCACGGACTTTGTGCG
GGCCAGCACTCGACACAGCTGGCGCTCCTGACGTCCCAGTCCCTGAGAATTCCTCTC
TGCAGGTTGTGGCAGTTCGAGATGGTTGATTTGCGCGCAGCCCTGGGGCGTTTGGGG
CCCGGCCTTTGGTATCATGGGTTCTAAGCCCTTTGCTTCTCTGCGTAGCGGACAACGC

3:143119740-143121239 (SEQ ID NO.: 39)
CACCAACCGGGCGCCGGCTGGCAGGAGCCGCGCAGAGGCTGGTCCGAGCGC
GTTGCGGGCGCCCGGCGTAAGGGGAGTCGGGTAGCAGCATCCTCCTGGGCGCCGCT
TTCGCGCGGCGGCGGCGGCTGCGGCGGGGTCTTTCTTTGCTTAAATACCTCGTTGGC
CAGAAGCGCTGGTACCGGGGGCGGGTTGGGTCGGGTCGGGCAGTGCTGCACACCTG
GGTTTCCTTGCCTAGAGCTGTGTGTTCGGGGTCCTTTGGTCCAGTCGGAGGCTGCGG
AGCGGCGGGGGTTGCCTGCGCTGTCCGCCCGGGCATCCTCCCGGTGATGGAAGCAG
CCGCCGCCGCCGCTGCGGGGTCGCGCTGTGCCCCATCCACCGCTGCCAGAGAGGTG
GGAAAATTCGCCGCACGGAGGCCGAAAGCGAGAGGGGCTGCGCCGCTATGCCGGG
AGCTGAGTCCCATATAAGCCGCCCCCAGCCATCGCCCCCAGCCGGCTTCGTTCCCCT
GAGCGAGACAGGAAGCTGCGGTCCCGAGAAAGCGGAGGAGACGTCGCTGGAGCCG
GGAGGCGCCGGGTTCGGCGGAGCGCGGAGCGGGGCTCTGGGCCGCGTGAAAGTTTT
TCTTCCCGAGCCGCAGGGCGCCCGCTGCCCGGAAACTGCCCAGGGATAAGTCGGCC
GACTCCCCAGACCCCTCGAAGGTGCGGGGACCCCCAGCGGAAGCGAGAGGGAGCG
AAATCGAGGAACGAGTGACAGCCGGACAGTCCGCCGGGCGGTGATCCGGGGCCGCT
CCCGGGCGCGCCCTCGGCTCCAGGTGAGCGGAGGAACCGGGCAGAACCGAGGGTG
GGCGTTACTTAGGAGGAGGAGGCTGGGAGGGAGATTGGGGCGCATCCTCCTCACTCC
GCTTCCCCTCGCAGGTCCTACCCGGAGCCGCTGCCATGGGAGAGCCAGCCTTGGGCG
CTGGGGACCAGCCGCCGCGCCCGCCTCGGAGTCGCGCGCCCGAGTCCCGGCGCCAGC
AGCCAGCCCGCTGCGTCCCCTTCCCGGGCTGCAGGGCTGCCTCCGCCGCGCCGCCGG
CCCGGATTGTGCCTGTGATGAGCCGCAGCCCGCAGCGAGCTCTGCCCCCCGGGCGCG
CTCCCTCGGCTGCTCCAGGCTGCGCCTGCAGCCGCGCCGCGTGCCCTGCTCCCGCAG
TGGCCCCGGCGCCCAGGACGCCGCTGGCCCGCGTCCCCTCTCGGAATGAAGGTGTTC
CGTAGGAAGGCGCTGGTGTTGTGCGCGGGCTATGCACTGCTGCTGGTGCTCACTATG
CTCAACCTCCTGGACTACAAGTGGCACAAGGAGCCGCTGCAGCAGTGCAACCCCGA
TGGGCCGCTGGGTGCCGCAGCGGGGCAGCCGGAGGCAGCTGGGGGCGCCCAGGG
CCGCCTCCGGCCGGGCCGCCCCGTGCTCATGCCCGTTTGGACCTCCGCACTCCTTAC
CGCCCTCCCGCTGCCGCCGTCGGGGCGGCTCCTGCAGCCGCGGCA

-continued

| SEQUENCES |
| --- |

3:192409037-192410302 (SEQ ID NO.: 40)
GGCCAGCAGCACTGCAAAGAGAGCGGGAGGCGAGGGAGGGGGGAGGGCGC
GAGGGAGGGAGGGAGATCCTCGAGGGCCAAGCACCCCTCGGGGAGAAACCAGCGA
GAGGCGATCTGCGGGGTCCCAAGAGTGGGCGCTCTTTCTCTTTCCGCTTGCTTTCCG
GCACGAGACGGGCACAGTTGGTGATTATTTAGGGAATCCTAAATCTGGAATGACTC
AGTAGTTTAAATAAGCCCCCTCAAAAGGCAGCGATGCCGAAGGTGTCCTCTCCAGCT
CGGCGCCCACACGCCTTTAACTGGAGCTCCCCGCCATGGTCCACCCGGGGCCGCCGC
ACCGAGCTGGTCTCCGCACAGGCTCAGAGGGAGCGAGGGAAGGGAGGGAAGGAAG
GGGCGCCCTGGCGGGCTCGGGATCAGGTCATCGCCGCGCTGCTGCCCGTGCCCCCTA
GGCTCGCGCGCCCCGGCAGTCAGCAGCTCACAGGCAGCAGATCAGATGGGGATTAC
CCGCCGGACGCAAGGCCGATCACTCAGTCCCGCGCCGCCCATCCCGGCCGAGGAAG
GAAGTGACCCGCGCGCTGCGAATACCCGCGCGTCCGCTCGGGTGGGGCGGGGGCTG
GCTGCAGGCGATGTTGGCTCGCGGCGGCTGAGGCTCCTGGCCGGAGCTGCCCACCA
TGGTCTGGCGCCAGGGGCGCAGGCGGGGCCCCTAGGCCTCCTGGGGCTACCTCGCG
AGGCAGCCGAGGGCGCAACCCGGGCGCTTGGGGCCGGAGGCGGAATCAGGGGCCG
GGGCCAGGAGGCAGGTGCAGGCGGCTGCCAACTCGCCCAACTTGCTGCGCGGGTGG
CCGCTCAGAGCCGCGGGCTTGCGGGGCGCCCCCCGCCGCCGCGCCGCCGCCTCCCC
AGGCCCGGGAGGGGGCGCTCAGGGTGGAGTCCCATTCATGGGCTGAGGCTCTGGGC
GCGCGGAGCCGCCGCCGCCCCTCCGGCTGGCTCAGCTGGAGTGCTAGCTCCGCAGG
AAACTCGGGGCCCGGGCGAGAGCCACCGAGATGGCAGGTGGGACGCAGAGCCCGC
GGCAGCCAGAGTTCCTCCCGCACGGCCCGCCGACCCACGGAAGAGCGAAAGAGCGC
CCAGGTGGGGCCGAGCTGGGGGCCGGGCCCCTGGAGCGCTGGGAAGCACAGCGCG
CTCTAGTCAGGTTCCCTTTCCTGGAGCCCTCCGCTTCCAGACTCCCTTCTTTCCTCCCT
CCCTCCCGCCACCCCTCTCCCTCCTCTCTGTGTCTTCT

3:38039219-38039410 (SEQ ID NO.: 41)
GGTTGCCATGGAGACCAGGAGCTCCAAAACGCGGAGGTCTTTAGCGTCCCGG
ACCAACGAGTGCCAGGGGACAATGTGGGCGCCAACTTCGCCACCAGCCGGGTCCAG
CAGCCCCAGCCAGCCCACCTGGAAGTCCTCCTTGTATTCCTCCCTCGCCTACTCTGA
GGCCTTCCACTACAGCTTCGCAGCCCG

3:96813876-96814374 (SEQ ID NO.: 42)
CGGCGCTTTGCTTTTCTACAACTGGAAGCCGCGAAGGCGGCTACTGCGCTGA
GCCGCTCGCTCTGCTGGTCAAGTTTGGGCGACCCGCGCGGAGGAGGGTCGGGCTGA
CTGCCGCCGCTGAGCTGTCCCCGGACGGGAGCGCCTGTCCACGGCACTCACCCCCTC
CAGCGGTGGAAATGTGGAGAAGTAAGTGGGAGGCGGTGTCGGGAACTGACTCCTCT
TAAAACGGTCGGCGCCGCTGCTCTGAAATGGGCGGCTAAGTGCTTGTGGGACTAAG
GGCGGCCTCAGAGATGCCCGGAAAATCGCTGCCACGGCCAGAGTGCGGCGCAGACG
CGGCAGAGTTGGAGGTGTCCGCGGTGCAGGCTGCTGCCCACGCCGCTCAGGCCAGG
TGCTGAGGGCTCAGCCCGCGCCTCGGCCGAACCACTCTCAGCCCCGTTGAGCCACCT
CGTCCGCCCGGCTTTCATCGCACCGGCCAGAGGAAAGTTCCCGCGGCCCCCAC

4:143699944-143701144 (SEQ ID NO.: 43)
AGCCTCACAGTCTACGCCCTTGCCCCTGGGGAGAGGGGCCCCCACCGCGTCC
ACCAAGCGCCCGTACTTGGGCAGGGGGCCGTCCTCGTGAGGAAGTGGGGTAAGCCG
GCACCTGCGGGTGGCCGTGGCTCCAGACTTCAGGGAGGCGAAGTCCAGCACTCTCC
TGTCTATGGCGCGGCTCCAGCTTCGCAGCTTCTCCACTACCAAAGGCCTGTTACGCG
TCACCAGCTCCAGCTGGGAGAAGACCAAGTCCACCGCCAGCGTGAAGGGCAGCACC
AGAGTGTGAGTCGGGCGTCGTAGCGCAGCTGCAGCAGCACCCGGGCGCGTCCGGG
GCTGTGGGAGCCGAAGTGAGTGTACTGGACTTGGCGGGGCCCGAAGGTGCAGGGGA
AGCGGCGCGGGGAGAGCGCGCCCTTGAGCCGCGGCAGGGCGTCCAGTACCGTGACT
TCGCACCGGTCCCCCGGCTGCACTCCAATCACCAGATCCCGGAGCGGGTCGAGCCA
AAGGGAACGACCCAGGGGCACCCGGAGTCCAGGGTTGGCAATCAGCACGCTGGGG
CCGTCGGGGCGAGTGCCGTCAAGCGCACCCCGGGCGGGCAGGTAAAGCGCCGGGTC
GGGCTCGGTCCCAAGTGAGGATGCCCGTCCCTGCAGCGCGGGGCGACTCAAGAGCA
GGCAGGCGAGCGCCACAAGGAGCTGCCGGGGCGTCCCAGTCGGGTGCCGAGAAGC
CCCCGCCATGGCCACGGATGGCTCCTGGCGTTGGGATTCCCGGGGTGGGGTGCCCTG
TGCAAAGAGGGATCTGCTGAGCGGCAGGTGCAGGCAGTGGAAGCAGTAGCTGCTGT
CCAGTCGGTAGCCGACTTGCGGATCCAGCAAGAGCCAGCGGCTGCGCTTCGGCTGC
TGCAGGTAACGGCAGCGGGGGAAGGGGCTCTGCCCACTTCCTGCTCAGCCCCGGTC
GCAAGTCTCTCTCTGCTGGCTTCTGGGGACCCCAGATACGCGCCCAGCGCGGCGAGA
CTTAGCGAGGGTGCAGCGCTGTCCCCTCCGCTCCTGGGCGCTTCACCCAGCCTACCT
TACACACCTTCTCGCCGGGAGCCGTGGCCGCCGCACTGCTGCCCGCGCTGCCAGACT
CCGACCAGCTGTCTGGATACTCTCTTCCCCAGGTGCCACAAAGGGATTGTCCCTCAG
GGTTGGGAGAGAGACGGTGACTGTA

4:183904790-183906478 (SEQ ID NO.: 44)
CCCCCTCAAATAATTCAAGCCTTGGAATAGCACAGATTGTGTTAGAACTTCCT
GAATCCTAACCAGCTAGAATCCACTGGCTTGTTTTTGCGATATCAGCCTGTTAGAAG
CATATCCCTATAAAGATTTAATATCCCTGTCTCTGCATCTTGGCACCTGTGAATATGA
AACAACAGCATAAATATGATTTTGAACGTTGCATTGTCACAGATGAAAAAATGCAC
CAACATGTCAAATGCAGCGCTGAAAAAGGAAATCGGGCTTATTTTTGTCGTTGTTTA
CTGTACCAAAGCATTTTTGAAAACCCAAATCGAGGAGATAACCGTTTTTGAATGAAC
GGCAGTGCAAAGCGTGGTCGGGGTTAGCAGCAACGTGGCTGGGCGCCTTTAACTCG
GCGTGACCTCCGGGTCCCAGGCCCGCGTCCCGGGCCCAGCGCCCAGGCCCGGGCGG
CGCATTGGCCCCTCCTCCCCTCGCGCGCCGCGCGCATTGTTGTCCTTTAGCGATTGGT

| SEQUENCES |
| --- |

```
TGTTGGACCAGAAACAGCTGTGCAGAGCCGTGCCATCTAAAGAGCTGTGGACCTGA
ATGCAGCGTAGCGGGCTGGCGGTGACTTACACCGGGACTCCAGAGGGAGAGAGGAA
GCGCTGCAGGCCACTTGCATTGCGTCTTCCAGGCTGCGTGGACCCGGCGCCCCGGCG
TGTGCGGTTGTGGGGGAGCTCGCCGTGGCCTCCCCTCCCTCTGGCTTTAGCTTCCTTT
GGGGTTGGCGCAGGTGGGCCAGGCAGCGCACCGCAGATCTCCCCGTTCCCACGAAG
GCTGGCTCGCTGTCTCTCTCCGAGCGGGAGGGACCATCCTAAAAATATGTAAATATC
CAAGCGCTGGCTCCAGGCTGGGGCAGCTGCCAAGGTCCCCGCGCCGCGCCGGGTG
TTTTACATGAAAATGAGAAGCCTGATGGGAACCGCGTTCTAACTTAAGGCAGCCTGG
TGATTAGCATGAGACTGGGCGGCTGTCCTGCTTCCTGCCCTTCAATAGCCGTTCCGC
GCGCTCGCGCCGGAGCAGCGCTGCCGCCGCGCGGGGGTCGATCGCAGGCTCGGCGT
CCTTGGCAGCCATGGCTCCGGCGCCGCCTCGGCCAGTAAGTAGGAGCATGCATGTGT
AGGGGGGCACATGCGTGTCGGCGCACCCACCCAGCCATCCACCCGCGCGCACGCACA
GCGCCCGGAGCCTCGGCAAGGGGAAGATTGACGAGGCGCTGCAGTCGCGGGGACG
ACGCGGGCTCTTCCTGGATTCCGCAGGAGCCCGCCCGCCGCAGCTGCTGTCTGCAGA
GCCTGCTCGGATCCTGTGCACACGCGCCCCCCGCTCGAGCCTCTGTGATGAAGACTG
TCTCCCGGGGACTGCAGCGGAGGCAGAGCCAGCCAGCGCCGGGGACTGCGGGCCGT
GCGGCTGATAGGCCCGCGGGGACACGACTCGGACACTGTCATCCCCACGCCTCGCG
CTGAGCTGCCCGGCGCGGAGGGTCTGCCGCCGCCCCTCCGGCCTCCCGCACGCCCGA
TCCCGGGTCAGCCCCGGAGGCCTCGGCTGCCTCATTTGTTTGGGTCTTTTGTGCCGTG
GCTCCCAGTTGGCCAAGCACTCCTGCGCTGAATCGGGCCATTGTCTGCGCTCCCATT
GCCTTCACGCTGCAAGTCTCGGCGCCCCCACCCCGCCCGCCCCCTCCCC

4:20252431-20252893 (SEQ ID NO.: 45)
ACTGCGGCCGCCGCGTCAGGTGCAGCGCCAGGAGCCGGGCGGCGTCGCCAC
GCCGGCAGGGGTACCGCCACTGTGGCCTTGGGGGACGGAATTCAAAGCCTGGGAAA
AGTTGCTGCACTTTGAGAAGGACGAACCACTAGTGGGAGACCGCCGGGGGCCGGCC
GTGGCTCTGCGCCCTCCGGAACCCGGCTCTTGTTTCTTCTACCTTTGCCATCAGGTGT
CTGCCGCGGAGCTGCGGCTTATCTGGGAGACGAGCGGGGTTGACACGCGCGCACAC
ACTACTGCCATTCAGCTGCCGCCTGGCTCTGCCTGGAGTAGTGGATCCCACCCGCCC
ACCTGCCACCGAGCCATTCTCCAGTACGCCCCAGCAGGACGCTGACACCTCCAACCT
TGGCCTTTGCCTTTCCACTCCTTCCGGTCTGCCTGGTTTTTAAGTCCGCCCCCAGTCA
GTCCCCACTCAGTC

4:81030777-81031022 (SEQ ID NO.: 46)
ACTAAAAAACTCGGACCAGCCGCGCCGCAGCTGCTCCAATCCCTGGAAAAGG
CAATCGAGCGCCCTCCGGACCGCTGCGCACAGCCCCGGCTCCGACCTGGCGCCCAA
AACAGAGCTAGTCCTAGTCCCTCGCGCGGCCAGTTTGGCCGGGTGTTCCCAAAAATA
AAGCGAGGAGGGAAGGTACAGACAGATCTTGAAAACACCCGGGCCACACACGCCG
CGACCTACAGCTCTTTCTCAGCGTTG

5:179343982-179344854 (SEQ ID NO.: 47)
TGCCAGGCTCCTCCTCGTTGCCTCCGGGGAAGCTCGGGGTCCGGACCGGGGC
GGCCCTGCGGGCTCGTACCCCTGCTCTGGACGTAGCTGCCGACACCACGTGGGACAC
CAAGCGGCCCTGGGCGTCAGTGCGCACGGGCACCGCCAGGATGCGCTCCGCTCCGT
GCCCCAGGGGCCCGCCTGCAACGGGAAGGGGCGTTAGATCGGCGGAGACCACGGA
GCCCCAGTGCCTCAGAGACCCGCCGGCAAGCCACGCCCCCCCAGACCCCGCCCCAC
TGCGAAGGGAAGGGGCATTCCGCCAGGCGACCCCAGAAGCCAGCCTGCACCTCCCC
GGCTTTCCTGCAACCGGGAAGGGGCGTTAACAGGGCCACCACTCCGGGGCTCCGCC
ACTCCCCAGCCGTTCCCTCCTCCGGAGACCTTGCCTGCCAAGAGCTCTGCCCCCTGC
CCCGTTCAGGGTTGGGGCTCGGTGGGAACCTCCCCGTGCCCGAAGGGACGACCCCG
TCAGAGAGTCCCCCGACCCTTGCACCTACCGTCCTTGGCAGGACGTGGAGCTGCTCG
GAAGCCATTCCGGGTTGGCCCCCTTACCCGTGTGCCACGACCCCTCGGCGGGCCCCT
GCCGCCCGAGTGCCCTCACCGCCAGCCTCCGGAGCGGCGGAGTCTCGGCTTCCCCGA
GCACGAGCGGCCTGTCCTGCCTGTCCAGCTCCCGCTCAGCCCGCTGCCGGCCCCGTC
TCCCCGAGCGCCCGAGGACTGGGAGGGGTGGAACAGGGTCCCTCCGATCTCCGGGG
ATTCCCTGCGGGGCGCCCCAACCAATCCTTAGGGCCCAAGGCTACGCGCTCGGCAG
CCGGCTCCTCCGGAGCGTCCCCGGACGCGAGC

5:180353618-180354114 (SEQ ID NO.: 48)
CGTGGAAGCCGGGCAGGGCCCGATCGCGCTGTGCCTCCGCTTTCCCGTCTGT
GAAACGGGGCTACCCAGGGAAGCTCCCTCCCACGGGGTGCTGAGAAGTCAGACGGG
CCGCGTAAGGGGCAGAGCGAGGGGTCCGGCATCACTCGCGCGCTCCGGAAACCCGC
GTGAGCCGCTGTTCCTGCCGCGCTCCCATCTGAGTGACAGGCTTGTTTCAGAGCTCC
GCAGACCTCTAAGCCTGGCCCTCACCCTGCGTGGAGAGAACGCCCGGGCTTGGCGG
AGAGACGAGAAAACCGAGGCTCCCGGAGGCAGACAAGGACTCTGCCAAAACCGGA
CGCCGCGGCGGTGGCAGAATTCGACCCTGGGATTTGCCGCGGAGCCCGAGCTTGAA
GGCGAGGGTTCCGCAGGTTGTGAACGAAGCTGGAGGCGCCCCAGGAAGCCCCGACC
CCACCCGCGCCGAGCTGCCCCCTCCCCAGATCTGCCTCGCGCTGCAGGCCCGC

5:32711664-32712564 (SEQ ID NO.: 49)
GCCCAAGGGGGCGCAGGGACCTTGGAGAGAAGAGTGGGGAGGAAAGAGGA
AGGGTGGGTGGGGGGCAGAGGGCGAGTCGGCGGCGGCGAGGGCAAGCTCTTTCTTG
CGGCACGATGCCGTCTCTGCTGGTGCTCACTTTCTCCCCGTGCGTACTACTCGGCTGG
GCGTTGCTGGCCGGCGGCACCGGTGGCGGTGGCGTTGGCGGCGGCGGCGGTGGCGC
GGGCATAGGCGGCGGACGCCAGGAGAGAGAGGCGCTGCCGCCACAGAAGATCGAG
GTGCTGGTGTTACTGCCCCAGGATGACTCGTACTTGTTTTCACTCACCCGGGTGCGG
CCGGCCATCGAGTATGCTCTGCGCAGCGTGGAGGGCAACGGGACTGGGAGGCGGCT
```

-continued

---
SEQUENCES
---

TCTGCCGCCGGGCACTCGCTTCCAGGTGGCTTACGAGGATTCAGACTGTGGGAACCG
TGCGCTCTTCAGCTTGGTGGACCGCGTGGCGGCGGCGCGGGGCGCCAAGCCAGACC
TTATCCTGGGGCCAGTGTGCGAGTATGCAGCAGCGCCAGTGGCCCGGCTTGCATCGC
ACTGGGACCTGCCCATGCTGTCGGCTGGGGCGCTGGCCGCTGGCTTCCAGCACAAG
GACTCTGAGTACTCGCACCTCACGCGCGTGGCGCCCGCCTACGCCAAGATGGGCGA
GATGATGCTCGCCCTGTTCCGCCACCACCACTGGAGCCGCGCTGCACTGGTCTACAG
CGACGACAAGCTGGAGCGGAACTGCTACTTCACCCTCGAGGGGGTCCACGAGGTCT
TCCAGGAGGAGGGTTTGCACACGTCCATCTACAGTTTCGACGAGACCAAAGACTTG
GATCTGGAAGACATCGTGCGCAATATCCAGGCCAGTGAGAGAGGTGAGCAGGGGCG
CGTCCC

6:123803544-123804226 (SEQ ID NO.: 50)
CGCCGCTGCTGGGACGCGGCGCGGACCCGCATCATTGCGCGCAGCAGCCGCT
GCAGCAGCCGCCGGGGACCGCGGAGCCGGGACGCCCCCGCTCGGCCCGCGCCCCGC
TCCCCGCCCCACCCCCGCCCGCCGGGCCCAGCAACGCAGGGTGCCTAGGAGCCGCG
GGCTGCGCAGGGAGGCGGGCAGCGGCCCTCGCGCGCTTCTGCCGCCCCCGGAGCCG
GCGCGCGGCGAGCGCAGGGCGAGCGCGCGTCGGGCGGCGGCCGCGCTGGGGGGCG
TGAGGCGAGCGGCGCGGAGAGCGGCAGGGGCGAAACTTCGCGGGCCAGATGCCCG
AGGGCGCGGCGGCGCTGCCAGGCTGCCGCTGCTGCCCCTGCGGGCCCCGAGCGCGC
CTCCGCAGGCGGCACTGCCCGGCGCGGCGTGTGCACCGAGCGAGTGAAGGTATG
TGTGGCGGGCGCGGCTGGAGCTGCCGCCGCCGCCGCCGCCGCGCCGCCAGCAGGTCCTA
ATGCCTGTCACTTCCCAGGACGCTGGCAGCAGCAGCAGCCCGGAGCCCCCGAGCCC
TCGGCAGGTTTGCGTGTCCTTCCCCGCGATCTGATTGGATAAAGTGGGGGCTCGACG
GTGGCCGACGTGGGACAGTCTGGCTGTGGCAGGGGTCTCGGAAACCATGGGTTATT
GCAGTGGCAGGTGCAC

6:163413181-163413961 (SEQ ID NO.: 51)
AGGAAATTCTTCCAAACAAGTCTAAATGTTGGAAATCCACCAAACTGCAGAG
AAAGACCTCTTGCCTCCGTATTCTTTCTTCATCTGTAAAAATGTTGACTTCTGCTTTTC
AGACTACGCGCACAGCCTCTTTATTTCCTACTGCGGCTTCATTCCCTCACGGAACACT
GACGCCATCGCGAAGGAAGCATTTCGAGCACGACTGACGCTCCCCTTATTATTTGCT
AAGCCGCTGCGCTCGGGTCTGGCTACGATTTGCTTTCAGAATAACGGGAAGGTGCAA
CAAGATCGCTTCCCTAGAGGCGCGTCGCCCGCGTGGCCCGGACCCCCCACGCCCGCC
CGCCGCCCCGTGGGTGCGCACGCGTGTCCGCGCAGGCTTCCCGCCCTGGCGAGTGCA
AGGCTCCTCTCCGCCGTGCTGCTTTCCAGCCTCTCAGCAAATCACGAACACCGAAAG
AAGCCACGGCGGCGACGGGAGGGGCGTCGCGCGTGCTTCCCTCGGCGACAAAGCGG
GAGCCGGGCGCGCCGGCCGAGGGCGCCCGGCGCAGAGTCCCGCAGAGGCGGACGC
CGCGGCCACGCGCCTCGAAAAGCCTCAAACTCTTATCCTCGGCTCTCCCGCCCCCACCT
CCGCCCCGCAGCCAAGACCCGCGCCGTGGCGGGCCCGACGGCCAAGGAAAGCCCAC
CAGCCCTCCGCACCGTGGGCGACGGGCCAAGACCCGGCCCTAAACGGCCAGACCCA
GCCCCTAGTCGGCTGCCGCCCCCGCCCCACGCAGGCGCGCTCCGGGGC

6:31815355-31815955 (SEQ ID NO.: 52)
AGAGTTCTGAGCAGGGGGCGGCACTCTGGCCTCTGATTGGTCCAAGGAAGGC
TGGGGGGCAGGACGGGAGGCGAAAACCCTGGAATATTCCCGACCTGGCAGCCTCAT
CGAGCTCGGTGATTGGCTCAGAAGGGAAAAGGCGGGTCTCCGTGACGACTTATAAA
AGCCCAGGGGCAAGCGGTCCGGATAACGGCTAGCCTGAGGAGCTGCTGCGACAGTC
CACTACCTTTTTCGAGAGTGACTCCCGTTGTCCCAAGGCTTCCCAGAGCGAACCTGT
GCGGCTGCAGGCACCGGCGCGTCGAGTTTCCGGCGTCCGGAAGGACCGAGCTCTTC
TCGCGGATCCAGTGTTCCGTTTCCAGCCCCCAATCTCAGAGCGGAGCCGACAGAGA
GCAGGGAACCGGCATGGCCAAAGCCGCGGCGATCGGCATCGACCTGGGCACCACCT
ACTCCTGCGTGGGGGTGTTCCAACACGGCAAGGTGGAGATCATCGCCAACGACCAG
GGCAACCGCACCACCCCCAGCTACGTGGCCTTCACGGACACCGAGCGGCTCATCGG
GGATGCGGCCAAGAACCAGGTGGCGCTGAACCCGCAGAACACCG

6:391674-392694 (SEQ ID NO.: 53)
AGGCCTCGGCGCCCCGCCCCGCCCCAGGCCCCGCCCCAGAGAGTTCTATAAA
GTTCCTCTTTCCCACCTCGCACTCTCAGTTTCACCGCTCGATCTTGGGACCCACCGCT
GCCCTCAGCTCCGAGTCCAGGGCGAGGTAAGGGCTGGAGTCGGGCAGGAGGAGGG
GTGTGAGGCTGATACCAGAGAGGACCCGGAGCGCGAACCAGAGGTTCGACCTCCAG
GGCAGCGCAGGGTACCCGGCTTCGGAGCGGGAAGGGAGCGCGCCCCGTCCTGGAG
CTCCGACTCCCACCCCATCTGCGCTGAGCCGGAGGCGCTGGTTTGGGCTCCAAGGCC
CGCCTCCTTGGCTCTGCCCGAGCCTCCCCGCCTGCCCTCCGCGCTCCTGCGACGGGG
TCGCCACAAGCTGGACGGGATGAGCTAACCGGACTGTCGGGGCCCCAGGAGTGGCT
GAGGCGGGGCCGTCCAAGGCACCCACACAAGACGGCACAACTGCCTGCGAGAAAC
AGGCCCGGCCCTGTGGACCCCAATCCGAGGCTCCTTCCCCTGCTCTTCGTTCCTAAG
GGGCCCAAGCTCACGGCGGCCTCCGGCGCGGTGCTCACCCGCTGGCGCAGGAGGAG
GAGGAGCTCCACATTTGGGTCGCTCCGAGCCTTGCGTGCGGTGGCCTAGCCGGCCTG
GCGCGGTCCCTGCCTCCCAGGCTCCGCAGCTGTCGTCGCCCTCTCCCGCGCCCTCCC
CGCCTCCGCTCTCCCGGGCCTGCTCCGGGGTCCGGCGGACGCTCTGCGCGCGGAATC
CCCCGTACTGGGGCTGCAGCCCCCGCGTCTGCGCCACTTGTCGTTTGCAGAGCCCAC
TTAGTGCGCGCTAGCTGGGCAGGGATAGGGGTCCTATTCGGGGCGAAGGGTCTGGA
TGCGAGCAGAGAAAGCGGAGGGTGGAGGAACCCGGGGCTGCGCCCCTGGAACGCC
CGGCCGCAGGCGAGGTCCTCCGCGCGTGGAGGCCGCCAGGGGAGTGGAAACTGACA
GAGTCGCGGGG

-continued

SEQUENCES

6:72621373-72622257 (SEQ ID NO.: 54)
CTGGAGTGAGGCGCGGGAAGATGCCTGGTCCTTGCCTCGCGGACTTGGCAGC
CGCGTCCTGCGGGTCTGTCCACTGAACTGCTGAGGACTCGCCCGTGTGCGGGGACCC
GAGTGCCACTTCCCGGAGCGTTACCTTGCGCTCCAGCCTCCAGGCTAGATAATACCT
GGAAGGCAGGGCAGGGCTGTTCCCGCTCTCACCCCTTGCGGAAGGATGGCAGGATC
CGGCGCAGCGACGTAGCAGCGGGAGGGCACAGCGACCTGCATCTCCAGTTTCTCCT
CAGGACACAAGGCTGACTTCACCTTCCGGACAGCTGCAAAGCCCCTGCCAGAACCA
AACCGAACTCGCGCCTCGGAGAGGGGCTTCTGGGGCCGTTTCGCTGCAGGGCGTGG
GGAGTGGAGAGAGGGAAGGGGAAGCCTGGGGCTGGGTGTGCGCGCGTGGGAGCGC
GCCTCGGAGCGCCCCGCACTCCCCCACTCTATCCCCGGGGGCAGTTTGGGAAGGAG
GGAGTGGTAGTCGCGGGAATGAGGGAGCAAGAGAAACCCTCTCAAAGTGACGCCCC
AAACAGGTCCGGATTTAGAATTCGAAGCTAAAGGCTGTTAGAAATTGGGACTCCTC
GGCCTCCTCTGCAGCCCCTCCTTTCCCGCCCCGAAGCCCGGGCGGTTTGCTGGCTGC
CTGCTTCCCCGCCCCCGGCTCAGAGGTCTCTGGCTGGCGGGCGCCCCGTCGGCCGCC
GGCTTCCTCCTTGAAACCCGCCGGCGCACATGAGGCCGCTGCCCCCGCCGCAGGCGC
TGGCCGGCCCCCTCGCGGTGCCCGTGGTGATGCCATGCCCCGCCACCACGCGGGAGG
AGAGGAGGGCGGCGCCGCCGGGCTCTGGGTGAAGAGCGGCGCAGC

6:72622261-72623373 (SEQ ID NO.: 55)
GGCGGCGGCGGGCGGGGGGCGCTTGGGCAGCGGCATGAAGGATGTGGAGTC
CGGCCGGGGCAGGGTGCTGCTGAACTCGGCAGCCGCCAGGGGCGACGGCCTGCTAC
TGCTGGGCACCCGCGCGGCCACGCTCGGTGGCGGCGGCGGTGGCCTGAGGGAGAGC
CGCCGGGGCAAGCAGGGGGCCCGGATGAGCCTGCTGGGGAAGCCGCTCTCTTACAC
GAGTAGCCAGAGCTGCCGGCGCAACGTCAAGTACCGGCGGGTGCAGAACTACCTGT
ACAACGTGCTGGAGAGACCCCGCGGCTGGGCGTTCATCTACCACGCTTTCGTGTGAG
TACCCGCGCCCCCTGCTATGCCCGCTGCAGGGGACCACTGTCCCTGGCCCCCTGGGG
CGTGCTCCGCGCTCGCGCCCTTGGGCCCCGCGCGTGCACACGTGGTGGCTTTTA
TTTCTTCGCACGTGTTCGTGGTCTTCCTTCTGGAGCCTCTCCCCTCCCCCAGCCCCAC
TTCTCTCATCTCTACAGCTTGAACCTTTTCCCCGAGGACACCCAATGAACTGCCCGGT
AGCTTCAGGCTCCCGGGGCGAGAGCCAGGCAGACGCGGGACTTAGGCTGCGCGGAT
AATTGGGAGCAATTAGGTCCCAAGATACGTAAACTTCAACCGAACGGGGCGCCCGG
GAGCTAGGGAATGCAAAGGGAGGACAGGCGCCCGTGTGAGGCTTGAGAGTATACTG
GAGAGGTTAGGAGGTGATGGCGGGGTAGGACGGGGAGAAGTGAGGGGGCATCGAG
GGCTAGGTCCTCAGTCCTAGGGGCGGAGTAGGGGAAGCTGCTACTTGGAGAGAGCT
GCTAGGTTTTAAGCGCGCCCGGAAACACGCCTCGCCACCACCCAGCCACCACCAAC
GGAAAATCTGTCAGTGCATGTAGCCCTTCCTGCCACGGAGAAGGTGGCCAAGGTCT
AGAGGAGGCCAGCAGGCCAGGCGAAGCAACGCTCCCGCGCTGCAGGGGGCGGGGA
GGCAGCGGGGAACCTGGGGCGCAGGAACGCGGGCGGAGGTGCGATAGCAGAAGCG
CAAATGGGTCGCCTCTGACAGAGATCGGGCAGTGGGTTAAGTCCCCGTTT

7:103989079-103989646 (SEQ ID NO.: 56)
CGCTGGCGGGCGCACCCGGCGGCGGCGAGCGCGGAGGTGCTGCGGTACCTA
CCATGGTATTCTTGTCCCGGAACGTAGTAGGTGGGGTTGCCCGCAATATGCAGGGAA
ATGAGCACCTCGCCCTGCTCCCCATCCCCTTCCAGCTCCCCGTGGTGGGTGCACAGG
AAAAAGAAGGGCGAAAAGCGGGGGTAATAGCCAGCCGCCGCGCGCGCCCTCAGCG
TCGCCCCCAGCAACAGCGCTAGGAGGAAAGTCTGCCGGGCCCAGCCACTGCGCTCC
ATGCCGCCGCCGCCGCCGCCGCCGCCGCGCCCTACGCGCCGCTCGCTCATTCAGT
TTTGGAGACGCCGGGACGGAGGAGCCACGCGGAGAGAAGGCGAGAAGAAGGCGGA
CGGGAGCGGAACGGGCTCGGGGAGCGGGCCTGGGAGCGGGCCCCCGCCGAGAAGTT
CCGCGGGGAGACGGCGGCTCCCAAAGTTACTTTGGGCGCGGGAGCGCGGGACCGGG
GCTGCGGGCGCCGAGAGCGCGTCGTCTGCCGCCTCCGTGCGCCGCCGCCGCCTCTGC
GCGACGCCCCTC

7:141073222-141073810 (SEQ ID NO.: 57)
CGGCGCTGGGAAGAGCTGCGTGACGCTCGGGGGCTGGCGGCTGGGCCGGCA
GCGCGCCGTGGCGGCGTGACCTGTCCATGGTGTTGAAGGCGCGGTGGGCCGGAGCCC
CTAGCGCCGCGCGCAGTGAGCGCTGCCTGGTGCACCCTCCGCCGCGCAGCCCGCCCC
TCGCGTCCGCCAGCAGCCGCCCAGTCTCCGCAGATCCCAGGCCGGGTCTCGTCCGGT
AACGCCGCCCGGGTGAACACGCTGTCGGCCCGAGGGGCCGCCTGAATGGCGATGCC
AGAGGCAGGGCACCGGGGAGCTCGCGGGGAAAGGTCGGCCGAGAGCGTGCGTCCG
CGGGGAGTGCGCCTCTGAGCGCAGCACGCGGGTCAGAAGGAGCAACCGACCTGCTG
GTGACCAGAGAACGGAGATTTTAAGAGGACCCGACCCAAAGAGGAAGAACATTTCT
GGGTGCGCGCCCCCAGGTCTTTGCTTGCAGACGGGGAGGGGGAGAGGCTCTGAGCCA
GAGACCCAGGAGGGACTCCGAGAAGCCGGCCCCAGCACCTGGAGGTTTCTTTCGCC
CGCCGGCCGCATCCGGGGCGTTCTACTTCACCC

7:141074279-141074546 (SEQ ID NO.: 58)
TCATGCCCATGGTGTAGCCGCCAAGCGGAGGCATGGCTGCCGGAAGGTTACT
GCTCTACACTGGCCTCTCGCTAGCGCTCTGCGCCCTCGGCATGCTGGCCGTGGCCAT
CTGCTCGGACCACTGGTACGAGACGGGACGCCAGGAAGCACAGGGACCAGGTGCAAG
GCCTTCAACACCCGCCGGGTCGACCCCGGCTTCATTTACAACAATAACAACAACTTG
CCGCTCCGGGCGAGCCGCTCGCGCCTGGACCGCTGGGAGGGCAAACT

7:151409258-151410098 (SEQ ID NO.: 59)
GCGCTCAACAGCCAGATGCTGGGCCCAGACAAGCGCTCTTCCGCTAGTGTGC
CGGGATGAGCGGGGGCTGGACTTCTAGAAAGGGGTCTGCGGGCGCAGGAGCTGGGG

-continued

| SEQUENCES |
|---|

```
TCCGCGGTCTGGGGCCGGTGAGCTGCGGCGAAGAGGTCAGGGAGGGAGTGGGAGG
GTCTACCTTGCAGGAGCGCGCAGCACTGGCCGTCCGCGGTGCTCCAGAGCCGGGCC
GTGCCGTCCTCGCTGCCCGTCAGCAGGCGCTGCCCGTCGGGCGTCAGGCTCAGCCAG
TTGATGCCCCCGCGGTGGTCGGCGCAGACCCTCAGGGCCGACCCGCCGCCCCCCATC
CCGCTGGCAGGGCGGGGAACAAGAAGGAGCTGCGCCCCGCTAGGGAGGGGCGCCC
CGGGGTCCGCGCGGCGGCTCCGTACGACTGCGGCCCGCGGCCATCGCGGGGAACGG
GGAGCCCGACTCCTGCGGAGGCACGCGGCGAGGGGAGGGTGAAGGACCCTAGCTCC
CCGCTGCCTCCAGCCTCTGGGCCCGCGAACCCAGGGCGCTGCGGGGGCGGCCCAC
TCGGGACCTCCGCCCTGGGTAGAGTCCTGGGCGCGCGGGCAGAGAGAACCCCCTTC
CCAGCACCGCTCGGAGGATCCACACCCCACCGGGCGAACAAGGCAGCTGCGTCTCT
GGTGCACAAGGAGCCCCCGCCTCCTCTCGCGCCCACGGGGCTGGGGGGGGGAGAG
GAACACGGGAAGCCGAGCGCCCCGCGCCCTCCCCGGCCGAGCGCGGAACAATACGG
TCCAGCCTGGCTCCTCCTCAGAGACCACCCCTCACCCGATCCCCTCCCACTTCTCGG
GCTG

7:153886164-153886404 (SEQ ID NO.: 60)
TCTATCAGCTCTGAATCTGGTTTTTCAAGTGGCTTGGGTGGGTCTGCATATGA
ATTTGACCAACCTCTGCGCGCGCTCCTGGGAGCGCGCATCTGTGTGTGGTCCAGGGA
GCCAACCGCGTTTGTGAATGGATGATTGATGGGAACAGCGCCCAGGGGCAGCAGGT
GGAGACGGGAACCCAGGTCGCGGTCACTGGTCAACCCGCCTCTTGGGGTGGAGGTT
AGAGAAATGGGCGCTGGGA

7:157336370-157336577 (SEQ ID NO.: 61)
CGTTTCCTTCAGTCACTATTCCCTGGCGAAGTCTCCACGCGCTCCCGTTCGCC
GGGGAACTTAGGGTATCCGGGCTTCCCTAAATTGACAAGCGGGGGCCGGCGCCTTC
GCCCGCCTTCGCTGGCCGCCGCTTGGTTTGTTCTTCTTCTCCTTCGGGGACTTCTCCG
CCCGCGCCCGCGCCCGCGCCCCAGCTTTCGTCCCGCTGTGC

7:159144190-159144938 (SEQ ID NO.: 62)
ACAAACTTATGAGCAGTTAGTTCCTCCAGTGCCCTTGGGAAAAAGCAACTAT
TTCCAAAAGGAAACTTTATTTAACCGACGCCACGTCCCCCCGACACTAAAACTAACC
AGTAAGTACAGGGAGGGACCGAGAGGCATCTGCGGCCAACGCCAACCCCGATCTCC
CCGTGAAACGCGCAGCCCGCGCAGGCGCCCGCAGCTCCCAGCTCCCGGGACGGCCC
CGAACGAGCTCATCGTTGACGCGTCCAGGAAGAAACGATCCCGTTTCCAGCAAACC
CCGGACGGTGGGGCGCGGGGAAGGGCGCAGGCAGCCTCCCAACCCGAGTCCCGCA
ACCCGGCGGGACCGGAGCTCAGCGCTTCACGCTCTCGGGGAGGAAGCTCCGGACCC
CGGGCGACCCCGCTCCCTCTCCCGGACCCCGCCCGCGCTCCAGCACCCGGGAGGAA
GGCGAAGACCGGCGGGAGGAGCGCTCTTCTCGGAAGGGGAGAACCGGGTCCGAGG
CGCCGTGGGGCGGGGGTCGCGGGCGCACTCACGGGGGCGAGCAGCCAGCAGGTCA
GCAGCGCGGGAGGCAGCAGCGTCCGCATCCCGAGCTCAGCGTGCCGGGGGCCGCCC
AGCGCCCGCCGCCTCCGTCCTAGGTCCCCGCGGTTCCGCCGCTCCAGCATGGGCCG
GGAGCGAGTGCGCGGAGACCTCGGGCCCCGCAGCTGTAGCCGAGCGCCCGAGCGCG
GGGGCCGCCCCCTCCGTCCCGGCAGC

7:19117486-19118112 (SEQ ID NO.: 63)
GGGGGAGGCGGGGAGGGAGGCGGGAGGGGGAGGGGACGGTGTGGATGGCC
CCGAGGTCCAAAAAGAAAGCGCCCAACGGCTGGACGCACACCCCGCCAGGCCTCCT
GGAAACGGTGCCGGTGCTGCAGAGCCCGCGAGGTGTCTGGGAGTTGGGCGAGAGCT
GCAGACTTGGAGGCTCTTATACCTCCGTGCAGGCGGAAAGTTTGGGGGCAGCAGTG
TCATTGGCCTGACGTGAGGAGGAGGGACTTTTCGAAGTTTTATAGGAAAGTTTCCGC
TTTCCAGTCCCCCTCCCCCGTCCCACCTCCCTTCCTCGGGGTCTAACAATTCGTCCTC
CCAAACCATTCAAAAACGACCTGGCCCGGGCGGCCGGCCCCTCCACCCGCCTCCTA
GCCGCCCTCCCCCTTCCCTCCCCGTCGCCTTCCTCCGGCGGCGCGGGGCGATTTCCT
TCCCCGCCGGAGCGTGCGGGCAGCGCCCCCGAACCCTAGCGCAGCCCAGGAAGCGG
TCGGAGGAGACTGTCCTGGCCGCGGTGGCAGCCCCATCCGGAGTGGCTGTGACAGC
AGCAATGGCAACAGCTTCTACACAGTGGGTGATGTCTCATCTCGCCCAAGAGCCCTC
TAGGTCCGTGG

7:28409622-28410342 (SEQ ID NO.: 64)
GGGTGATCTGTGTTTGTAAACATTTTGGCGGACCAGAGGGAAGTCCGGCCCC
GAGTGCTGGTAGACTGTGGAATTCGGCTGTGTCCTGAGGCCACCCTAGAGACCCCGC
GCCGCGTGAGTGCCGGAGCGCTCGGTGGCCGCCGCGCCGCGCGCCTGGAGGGATGC
TAACGTGGAGCCGGCGCCGAGTCCGCCCGGCGTGCGTGCGTGTGTGGGAGCGCGCG
AGTCCCCTGACGCGGGGACCAGTTATGAATCGGGGGTGTGTGTTTGCCTCCAGAGAC
CTGGCAAGGTGCGGAGCCCTCCAGAAGTGCGGTCAAGCGGCAGCGGAGCAGGCGA
GCCAGGAACCTCCCCCCGCGTCCCCAGCTTCCCAGCGTGGCGGCGGAACCCCCCGGA
GAAAGTTTGCAAACTTCCAGCGGGCGCGGCGAGGACGCCGGGTCACCTAGGGGGCG
GGTGGGCGCGCGCGCAGGGGGCTCGCTCTCCCCGGTGCGGAGCTGCAGCTGCCACC
TCTCCCGCCGGGCTGCCGGCTGCAGCGGGTGGGCGCGCGCCCGGGGAGGGGAGGTC
GCCCTCGGAGGGCGCTTGGCTTTCGCTCCAGGCGCTCCGGGCTGGAGAGCGGCGAG
GCTCCGTCCGCTCCAGTCCACTCCTCCGGCCGCCTCCTGCCTCCGCTGCTTTCTTGCT
GGCATCGTTACCTCTTCCCGGCCGCGTGCCCCAAATGACAGCTCCGGCTCG

7:37448742-37448854 (SEQ ID NO.: 65)
ATTGAAGGGGAACTGGAGGCTCTGTCGCCCAGCGTGGGGCCGCGGCGGCGTG
GGTGGCTCTGCCTCTATCCTGTGCCCATCCTCGCCCGCTCCCGCTCGCCCCAGCACAC
GCA
```

-continued

```
                         SEQUENCES
```

7:38630658-38631461 (SEQ ID NO.: 66)
AAAGTGTGTATATCTAGATCTCTGTTTTGAACTCCAGAACTCACCAGACAGCA
CTGTGTGATCACGATCCTACCCTATTGGTCCTGGGAGATTTTTGGTGGCTTCTCTGTT
AAATCGTTCGTGTCTGCTGCACTTAAGTAGCCACAAAATCCCCCGCAAGAAGGAAG
GCTGCTGCAATCTCCCGCCCCGATCTGCGGGCCGCGTCCCCGCGAGCTGCCTGCGGG
CGCGCTGGGAGCCGGCCCGGGGAGATGCGAGCGCAGGGAGATGCGCTCTGCTCCGG
GCGCAGCGGGCAAGCTGCCGCACCTCCTACTTCTGTTGCCTGGCTTGGGGCCAGGAG
AGCGGCAACCCGGGGCCGGCTCCGGAGCTGGACATATCCGGCGTCTCCGGGGCCAG
GGTCTGCGGGTCCCCGGCGCTGCGTCCTCCCGACCCGCTCCCCGCGGCGCCCGGGTC
GCGCCTTGCGGCAGTCACCGAGCTGAGGGCAGGGCGTCCCAGCGTCCCTGGCCCCG
GCCCCGCTCCGCAGCGCGCCGCACCCCGAGGCTCGGGCCCCGCACAGCTGCAGCCG
GTGCCCTCCGGCCAAGCCCCCGCCTGGCGTCCCCGGCCCCAGCCCCGGCCGCCCGCC
GCTGACCTTTTCCTGCGCGCGGTTGAGTCGCTTCTGGACGTTCTTGGCGAAGATGCC
CGTCTTGATGTCGGCCATGGCTGCGGGTCCGGGGAGCTGCGAAGAGCAGAGCGCGC
AGCGGGGCTGGCGGCGGCGCGGAGGAGCGGGAGGAGGAGCGGGAGGAGGAGGAG
AGGGCCGAGCAAGGGAGG

7:43112316-43113632 (SEQ ID NO.: 67)
CACAGGGTACCCGCCTAGAGTGTCTGTACCGCATCCTTTCTGCTACACTGTTT
GCACACACACAAAAGGGCCGAGGAGCCAGGGTTGGTGTTGGATATGCCCAGTACGC
GTGCTGGGTGTTGGAAGGATGGGGCCGGCGGTAACAAGAATCGATATATATTTACC
GCGGGGGGGGGGTGGGGGTGCGCGGAGGCTGCAGGGCGGGGCAGCGCTAATGAG
AGCAAGCCCGGCTTGTGGTTGGTTCTGGAGTCTGGTACCCACAGAGGAGCAGGCAG
GGAGGGAGGGGATGCAAGCGGGAGGATAAAGCGATGAAGTGTGCTGCGTTACCGC
GCATCAGGCGCTGTTGTTGGAGCCGGAACACCGTGCGACTCTGACCGAACCGGCCC
CCTCCTCGCGCACACACTCGCCGAGCCGCGCGCGCCCCTCCGCCGTGACAGTGGCCG
TGGCCTCCGCTCTCTCGGGGCACCCGGCAGCCAGAGCGCAGCGGAGAGCGGGCGGTC
GCCAGGGTCCCCTCCCCAGCCAGTCCCAGGCGCCCGGTGCACTATGCGGGGCACGT
GCGCCCCCCAGCTCTAATCTGCGCGCTGACAGGAGCATGATCTGTGCCCAGGCCAG
GGCTGCCAAGGTAAGCGGGCGTAGCGCGGGGACACTGTCTGCCGCCCCTTCCCCCC
CGCCCTTCTCTGGGCGGCTTCCCCGCCGCACGCGAGGCCCCGGCAGCGCCCTCCCTT
CTCGGGGCCGAGATCCACCCTCCTCCCCACCCTCTCGCTTCTCCCGCGAGGTTCAATT
GTCAGCCTGGGTCGCGCCGCCGCCCGGTCCGGGCCGGCATCCCCGGGTGGCGACCC
CGGCTTGGGTACTGCAGGCGCACCCGGCCCTCCTGCGGGGTACGGAGAGAAACAAA
GAAGCCCCCAAGCGGGTTCGCAGCGCCTCCCCCGCCCCTCAGCGCCCTCCCAGTGGC
GAGGAGGTGTCAGGGGAGGGGGCGGAGAGACCTACGTAATCCCCCTTCCCAGCCCA
CACCCACCCCTTGTGAACCAAAGCTCTGGATTTGCGCTTCGCCTTGGGCTCGCTTTTG
AACAATTGTGTCCCATGCAATGCCCGTGGTTAGCCCAGAGAGCGCCCAGAGCCTCC
GCACGGGCTCGCCGGTGCTCGCTCGAGGGGCGCGTGGCCAGGTCCGGCCCTTGCTCC
CATGGACGGGTGCAGGAGGGGAGGAGGCGCTGTGTGGGTGCTCCCCCAGCGCCTCC
CTGTTACCGGCCGGCTGCGCCGCTCAGCCGGGCCTGCCACCTGAGTTTTAGCGGGAG
CAGTCATGTCGCCTACCGTATTGCG

7:50304073-50304411 (SEQ ID NO.: 68)
CGGCGCGGGCGAGCGGGCTGCAGCCGGCGGCGGCGCCAGCAGGTACGGCCC
GCACCCGCCGCCGCCCCGGCGGCCTTTGGGGGCTGAGCCGGAGCCCGGCGCGATTG
CAAAGTTTTCGTGCGCGGCCCCTCTGGCCCGGAGTTGCGGCTGAGACGCGCGCCGCG
CGAGCCGGGGGACTCGGCGACGGGGGGGGACGGGACGACGCACCCTCTCCGTGTC
CCGCTCTGCGCCCTTCTGCGCGCCCCGCTCCCTGTACCGGAGCAGCGATCCGGGAGG
CGGCCGAGAGGTGCGCGCGGGGCCGAGCCGGCTGCGGGGCAGGTCGAGCAGGGAC
CGCCAGC

7:50304762-50304947 (SEQ ID NO.: 69)
GCAAGCCCCTGGGTCCCCGCGCGGCGCATCCCAGCCTGGGCGGGACGCTCG
GCCGCGGCGAGGCGGGCAAGCCTGGCAGGGCAGAGGGAGCCCCGGCTCCGAGGTT
GCTCTTCGCACCCGAGGATCAGTCTTGGCCCCAAAGCGCGACGCACAAATCCACGT
GAGTGTTTTCAAATTGAATTTCA

7:93889427-93891122 (SEQ ID NO.: 70)
TCTTTCAAGTTCAGTAGAAAGACTCTCTGTTTTCTCTGGGTGTTCTCTGATTGT
ACATATGCAGTGAATCAAAGCTTATTCACATGAATACGCATTTTCCCCTGGCTCAGT
TCCTTGAATGGAAAAGCCCCATGTTCTCTTACAGGCCTTAACCGATATAATTTAAAA
ATTAAAAATAAATTAAAATATAACAGTATTATGAATCTCCACCATGTCCCGCAACTA
ATCCAACACATGTTTGGGTATCGGGACAAAAGTAGAGTTATATAATGAGCTAAGTC
ACACTTCAATAATAAAATCCACTAAAAATATTTCAGATTGATGGATAATCGACAGAA
GGAAATGATGTACTCCAGGAGAGATAAAAATCATAGGTTTGGAATTAATGAAAAAT
ACAGAGAAGCACTTACGTTGTACCTAACACGTTATTCTCTTGCATTTATTATACCCCA
TGGTGAGGGAACAAATCTTTCCCTGAGTCCGCACAGGCACTGAATTATGATCAATGT
CAGTTGGGAGACAGGAAATGTGTTAGTGGTTGTAAATTTGTGATTACTTTTAAGAAA
CTGAAAACCATGAGGTTTGCTTAACACTTGAGAAAACCCAGGCTAAAACTTCCTGTA
GAAAGCGAGACGTGGGAAACTGGCGAAGCTGCTACCAGCCGCCGGCGCAAGGAGC
GCGAGAGTCCTGGGTGCGCGCAGGGCACTTACTTTCTATCCTCCAGCAAGCATCGTC
GCAAGCCTCCCAGGTGTAGAAATTGTTGGCGTTGCCCTCGCAGCCCCCGTACAGGAA
CTGGCGGCAGCTCTGCGTGTACCTGTCGTAGTAGTAACGGAGAAGTAGGGCCCGGC
AGGGTCCGTAGTCTAGGGGCAGGAGACAGATCTCCGCGTTATTTCCTGAAGAAGGG
GCAGAAGGAGAGCAAAAGAGAGGGAAAGTGGTCAGGCGTAGCTCCTAGGAGGAAA
```

-continued

---
SEQUENCES
---

```
GAACATCCCGGGGAGTTCTGTCCCCTTCCGAGCGGAGGGGCCTCTGCAGAGAAAGT
GCAAACTTGGGAGCGAGTCCCCCCTGCCAGCGGAGCGCGCGGCAGGGACCTGGAGA
AAGCGAGGCTTGGAGGGCGCCTACACGGGGCCCCATGGCCCGCTGCGCCCTCTCCG
CCGGTTGGGGAGAGAAGCTCCTGGAGCGGCCAGATACCTGTTGGCTCCTGAGCAGC
ATCGCCCAGTGCAGCCTCCGTCAGGAAAAGCAGCAGAATCGACAGCCCCAGGGGGC
GAGCGGGGTCCATGGTGCAGGGGGTCGGGCGGCCCGCTGGGCAAGGCGTCCGAGA
AAGCGCCTGGCGGGAGGAGGTGCGCGGCTTTCTGCTCCAGGCGGCCCGGGTGCCCG
CTTTATGCGGGGCGAGCGTCCGGCCGACCCCCGCCGGGGCGGAGCCTGAGGGGTGG
CTGATTCATGCACGGGGACTGTCACCCCGCCGCCCCCGCGCTGCAAACTGTGTAAGA
GGGAGAGGAATTCCCCGCCAAGTTGAAAAGTTGAACCTGCCTCCCAAACTTTCTCCT
GTAGTCCAGACGGGGACGCCCTGAGGGAGCGTTTGTGTCAGTAATGGGAAATCTGC
AAGCTAGACGGAAATGACCTGCTAGTGATTGCGCTGTAAAGAAGCCGGAATCCACC
TCTTGAAGGCATGAAGTTCAGGTATTTGAAAGGCTGGTGGAGAGAAAGTGCGGAGT
TCTTGGGT

8:142451692-142452592 (SEQ ID NO.: 71)
GGGAACAGCAGAGGCCGCGCGGGCGGAGGCGGGGGAAAGGGGAGCTGGGT
CCCTTTTCTATCTGGGAGGGAGGTGGTATACGGTGTGTGGGGTCTGGGGAGGCGACT
GTCACGTCTCCTAGAACCCTCATGCCTTCCACTCGTCTGCGACCCCGGCTGCCGAGG
AGGCAACGAGGGAGGTCGAGCCGCTCCCTCCCGTGGGCGGCAGCGAAACTCTGCGC
CCGCACGCCGGGGTGCCGCCGAGTCCGGCTTTGAGTACCCAGCAAGGTCAAGCAGG
CGAAGGAGGGGGCGGGGGTTCCTGGGCGCGCCCCCGTCCGCGCACAGTCGGGGCCT
TGGAAGGGGGTGTGCGCAGCCCGCCGAGTCAGTCCCGCTCGCCTGCCGCCCGCGCC
CGGTCCCCGGAGGCGGACGTTGCGCGCGTTCGGGGATCCCGGAGCGCCCGGCGCCC
CACGCCCTCCCTTCGGCTCGCTAGCTGCTCCTTGGCGCTGCTTTCAGACTTGTTGCGC
CTCGATCTGGGGGGCAGAAGGCTGGCCCGGGAGACCCGGCGGCTGAGGGCCGAGCC
GCGAAGCCCAGGGATGCGCCAGAGAGGCGCGCGGCTCCGCGGGTGGGCGCTGCGCT
GGGGGGCTCGAGCCTGGGGTTTGCCGCCTCCGATCCCAGGGACGGGCGCTTGTTCCT
GCCGGGGTCCCGCGCAGGGGCGGATAGAGGGCGATTCGTCGCCTCGGCCTCAGGCA
GCACTCATCCGGATCCCGGGCTAGGGAGGGGGCGCAGCCAAGTTGTGGAGCCCTCG
GAGGCCCTTCCCTCTCCCGCAGGCTCCGGCCCCTCTCGGACCTCGGTGGCCGCGTCC
GTGAAATGGGGACGCGGGCTCTGCTCTCGGATCCCTTCCAGCCCCCGACCCTCCGCA
CTTG

8:66961046-66962606 (SEQ ID NO.: 72)
AAACATTATCAGGATGTGCAACCAAGCCCCCATTTCTCACCTTGGTAGGCAC
AAAAATCCTTCGGAGGCATCCTGTAAGAGGCTTGCGAGACTCTTACCAAGCCACCCC
GGCTTTAAACGCCTCTCCAGCCACCTGTGAACCGCGAAGGAGCCGGCTTTCGCGGCG
GGGACCTTGCCACCAGTACCCTCGCGGGCCGAGGTCGTTCTCCCGGTCGGCTTCCCG
CCTCACCCGAAAAGGAATTAGAGCATCTACCCAAGACGGTGACTGGCAGGGCAGAT
CAAGGTGTCCTGGTCTCGGCCCCAGCCCCGCGGTGCGCCCCGCCCGCTTACCTTGAC
CGGGTGCAGGTAGCCATCGCCCGCGCAGGGCGCCCAACCCGGCGTCCGCCGGCGCCT
CGGCGTCGTCCTGCAGGCTGCGGGTGAGATGCGCGATGTAGGTGGTGGCCAGCAGC
AGCACGTCCAGCTTGGACAGCTTGGTGTCGGGCGGCACGGACGGCAGCGTGCGCTG
CAGCTCCAGGAAAGCGTGCCGCAGGGTCTGCACCCGGCTGCGCTCCCGCGCGCAT
TCGCCGCCGCCGGCCGCCCGCTCCCGGAACGCGAGCCGCCCCCAGGGCCCGCCGGC
CCCGGCCCGGTCCGCCCGGGACGCGAGTCGCGGATGGCGGCGGCCAGGGGCGCGGG
CTCGGCGCTGGCGCTGAGGGGGCTGCCCGCTGGGCGGCCGCGGTCCATGGCAGCTT
CCCGCGCCGCGCGCGCTGCAAAGGACCGAAGGTGCGGTGAGGCCGGGGGGCGGTC
GGGCTTAACCCGAGAGGCGCAGCCCCCTGGTTCTCCCCGTGCGCCCACCAGCAGCCC
AACGGGGCTAAGGGCGCTCTCAAGCGAGCTCGTTTTGCCTGGGACGCGATTTGCTTC
CGGACGTCTGGGGAGAGTTGCGGAACTCCGGAGTTCTTGGGCTTCCTAGAAGGATA
AGAAGAGGCGCAGTGCCGGCTTTGCTTTTCAGGGGCAAATTAAGCAAAAGGTCTAC
TCTACCCGGGAAGAAAGATCTCGGAAGCACAGCTCAGGATCAGCACTCGTTCGCGC
TTGGGTGACTTTATCCAACCCGGCACGCACGAGAGGTGGCGCGGCTCCTTCTCGCCG
ACGCCGCGGAAAACCACGGCTCACCAGCCGCCCTCGGCCTTTCACGCCAGGGGGGA
TTTCTGCCCGAGGAGCGGGGGACCCTTAGCCTCACCTCGGGGTACGGCACCCGCCAC
CGTTCCGAGCCCGAGAGCTGCGCAGTACGCGTCTGACGGGCCCCTCACCTTTCCTGG
AGCGGCTGAGTGGAGCTCCGCTCCGTCGTGAGGGCGGGCGAGGGGCGTGGAGCAGG
GCCTGTGTGGCCAGGGCCGCGCTGGTCACTCCATCCTCGTCCGGCCGATGCCCAAGT
CGACGGCTGTTTCCAACCTCCGCTGGCTGTGACTTTTATGCGGGCGCCCCGCGGCCA
GGCGTGTGTGCTCCGACCGGCTAAGGCAGGTCGGGCGGAGGACCTGGCCCACCGGA
GAGGCTACGCCGGGGGCTGAGGCGGCTTAGAGGGTCATTAATC

8:68330607-68331757 (SEQ ID NO.: 73)
GTAGCTGCCAAGGAGTAGCCAACAAGCACCAGATTTATGTGCACTTTGAAAG
AAGCACCTTCACCATTGGCTTTTTAAGCGGCGCTGTCGCTAGGGAGCGGCTGGTAGG
GCGAGCAGCCTCGGGGAGCAGCCCGGGCTGTTTGTTCCGTCACCGGGGAAAGGAGG
TACACACAGTCGCGCGCGCACGGACACACACACACGCACGCACGCACACACACC
GGTGGCGAGTTCGAGCCCCGCGGCCCCTGTCCGCCCGCGTGCGCCCCTCGACACAGC
TCGCCTCCCGCCCCTGATTCCTGCTGCTGCCGCCCAGAGGAGAAAGGAACCTCTGC
CTCGAATTTCCCCACTGCGCCGGGCGCTGCGGAGAGCGGCGAGGGTGGGCGCGAGG
CGGAGAACGCGATGAATGAGTTCTCCCCTCGCCTCGGAGTTGTCTGAGTTGGCGGCG
CTGCGCCCAGGCTTCCGGCTCTCAGCGCCCCACGCGCGCGTGGCTCCCCGGGCTGCC
ACCCACGCCCGCGGCCGGGGCCGAGCCAGCCACGCAGGGCAGCCGAGGCTCCGGA
GCTCCTGTCCCGGCCCCAGTCCGGGTAAAAGGAGGGGTTGTCCCCAGCGGAGGCGCA
CAGCCGCGCGTTCTCCCTGCACTCTCTTCGCGGTCCCATCTGTTCCCCATGGCGTCTC
```

-continued

---
SEQUENCES
---

ATCCGCAAACCCGGATCCAGGCTTACCTGGAGAAGAACAAGATCGGTCCCCTGTTT
GAGGTAAGGCGCTGTGGAGGAGGGCAGTCCCGTTGTCTTTAGGGGAAGGGGTGCAG
TAATGAAAACAGAACACTCCCAATCCCACCCCTCCCAGGGAAGGAGGGCTAGAGAA
CCAACGCGCGGGAGAGGGCGCCCTGGGATTCACTGGCATTCGCTCTGTCCCGGCCA
GGTGTCCTGGAACGCGGCCGGGCGGGCACTTAGCCAGTTACCTGAACGCGGACAGG
TGAGCTCGGGAGGGCCCAGCCTCAGCCTGGCAGGGGAAGTTTTGGCCCTCTGACTGT
CCTGCACCTCTCAGCTACATGTTCAGGACCCGGGCAGGCTGAGGCAGGCGACGCAT
ACGGATGCACACACTCAGACTGTGTTGCACACGCACACTTTCTTTTTTGAATTCACG
CTATCTTGAGTGTTCGTGTTGGATTTT

8:71843436-71844516 (SEQ ID NO.: 74)
GCAAACAGACACGGAGGGTTGATTCTTCTTCAGGGAAATGGCTGGCCACTCC
CTTGATTTGGGAGAAACTAAACTGGCCTTCTCGTTCCCAGTCCCAGAACCTCCACCC
CTTTCGAATTCTTCCCAACGGGCTGACCCTGCCCGGCGCCCAGGAGCGCCCTGGGTA
TCTCCTGGCTGCTCTCCCGAATCCTTGCGCGCCGCGCCCCTACCAGGTTCACTGGGT
GCACGTAGCCGTTCTCATAGCGGTCCTCCTGCAACAGCTGCCGCAGGTGAGCGATGT
AACTGGAAGCCAGCCGGAGCGTGTCCAGCTTGGAGAGCTTAGTGTCGGGGGGCACC
CAGGGCAGGCTGGTCTTGAGCCTGGAGAAGGCTTTGCTCAGCACGCGCATCCGGGC
ACGCTCACGGGCGTTGGCCGCGTTCCGCTGCGACTGCTTGCACTCTGCGGCTGAGCC
CTTGGCCGGGAGGGGCTTCTTGCCACCACCGCCCGCGCTACCACCTGCGCCGCCGCC
CCCAGCCACACGGGGCCGCTTCCTCTTGCAGCCTTCCGCGCTGCCGGCTGTGCCCAG
AGCGCAGCGCTCCTCCTCGCCGTCGGGGTCCTCCTCCTCTGCCGACGAGTTGTCACT
GGGCGAGGCGTAGCTGCGCTCTACGCCGCGGAGGGGCGGCCTCTTGGAGGCGGGGA
CCGGGTACTCCCGCTGCAGCCCCCGAAGCTCCATCTCCTCCGGATCACTCACCGAGC
CCGTGGACATCCCGTTGTCCCCCTTGCCCACACGCGTCCTCTTTCCTCCCCCCTGGCC
AGTCTCGCTGTCTCCGCCTTCCGCTCCCTGGCGGAGGCGGAGGCCAGAGAGCGCTCC
AAGGAAGACTAAAAACCCAGGCCGGGAAGCGCGGGGTGAGAAAGCGAGGTGGGTG
GCGAGAGCGTGAGCGCCCCTCTGCTGACCCCGGGGAGCGTGGACTACGAGTTGGCG
CCCAAGTCCAGAATCCGCGCGCACCGCGGTAAGCTGCGCCTTTTGAAAAGGCTATCT
GTACTCCTTGGAACAAACCACCCCGGGCAAAGAAGAGGGGGTTGTAAAGGGGGCCA
AGAGGTGGG

8:96145538-96145718 (SEQ ID NO.: 75)
AATAATTACAGTCAGTTTCACTTAAGGGGGGAGATCAGCCCGGTGCTCTTCGG
CCGCCCCGGGAGGAAAAGGGCGGGGAGTGGGGGCAGGTCGGCCGGGCAGTCCAGC
TTGCCCGGCCCAGGGCCTGACCACCCCGGCTCCCCATCTGGCTGGTGCATGGCGCGG
GGAAGGGGGCGCGCCAG

8:96160146-96160866 (SEQ ID NO.: 76)
TTGAGAAAAACAATTTAAGAAAAGTAAAAAGGAAGTGTCCAGAGCAGGAAG
GGAATTCACAAATGTAGCCTCCAGCGGGAACAGCTCCCTGGCTGCCGAGCTCCAGC
GGGAGGGGAGTCGAGCGTTTTCTTTGCCACTTACCTAGTCCCCTGTCTACAAAGCTG
GTGATCGTATTAGCCGACTTGGAAGACTGGAAAAAGCTGGCATTGATGCCCAGCTTC
TCAGCGATGGAGTAAGTCCTGTAGATTGACAGCATGTACTCGTGGGGCACCACGCG
CGGACCCCTGCCTGGCGGCTCCTGCGCCCGGGGCTGCTGAGCCCGGGGTTCGTCCTG
AGGCCGCGGCTGTGGTTCCTGGCCCTCCCGGCCCGCGTCACTGTCGCGGCGGCGCCCG
CTGCATCTTGCCTTCCTTGCGGCTTCGCATGCCCTTGGTGGAACCCAGCTCGGCGGA
CGACGAGGAGGATGAGATGGAAGCCTGCTGGAAACCGGGCAAATCCCACAGAAAA
CTGATGAGGAAGACGGCCGAGAGCAGGACCCTGGGAGTATCCATGGCGGGCAAGTG
GCTGCGTCTCCCCAGGAGGCGGTGGCGGCGGCGCAGGACGCGCGGGGCACGGAGC
GGCTGGACAGCGGCCGGGGCCCGGCTCCTCGGGCGGACTCGGAGTGCGAGGAGCCG
GGTCCCAGCCACACAAACCCCGGCCCCGCCACGCCCCCTCCCGCCCCTCGC

8:96494109-96494705 (SEQ ID NO.: 77)
CGAGCGCCCCCGAGCCCCGAGCCCGAGTCCCCGAGCCTGAGCCGCAATCGCT
GCGGTACTCTGCTCCGGATTCGTGTGCGCGGGCTGCGCCGAGCGCTGGGCAGGAGG
CTTCGTTTTGCCCTGGTTGCAAGCAGCGGCTGGGAGCAGCCGGTCCCTGGGGAATAT
GCGGCGCGCGTGGATCCTGCTCACCTTGGGCTTGGTGGCCTGCGTGTCGGCGGAGTC
GGTGAGTGGGCCAGGCGGAGGATGCGCGCGCCGTTTAGGGTGTTTGAAGCTACGAG
AGGAGCCCGCAGGGAATAGGGGAGCGCCACCTGGGGAACCCCCAGTCCCCAAGTAT
ACACCGGAGATCCGCTGGGACAAATGCGCTCGTCCGGTCACCCTTTCCCCCTCTTCC
CTTCCTCAGAAAAGCGCTGCTCGCTGGCGTTACCCCGCGGTCCGCGGGAATGGGGG
CACCGAGAATTGCGGTTTGGTCTAGCCGCAGAGGCCCCTGAAGTCACTCCCAACTTC
TTCGCCCTCGGCGGGTCTTGCTGCGTGGTCTGGGAAGGACGGAGGGGAAAGGGTGG
CAGGAGGGGGGAGCCTGGGTCGGGCCCGCGAGGGAAC

8:96494903-96495378 (SEQ ID NO.: 78)
CGGCTAGGGCGAGGTAACCGACACTACGTGGAATCGCAGTAGGCGATCCCTC
AAGGGGATACTGGGGGAGGCACGGAACGCGTCCGAAAATGCTGGGACGCCGGCCA
CTGGATTCCCAGTCCTGCGGCGACCCCCTCCTCGTTGAGGGGTGGAGGTTGCACCGC
GGGGCGTCAGGGACGGGAGGACATTTTCATAGGAGTTACACGGGAGTGCCGCAAGC
AGGGCGAGGCGGGGTACGTGTGACACGGCGCTCGGCTTCGGGTCGCCTGGCCGCTG
GGGGACAGAGGCTTCCCTCCCGCCACGCTCGCCCTCTCTGGCCCTGGCGGGGCGCTT
CTGGGGCCGGGAGGAGTCTCGTCTCCGGCGGAGCGCCTGCCGGCACCCAGCTTCCCT
CCCCCGCCCTGGCGGTGGGAACTTGATTTCTCCTTTTGGTCGCGCTTCGGGGGCTGG
AGCTTGTTTCCCCACGTCGCCCAATGAGC

---

SEQUENCES

---

8:96495148-96495525 (SEQ ID NO.: 79)
CGGCGCTCGGCTTCGGGTCGCCTGGCCGCTGGGGGACAGAGGCTTCCCTCCC
GCCACGCTCGCCCTCTCTGGCCCTGGCGGGGCGCTTCTGGGGCCGGGAGGAGTCTCG
TCTCCGGCGGAGCGCCTGCCGGCACCCAGCTTCCCTCCCCCGCCCTGGCGGTGGGAA
CTTGATTTCTCCTTTTGGTCGCGCTTCGGGGGCTGGAGCTTGTTTCCCCACGTCGCCC
AATGAGCGCCCTCTAAAGGGAACTGCCTCCTTGGCCTCCTCTCGTCCGCAGCTGCCT
CCACCTGGGCGCCAGGAGCTCTGTCGGGCAGGTGGAAGCTTGAGCACCCCAGATT
TCGTCTGCAGCCTCAGTGCCCTCTGGGGTCTCAGGGAGTGC

8:98951212-98951512 (SEQ ID NO.: 80)
TTTCCTTCCCCCTTTTCCTGCCTATGACATGGTGATGAAATGTGAAGAGCTGG
AAATCACAAAGCCCACCGAGGTGGCTGCGGGTCTGCCTCCGAAGTTATCAGTGTAAT
CGGGCCTCTGTGTATGCCTGCACGTGTATTTTCATGATTGGAAGATTAGGAGCACGG
ATTTGTTCCTGCAAGTCTCCTCTTTTGTTGTCATGAGAGTGTTATGTTAACGCTTGTG
ATAACGATAAGACAGAAACTATTGAAAAGGGTGCAGTGGTGGTGTGAAGGATTAAT
CCTTTGCTTGCTTCACATCT

8:98951542-98951902 (SEQ ID NO.: 81)
ATGTGGAAGAACCTTTAATCAGAGAAGTAATCTGAAAACTCACCTTCTCACC
CATACAGACATCAAGCCCTACAGCTGCGAGCAGTGCGGCAAAGTGTTCAGGCGAAA
CTGTGATCTGCGGCGGCACAGCCTGACTCACACCCCGCGGCAGGACTTCTAGAGAA
GCCCAGGATCTGTCCCGTGCCGCCGCTGCTCCCCTCCCCAGACACCTCTCCACGTCT
CCTACCCAGGGGGTCGCATCCCTAGCCCTTCACTGACCCCAGCTCTTCCCTTGCTGC
AGCCGCACCTGCAGCTCCAGGGAGTTAACTCTTCTTCTGGGGGACTGAGAACTGTAG
AAAGCCACACTACTACATCCCTTC

9:134407349-134407680 (SEQ ID NO.: 82)
TACCGCCCTGCGCAGCCAGGCTGGCTGGCAGGCTGCAGCGGGAAGCGCCTGT
GGGTCCTCGGCGCTGACTGCAGAGCTGGGTGGAGGCAGCGGAACCAAAACTGCTGT
GTCACTGCACGCTGCAGCTGTTGCCAGGGTGACCGGGTGAGTTTCCCACGCTTGCCC
GGGCGGCAGCGTGCGGGCCGGCGGGTGGGGCGGAGGGGTGTGCAGAGAGGCCAGT
GGTGTCGTGCCACCCGATGCCCGGGGGTGTCCACTCCCCTCTCCTGGGTCACGTGAC
CAGGGCCCCTGCCCTGCGGTGTTGTGGGGTGTATGTGTGGTTCTTGGGGGGGTCC

---

SEQUENCE LISTING

---

Sequence total quantity: 82
SEQ ID NO: 1              moltype = DNA  length = 1155
FEATURE                   Location/Qualifiers
source                    1..1155
                          mol_type = other DNA
                          organism = synthetic construct
SEQUENCE: 1
tctacagtca caactaccca actgttattg atcctttata actgcaattg agtacagatg    60
taggaagatt gagagggaac tgggatctgg cgcctggatt gctcaagaga ggtcagggaa   120
acccctcaga actcctgaga cccagagatt gagggagggg ttgaggcgga gtctgcaatg   180
ggggctgtcc agcagtagca agcagcgggc cgatcctggt ggagggttgg gaggctgctg   240
tcattttatg ggtcggcagc cagagtgaga gtgtccctgc tgccagagga ctacggcggg   300
ctgggcgcgg ggtccccgcc tctcgctcac cacacagacc ccgcgcctcc tctggcagcc   360
gcggtggtgg cggcggcaga gcctcgccca ctccaatccc caccctctcc atccttagtc   420
attaaagaac agcagcgcct ggcacgttct tggaggaccc cgggcgcaga ggaggaaagg   480
gagcaggcgc aggggactg gaaaggcagc atgcgctcgc caggagcaac ctcggcgccc   540
agggtctgag gctgcagccc cagttcgcca ttgtgagccg ccgccggggg agtccgctag   600
cgcagccgtg cccccgagtc cccgtccgcg cagcgatggg gcacctgccc acggggatac   660
acggcgcccg ccgcctcctg cctctgctct ggctctttgt gctgttcaag gtaggggagc   720
tcctccaccc cttttttccca gcggtccggg cggcagccgc gctccggagcc cctcgctctg   780
ccgttgggag cggcgcgccc cagggcacga tggcccagcc gcgggaagcg cctgccgtgc   840
agcctgggcg cacgctttgt tgtcctcgcg tgtgcgtgtt cctggtggtc ttgagaggta   900
gggggcgggg ggaagaataa gggaagtttg ctccctccgg ctttcgccct ttgtgctctt   960
ttatcgctgc tgaaatccac atcaaaggtg ggcttgttgg atcgtgcttt ctcaggcaaa  1020
atgaggtcac tttctttct ggtttccact gcaccccaac tgctcttaac ctttccgccc  1080
tccctcgcac agaatgcttt gtcttaattt tccttactgc tggaattata cactggagag  1140
tggaggggga ctgag                                                   1155

SEQ ID NO: 2              moltype = DNA  length = 1209
FEATURE                   Location/Qualifiers
source                    1..1209
                          mol_type = other DNA
                          organism = synthetic construct
SEQUENCE: 2
ctcctggcgc cccctggcag tttcccgccg cctaggccg acttttccac ctccagctcc    60
cgggcggggg aggcccgta cggccgctta gacgggctgg ggcgggaaga ttgcagcggc   120
tttgggttta ctccttgttt cttcataatc cctagtggag ctgggtcaat ttcaggcaca   180

-continued

```
gcccatccga gtcaggcgag gtccagaaag gcctgactcg cctggcagcc tcaacggact   240
tgtccccgca gccgttgact agccgttgac gagcggacct cccggtcgtc atggcgactg   300
tgaaatgtag ggtggagcgc atgcgttcga agccattcgc gcgggcagtc cctgcgtgtc   360
cccctgcgtg tcccccacg tgctccccag cgcgcgcagc accccgcctc tgcgcttccc    420
cgagcgtgca gcttccggtg agggcagccc cacgcacagc cccaacacc ctccccagcg    480
cctgcagcct tcggtgcgcg cagtccccaa gcccacatgc gcagttctca ccttgcgcgc   540
agccccacgt acagccccca acacgctccc agccccactg gcgcagaacc catcaccgct   600
tgcccttcac gcgcttcatt gggagtgcag ctcccacccc gagcgcgcag ctccacgcag   660
cctctccaca ctctccccag cgcttgcagc accccccagt gcgcacagct ctgccagtag   720
cttcccggcg cgccgcccct gcaccgcttc gggccataac cttgctggcg actaagtctg   780
aagaacttcc tgtggtttca ttcttttctt caggtttagt cttagctctg acattttaac   840
caaaaggtta cacgttaatt aacgaggtat taaaggggaa gatctcagct gaaagaaatg   900
actgtaggaa gtgtgtcagg gaagccaacg gaaccgctgg cccgccggtg gtgcgcccgg   960
cattaggaaa gtctctacga tcgctgaggt atcgggcagt cagtgcccgt tgccaacgcg   1020
gagggaacgg gcggagactg cgggcaacac gtgcagagc cggcgtcgagt ccggtgggtc   1080
tgatcccaga gcctcaggtt gacgccactt ccttggcacg gaacagcgtt tactgaatct   1140
tagagcaaaa tgcttttcca atgaggttcc tcagaagtca tcggccctag gagcggtgtg   1200
ctcaagcgc                                                           1209
```

```
SEQ ID NO: 3          moltype = DNA   length = 192
FEATURE               Location/Qualifiers
source                1..192
                      mol_type = other DNA
                      organism = synthetic construct
SEQUENCE: 3
ggaccgctca ccactgctca ctgctcttcc tccctggtct ttccaccttc aaccttgccc   60
aacccagagc tgttttccac gctgtagtca taatggttgt ctaaagggta gatatgatca   120
tgacacagaa gagagctcac gatctgtgcc tcactacctt gcaaccccac tcactacctg   180
ccactcccta ga                                                       192
```

```
SEQ ID NO: 4          moltype = DNA   length = 661
FEATURE               Location/Qualifiers
source                1..661
                      mol_type = other DNA
                      organism = synthetic construct
SEQUENCE: 4
gtgggggaag gacgccgcaa caccctcata ccctccccca ccccgccccc tgtcccccgc   60
cccccagcgg agacgcggaa aaccactcgc agccggagag acacccggac acaaagacct   120
cgtgccagcc gcagacccaa gtttctcccg gagagactgg gggtccgccc gcgttcaccg   180
cgagaacaca caaacggacg gacagaccga cgcacggacc cggggacctc gacactcgct   240
aggaggcaag ccctattcct cagccgggcg ccctcgtct cccgctctct ccatggaccc    300
ctctcctggc aaatcgcccg cagagcgagc ttggagatgc gagggaaact gaagcccaa    360
gggtgccccg tcctgggagc ctggctgtct gcggggtccc gccattccg cagtagtaat    420
acaggagggc cggggggcttc tacccaccc tccgctcccc ttcgggtctc tcctggctgt    480
gcaagcgatg ggccagaggg ctggacgagg ctggctccca atccagaatc ccgagctggg   540
gagttctctc taggttctgg ggctcctggg accggggctt tggggaaggg agatcgcagg    600
acggatatcc aggaagggag ggggccctgg gtctcccgtt acctgcgcct gccgcgctgg    660
g                                                                    661
```

```
SEQ ID NO: 5          moltype = DNA   length = 481
FEATURE               Location/Qualifiers
source                1..481
                      mol_type = other DNA
                      organism = synthetic construct
SEQUENCE: 5
ccaccttgga tttcagatcg aggaaaggaa gccaaagcaa aggtgtggtt acacaggaca   60
tccatagaca aatcgttgcc tctctaagtg ggcctgagct ttgcggctcc agaagcgcga   120
ggcgcggttg gtgcggacgc ggggggcgtgg gagtcatcgc tctccccgca gccctggccg   180
agctctctgc tgtcctcccg agtttgggcc agagaccacg gctcactccc taacgccctc   240
gcaaggacgg ctgcccgtcg ggccaagggc gccccgggct ggaggccgga gcaagacggc   300
cccgcgggac tcgggagcct tggtaaggcg gaggctcaga ccccgttcac gaaaacgcct   360
ggctcctcca ggatttgtca ggtcttaagc agctccgaga aggctccgct ggctcttggg   420
gaaccccgct gtgcggctca cccccgtttg tctctctcaa gctctcgccc tcctcccctg   480
g                                                                    481
```

```
SEQ ID NO: 6          moltype = DNA   length = 481
FEATURE               Location/Qualifiers
source                1..481
                      mol_type = other DNA
                      organism = synthetic construct
SEQUENCE: 6
caaaatgacc gatgcgcagg tcaaaacctg gttccagaac cggcggacaa agtggaggtg   60
agcaagcggg gcgggccggc cgcccgcgag cggcgcggtc tcaggcagct ctcggttcat   120
tggcctctcg tggggcgcac atactttttc cgctcgcggt ttctgatcct ttcggaggag   180
cgagctcccg ctaggcttgc ggggagctgg aagcaaccga ggccgatagc tgggatgggg   240
ctgaagagcc ctggctctgt tttaccggag gcttcagggc tttctggttg gcacactctc   300
tgccggtgta gacgcggcag gtctattccg ccgcttgggc aaacaggcgg gttagtgcac   360
tccacgcagt ccaggctcca gggatctgtg agtcctgggg agcttttgt ttgcgcaaac    420
tcttgcttat ggaatcctgc tctgtcctgg agactggatg cagaacagcc cgcaccttgt   480
```

-continued

```
t                                                                  481

SEQ ID NO: 7          moltype = DNA  length = 1501
FEATURE               Location/Qualifiers
source                1..1501
                      mol_type = other DNA
                      organism = synthetic construct SEQUENCE: 7
gctgcatctc agatataccg aagtgtgtac ccgctacgca cagtgcggtg atgcctggcc   60
acctccagcc tccagcgggg acctcctgcc caggtggagt ctgaatgccc accgccacca   120
gcccacgcgc gcagtgggcg tacacgtggt gacctgcctg cggctgggtt cccagctccg   180
gctcctcctc cctccagctc tcgctcggct tcctgcagta tcacgtgcag ctgcgctggg   240
tgcaggatgg cggcggccgc ggcggcggca gcagcggtgg gtgtcaggct ccgggactgc   300
tgcagccgag gcgctgtgct cctgctcttc ttttccctgt ctcctcggcc cccggccgcc   360
gccgcctggc tgctgggcct gcggcccgag gacactgctg gaggccgcgt gtccctggag   420
gggggcaccc tgcgcgccgc cgaaggcacc agcttcctcc tgcgtgtcta tttccagcca   480
ggaccgccgg ccaccgccgc accggtgccc tcaccgaccc tcaactcggg ggagaatggc   540
accggcgact gggctccgcg gctcgtgttc atcgaggagc cccggggcgg tggcggcgtg   600
gcccccagcg cggtccccac tcgccccccg ggaccgcagc gctgcaggga gcagagcgac   660
tgggcatcgg acgtggaagt cctggggccc ttgcgtcccg ggggcgtggc aggctcggcc   720
ctggtccagg tgcgagtgcg ggagctgcgc aagggcgaag cggagcgggg cggcgcgggc   780
ggtggcggga agctctttc actctgccgc tgggatgggc gcgggtggca ccaccaggc    840
gccgccggcg gcttcctgct gcgcgttcgc ccgcggttgt acggcccagg cggggacctg   900
ctgcccctg cgtggctgcg ggcgctcggg gcgctcctgc tgctagcctt gtcggccctg   960
ttcagcggcc tgcgcctgag cctgctgtcg ctggacccgg tggagttacg ggtgctgcgg   1020
aacagcggct cggccgccga gcaggagcag gcgcgccggg tgcaggccgt tcgcggcagg   1080
gggacccatc tgctctgcac cctactcctg ggccaagccg gagccaacgc ggccctggct   1140
ggctggctgt acacctcgct gccgccgggc ttcggggca ccgggaaga ctacagcgaa    1200
gaggggatcc acttcccgtg gctgccggcg ctcgtgtgca ccggcgcggt attcctgggc   1260
gccgaaatct gcccctactc agtgtgttcg cggcacgggc tggccatcgc ctcgcacacg   1320
gtgtgcctga cccggcttct gatggcagcc gccttccccg tgtgctaccc gctgggccgc   1380
ctgctggact gggcgctgcg ccaggagata agcaccttct acacgcggga gaagttgctg   1440
gagacgttgc gggccgcaga cccctacagt gacctggtga aggaggagct caacatcata   1500
c                                                                  1501

SEQ ID NO: 8          moltype = DNA  length = 433
FEATURE               Location/Qualifiers
source                1..433
                      mol_type = other DNA
                      organism = synthetic construct SEQUENCE: 8
aaataaaatg agtctcttac catctcgcct gaggttggcg ttgcgcaaag ctttgatgga   60
tgcgctctgc ggggttgcag aagtgtcccg acagctgcaa aagtttgcgc agattagagt   120
gtagacaaag atgagccggt gcatttggga tcagcgacta gagacagcgt cgctccaaga   180
aaaagccggg ttctgctccc gggaccgacg ccgcgccgcc ctgcgctctc gccgcctgcg   240
ctcgccctgc gctggcccgg gtcgctgtgc taatcgccga gctctcccca aacttcctgc   300
atgctgaact ttccgagcgc gtgtgggtgc cgcacttcct tgtggtgctg agctgataaa   360
tggtgacggg acaaacaaca ggttgacgtt tgtttgttcc cccctccgg tggccggcag    420
ctgcagcaca ggc                                                     433

SEQ ID NO: 9          moltype = DNA  length = 901
FEATURE               Location/Qualifiers
source                1..901
                      mol_type = other DNA
                      organism = synthetic construct SEQUENCE: 9
aatcttggac ccaaaccctg catttgggca tctgacaccc ataggcccat ggttcaaacc   60
caggcggctc tttccaagtt cgaagcaggg actcggttct gcgcatctgg cgggtgtgcc   120
cagattgtaa ccttcgcact aggcatccaa gaacgtgctt tggacacact cggcggtggg   180
agcgggtgct tggtttgcat cagggatgag gggtggagta gcgaaagcgc gcggagcgcg   240
cactcactca cactccccaa gccagggcgc ggccgctctg ggcgcgaggt cccaagccaa   300
gtctcgcgct cggccaggag ccggggagta ccccaggtcc ccggtctggg gccgccgcta   360
tcctaccctg cggcgcgcac tcctgacctg gccccgcccc ccggcggccg cgagtagcgg   420
gcggagcgca agcagagagg cgctctgggc tgtgcggcac tggccatcgc cggtgtctcc   480
ggagggacgg agggaccggg cgggagagag agaaagcctg accgaccggc tggcgaagag   540
ctgcatgcaa ccggtgggag gccgggccgg ctgggtctgg ggctcgggct caggctcgca   600
ccgtttctcg gcaggtccct ggcggtgagc gcggacggcc cggaggcggc ggctctgagc   660
tggcaggcgg agggctgtct cctgcgcccg cctgcccggc gcggtccgag gatgcggggg   720
ggcgatgccc ggggccaggg acgcgctctg tcaccaggcg ctgcagctgc tggccgagct   780
ctgtgcccgt ggggccctgg agcacgacag ctgccaggat ttcatttacc acctgcggga   840
ccgtgccaga ccccggctcc gcgacccagg tgagtgccgc caccgccgcc tggagggacc   900
t                                                                  901

SEQ ID NO: 10         moltype = DNA  length = 293
FEATURE               Location/Qualifiers
source                1..293
                      mol_type = other DNA
                      organism = synthetic construct
SEQUENCE: 10
```

-continued

```
cggggggtgtg ggaactcgga ggtgggggtg agggaaggcc aacctccacg cttcggcccg  60
gaggttcccc cgcctcttcc tgcacgactg gattccttct ccatccgcgc ctccggcccg  120
gtccctgccc cgccaaatcc gcgcatcggt ttcccatccc atagcgcaga taggtagggc  180
aggtacacag ggaggtgttc gaatgatccc cgtttcacag aagacgaaac tgaggctggg  240
aggcctgggg actggcccgg ctgcagcgcc gccgttagcc gaaggtggga gcc          293

SEQ ID NO: 11          moltype = DNA   length = 521
FEATURE                Location/Qualifiers
source                 1..521
                       mol_type = other DNA
                       organism = synthetic construct
SEQUENCE: 11
cgcgcagcca gcgggtccac gcatctcagc acttccagac caactccggc accttccaca  60
cccctgcccg ggctggggc tccgagagcg gccgcgaagc gactccgatc ctccctctga  120
gccttgctca gctctgcccc gcgcctcccg ggctccggtc cgcgcggcgg ggtccctgct  180
cctgcgcccc gggcgcgctt cccggacacc ccggtccccg cagccaggac aaagccatga  240
agccagcgct gctggaagtg atgaggatga acagaatctg ccggatggtg ctggccactt  300
gcttgggatc ctttatcctg gtcatcttct atttccaaag tatgttgcac ccaggtaggg  360
ggcgcgttag cgtggttttg ttggatattt tcttctctct cgcgctctag ctcgctccgc  420
ctgatttctg cctcttccaa ccctacctct ccgccttcgg cctcttcggg gctcctggct  480
gcccagagct cctggctgcc cagatctacc cgggtcaccg c                      521

SEQ ID NO: 12          moltype = DNA   length = 329
FEATURE                Location/Qualifiers
source                 1..329
                       mol_type = other DNA
                       organism = synthetic construct
SEQUENCE: 12
tttgatcctg accaggcgac ttcgtcgcct gcggatcacg gaagtggctg cggtcggcgc  60
catgttatgt tggggcagaa gggacgggga acttccggat tggaagcccc aaggattctg  120
agagccccgc taatctgggg atgactccta ggagtagaag acggtccatc ttagttgtca  180
cgaggtagtg cacgtgggga cccttgcggg tacagttgca cacagtggat cacacagatc  240
cgaagtctga ggcacagggc gcggtccgcg agtgggagcg gctgcttgtg ggcagggtgg  300
acgcggggc acgtcttggc cggcgtttt                                     329

SEQ ID NO: 13          moltype = DNA   length = 815
FEATURE                Location/Qualifiers
source                 1..815
                       mol_type = other DNA
                       organism = synthetic construct
SEQUENCE: 13
catgggctgg agttgcccga gggcccccgcg tcgggaccgg cggagagacg catgctgtcc  60
atgcagctcc tactcggccc tcttcggagc tccagccctc gcgggccgct ccctccccgt  120
ctcggaggac ttgggctcct cgtccgaagc gcagggtctt tggcgcgctc gcagcttgcc  180
gggctctgcg atccctccag tgggcgtctc ccggagcagc gtcccgcctg cccactgagc  240
agctctcagc agggtgagct ggcccctctc cctgctctgc cttttttcaa cttcggcgag  300
gtcgggaagg tgagctccga gcttccggaa gcactgggtt cccaactcaa gtatttatgc  360
ggtgcttgtt tccttgggac gcgctccctc ccgccctatt gccggaagac tgctggttgc  420
ctactccccg ctccctggag ttttattttt tcctctccct acgtcggtgt ttgtcctctg  480
catcactgtg gaggggtgg agctgggaga ctcgcagatt cctcctcaca gtaggtggga  540
tcgtgggatc ttcccgcttt tcccttccaa aaacttggac aactggacga gtcatgcctt  600
ttctgggctc gtagccgttt ccacaagctt ccctcactag ccttcctcgc tagcctcctt  660
aaccatgcat ttgacttcaa caggcacgct aagcgcggta cctggaaacc tccagtccac  720
gcaccggcgt ccacgcatct agctcctgca cctgaacctg gctctcgacc tcacctcctc  780
cagtccgggt ttcttccttc tcaccgagct caccc                             815

SEQ ID NO: 14          moltype = DNA   length = 541
FEATURE                Location/Qualifiers
source                 1..541
                       mol_type = other DNA
                       organism = synthetic construct
SEQUENCE: 14
gagggggtgc caggcgggac tggggagagg ggaaggggg ctcagtcctg accgggaccc  60
atcgccctct ccgcggggcg cggggccagg cgcgcagatg cgccagggc gcagccggac  120
gatcccggga agccggacgt cgtggccgcc gccgcttggc cacgtccgag tggagagcgg  180
gaccgcggct gcgggcgctg ctggtcaccg ctcgtcgcag gaacccggc ggggggtcgcc  240
accgccactc gcgctgcctt ctcgccctgc ccggctcccg ggcgggaggt agagccggc  300
ggcggctccc cgggcgccgg ctggagggcg ggtcccggca gggtctctgc gcgtccgtcg  360
gtccgggtcg cgctgggcag gactcagcgc cgggctccag ctgcccgcgg gccggtgccg  420
ccgccggcgc cgcccgctct cggcttctgc cggtgattgt caagtgcttt ggaaatcagc  480
atctggagag accaatcttc tcccctgaga tctctaatca aacgctccgt tcccaccccca  540
c                                                                  541

SEQ ID NO: 15          moltype = DNA   length = 602
FEATURE                Location/Qualifiers
source                 1..602
                       mol_type = other DNA
                       organism = synthetic construct
SEQUENCE: 15
```

```
cgcgccctgg cggctccgag ggacctgggc tcgggcttgc ggtcgcgtcg cctgggcttt   60
ccctgggctg ggagcgcgcc gggtctccgc cttgcacgct gtcaccgcgg gagacgtctc   120
ggcctcgccg cgcgcagagg ggacgcgcgg agaggctggt ttctgggcga gcggagagct   180
ttgcccatta agctgccgga agaagccaaa tcaaaaagcc aatctccaag cctccaaacg   240
gaacgtcacc ctatcagctg ggagacagcg ccgcactgac tgacaagccg cgcatattta   300
tcctcgcgcg cggaggggag actctcagaa cgctcctcga ccagcagcga ggaagtcgag   360
cccgcatccc gcatcccgca tcccgcatcc agagcccccg agggacgaat tcagatccaa   420
cccctgcccc gcgccaccc acctagtcg ttggagcctg gcgcccgcgc ctcccggccg   480
gcagcacgtc aaaacggcgg cgcgtcctga cctggattcc gccgagttgg gagctccagg   540
cagcaggcgg gcgcgcggca ccggctttcc ccttgtcctc aggagacgct gcctgcaatt   600
cc                                                                 602

SEQ ID NO: 16            moltype = DNA  length = 304
FEATURE                  Location/Qualifiers
source                   1..304
                         mol_type = other DNA
                         organism = synthetic construct
SEQUENCE: 16
cgcaacggggg gaagcctcca ggacgcactt ggctctgcct gtttgttccg ccccgcgga   60
aaccgctgct cgctgggcag gggctttctg ttttgcagcc ggaacaggaa cacagatagc   120
ccgccaagcc gccggcgaca ccttccaacc cctttagctc tccgcaccgt ccctccccac   180
cgccccgcct ccacccgcgc cgcgatcaag tcctcatagc ctttttaggga atttgctcag   240
caaactagcc gaaccccaaa ggcaggggag aagcacgcaa atacccgac tccaccggct   300
ggcc                                                               304

SEQ ID NO: 17            moltype = DNA  length = 241
FEATURE                  Location/Qualifiers
source                   1..241
                         mol_type = other DNA
                         organism = synthetic construct
SEQUENCE: 17
tccagcctcc cgagtccgcc cgctctctgg cctctcgtcc tggccgcggg aggtcacttc   60
ccgggtgtcc gaggaacgtg cggaaaaagtc cgcggaggct cgaaggtctg gctgcgggcg   120
gcgccggggg acgagccga gtgtcatttg agtcttttgt cagggatcag atcggtatcg   180
ggacctcctg ctgcctttgc atttcctgca actgacacca gcggccagtc gcatttcctg   240
c                                                                  241

SEQ ID NO: 18            moltype = DNA  length = 462
FEATURE                  Location/Qualifiers
source                   1..462
                         mol_type = other DNA
                         organism = synthetic construct
SEQUENCE: 18
cgtgtgagcg tctgcgagtg tgtggaggcg gctgctgtgg cagcgcaggc ggctcggctc   60
cggcccggag cgcagcggaa gccgcgaggg atgcagcggc ggggaccttg gccggtggag   120
gatgtggagg tggaagtgga gcggatggcg ctccccaaga gctccgccac gcgaggtttc   180
gggctcgtgg ttttgcttcc tccgggtccc cgctccaggg cccgggcg cgacgaaagc   240
gccggggaca gcgccgcggg gagggcgctc cgggtcgtgc gtgctgcacc cacaaagagc   300
agcagtcccg ccactccgcg cctccgctgc gtgggggccg aggggcgctt ctcggctcct   360
ctttccggtc ccccggcgag ttggagactg ttctccggcc tcggccgcaa gggggtgagg   420
cgaggggccg gcgcggtctc tcccgccgcg gctccgtccc gc                      462

SEQ ID NO: 19            moltype = DNA  length = 241
FEATURE                  Location/Qualifiers
source                   1..241
                         mol_type = other DNA
                         organism = synthetic construct
SEQUENCE: 19
ccggggagac gcggccgtgg agcgtgaaac gcttcttgca agcgaggaaa cggtgagttg   60
gccgacaccg ccggcggcct caccattctg gtggccgcgc tgagctcctg tcgcctggag   120
gcgggttgcg ccgcacgggg tcagctcccg ccggctccca gctcaccttc gaagctccca   180
cttaggcgcg cccggtgcgg cgtgtgcaca gcgcggggcg ccgcacacgg aagcgtgtag   240
t                                                                  241

SEQ ID NO: 20            moltype = DNA  length = 555
FEATURE                  Location/Qualifiers
source                   1..555
                         mol_type = other DNA
                         organism = synthetic construct
SEQUENCE: 20
cgccaggagt gacgaaacgt tcgaattcct gcgagaaaag tggcaggcca ccaggccctc   60
tgggaaatgt agtccagagc gggacccacg ccgattcctg tcagctcctc gcctgggccc   120
acccgaaacg gctgctccct caactctcaa catccagccg agcctcggag ttgcgggtcg   180
ccgtagcgct gcgcaatgga gatgagcctc cggggaacc cggccaagc ctcaccctca   240
cacaggaaag cagatgtgtt ctggccggaa gttgagtggg gccgcggggc ctgctgggag   300
gtgttgtcct cggaaacgtc gctggcgcgg aggatggtt cggcgcttta ggcgtctgtc   360
acagacctat ctgcgggtcg ccttcaccca gcatctcaga aactgcgcgc gggatgaaca   420
ttcgggtgtt tccggcaggt gacgctgccg agtccccgca gcagggggcg agcaagggac   480
tcgcggttga cgggacacgg atcctctaag gcccagagtg tcccgagtag cggcagtggg   540
```

-continued

```
gagtgctcag ggtac                                                       555

SEQ ID NO: 21            moltype = DNA  length = 361
FEATURE                  Location/Qualifiers
source                   1..361
                         mol_type = other DNA
                         organism = synthetic construct
SEQUENCE: 21
ggtgggcggt cggtgtccac actgacctaa agcaaaaagg tcggggccag tacccacttc   60
agaacgattt taatccgaaa tggacgcaga tctctagacc ctctcggagc gacgggactg   120
ggaacgtctt agggccacgc cgcgagagga atgagcaggt tcggggtttt aacctacagg   180
gcgaccccaa aacccgacag cggagcgtgg gaacctgtgg cccgcgaggc gcaggcttga   240
acccgaaaga cggagactca cccgagagcg ccagtagccc cgcgagatcc gcttccgggt   300
cggcaggaac ctgcgcgtac gcgagtgcac tggggcggcg caaggggcaa gggcaggggc   360
a                                                                      361

SEQ ID NO: 22            moltype = DNA  length = 1514
FEATURE                  Location/Qualifiers
source                   1..1514
                         mol_type = other DNA
                         organism = synthetic construct
SEQUENCE: 22
ccacctttca ccttcccatc cttaggaagc aaagtgaccc ctaagcctag acaaagctct   60
cgaaagccca aagcctcggg cccaccggcc agctccccac cccgctgctg ggccggacag   120
gtgtagggga ggcggacccg ccccgcagcc gactcacccg gctccagggc ctggtcgcac   180
ctgagcgagc cggcctccgg ctgctgctgg cgctgcaggc tccgcgcctg gcctgccagc   240
ctgcgcagcc ggcactcggc cgggaagcac ttctccagca ggccgctcag caccacgttc   300
acgcgccgca cctgcggccg cgcggggccct ggctccacgc agcgcttgca gactgtgagc   360
ccgcagggca gcgtcaccgg cttatgcagc agccgccggc agcgcgggca gccgagcagg   420
tcgcggggcg cgcgggggctc cggggccggc cctccctgcc cgggcgcctc gggctcgccg   480
cccgggttct ccgcggacag cggccggtcg cgcaggccca cggcgcgcac caggccgccc   540
gccagctctt ccagctcctc cggccggcagc gccccgagcc gcgcggcgcc gcggaacgcg   600
cccagggctt cggggaggcg gccggcgcgg gccagcgcgt cccccagcct caggcacagg   660
ccgcggtccg gctgcgccag cccggctagc atggagcgaa agagctcggc tgccatctcg   720
tagtcgcccg cgcggaaggc ctcgtcgccc tcctctagca gctgggcgat cggctccgcg   780
cggtcgcagc caggacactg gggcggcggc ggcggcggga ccggctcggg gctcatcacc   840
gcgggggctgc gacgacgcgg gtccggagcg aaggcgcgga gcaggagga tgcgctgctg   900
ctgggaactg gccggcggga gcgcggtctc agccctcgcc agcagccacg cgcgtctggg   960
ggcggcgcgc tgcgagcggc tgagaccgcg ggcgggggcg ggcgcctggc ttgggcaggg   1020
tcctcagcgc ggtgtgggcg gcgagccccg cagggctgca atcgttccgg ggtggggggc   1080
gggacaggca ccgcgggcgc aatctgagcc cctgcccacg cgcagcggcc tctcagtccc   1140
gccggcttag gtaacccagg tcgctgcggt aacgcagtga ccgcgctcca ggtccgcgtc   1200
tcttgcgatg cttcccccac tcgcctgagg gctcctgcgc gactgcgcgc gcgtcctctg   1260
cctgccgcct ccccgcagag gtgccgggggc cctgggagca ggtggccttg gccgcgcgggct 1320
gctggcgcgc cggcaccgcg gcacctgctc ttccccagag gcctggccgc ccccacaacc   1380
tgtggctccg cttaagcaag aacccaggaa aagtcaccaa acgcatcacg catctctagc   1440
ttcgacttag gaaattgtcc taaatgactg gggaggctga agtgggcacc cagaggcccc   1500
gcctcagcga gctt                                                        1514

SEQ ID NO: 23            moltype = DNA  length = 505
FEATURE                  Location/Qualifiers
source                   1..505
                         mol_type = other DNA
                         organism = synthetic construct
SEQUENCE: 23
tggaagcgga tcttctcgga cgcctctggc ttggggctgc gggaagcgtg ggctgcccgg   60
ggcgcagtgt gcggagaccc tctaggcggg cggggacgcc ccacgcggcg acctgagcac   120
cgacctcatg caacgggacc gaaccttggg acccgggcag caggagctct gttcccttca   180
cctccagctt ggtttgaggg atactgatga aggaaaccgg gggtttcccg tcctgcgcgg   240
agagcctcgg cgcccaaaat cgaaaggccg ggagttgttc tgcaggcttt gcaaacaggt   300
tgactgaggg tttcctttcc cgtagcgctg actgcgaaat ctgtgcatag gcgttcagtg   360
ccagtggagg atagctgagc aagccaagaa gttttgcagc ttcctctgat ttatcggtgg   420
agtgtcagga ggctgtagca acagtttaca tttcccctgt ccctgcgagt ggctaggggc   480
aagctgggct cggacgtgat atcct                                            505

SEQ ID NO: 24            moltype = DNA  length = 1381
FEATURE                  Location/Qualifiers
source                   1..1381
                         mol_type = other DNA
                         organism = synthetic construct
SEQUENCE: 24
ttgcgttgtg ggtctccggc acatttcaga ggctcattag gaccctgacc ccacactggg   60
gtttacaccc ctaaaagcag gtgtgtcccg tggcaactga gtgggtgcgt gaaaaggggg   120
gatcatcaat taccagctgg agcaatccga atcggttaaa gtgaatcaag tcacagtgct   180
tccttaaccc aacctctctg ttggggtcag ccacagccta aaccgcctgc cgttcagcct   240
gagaggctgc tgctagcctg ctcacgcatg cagcccgggc tgcagaggaa gtgtggggag   300
gaaggaagtg ggtatagaag ggtgctgaga tgtgggtctt gaagagaata gccataacgt   360
ctttgtcact aaaatgttcc ccagggggcct tcggcgagtc ttttgtttg gttttttgtt   420
tttaatctgt ggctcttgat aatttatcta gtggttgcct cacctgaaa aacaagacac   480
```

```
agtgtttaac tatcaacgaa agaactggac ggctccccgc cgcagtccca ctccccgagt    540
ttgtggctgg catttgggcc acgccgggct gggcggtcac agcgaggggc gcgcagtttg    600
gggtcacaca gctccgcttc taggccccaa ccaccgttaa aaggggaagc ccgtgcccca    660
tcaggtccgc tcttgctgag cccagagcca tcccgcgctc tgcgggctgg gaggcccggg    720
ccaggacgcg agtcctgcgc agccgaggtt ccccagcgcc ccctgcagcc gccgtaggc    780
agagacggag cccggccctg cgcctccgca ccacgcccgg gaccccaccc agcggcccgt    840
acccggagaa gcagcgcgag cacccgaagc tcccggctgg cggcagaaac cgggagtggg    900
gccgggcgag tgcgcggcat cccaggccgg cccgaacgct ccgcccgcgg tgggccgact    960
tcccctcctc ttccctctct ccttcctta gcccgctggc gccggacacg ctgcgcctca   1020
tctcttgggg cgttcttccc cgttggccaa ccgtcgcatc ccgtgcaact ttggggtagt   1080
ggccgtttag tgttgaatgt tccccaccga gagcgcatgg cttgggaagc gaggcgcgaa   1140
cccgcccccc gaagggccgc cgtccgggag acggtgatgc tgttgctgtg cctgggggtc   1200
ccgaccggcc gccctacaa cgtggacact gagagcgcgc tgctttacca gggccccac    1260
aacacgctgt tcggctactc ggtcgtgctg cacagccacg gggcgaaccg atggtgagta   1320
gagttggact gatgcgccct cagcagctca gagcggcgtg agaatggcgc cctagggatt   1380
c                                                                  1381

SEQ ID NO: 25            moltype = DNA   length = 421
FEATURE                  Location/Qualifiers
source                   1..421
                         mol_type = other DNA
                         organism = synthetic construct
SEQUENCE: 25
gaggcaggag ggaaacgctg cgagagccag ctcgctggaa atctgccagg gaaactaact     60
tatcttgggg cggcagcgcc ccgggtgcgt tatggtgcaa ggtcttggag cttcgagtcg    120
ggggtggtgg gcggaggagg aggtggggaa gctgccctgc tgcggactgc acatctgtgg    180
cgacagggag ctcagtgggc agcacagctc acgtctgagc gcacgtgcac gtgtctcgct    240
ttaggctcct agtgggtgcg cccactgcca actggctcgc caacgcttca gtgatcaatc    300
ccggggcgat ttacagatgc aggatcggaa agaatcccgg ccagacgtgc gaacagctcc    360
agctgggtga gttgggtatg ggaccaggag ttagtgacct cccgacccc catgtggacc     420
c                                                                   421

SEQ ID NO: 26            moltype = DNA   length = 541
FEATURE                  Location/Qualifiers
source                   1..541
                         mol_type = other DNA
                         organism = synthetic construct
SEQUENCE: 26
ttgctcaacg tgggtgtagc acggattagg ccttttacag caagcgctgc cagcagggaa     60
ctggtggatg tactcttgac cacgctcggc tggactctgg ggagcccaag acgggtaaga    120
ctaggtcccc ggccccagca gctggtgggg gcgccgcagg ttagagacgt gaggccgcga    180
ggctgagggc tgtgaaggcg gtgggcacgc acggcgtgcc ggggccgcct ggcttcgcgg    240
cggggagggt aacactgcga caccccgcag acgctgtcag ccggggtcgc ggccccgcgt    300
gcgcccgatc atctgactgc tggggagtgc gggggcgcgg gagccaggcg agccagcgca    360
ggcgcgcgct gcctcctccg tccccaccga gtccccagcg cgtgcgcggg gccgtggccg    420
aggcctgcgc gccgcccggc cgcctgcact gcgcgcgcgc ccaccccgcg tgggaggcag    480
cgggagggc ccgagaggt gtggagcggc gcggcggag gctccgtggg cggccacggg       540
a                                                                   541

SEQ ID NO: 27            moltype = DNA   length = 959
FEATURE                  Location/Qualifiers
source                   1..959
                         mol_type = other DNA
                         organism = synthetic construct
SEQUENCE: 27
gccccgcggc cgcctcccgt gggcaccggt gtcgctggcc gcggggaggc cttctcgggg     60
cggagcggcc cacccggcgg ggatggggac tcctcgtggc ggccgctgac ggacggccca    120
actttaggtt gaggggcgcg gggtgtgcgg gaccccggcg cggagctggg ctctgggcca    180
cgaccgccag ccgcggctgc cccgagagtc cccgcacgcg cagtggcttt ccaacgcggc    240
ctcttcccat ttctcacttg actcccttg cgcattaaat tgtcgagaaa cctttggcca    300
gtgggtcttc aaagctaaac caaatggctg tccttgcagt ccttggctac ctgagatccc    360
ttaattctga accatccgca cctgggaggg gaagttgaaa ggagcgctgg agctgagccc    420
gcatccttaa ggatcccatt cactgcttat gatggtagag ctttgaatta gatgtcaggc    480
tgttcacgtc atccagactc tggttttcag ctctgtgctg agacagtgtt ttgatacgta    540
tcagaggatg atgttcctat gggacaataa cttgctgtat gttctgagat actagactgc    600
gttcatattg tagcaccatc atcgtataaa acgggcgcct ttgaaaggtt tcagtaaaca     660
ccttcctcag gaacatccgc cagcacttaa attgtacttc actttcactt tgacgtttgt    720
tgtttgtgaa tcttgtgcac aatttaaagt gagtcgtcta aacagcacag gatcacgtgg    780
tgcggggcat tgagcaactg gggaggaaag cagagacttg aacctgctgg agtctagttg    840
gtctgcgttt ttatgttgga gaaccatcct ggttccagct tattttgctt tcgtaaatat    900
gatgcatttt ttaaatgctt tcatttgata cggtctatct ggactgtaag attgagtct     959

SEQ ID NO: 28            moltype = DNA   length = 1320
FEATURE                  Location/Qualifiers
source                   1..1320
                         mol_type = other DNA
                         organism = synthetic construct
SEQUENCE: 28
ggacagcctt ccctctctgc ccacttccga cgccttcttc tcgggcatca ggcggatcct     60
```

-continued

```
cagtcgccct tcgccttggc gaatccacca actgaacagc tcgctgagat tgaactggag   120
cagccccaca gccgcctccc cggggggccc gacgcaaccc tccaagatcg cctcctcgcc   180
cagctccagc accaactgct tggcacgccg gagcttgcgc acggagccgc ccttcagcac   240
cctggacagc gtccgggcct ctgccggggc tggtgaaccg gcggtccagg agacccccgg   300
cgccggcccc agcaacctga gcagcggggc gcagtccaga gctagcgagc cgcgggcctc   360
gggcctgcca gccttcagct ccgaggagga tggtggcagc agtaggtccc gggcgtagac   420
acggaagagc gagggcacca cgaagtcaac tgccagactc ttcctctgca ggcgcgagta   480
gctgagtggc tccgggggct gcagcggcgg ccccgcagct ggggagcccg cgcgctggcc   540
ggtccccatc ccggagccca cagctgccgt ggaaagcagc agcggcagga gccacaggag   600
cccgatggct cccatcccgc cggaggaggc cgtttacact gctctccggg cccagcctca   660
cccttcgctc tccccgagat gggaagaggc tctgaacagt ccttggtacc cagcggctcc   720
ttccacctga tctccagagg actgtgcgtg cgcgcaagtc tcttgctttc ccccaactgc   780
acggaggcga gcaggagtct aaatgaaaca gacctggaag ctcaggggcg agtccagaga   840
cactcaagca cactgggctc actggctggg accttgagc tcccgctctc cgcgccgagt   900
gccgcgcccc cgtctgtagc tcgctgcgct cggtacagag gaactactat ggttgaaggg   960
aggtggcagt tgggtaccgt cctctcctgc ccccgcagt cggagctggg gtctgtcccc  1020
tctcggggca gcctccaatc tctgcaactt ttaaggctga gaacgcggc tcccagctgc  1080
tgcacgctgt cctggccgcc tttttgcgttc cttttggct ctccaagctc ttctgcccgg  1140
tctgggcggg aaccgagggc ggaggctgcc gtcttgcgca ccctcaagct atctctccgc  1200
tgcgggaagg cttcggactg tctgcctgct gaacttctgg gcgtgaatcc cagccccgc  1260
gctgcgcaag tttgcagcgt ccttgctctc accggcgcct cggctcctca gagttcgcag  1320
```

SEQ ID NO: 29          moltype = DNA   length = 1495
FEATURE                Location/Qualifiers
source                 1..1495
                       mol_type = other DNA
                       organism = synthetic construct
SEQUENCE: 29

```
gagacgccac ctcccgccca catcttcctg tttttcagtc tcccatttcc gaccataagc   60
tcctccaagg cttttgccca gaccectaga cgactgttct ggacccagtt tataaagact  120
gcctggctgg ccaggaaatc ccccagaggc ctccttccgt gtccccgggc caaatctgtg  180
aagagaaaac ggaaggctac catgtcacga aaaactatga tcaaataaat tattatgcct  240
tttctcctat tgatctgcct tttgtcaact gattttcagt gaaccttcgg agagccatgg  300
ggaagttttc cctttccccc tacagggctc tgaatctgaa ggtaagagtg agcctatagg  360
gggaaccttc tggctccctc acaggaactg actgagcagg agttggaaaa gccacttgga  420
ttcccatttc ctcaactccc cgccaatacc aaggcgtctg tttttacagg ctctttcgtg  480
gtgttctggg cacattcaac ttccaatgca gctgagaggg tcgggaacag ttagagaaca  540
ggggtggcag ccgcccggga ggctgcaagg cgctcgcccg caacgcacag gcgcgcgcgg  600
cgcacccggc ctccggcctc cccaggtcgg gcctggcagc tgcgggaagg aggtcagcgc  660
agccgccaca cttcgcccgg gcgctggccc gacccgaccg ccggcgactc tctggcagcg  720
cccggagacc gccagcccct gggcgcccg tccgcagagc ccctccgcc ccgggaccct  780
cgcgcgcagc tcaagttggg agcccgctc cgcaggcgag cgcgcgccca ccacccacac  840
ccactgccac tcatgcacac cgcgggtccg gagatgcccc cgcgccgtttt aaaatccgag  900
aacatcacat ggtagccaca tccggcggct gttacctgct cgcagcaccc agaccctcgc  960
cctggtttcc cgggagcccg caaacccggc acgcgggctg cgcgccctcc cgcaagccac  1020
cgctcagcgc cagcgcgccg gcaagccgcc taccttaggg gtctgcactt caggtccgt  1080
cggcacctcc aacttcctct tggttaccca gaagaacagc agcaccgtga tccagagcac  1140
cccgaagact ggcagaacca gccgacgagt caggcgccgc atggtcccct ttgccgcttc  1200
ctctccgcgg cgctacgtcc cggggcacc ccccggcggt cagggttggc ggggcaggag  1260
tcctggcgag cgcctcgctc tggggagctc tagacccagg atccggttgg aggggcggca  1320
ggatcctgca aggcgccctt cccgcttcga agagaagcga gcctgggtgg ggggtgcagg  1380
gcgacccgaa acgtggcagg gaaggaccga gggcagccaa gctggacgcc cgctccagcg  1440
ggagaagcgc ggtggctgcc gagatgttcc ccacgccgcc accgcggctg ccgcc         1495
```

SEQ ID NO: 30          moltype = DNA   length = 302
FEATURE                Location/Qualifiers
source                 1..302
                       mol_type = other DNA
                       organism = synthetic construct
SEQUENCE: 30

```
tcggtcttca ccaccttgcc cgacttgctc ttcatctttg agtttgtgag tggctcctgg   60
ccggggaagg gacggggtgg gctgagccgt gcgctctctc gggcgcccag cacagctgtc  120
ggacgggatc cgctagctgc gcaggttctg ggagcatcgg ggcagcaggc gcaggcgggg  180
gactaagcca gggaagtccc ctcccacctc cggtcctttg tgcccttcta gaccaacaga  240
atgaggggaa cagtctacag gactatggag gaaaaactgg gttcccaact ggggtcagat  300
gt                                                                    302
```

SEQ ID NO: 31          moltype = DNA   length = 721
FEATURE                Location/Qualifiers
source                 1..721
                       mol_type = other DNA
                       organism = synthetic construct
SEQUENCE: 31

```
acataagccc ccaaacattg ccaagctagt gtggagaaca aagggagacc ttttagcatt   60
tagaaaaact gccctttccc cgaggatgag cccggagatg ggaaaggacc tttactgggg  120
tattagaaag acttccgagc cctcaattat ccaggggcgg tgtggaacgc gggaataaag  180
tgtcatcgcg tccctgggct gctgcgcaga gtgctatcga cgcacagatt tggtcgcacg  240
gataatcatg tttgctttag atattgaatt aaacctgatc atcaactaca gggagcgaga  300
aagtcagctg ggaccgctcc ttttgcccgg cctcctcact gccacccaac cccccagcct  360
```

-continued

```
tgatggtgca gcttcggaga gaacagagat acaatttcca aatgcgccga cgttcagtcc  420
ctcagcgtct gcagcacccg ctgggctctg agctagagtc ccaagtattt ttagaaaccc  480
gcgagataga ggagaaaggc tcatcctcca gttggccagg cttcctaaga cgctcccccg  540
cgtggccaag tgtgcgccag catctgccaa ggagatcttc ctccagcaac aagggtggga  600
cggaatccgt tccccgccgg aaagatggat gcgcccttcc cgggcgtgcc cggggctgtg  660
tgcccacttc ccatccgggg agctcacccc acccccaaac ctctacttcc tagcaatcca  720
c                                                                   721

SEQ ID NO: 32          moltype = DNA  length = 2986
FEATURE                Location/Qualifiers
source                 1..2986
                       mol_type = other DNA
                       organism = synthetic construct
SEQUENCE: 32
ggaatgggcg cgaagccctc ggcgcagacg cagaggtagc tagtttggtt caggggctgg  60
cactggtact cgcagttggc tctgaagcac gggtccacgg gctccacaca ctcgccgtcc  120
accaggtcgt agttagggta gcagtggcac tcgaagccac cctgtgtgtt gacacagcgc  180
tgcggacacg gactgggctc cagtatgcag tcatccacgt cctcgcaccg gtgttggtcg  240
gccgccagcc ggtagccggt ctcgcacatg cacgagtagg agcccggctg gtcggggttg  300
ggaacgcaga agtgctcgca gaggtcgttg caggactgcg tcgcggatgc ggtgcaggag  360
cgcccgtctg cctgcagggc ggcgccggct gggcactggc agcggggagc cccagggatc  420
gcattgcacg cgtgctcgca gccgccgttc tccacgctgc agtcccaagc gcccggcgcc  480
tccctggccc agtgcccctg gaccgctccg ggcggcgcgg tgcacattag ctgtaagccg  540
aggggagcca ccgcggcgga gctgcccacc ggcagcgcct ggaagtccgc tccgcgggcc  600
gcgaacgggg tgccgtaggt gatcgagacg gcggcagccg cggcgccggg ctccacagcc  660
agtggcctgc aggtggctgg gaagtggaac tcgcagagga agccatcggc cttcacttcg  720
cactgctgct cctcccagat cggctcgctg ggcacagtgg cctcagcagc ggagacagcg  780
acgcacaacg ggccgcagag gggagcccca ttgaggtcga gccgtgccca cctgctatag  840
ctggtgttgt tgtctcccgt aacccactgg aagccgcgca ggggcccgag gcgcttgggg  900
tcgccgcagc cgggtggcag ctgcaggccg atccagaggc gccggcggcc aacgccgccg  960
tcgccgttca gtagcaagga aatgacatcg gcagccaccg aggagcgcac tgtcattagg  1020
tggccccgca gtccgtcgca gatctgactg gcattgagga aggtcgcggg gcccgggtag  1080
agcgcgaagc agtcgtgctc gacgcactgg ctgccacccg gctgcggctc tgcgggtgcg  1140
gggaacccca ggccggccag ggccagcgcg ccaaggacca ggacccaag catgttaccc  1200
aggcgcgccg cgtgcaggcg ccgggggaag cgcgggcact gcgacagggc cgtgccggag  1260
cagaggggca caggacgccg atggcgcag cctctcctgt ccgtcccagc ccagacactt  1320
cttgccgctg cgcgcagccc ctgcgaggca gcctctgaca tgcggatcgg ccagggctcg  1380
agtttataag tgcccggccc tccctccctg gacgttcggg aaaaggaagg aagtgcctgg  1440
tgggaagggc tgatgccgca tactcggatt gctgggttct ctggccgccg ttgcgcccgc  1500
cctcgcgcat gggatcacct cgccgggatg agtaaaccct gccctggcgc agggaggttc  1560
tcgggcgggg ccgacagggg caggcgccag ggaaggccag caccctgta acaagacgac  1620
tgtccccgcc caccactcgg gcccccacgc gtgcagccct ctttcatctc ttggtcctcc  1680
tttctttctt ttcatacatg ttacagccac ttccaaggaa agcctggatt gcaagagctc  1740
tgggaaccgg agacttcaga gaagagggct ttgaatgggg agtgggggag gtggtgcaca  1800
ggacctgcaa gacgctggga ggggtgatcg gcaccaaggg cactttggga ggacctgcct  1860
aggacgtgga cttccccgaa gacaggatcg caaggagaga cagctggatc ctgtccgcgg  1920
ccaaggtgcc tggctcagga aaccagcgga gcgcgcttgg cctcacagga cagtgggtgt  1980
ggctgggggtg acggggcagg gtggggaaga ctggcctaac accagcgccc tctgccccat  2040
ggctggccag ggaccgcga gtccctggac acgcactggc caacgccaga ccccatctca  2100
tcgggtgggg aagtcgcggg gacactgtca gggcgccgaa gtccggaccc ggctcagagg  2160
cggtgcagg tgaattgctg cggcgccggg tagggcgggg cgcgtgggag cgagtcaggc  2220
tggccagttt cggcccagct tccgaaggat ggtgcttctt gcaccccaac agagtggctg  2280
gcaacccccc aggggagcgc gcaggatccc agctgatccc acccgggtcg gctaaggagg  2340
tttccatttc gtccagagtc cgaattgata cccacgtgca tagaaacgcc acttgctcgg  2400
caaagggcac tgaagagcca ccgtcctgtg gatgggcagg gtggggggg ggctggagga  2460
ggacatggga atccgtcact ttcgacctct tccggtggtt cacttaccgg gaatgcggaa  2520
gagtgggtct cccctcgggg tcgcccccat aatggtgaga ggcaaactgt ttaaaaacac  2580
ccttgcctct ctcctctact gtcctcacaa cgagcgccag ggggcggcgc tgtcgagctc  2640
taaacaaagc caaggaagtt ggagaagttt cgggctaaaa agggttaagg tgtaggagca  2700
cagagtcctc cttctggggt tggaagctcc gttcccgggc agctcagcgt ggattccgct  2760
gcgttcacct cttgcctcca gggcccagta gatcctgggc tttaaacaag aacagagagt  2820
atggcgtctg ccacgtgcga cagacacgca ccggtggggt gggccgggct ggactggact  2880
gacctgcagt gaccaaacgg gtggggcgtg gacactctga aagtgaaaaa ggcaagcacg  2940
actgtcccgc cgcacactcc ccagcgcctt ggggcagaga gcctcc               2986

SEQ ID NO: 33          moltype = DNA  length = 901
FEATURE                Location/Qualifiers
source                 1..901
                       mol_type = other DNA
                       organism = synthetic construct
SEQUENCE: 33
tgcctttagg agcacggcag gcaccacccc cccgccccg ctcccctac tctggggaac  60
tacctctgct caccgccttc ccgtggccaa acccaaatat gagttccccg aactttttcag  120
gagcggacgc gctcacgggt caaatccact ccctccaag ggccttaaca cgggcgccca  180
gctacctcgg agaaaagcca gcgggtaggg cggaggtatt gctctcggtc atcaacgcaa  240
acatcccctc gggtgcctac agcggcctgc ttaggggagc agcgtgttca gagcaaatgg  300
agagcttcct gtatctccga ggaaaaaaga aaagccgccg ccccggcagc ctcggcctgc  360
tggggacctg tcctccccac taaaagcgcg cgctgcccga ggagctgccc gggagagaac  420
gctcacccc gggcgtcggt gccgctcctc gtctcgccgc cccaaacact caagtggcag  480
```

-continued

```
attccgacaa gtgggaggca gcaagtggaa atattcgcaa caaccgcgga aagttactcc    540
agcccggggg gccggcagga aactgaagcg gggaacttcg ccaaacgcgg gctgccgagg    600
gacgcgaggg gccgggctcg ctggccgggg cgcgcgggga cactgcttcc cgcgcctgca    660
agctgagacc cggggttccgg ccatggggac ccgcgccccc gcgagcccac acaactttct   720
cctccgaggc cccgcggct ggggcgcccgc gcgcatccag gagggagcgg ggagcccagg    780
ggagccgggc gggcgcactc acctggcgcg ctctgagccc gggcgccggg cagtggcggc    840
agctgcagcc tcaggagcag gctgagggcg agcgcggcga ggctcgccat ccgggcggcg    900
g                                                                    901
```

SEQ ID NO: 34          moltype = DNA   length = 1902
FEATURE                Location/Qualifiers
source                 1..1902
                       mol_type = other DNA
                       organism = synthetic construct
SEQUENCE: 34

```
tcccggtgcc gggcaccggg cgggcggcgg ggaagatgac cgcgggcgcc ggcgtgctcc    60
ttctgctgct ctcgctctcc ggcgcgctcc gggtaagttg ccgcctcccg cccccgccgt    120
tcggaagccc cgggcagcgg gaggtcgtcc ccggatcccg cggggcgctc acacacccgg    180
cgggggctctc ccgggctccc ccgccgcgct ccccgctgca tccagcccgg cgcccgcgct    240
cggcgaagct gcctgcggtc ggcaggagcg ggaagccgcc tgggcagcgg ggagcggcgg    300
agcagggtgg gagtgggggct cggtggagga cccgggggagc tccgcctgca ccggaccccgc   360
cgagcctccc tcgaacgccc aaagcccgta gccgctaccc gccgctcggc ttgcctgcat    420
ggggcaggct tccactggcg gagccggcgc gccctccatc gcccgggagc cgcgcgcgcg    480
gggagttgcc gagcccagcc ccggccgtgg ctgaaggcgt ggggcgcccg gcggctgcgg    540
gccagggatc cgcgagtgcg gggcgcctgc ccgacctctc ctgcccaagg cctgggggtc    600
cgtctagcgg cgccgctcag ttctgtgggt gccggcagga cccgcgctgc gggtgggcag    660
cggggtagga ctgcgggca ctctcacccc cgagccctcg gcggggctgg agcctgcgtg     720
tccggcgggg ccccggggc tgggagctgg gccgggcttg ggccgggaag ccggacgccg     780
ggcgggcgcg gcgcgggagg gcgccccggg agggcgagcg ggtctcccgc tgcctctgca    840
gagccccgcg ggccggattg ccagctttgc tctgcgcctg gcgaggtgcg cggcccgcgg    900
gggcagagag cgcggcggct ccggggggcgc ccctgggcgg aggcggaggg gcggcgggga    960
ttgcaggaac cccctctcgt ggccgatcgg cctcgctgcc ttctcccggg cagcgctgtt    1020
gtaacctcgg aaataaacaa gtgccagcgg cgggaggccc gctccgaggc cgcggggcgc    1080
tggggggacgc gctgggcaca cgcttcgggc gggcggaaac tttcctgggc gagttgagcc    1140
tcccaccggg ctgcgggtgc gatttggagc ttcgtggccg atgaagaaag ccgcggttta    1200
gagctttttcg taaggaatga ccctgcgtcc cgctctcctc cctcggtgct gggggtagag    1260
gggcgccctc cgcggtgccg gcgtcgggaa gcctggagct ccgggctggg ggcggcctcc    1320
ggagtcgaag catgggcggg cgacggcagc gcgcggagct ggaggaggcg gcgggcggga    1380
ggcgccactg cccggtgcgg gctgcacccg aggcttcctg cgctcgccgg ggagccaagc    1440
accgctgtgc tcctgctcct tcagcggggc tggcttcccg cttgcacaca ctgcctctcc    1500
ctccaccacc tcctcctgcc tgtcacgccc cctcccagaa gcttggtcgg agggccctgt    1560
cgtccacccc atccttccct ggccctgtgc catgggctct agacttcccc actgagcagg    1620
aaaggcgagc gagctccgga ggacaggagg agaccccctt tccggtcagt taggggagcc    1680
gtctccctgc ctgggctgga gatggggggct ccgagggtga aaatgcgggc tgaagactag    1740
aaggtggaag cgcccccact gcctcctcac cccagccacc ggcagcctcc cgcagagctg    1800
ccttcttcga ccggctccgg acctagtcct agagaatctt cttccttct ctcctctttc     1860
tcctccctcc cggtgacctg gagaggagac aagaagctgc ct                       1902
```

SEQ ID NO: 35          moltype = DNA   length = 721
FEATURE                Location/Qualifiers
source                 1..721
                       mol_type = other DNA
                       organism = synthetic construct
SEQUENCE: 35

```
gcatttcgaa ccttccagtc cagaggaagg gactgtcggg cacccccttc ccgcccccca    60
cccctgggac gttaaagtga ccagagcgga tgttcgatgg cgcctcgggg cagtttgggg    120
ttctgggtcg gttccagcgg ctttaggcag aaagtgctcg ctctcaccca gcacatctct    180
ctccttgtcc ctggagttgc gcgcttcgcg gggccgatgt agaacttagg gcgcccttgcc   240
gtggttggcg cgccccgggt gcagcgagag gccatccccg agcgctaccc cccggagcg     300
gagcacgccg gctcccagta ctaggggctg cgctcgagca gtggcggggg cggaggggtg    360
gttctttttcc ttctcctccg ccagaggcca cgggcgccct tgttcccgcc ggccaggtcc    420
tatcaaagga ggctgccgga actcaagagg cagaaaaaga ccagttaggc ggtgcagacg    480
gtctgggacg tggcagacgg acggaccctc ggcggacagg tggtcggcgt cggggtgcgg    540
tgggtaggggg cgaggacaac gcaggggtgcg ctgggttggg acgtgggtcc acttttgtag   600
accagctgtt tggagagctg tatttaagac tcgcgtatcc agtgtttgt cgcagagagt      660
tttcgctctt aaatcctggg ggtttcttag aaagcaactt agaactcgag attcaccttt    720
c                                                                    721
```

SEQ ID NO: 36          moltype = DNA   length = 841
FEATURE                Location/Qualifiers
source                 1..841
                       mol_type = other DNA
                       organism = synthetic construct
SEQUENCE: 36

```
tcccccctgc ccagaaagac acaaatcgcc tcccggagtg gcgcctccag tcgcggcgga    60
gcgcggcgtt ggcggcggat ggagggcgcg agcgggcggc cgcggaggct gcacccggcg    120
gggcgctgat gcgcgcgcctg gaccttcgct gcgcgacttc gggggcgtcg gccgagttgg    180
gactccgcga tgcagctcct gaaggcgctc tgggcactgg caggggccgc gctctgctgc    240
ttcctcgtcc tagtgatcca cgcgcagttc ctcaaagaag gtaattgtcc ccgggcgcgc    300
```

```
ggaccggtcc tccgcgctct gcccggctcg cggcggctcc ggcgcccgac ccggcttcca    360
gcacgttccg ctgccgccgc gctcggctga ggctcgtgga gcgccactgc gggcccggag    420
cggcggcgg cgcgacccta ccaggagccc gaccccccgc ggatctcgct gccccgcgcc      480
catcgggget caccggcagg gcgcggggtc ggggcgcgct gcgttctcgg tgcctctggc    540
gccgccccgg atcccagcc caagccgagg ctgccgttcc catcccctgc cccactgggc      600
tcggtggcag cggcgcccgc ccgcacgccg ccgggccctc ggtagatggc accagcgctc    660
cacggtggcc ggcggggctg gggcgggagc ggagctggga cccgccaggg tgggcgccgg    720
gctgggaccc gcggacgtcg ggaaaccggc ctgcgcacct gttccccagg gcccaagccg    780
ccttccagag acccataggt ttgggaagca ggggcttggt caccggggtg cgcaggtccc    840
c                                                                    841
```

SEQ ID NO: 37          moltype = DNA  length = 781
FEATURE                Location/Qualifiers
source                 1..781
                       mol_type = other DNA
                       organism = synthetic construct
SEQUENCE: 37

```
gagcctcggc cgctgccgag cgcggggctt gggcggcacc caccagagcg ccccccggctg    60
gctcttagcg cccgaaactg gctcgcgagt cccccggctt cctcgccccg gcactccctg    120
gtagcctcgg tctcccgcag cccccgctcg gagagctcgg agcccgctgc attgcggtgc    180
atgctcctta gctctgggc agagccagag ctgggcgttg gggagaaagg ggtgcctctg    240
gccatccggc tcctggagta ctggcgcccg tctgctcca agcgcacggata cgcttctgag    300
cagccgcgcg ccacctcctt ttctccagct cgcagtccac gggctagtgg actctgcttg    360
gcgtgcaagc actgcgcgcg ggggccgag aagctctgcc gtggtatccc gcaagtggcc     420
gccgaaggag aggggtggag ttcattggcc gtacccttgg ggaccagtct ggtggtccgg    480
gcgcctgcgg gactgcaggt ttccagggtc agtcgggag aggtggaaac cctttcgcc     540
tcttgagcct tggaacagga gtgggctggg gtgagtggtc ggtcctacct aaagtctccc    600
agcctctcca ccaccccgga gaggatactc ggcggccggg agtcgtcggg cagcgtcact    660
ctctgccagc tcagacttgg cggtgcctcc ggcttggtgg ctgggaaagc gcgctccaaa    720
gacaccgtgc ccggcgcagc ggggagcctg ggcgctcggt agcgctcgcg aatccctgtg    780
g                                                                    781
```

SEQ ID NO: 38          moltype = DNA  length = 841
FEATURE                Location/Qualifiers
source                 1..841
                       mol_type = other DNA
                       organism = synthetic construct
SEQUENCE: 38

```
cggcggcggc ggaggagggg gaggcggcgg cggctgcagc atccagagct ggccgtggcg    60
gccggcgcgc cccgcgcaca aaagcaccca gccccagggg agggcgatga acacaccaca    120
tcccgggccc gggccccagc tgctgctacc gctgcgtgcg ctcagggcgc tggggaagac    180
gcccggcgcg ccggggggcca gcggccgagg cgcggcccgt gcgccctgag cgcgggactc    240
gtcgccctcc gggtcaggcg ccaagcttcc aagcggctag agcgcgggata cgcttctgag    300
cccaggatcg cttcagtaag gcgcttcccc actccaggcc cgaccccggg cgcctgagcg    360
ccaacttcgc caagaacgct cctaactcca ggccatcctg cagcgcagag ggggcgctgc    420
tgccgggcat cagccgtgag gacgcgcccc tggccgtgcg gagagagccg gcatttgcgg    480
gtcactcggg cgcccctgag tgggcggcgg cggcagcaga cccctctcca gggagtccag    540
gacctgccag cgctggggat tcttcccgaa caggcgcttg ccctctcttt tatggtaagt    600
actctccagc tcctggtgag gggcgcgcgg gggccgggag ccgagatccg gctgcacgga    660
ctttgtgcgg gccagcactc gacacagctg gcgctcctga cgtcccagtc cctgagaatt    720
cctctctgca ggttgtggca gttcgagatg gttgatttgc gcgcagccct ggggcgtttg    780
gggccccggc tttggtatca tgggttctaa gccctttgct tctctgcgta gcggacaacg    840
c                                                                    841
```

SEQ ID NO: 39          moltype = DNA  length = 1500
FEATURE                Location/Qualifiers
source                 1..1500
                       mol_type = other DNA
                       organism = synthetic construct
SEQUENCE: 39

```
caccaaccgg gcgccggctg gcaggagccg cgcagaggct ggtccgagcg cgttgcgggc    60
gcccggcgta aggggagtcg ggtagcagca tcctcctggg cgccgctttc gcgcggcggc    120
ggcggctgcg gcgggggtctt tctttgctta aataccctcgt tggccagaag cgctggtacc    180
ggggggcgggt tgggtcgggt cgggcagtgc tgcacacctg ggtttccttg cctagagccg    240
tgtgttcggg gtcctttggt ccagtcggag gctgcggagc ggcggggggtt gcctgcgctg    300
tccgcccggg catcctcccg gtgatggaag cagccgccgc cgccgctgcg gggtcgcgct    360
gtgccccatc caccgctgcc agagaggtgg gaaaattcgc cgcacggagg ccgaaagcga    420
gaggggctgc gccgctatgc cgggagctga gtcccatata agccgcccca agccatcgcc    480
cccagccgac ttcgttcccc tgagcgagac aggaagctgc ggtcccgaga aagcggagga    540
gacgtcgctg gagccgggag gcgcgcggtt cggcggagcg cggagcgggg ctctgggccg    600
cgtgaaagtt tttcttcccg agccgcaggg cgcccgctgc ccggaaactg cccagggata    660
agtcggccga ctcccagac ccctcgaagg tgcggggacc cccagcggaa gcgagaggga    720
gcgaaatcga ggaacgagtg acagccggac agtccgccgg gcggtgatcc ggggccgctc    780
ccggggcggg cctcggctcc aggtgagcgg aggaaccggg cagaaccgag ggtgggcgtt    840
acttaggagg aggaggctgg gaggggagatt ggggcgcatc cgctcactcc gcttccctc     900
gcaggtccta cccggagccg ctgccatggg agagccagcc ttgggcgctg gggaccagcc    960
gccgcgcccg cctcggagtc gcggcccgag tcccggcgcc agcagccagc ccgctgcgtc    1020
cccttccegg gctgcagggc tgcctccgcc gcgccgccgg cccggattgt gcctgtgatg    1080
agccgcagcc cgcagcgagc tctgcccccg ggcgcgctcc ctcggctgct ccaggctgcg    1140
```

```
cctgcagccg cgccgcgtgc cctgctcccg cagtggcccc ggcgcccagg acgccgctgg   1200
cccgcgtccc ctctcggaat gaaggtgttc cgtaggaagg cgctggtgtt gtgcgcgggc   1260
tatgcactgc tgctggtgct cactatgctc aacctcctgg actacaagtg gcacaaggag   1320
ccgctgcagc agtgcaaccc cgatgggccg ctgggtgccg cagcgggggc agccggaggc   1380
agctgggggc gcccagggcc gcctccggcc gggccgcccc gtgctcatgc ccgtttggac   1440
ctccgcactc cttaccgccc tcccgctgcc gccgtcgggg cggctcctgc agccgcggca   1500

SEQ ID NO: 40           moltype = DNA   length = 1266
FEATURE                 Location/Qualifiers
source                  1..1266
                        mol_type = other DNA
                        organism = synthetic construct
SEQUENCE: 40
ggccagcagc actgcaaaga gagcgggagg cgagggaggg gggagggcgc gaggggaggga    60
gggagatcct cgagggccaa gcacccctcg gggagaaacc agcgagaggc gatctgcggg   120
gtcccaagag tgggcgctct ttctctttcc gcttgctttc cggcacgaga cgggcacagt   180
tggtgattat ttagggaatc ctaaatctgg aatgactcag tagtttaaat aagcccctc   240
aaaaggcagc gatgccgaag gtgtcctctc cagctcggcg cccacacgtc tttaactgga   300
gctccccgcc atggtccacc cggggccgcc gcaccgagct ggtctccgca caggctcaga   360
gggagcgagg gaagggaggg aaggaagggg cgccctggcg ggctcgggat caggtcatcg   420
ccgcgctgct gcccgtgccc cctaggctcg cgcgccccgg cagtcagcag ctcacaggca   480
gcagatcaga tggggattac ccgccggacg caaggccgat cactcagtcc cgaccgccc   540
atcccggccg aggaaggaag tgacccgcgc gctgcgaata cccgcgcgtc cgctcgggtg   600
gggcgggggc tggctgcagg cgatgttggc tcgcggcggc tgaggctcct ggccggagct   660
gcccaccatg gtctggcgcc aggggcgcag gcggggcccc taggcctcct ggggctacct   720
cgcgagggcag ccgagggcgc aacccgggcg cttggggcg gaggcggaat caggggccgg   780
ggccaggagg caggtgcagg cggctgccaa ctcgcccaac ttgctgcgcg ggtggccgct   840
cagagccgcg ggcttgcggg gcgcccccg cgccgcgcc gccgcctccc caggcccggg   900
aggggcgct caggtggag tcccattcat gggctgagc tctgggcgcg cggagccgcc   960
gccgcccctc cggctggctc agctggagtg ctagctccg aggaaactcg gggcccgggc  1020
gagagccacc gagatggcag gtgggacgca gagcccgcgg cagccagagt tcctcccgca  1080
cggcccgccg acccacggaa gagcgaaaga gcgcccaggt ggggccgagc tgggggccgg  1140
gcccctggag cgctgggaag cacagcgcgc tctagtcagg ttcccttttcc tggagccctc  1200
cgcttccaga ctccttctt tcctccctcc ctccgccac ccctctccct cctctctgtg  1260
tcttct                                                           1266

SEQ ID NO: 41           moltype = DNA  length = 192
FEATURE                 Location/Qualifiers
source                  1..192
                        mol_type = other DNA
                        organism = synthetic construct
SEQUENCE: 41
ggttgccatg gagaccagga gctccaaaac gcggaggtct ttagcgtccc ggaccaacga    60
gtgccagggg acaatgtggg cgccaacttc gccaccagcc gggtccagca gccccagcca   120
gcccacctgg aagtcctcct tgtattcctc cctcgcctac tctgaggcct tccactacag   180
cttcgcagcc cg                                                     192

SEQ ID NO: 42           moltype = DNA  length = 499
FEATURE                 Location/Qualifiers
source                  1..499
                        mol_type = other DNA
                        organism = synthetic construct
SEQUENCE: 42
cggcgctttg cttttctaca actggaagcc gcgaaggcgg ctactgcgct gagccgctcg    60
ctctgctggt caagtttggg cgacccgcgc ggaggagggt cgggctgact gccgccgctg   120
agctgtcccc ggacgggagc gcctgtccac ggcactcacc ccctccagcg gtggaaatgt   180
ggagaagtaa gtgggaggcg gtgtcgggaa ctgactcctc ttaaaacggt cggcgccgct   240
gctctgaaat gggcggctaa gtgcttgtgg gactaagggc ggcctcagag atgcccggaa   300
aatcgctgcc acggccagag tgcggcgcag acgcggcaga gttggaggtg tccgcggtgc   360
aggctgctgc ccacgccgct caggccaggt gctgagggct cagcccgcgc ctcggccgaa   420
ccactctcag ccccgttgag ccacctcgtc cgcccggctt tcatcgcacc ggcagagga   480
aagttcccgc ggcccccac                                              499

SEQ ID NO: 43           moltype = DNA  length = 1201
FEATURE                 Location/Qualifiers
source                  1..1201
                        mol_type = other DNA
                        organism = synthetic construct
SEQUENCE: 43
agcctcacag tctacgccct tgcccctggg gagaggggcc cccaccgcgt ccaccaagcg    60
cccgtacttg ggcagggggc cgtcctcgtg aggaagtggg gtaagccggc acctgcgggt   120
ggccgtggct ccagacttca gggaggcgaa gtccagcact ctcctgtcta tggcgcggct   180
ccagcttcgc agcttctcca ctaccaaagg cctgttacgc gtcaccagct ccagctggga   240
gaagaccaag tccaccgcca gcgtgaaggg cagcaccaga gtgtgagtcg gggcgtcgta   300
gcgcagctgc agcagcaccc gggcgcgtcc ggggctgtgg gagccgaagt gagtgtactg   360
gacttggcgg ggcccgaagg tgcagggaa gcggcgcggg gagagcgcgc ccttgagccg   420
cggcagggcg tccagtaccg tgacttcgca ccggtccccc ggctgcactc caatcaccag   480
atcccggagc gggtcgagcc aaaggggaac acccaggggc accgagtc cagggttggc   540
aatcagcacg ctggggccgt cggggcgagt gccgtcaagc gcaccccggg cgggcaggta   600
```

```
aagcgccggg tcgggctcgg tcccaagtga ggatgcccgt ccctgcagcg cggggcgact    660
caagagcagg caggcgagcg ccacaaggag ctgccggggc gtcccagtcg ggtgccgaga    720
agccccgcc atggccacgg atggctcctg gcgttgggat tcccggggtg gggtgccctg    780
tgcaaagagg gatctgctga gcggcaggtg caggcagtgg aagcagtagc tgctgtccag    840
tcggtagccg acttgcggat ccagcaagag ccagcggctg cgcttcggct gctgcaggta    900
acggcagcgg gggaaggggc tctgcccact tcctgctcag ccccggtcgc aagtctctct    960
ctgctggctt ctggggaccc cagatacgcg cccagcgcgg cgagacttag cgagggtgca   1020
gcgctgtccc ctccgctcct gggcgcttca cccagcctac cttacacacc ttctcgccgg   1080
gagccgtggc cgccgcactg ctgcccgcgc tgccagactc cgaccagctg tctggatact   1140
ctcttcccca ggtgccacaa agggattgtc cctcagggtt gggagagaga cggtgactgt   1200
a                                                                   1201
```

SEQ ID NO: 44       moltype = DNA  length = 1689
FEATURE             Location/Qualifiers
source              1..1689
                    mol_type = other DNA
                    organism = synthetic construct
SEQUENCE: 44

```
cccctcaaa taattcaagc cttggaatag cacagattgt gttagaactt cctgaatcct     60
aaccagctag aatccactgg cttgtttttg cgatatcagc ctgttagaag catatcccta    120
taaagattta atatccctgt ctctgcatct tggcacctgt gaatatgaaa caacagcata    180
aatatgattt tgaacgttgc attgtcacag atgaaaaaat gcaccaacat gtcaaatgca    240
gcgctgaaaa aggaaatcgg gcttattttt gtcgttgttt actgtaccaa agcatttttg    300
aaaacccaaa tcgaggagat aaccgttttt gaatgaacgg cagtgcaaag cgtggtcggg    360
gttagcagca acgtggctgg gcgcctttaa ctcggcgtga cctccgggtc ccaggcccgc    420
gtcccgggcc cagcgcccag gcccgggcgg cgcattggcc cctcctcccc tcgcgaccgc    480
cgcgcattgt tgtcctttag cgattggttg ttggaccaga aacagctgtg cagagccgtg    540
ccatctaaag agctgtggac ctgaatgcag cgtagcgggc tggcggtgac ttacaccggg    600
actccagagg gagagaggaa gcgctgcagg ccacttgcat tgcgtcttcc aggctgcgtg    660
gacccggcgc cccggcgtgt gcggttgtgg gggagctcgc cgtggcctcc cctccctctg    720
gctttagctt cctttggggt tggcgcaggt gggccaggca gcgcaccgca gatctccccg    780
ttcccacgaa ggctggctcg ctgtctctct ccgagcggga gggaccatcc taaaaatatg    840
taaatatcca agcgctggct ccaggctggg gcagctgcca aggtccccgc gccgccgccg    900
ggtgttttac atgaaaatga gaagcctgat gggaaccgcg ttctaactta aggcagccg     960
gtgattagca tgagactggg cggctgtcct gcttcctgcc cttcaatagc cgttccgcgc   1020
gctcgcgccg gagcagcgct gccgccgcgc ggggtcgat cgcaggctcg gcgtccttgg    1080
cagccatggc tccggcgccg cctcggccag taagtaggag catgcatgtg tagggggcac   1140
atgcgtgtcg gcgcacccac ccagccatcc acccgcgcg acgcacagcg cccggagcct    1200
cggcaagggg aagattgacg aggcgctgca gtcgcgggga cgacgcgggc tcttcctgga   1260
ttccgcagga gcccgcccgc cgcagctgct gtctgcagag cctgctcgga tcctgtgcac   1320
acgcgccccc cgctcgagcc tctgtgatga agactgtctc ccggggactg cagcggaggc   1380
agagccagcc agcgccgggg actgcgggcc gtgcggctga taggcccgcg gggacacgac   1440
tcggacactg tcatccccac gcctcgcgct gagctgcccg gcgcggaggg tctgccgccg   1500
cccctccggc ctcccgcacg cccgatcccg ggtcagcccc ggaggcctcg gctgcctcat   1560
ttgtttgggt cttttgtgcc gtggctccca gttggccaag cactcctgcg ctgaatcggg   1620
ccattgtctg cgctcccatt gccttcacgc tgcaagtctc ggcgccccca ccccgcccgc   1680
cccctcccc                                                           1689
```

SEQ ID NO: 45       moltype = DNA  length = 463
FEATURE             Location/Qualifiers
source              1..463
                    mol_type = other DNA
                    organism = synthetic construct
SEQUENCE: 45

```
actgcggccg ccgcgtcagg tgcagcgcca ggagccgggc ggcgtcgcca cgccggcagg     60
ggtaccgcca ctgtggcctt gggggacgga attcaaagcc tgggaaaagt tgctgcactt    120
tgagaaggac gaaccactag tggggagaccg ccggggggccg gccgtggctc tgcgccctcc    180
ggaacccggc tcttgtttct tctacctttg ccatcaggtg tctgccgcgg agctgcggct    240
tatctgggag acgagcgggg ttgacacgcg cgcacacact actgccattc agctgccgcc    300
tggctctgcc tggagtagtg gatcccaccc gcccacctgc caccgagcca ttctccagta    360
cgccccagca ggacgctgac acctccaacc ttggccttg cctttccact ccttccggtc    420
tgcctggttt ttaagtccgc ccccagtcag tccccactca gtc                      463
```

SEQ ID NO: 46       moltype = DNA  length = 246
FEATURE             Location/Qualifiers
source              1..246
                    mol_type = other DNA
                    organism = synthetic construct
SEQUENCE: 46

```
actaaaaaac tcggaccagc cgcgccgcag ctgctccaat ccctggaaaa ggcaatcgag     60
cgccctccgg accgctgcgc acagccccgg ctccgacctg gcgcccaaaa cagagctagt    120
cctagtccct cgcgcggcca gtttggccgg gtgttcccaa aaataaagcg aggagggaag    180
gtacagacac atcttgaaaa cacccgggcc acacacgccg cgacctacag ctctttctca    240
gcgttg                                                              246
```

SEQ ID NO: 47       moltype = DNA  length = 873
FEATURE             Location/Qualifiers
source              1..873
                    mol_type = other DNA

```
                         organism = synthetic construct
SEQUENCE: 47
tgccaggctc ctcctcgttg cctccgggga agctcgggt ccggaccggg gcggccctgc    60
gggctcgtac ccctgctctg gacgtagctg ccgacaccac gtgggacacc aagcggccct   120
gggcgtcagt gcgcacgggc accgccagga tgcgctccgc tccgtgcccc aggggcccgc   180
ctgcaacggg aagggcgtt agatcggcgg agaccacgga gccccagtgc ctcagagacc   240
cgccggcaag ccacgccccc ccagacccg ccccactgcg aagggaaggg gcattccgcc   300
aggcgacccc agaagccagc ctgcacctcc ccggctttcc tgcaaccggg aaggggcgtt   360
aacagggcca ccactccggg gctccgccac tccccagccg ttccctcctc cggagacctt   420
gcctgccaag agctctgccc cctgccccgt tcagggttgg ggctcggtgg gaacctcccc   480
gtgcccgaag ggacgacccc gtcagagagt ccccgaccc ttgcacctac cgtccttggc   540
aggacgtgga gctgctcgga agccattccg ggttggcccc cttacccgtg tgccacgacc   600
cctcggcggg ccctgccgc ccgagtgccc tcaccgccag cctccggagc ggcggagtct   660
cggcttcccc gagcacgagc ggcctgtcct gcctgtccag ctcccgctca gcccgctgcc   720
ggccccgtct ccccgagcgc ccgaggactg ggaggggtgg aacagggtcc ctccgatctc   780
cggggattcc ctgcggggcg ccccaaccaa tccttagggc ccaaggctac gcgctcggca   840
gccggctcct ccggagcgtc cccggacgcg agc                                873

SEQ ID NO: 48           moltype = DNA  length = 497
FEATURE                 Location/Qualifiers
source                  1..497
                        mol_type = other DNA
                        organism = synthetic construct
SEQUENCE: 48
cgtggaagcc gggcagggcc cgatcgcgct gtgcctccgc tttcccgtct gtgaaacggg    60
gctacccagg gaagctccct cccacggggt gctgagaagt cagacgggcc gcgtaagggg   120
cagagcgagg ggtccggcat cactcgcgcg ctccggaaac ccgcgtgagc cgctgttcct   180
gccgcgctcc catctgagtg acaggcttgt ttcagagctc cgcagacctc taagcctggc   240
cctcaccctg cgtggagaga acgcccgggc ttggcggaga gacgagaaaa ccgaggctcc   300
cggaggcaga caaggactct gccaaaaccg gacgccgcgg cggtggcaga attcgaccct   360
gggatttgcc gcggagcccg agcttgaagg cgagggttcc gcaggttgtg aacgaagctg   420
gaggcgcccc aggaagcccc gaccccaccc gcgccgagct gccccctccc cagatctgcc   480
tcgcgctgca ggcccgc                                                  497

SEQ ID NO: 49           moltype = DNA  length = 901
FEATURE                 Location/Qualifiers
source                  1..901
                        mol_type = other DNA
                        organism = synthetic construct
SEQUENCE: 49
gcccaagggg gcgcagggac cttggagaga agagtgggga ggaaagagga agggtgggtg    60
gggggcagag ggcgagtcgg cggcggcgag ggcaagctct ttcttgcggc acgatgccgt   120
ctctgctggt gctcactttc tccccgtgcg tactactcgg ctggcgttg ctggccggcg   180
gcaccggtgg cggtggcgtt ggcggcggcg gcggtggcgc gggcataggc ggcggacgcc   240
aggagagaga ggcgctgccg ccacagaaga tcgaggtgct ggtgttactg ccccaggatg   300
actcgtactt gttttcactc acccgggtgc ggccggccat cgagtatgct ctgcgcagcg   360
tggagggcaa cgggactggg aggcggcttc tgccgccggg cactcgcttc caggtggctt   420
acgaggattc agactgtggg aaccgtgcgc tcttcagctt ggtggaccgc gtggcggcgg   480
cgcgggggcgc caagccagac cttatcctgg ggccagtgtg cgagtatgca gcagcgcag   540
tggcccggct tgcatcgcac tgggacctgc ccatgctgtc ggctggggcg ctggccgctg   600
gcttccagca caaggactct gagtactcgc acctcacgcg ctggcgccc gcctacgcca   660
agatgggcga gatgatgctc gccctgttcc gccaccacca ctggagccgc gctgcactgg   720
tctacagcga cgacaagctg gagcggaact gctacttcac cctcgagggg gtccacgagg   780
tcttccagga ggagggtttg cacacgtcca tctacagttt cgacgagacc aaagacttgg   840
atctggaaga catcgtgcgc aatatccagg ccagtgagag aggtgagcag gggcgcgtcc   900
c                                                                   901

SEQ ID NO: 50           moltype = DNA  length = 683
FEATURE                 Location/Qualifiers
source                  1..683
                        mol_type = other DNA
                        organism = synthetic construct
SEQUENCE: 50
cgccgctgct gggacgcggc gcggacccgc atcattgcgc gcagcagccg ctgcagcagc    60
cgccggggac cgcggagccg ggacgccccc gctcggcccg cgccccgctc cccgcccac   120
ccccgcccgc cgggcccagc aacgcagggt gcctaggagc cgcgggctgc gcagggaggc   180
gggcagcggc cctcgcgcgc ttctgccgcc cccggagccg gcgcgcggcg agcgcagggc   240
gagcgcgcgt cgggcggcgg ccgcgctggg gggcgtgagg cgagcggcgc ggagagcggc   300
aggggcgaaa cttcgcgggc cagatgcccg agggcgcggc ggcgctgcca ggctgccgct   360
gctgccctg cgggccccga gcgcgcctcc gcaggcggca ctgccgcgg cgcggcgtgt   420
gcaccgagcg agtgaaggta tgtgtggcgg gcgcggctgg agctgccgcc gccgccgccg   480
ccgcgccagc aggtcctaat gcctgtcact tcccaggacg ctggcagcag cagcagcccg   540
gagccccga gccctcggca ggtttgcgtg tccttccccg cgatctgatt ggataaagtg   600
ggggctcgac ggtggccgac gtgggacagt ctggctgtgg caggggtctc ggaaaccatg   660
ggttattgca gtggcaggtg cac                                           683

SEQ ID NO: 51           moltype = DNA  length = 781
FEATURE                 Location/Qualifiers
source                  1..781
```

-continued

```
                            mol_type = other DNA
                            organism = synthetic construct
SEQUENCE: 51
aggaaattct tccaaacaag tctaaatgtt ggaaatccac caaactgcag agaaagacct    60
cttgcctccg tattctttct tcatctgtaa aaatgttgac ttctgctttt cagactacgc   120
gcacagcctc tttatttcct actgcggctt cattccctca cggaacactg acgccatcgc   180
gaaggaagca tttcgagcac gactgacgct ccccttatta tttgctaagc cgctgcgctc   240
gggtctggct acgatttgct ttcagaataa cgggaaggtg caacaagatc gcttccctag   300
aggcgcgtcg cccgcgtggc ccggaccccc cacgcccgcc cgccgccccg tgggtgcgca   360
cgcgtgtccg cgcaggcttc ccgcctggcg agtgcaaggc tcctctccgc cgtgctgctt   420
tccagcctct cagcaaatca cgaacaccga aagaagccac ggcggcgacg ggaggggcgt   480
cgcgcgtgct tccctcggcg acaaagcggg agccgggcgc gccggccgag ggcgcccggc   540
gcagagtccc gcagaggcgg acgccgcggc acgcgcctcg aaaagcctca aactcttatc   600
ctcggctctc ccgccccacc tccgccccgc agccaagacc cgcgccgtgg cgggcccgac   660
ggccaaggaa agcccaccag ccctccgcac cgtgggcgac gggccaagac ccggccctaa   720
acggccagac ccagcccta gtcggctgcc gccccgccc cacgcaggcg cgctccgggg   780
c                                                                   781

SEQ ID NO: 52            moltype = DNA   length = 601
FEATURE                  Location/Qualifiers
source                   1..601
                         mol_type = other DNA
                         organism = synthetic construct
SEQUENCE: 52
agagttctga gcagggggcg gcactctggc ctctgattgg tccaaggaag gctgggggc    60
aggacgggag gcgaaaaccc tggaatattc ccgacctggc agcctcatcg agctcggtga   120
ttggctcaga agggaaaagg cgggtctccg tgacgactta taaaagccca ggggcaagcg   180
gtccggataa cggctagcct gaggagctgc tgcgacagtc cactacctt ttcgagagtg    240
actcccgttg tcccaaggct tcccagagcg aacctgtgcg gctgcaggca ccggcgcgtc   300
gagtttccgg cgtccggaag gaccgagctc ttctcgcgga tccagtgttc cgtttccagc   360
ccccaatctc agagcggagc cgacagagag cagggaaccg gcatggccaa agccgcggcg   420
atcggcatcg acctgggcac cacctactcc tgcgtggggg tgttccaaca cggcaaggtg   480
gagatcatcg ccaacgacca gggcaaccgc accacccca gctacgtggc cttcacggac    540
accgagcggc tcatcgggga tgcggccaag aaccaggtgg cgctgaaccc gcagaacacc   600
g                                                                   601

SEQ ID NO: 53            moltype = DNA   length = 1021
FEATURE                  Location/Qualifiers
source                   1..1021
                         mol_type = other DNA
                         organism = synthetic construct
SEQUENCE: 53
aggcctcggc gccccgcccc gccccaggcc ccgccccaga gagttctata aagttcctct    60
ttcccacctc gcactctcag tttcaccgct cgatcttggg acccaccgct gccctcagct   120
ccgagtccag ggcgaggtaa gggctggagt cgggcaggag gaggggtgtg aggctgatac   180
cagagaggac ccggagcgcg aaccagaggt tcgacctcca gggcagcgca gggtaccccg   240
gcttcggagc gggaagggag cgcgccccgt cctggagctc cgactcccac cccatctgcg   300
ctgagccgga ggcgctggtt tgggctccaa ggcccgcctc cttggctctg cccgagcctc   360
cccgcctgcc ctccgcgctc ctgcgacggg gtcgccacaa gctggacggg atgagctaac   420
cggactgtcg gggccccagg agtggctgag gcggggccgt ccaaggcacc cacacaagac   480
ggcacaactg cctgcgagaa acaggcccgg ccctgtggac cccaatccga ggctccttcc   540
cctgctcttc gttcctaagg ggcccaagct cacggcggcc tccggcgcgg tgctcacccg   600
ctggcgcagg aggaggagga gctccacatt tgggtcgctc cgagccttgc gtgcggtggc   660
ctagccggcc tggcgcggtc cctgcctccc aggctccgca gctgtcgtcg ccctctcccg   720
cgccctcccc gcctccgctc tcccgggcct gctccggggt ccggcggacg ctctgcgcgc   780
ggaatccccc gtactggggc tgcagccccc gcgtctgcgc cacttgtcgt ttgcagagcc   840
cacttagtgc gcgctagctg ggcagggata ggggtcctat tcggggcgaa gggtctggat   900
gcgagcagag aaagcggagg gtggaggaac ccggggctgc gccctggaa cgcccggccg    960
caggcgaggt cctccgcgcg tggaggccgc caggggagtg gaaactgaca gagtcgcggg   1020
g                                                                   1021

SEQ ID NO: 54            moltype = DNA   length = 885
FEATURE                  Location/Qualifiers
source                   1..885
                         mol_type = other DNA
                         organism = synthetic construct
SEQUENCE: 54
ctggagtgag gcgcgggaag atgcctggtc cttgcctcgc ggacttggca gccgcgtcct    60
gcgggtctgt ccactgaact gctgaggact cgcccgtgtg cggggacccg agtgccactt   120
cccggagcgt taccttgcgc tccagcctcc aggctagata atacctggaa ggcagggcag   180
ggctgttccc gctctcaccc cttgcggaag gatggcagga tccggcgcag cgacgtagca   240
gcgggagggc acagcgacct gcatctccag tttctcctca ggacacaagg ctgacttcac   300
cttccggaca gctgcaaagc ccctgccaga accaaaccga actcgcgcct cggagagggg   360
cttctggggc cgtttcgctg cagggcgtgg ggagtggaga gagggaaggg gaagcctggg   420
gctgggtgtg cgcgcgtggg agcgcgcctc ggagcgcccc gcactccccc actctatccc   480
cgggggcagt ttgggaagga gggagtggta gtcgcgggaa tgagggagca agagaaaccc   540
tctcaaagtg acgccccaaa caggtccgga tttagaattc gaagctaaag gctgttagaa   600
attgggactc ctcggcctcc tctgcagccc ctcctttccc gccccgaagc ccgggcggtt   660
tgctggctgc ctgcttcccc gccccggct cagaggtctc tggctggcgg gcgcccgtc    720
```

-continued

```
ggccgccggc ttcctccttg aaacccgccg gcgcacatga ggccgctgcc cccgccgcag    780
gcgctggcgg ccccctcgcg gtgcccgtgg tgatgccatg ccccgccacc acgcgggagg    840
agaggagggc ggcgccgccg ggctctgggt gaagagcggc gcagc                   885

SEQ ID NO: 55          moltype = DNA  length = 1113
FEATURE                Location/Qualifiers
source                 1..1113
                       mol_type = other DNA
                       organism = synthetic construct
SEQUENCE: 55
ggcggcggcg ggcggggggc gcttgggcag cggcatgaag gatgtggagt ccggccgggg    60
caggggtgctg ctgaactcgg cagccgccag gggcgacggc ctgctactgc tgggcacccg   120
cgcggccacg ctcggtggcg gcggcggtgg cctgagggag agccgccggg gcaagcaggg    180
ggcccggatg agcctgctgg ggaagccgct ctcttacacg agtagccaga gctgccggcg    240
caacgtcaag taccggcggg tgcagaacta cctgtacaac gtgctggaga gacccgcgcg    300
ctgggcgttc atctaccacg ctttcgtgtg agtacccgcg cccctgcta tgcccgctgc    360
aggggaccac tgtccctggc cccctggggc gtgctccgcg ctcgcgccct gggccccccg    420
cgcgcgtgca cacgtggtgg cttttatttc ttcgcacgtg ttcgtggtct tccttctgga    480
gcctctcccc tcccccagcc ccacttctct catctctaca gcttgaacct tttccccgag    540
gacacccaat gaactgcccg gtagcttcag gctcccgggg cgagagccag gcagacgcgg    600
gacttaggct gcgcggataa ttgggagcaa ttaggtccca agatacgtaa acttcaaccg    660
aacgggcgcg ccgggagcta gggaatgcaa agggaggaca ggcgcccgtg tgaggcttga    720
gagtatactg gagaggttag gaggtgatgg cgggtagga cggggagaag tgaggggca    780
tcgagggcta ggtcctcagt cctaggggcg gagtagggga agctgctact tggagagagc    840
tgctaggttt taagcgcgcc cggaaacacg cctcgccacc acccagccac caccaacgga    900
aaatctgtca gtgcatgtag cccttcctgc cacggagagg gtggccaagg tctagaggag    960
gccagcaggc caggcgaagc aacgctcccg cgctgcaggg ggcggggagg cagcggggaa   1020
cctgggcgcg aggaacgcgg gcggaggtgc gatagcagaa gcgcaaatgg gtcgcctctg   1080
acagagatcg ggcagtgggt taagtccccg ttt                               1113

SEQ ID NO: 56          moltype = DNA  length = 568
FEATURE                Location/Qualifiers
source                 1..568
                       mol_type = other DNA
                       organism = synthetic construct
SEQUENCE: 56
cgctggcggg cgcacccggc ggcggcgagc gcggaggtgc tgcggtacct accatggtat    60
tcttgtcccg gaacgtagta ggtgggggttg cccgcaatat gcaggggaaat gagcacctcg   120
ccctgctccc catccccttc cagctccccg tggtgggtgc acaggaaaaa gaagggcgaa    180
aagcggggggt aatagccagc cgccgcgcgc gccctcagcg tcgcccccag caacagcgct    240
aggaggaaag tctgccgggc ccagccactg cgctccatgc cgccgccgcc gccgccgccg    300
ccgcgcgccc tacgcgccgc tcgctcattc agttttggag acgccgggac ggaggagcca    360
cgcggagaga aggcgagaag aaggcggacg ggagcggaac gggtcgggca gcgcggccgg    420
gagcgggccc ccgccgagaa gttccgcggg agacgcgggc tcccaaagtt actttgggcc    480
gcgggagcgc gggaccgggg ctgcgggcgc cgagagcgcg tcgtctgccg cctccgtgcg    540
ccgccgccgc ctctgcgcga cgcccctc                                     568

SEQ ID NO: 57          moltype = DNA  length = 589
FEATURE                Location/Qualifiers
source                 1..589
                       mol_type = other DNA
                       organism = synthetic construct
SEQUENCE: 57
cggcgctggg aagagctgcg tgacgctcgg gggctggcgg ctgggccggc agcgcgccgt    60
ggcggcgtga cctgtccatg gtgttgaagg cgcggtgggc cgagcccta gcgccgcgcg    120
cagtgagcgc tgcctggtgc accctccgcc gcgcagcccg ccctctcgcgt ccgccagcag    180
ccgcccagtc tccgcagatc ccaggccggg tctcgtccgg taacgccgcc cgggtgaaca    240
cgctgtcggc ccgaggggcc gcctgaatgg cgatgccaga ggcagggcac cggggagctc    300
gcggggaaag gtcggccgag agcgtgcgtc cgcggggagt gcgcctctga gcgcagcacg    360
cgggtcagaa ggagcaaccg acctgctggt gaccagagaa cggagatttt aagaggaccc    420
gacccaaaga ggaagaacat ttctgggtgc gcgccccagg tctttgcttg cagacgggga    480
gggggagagg ctctgagcca gagacccagg agggactccg agaagccggc cccagcacct    540
ggaggtttct ttcgcccgcc ggccgcatcc ggggcgttct acttcaccc                589

SEQ ID NO: 58          moltype = DNA  length = 268
FEATURE                Location/Qualifiers
source                 1..268
                       mol_type = other DNA
                       organism = synthetic construct
SEQUENCE: 58
tcatgcccat ggtgtagccg ccaagcggag gcatggctgc cggaaggtta ctgctctaca    60
ctggcctctc gctagcgctc tgcgccctcg gcatgctggc cgtggccatc tgctcggacc   120
actggtacga gacggacgcc aggaagcaca gggacaggtg caaggccttc aacacccgcc   180
gggtcgaccc cggcttcatt tacaacaata acaacaactt gccgctccgg gcgagccgct   240
cgcgcctgga ccgctgggag ggcaaact                                     268

SEQ ID NO: 59          moltype = DNA  length = 841
FEATURE                Location/Qualifiers
source                 1..841
```

-continued

```
                              mol_type = other DNA
                              organism = synthetic construct
SEQUENCE: 59
gcgctcaaca gccagatgct gggcccagac aagcgctctt ccgctagtgt gccgggatga    60
gcgggggctg gacttctaga aaggggtctg cgggcgcagg agctggggtc cgcggtctgg   120
ggccggtgag ctgcggcgaa gaggtcaggg agggagtggg agggtctacc ttgcaggagc   180
gcgcagcact ggccgtccgc ggtgctccag agccggggcg tgccgtcctc gctgcccgtc   240
agcaggcgct gcccgtcggg gctcaggctc agccagttga tgcccccgcg gtggtcggcg   300
cagaccctca gggccgaccc gccgcccccc atcccgctgg cagggcgggg aacaagaagg   360
agctgcgccc cgctagggag gggcgcccccg gggtccgcgc ggcggctccg tacgactgcg   420
gcccgcggcc atcgcgggga acggggagcc cgactcctgc ggaggcacgc ggcgagggga   480
gggtgaagga ccctagctcc ccgctgcctc cagcctctgg gcccgcgaac ccagggcgct   540
gcgggggggcg gcccactcgg gacctccgcc ctgggtagag tcctgggcgc gcgggcagag   600
agaaccccct tcccagcacc gctcggagga tccacaccc accgggcgaa caaggcagct   660
gcgtctctgg tgcacaagga gcccccccgcc tcctctcgcg cccacggggc tggggcgggg   720
agaggaacac gggaagccga gcgccccgcg ccctccccgg ccgagcgcgg aacaatacgg   780
tccagcctgg ctcctcctca gagaccaccc ctcacccgat cccctcccac ttctcgggct   840
g                                                                  841

SEQ ID NO: 60          moltype = DNA   length = 241
FEATURE                Location/Qualifiers
source                 1..241
                       mol_type = other DNA
                       organism = synthetic construct
SEQUENCE: 60
tctatcagct ctgaatctgg tttttcaagt ggcttgggtg ggtctgcata tgaatttgac    60
caacctctgc gcgcgctcct gggagcgcgc atctgtgtgt ggtccaggga gccaaccgcg   120
tttgtgaatg gatgattgat gggaacagcg cccaggggca gcaggtggag acgggaaccc   180
aggtcgcggt cactggtcaa cccgcctctt ggggtggagg ttagagaaat gggcgctggg   240
a                                                                  241

SEQ ID NO: 61          moltype = DNA   length = 208
FEATURE                Location/Qualifiers
source                 1..208
                       mol_type = other DNA
                       organism = synthetic construct
SEQUENCE: 61
cgtttccttc agtcactatt ccctggcgaa gtctccacgc gctcccgttc gccggggaac    60
ttagggtatc cgggcttccc taaattgaca agcggggggcc ggcgccttcg cccgccttcg   120
ctggccgccg cttggtttgt tcttcttctc cttcggggac ttctccgccc gcgcccgcgc   180
ccgcgcccca gctttcgtcc cgctgtgc                                      208

SEQ ID NO: 62          moltype = DNA   length = 749
FEATURE                Location/Qualifiers
source                 1..749
                       mol_type = other DNA
                       organism = synthetic construct
SEQUENCE: 62
acaaacttat gagcagttag ttcctccagt gcccttggga aaaagcaact atttccaaaa    60
ggaaacttta tttaaccgac gccacgtccc cccgacacta aaactaacca gtaagtacag   120
ggagggaccg agaggcatct gcggccaacg ccaacccccga tctccccgtg aaacgcgcag   180
cccgcgcagg cgcccgcagc tcccagctcc cgggacggcc ccgaacgagc tcatcgttga   240
cgcgtccagg aagaaacgat cccgtttcca gcaaaccccg gacggtgggg cgcggggaag   300
ggcgcaggca gcctcccaac ccgagtcccg caacccggcg ggaccggagc tcagcgcttc   360
acgctctccg ggaggaagct ccggacccccg ggcgaccccg ctccctctcc cggacccccgc   420
ccgcgctcca gcaccccggga ggaaggcgaa gaccggcggg aggagcgctc ttctcggaag   480
gggagaaccg ggtccgaggc gccgtggggc gggggtcgcg ggcgcactca cggggggcgag   540
cagccagcag gtcagcagcg cgggaggcag cagcgtccgc atcccgagct cagcgtgccg   600
ggggccgccc agcgcccgcc gcctccgtcc taggtccccg cggttccgcc gcctccagca   660
tgggccggga gcgagtgcgc ggagacctcg ggccccgcag ctgtagccga gcgcccgagc   720
gcggggggccg ccccctccgt cccggcagc                                    749

SEQ ID NO: 63          moltype = DNA   length = 627
FEATURE                Location/Qualifiers
source                 1..627
                       mol_type = other DNA
                       organism = synthetic construct
SEQUENCE: 63
gggggaggcg gggagggagg cgggagggggg aggggacggt gtggatggcc ccgaggtcca    60
aaaagaaagc gcccaacggc tggacgcaca ccccgccagg cctcctggaa acggtgccgg   120
tgctgcagag cccgcgaggt gtctgggagt tgggcgagag ctgcagactt ggaggctctt   180
atacctccgt gcaggcggaa agtttggggg cagcagtgtc attggcctga cgtgaggagg   240
agggactttt cgaagtttta taggaaagtt tccgctttcc agtcccccctc ccccgtccca   300
cctccctcc tcggggtcta acaattcgtc ctcccaaacc attcaaaaac gacctggccc   360
gggcggccgc ccctccacc cgcctcctag ccgccctccc ccttccctcc ccgtcgcctt   420
cctccggcgg gcgcggggcg atttcctttcc ccgccggagc gtgcgggcag cgcccccgaa   480
ccctagcgca gcccaggaag cggtcggagg agactgtcct ggccgcgcgtg gcagcccat   540
ccggagtggc tgtgacagca gcaatggcaa cagcttctac acagtgggtg atgtctcatc   600
tcgcccaaga gccctctagg tccgtgg                                        627
```

-continued

```
SEQ ID NO: 64            moltype = DNA  length = 721
FEATURE                  Location/Qualifiers
source                   1..721
                         mol_type = other DNA
                         organism = synthetic construct
SEQUENCE: 64
gggtgatctg tgtttgtaaa cattttggcg gaccagaggg aagtccggcc ccgagtgctg    60
gtagactgtg gaattcggct gtgtcctgag gccaccctag agaccccgcg ccgcgtgagt   120
gccggagcgc tcggtggccg ccgcgccgcg cgcctggagg gatgctaacg tggagccggc   180
gccgagtccg cccggcgtgc gtgcgtgtgt gggagcgcgc gagtcccctg acgcggggac   240
cagttatgaa tcgggggtgt gtgtttgcct ccagagacct ggcaaggtgc ggagccctcc   300
agaagtgcgg tcaagcggca gcggagacgg cgagccagga acctcccccc gcgtccccag   360
cttcccagcg tggcggcgga acccccggag aaagtttgca aacttccagc gggcgcgggg   420
aggacgccgg gtcacctagg gggcgggtgg gcgcgcgcgc agggggctcg ctctcccggg   480
tgcggagctg cagctgccac ctctcccgcc gggctgccgg ctgcagcggg tgggcgcgcg   540
cccgggggag ggaggtcgcc ctcggagggc gcttggcttt cgctccaggc gctccgggct   600
ggagagcggc gaggctccgt ccgctccagt ccactcctcc ggccgcctcc tgcctccgct   660
gctttcttgc tggcatcgtt acctcttccc ggccgctgcc ccaaatgaca gctccggctc   720
g                                                                    721

SEQ ID NO: 65            moltype = DNA  length = 113
FEATURE                  Location/Qualifiers
source                   1..113
                         mol_type = other DNA
                         organism = synthetic construct
SEQUENCE: 65
attgaagggg aactggaggc tctgtcgccc agcgtggggc cgcggcggcg tgggtggctc    60
tgcctctatc ctgtgcccat cctcgcccgc tcccgctcgc cccagcacac gca           113

SEQ ID NO: 66            moltype = DNA  length = 804
FEATURE                  Location/Qualifiers
source                   1..804
                         mol_type = other DNA
                         organism = synthetic construct
SEQUENCE: 66
aaagtgtgta tatctagatc tctgttttga actccagaac tcaccagaca gcactgtgtg    60
atcacgatcc taccctattg gtcctgggag attttggtg gcttctctgt taaatcgttc    120
gtgtctgctg cacttaagta gccacaaaat cccccgcaag aaggaaggct gctgcaatct   180
cccgcccga tctgcgggcc gcgtccccgc gagctgcctg cgggcgcgct gggagccggc   240
ccggggagat gcgagcgcag ggagatgcgc tctgctccgg gcgcagcggg caagctgccg   300
cacctcctac ttctgttgcc tggcttgggg ccaggagagc ggcaacccgg ggccggctcc   360
ggagctggac atatccggcg tctccgggggc cagggtctgc gggtcccggg cgctgcgtcc   420
tcccgacccg ctccccgcgg cgcccggggtc gcgccttgcg gcagtcaccg agctgagggc   480
agggcgtccc agcgtccctg gccccggccc cgctccgcag cgcgccgcac cccgaggctc   540
gggcccgca cagctgcagc cggtgccctc cggccaagcc cccgcctggc gtccccggcc   600
ccagcccagg ccgcccgccg ctgacctttt cctgcgcgcg gttgagtcgc ttctggacgt   660
tcttggcgaa gatgcccgtc ttgatgtcgg ccatggctgc gggtccgggg agctgcgaag   720
agcagagcgc gcagcggggc tggcggcggc gcggaggagc gggaggagga gcgggaggag   780
gaggagaggg ccgagcaagg gagg                                          804

SEQ ID NO: 67            moltype = DNA  length = 1317
FEATURE                  Location/Qualifiers
source                   1..1317
                         mol_type = other DNA
                         organism = synthetic construct
SEQUENCE: 67
cacagggtac ccgcctagag tgtctgtacc gcatccttc tgctacactg tttgcacaca    60
cacaaaaggg ccgaggagcc agggttggtg ttggatatgc ccagtacgcg tgctgggtgt   120
tggaaggatg gggcggcggg taacaagaat cgatatatat ttaccgcggg ggcgggggtg   180
gggggtgcgcg gaggctgcag ggcggggcag cgctaatgag agcaagcccg gcttgtggtt   240
ggttctggag tctggtaccc acagaggagc aggcagggag ggaggggatg caagcgggag   300
gataaagcga tgaagtgtgc tgcgttaccg cgcatcaggc gctgttgttg gagccggaac   360
accgtgcgac tctgaccgaa ccggccccct cctcgccgac acactcgccg agccgcgcgc   420
gcccctccgc cgtgacagtg gccgtggcct ccgctctctc ggggcacccg gcagccagag   480
cgcagcgaga gcgggcgggtc gccagggtcc cctccccagc cagtcccagg cgcccggtgc   540
actatgcggg gcacgtgcgc cccccagctc taatctgcgc gctgacagga gcatgatctg   600
tgcccaggcc agggctgcca aggtaagcgg gcgtagcgcg gggacactgt ctgccgcccc   660
ttcccccccg cccttctctg ggcggcttcc ccgccgcacg cgaggccccg gcagccgcct   720
cccttctcgg ggccgagatc caccctcctc cccaccctct cgcttctccc gcgaggttca   780
attgtcagcc tgggtcgcgc cgcgcgcccgg tccgggccgg catccccggg tggcgaccct   840
ggcttgggta ctgcaggcgc acccggccct cctgcggggt acggagagaa acaaagaagc   900
ccccaagcgg gttcgcagcg cctcccccgc ccctcagcgc cctcccagtg gcgaggaggt   960
gtcagggggag ggggcgggaga gacctacgta atcccccctc ccagcccaca cccacccctt  1020
gtgaaccaaa gctctggatt tgcgcttcgc cttgggctcg cttttgaaca attgtgtccc  1080
atgcaatgcc cgtggttagc ccagagagcg cccagagcct ccgcacgggc tcgccggtgc  1140
tcgctcgagg ggcgcgtggc caggtccggc ccttgctccc atggacgggt gcaggagggg  1200
aggaggcgct gtgtgggtgc tcccccagcg cctccctgtt accggccggc tgcgccgctc  1260
agccgggcct gccacctgag ttttagcggg agcagtcatg tcgcctaccg tattgcg      1317
```

```
SEQ ID NO: 68            moltype = DNA  length = 339
FEATURE                  Location/Qualifiers
source                   1..339
                         mol_type = other DNA
                         organism = synthetic construct
SEQUENCE: 68
cggcgcgggc gagcgggctg cagccggcgg cggcgccagc aggtacggcc cgcacccgcc    60
gccgccccgg cggcctttgg gggctgagcc ggagcccggc gcgattgcaa agtttttcgtg   120
cgcggcccct ctggcccgga gttgcggctg agacgcgcgc cgcgcgagcc ggggactcg     180
gcgacggggc ggggacggga cgacgcaccc tctccgtgtc ccgctctgcg cccttctgcg    240
cgccccgctc cctgtaccgg agcagcgatc cgggaggcgg ccgagaggtg cgcgcggggc    300
cgagccggct gcggggcagg tcgagcaggg accgccagc                          339

SEQ ID NO: 69            moltype = DNA  length = 186
FEATURE                  Location/Qualifiers
source                   1..186
                         mol_type = other DNA
                         organism = synthetic construct
SEQUENCE: 69
gcaagccccc tgggtccccg cgcggcgcat cccagcctgg gcgggacgct cggccgcggc    60
gaggcgggca agcctggcag ggcagaggga gccccggctc cgaggttgct cttcgcaccc   120
gaggatcagt cttggcccca aagcgcgacg cacaaatcca cgtgagtgtt ttcaaattga   180
atttca                                                              186

SEQ ID NO: 70            moltype = DNA  length = 1696
FEATURE                  Location/Qualifiers
source                   1..1696
                         mol_type = other DNA
                         organism = synthetic construct
SEQUENCE: 70
tctttcaagt tcagtagaaa gactctctgt tttctctggg tgttctctga ttgtacatat    60
gcagtgaatc aaagcttatt cacatgaata cgcattttcc cctggctcag ttccttgaat   120
ggaaaagccc catgttctct tacaggcctt aaccgatata atttaaaaat taaaaataaa   180
ttaaaatata acagtattat gaatctccac catgtcccgc aactaatcca acacatgttt   240
gggtatcggg acaaaagtag agttatataa tgagctaagt cacacttcaa taataaaatc   300
cactaaaaat atttcagatt gatggataat cgacagaagg aaatgatgta ctccaggaga   360
gataaaaatc ataggtttgg aattaatgaa aaatacagag aagcacttac gttgtaccta   420
acacgttatt ctcttgcatt tattataccc catggtgagg gaacaaatct ttccctgagt   480
ccgcacaggc actgaattat gatcaatgtc agttgggaga caggaaatgt gttagtggtt   540
gtaaatttgt gattactttt aagaaactga aaaccatgag gtttgcttaa cacttgagaa   600
aacccaggct aaaacttcct gtagaaagcg agacgtggga aactggcgaa gctgctacca   660
gccgccgggca caaggagcgc gagagtcctg ggtgcgcgca ggcgcacttac tttctatcct   720
ccagcaagca tcgtcgcaag cctcccaggt gtagaaattg ttggcgttgc cctcgcagcc   780
cccgtacagg aactggcggc agctctgcgt gtacctgtcg tagtagtaac ggagaagtag   840
ggcccggcag ggtccgtagt ctaggggcag gagacagatc tccgcgttat ttcctgaaga   900
aggggcagaa ggagagcaaa agagagggaa agtggtcagg cgtagctcct aggaggaaag   960
aacatcccgg ggagttctgt ccccttccga gcggagggggc ctctgcagag aaagtgcaaa  1020
cttgggagcg agtcccccct gccagcggag cgcgcggcag ggacctggag aaagcgaggc  1080
ttggaggcg cctacacggg gcccccatggc ccgctgcgcc ctctccgccg gttggggaga  1140
gaagctcctg gagcggccag atacctgttg gctcctgagc agcatcgccc agtgcagcct  1200
ccgtcaggaa aagcagcaga atcgacagcc ccaggggggcg agcggggtcc atggtgcagg  1260
gggtcgggcg gcccgctggg caaggcgtcc gagaaagcgc ctggcgggag gaggtgcgcg  1320
gctttctgct ccaggcggcc cgggtgcccg ctttatgcgg ggcgagcgtc cggccgaccc  1380
ccgccggggc gagccgcgag gggtggctga ttcatgcacg gggactgtca ccccgccgcc  1440
cccgcgctgc aaactgtgta agagggagag gaattccccg ccaagttgaa aagttgaacc  1500
tgcctcccaa actttctcct gtagtccaga cggggacgcc ctgagggagc gtttgtgtca  1560
gtaatgggaa atctgcaagc tagacggaaa tgacctgcta gtgattgcgc tgtaaagaag  1620
ccggaatcca cctcttgaag gcatgaagtt caggtatttg aaaggctggt ggagagaaag  1680
tgcggagttc ttgggt                                                  1696

SEQ ID NO: 71            moltype = DNA  length = 901
FEATURE                  Location/Qualifiers
source                   1..901
                         mol_type = other DNA
                         organism = synthetic construct
SEQUENCE: 71
gggaacagca gaggccgcgc gggcggaggc gggggaaagg ggagctgggt ccctttctcta   60
tctgggaggg aggtggtata cggtgtgtgg ggtctgggga ggcgactgtc acgtctccta   120
gaaccctcat gccttccact cgtctgcgac cccggctgcc gaggaggcaa cgagggaggt   180
cgagccgctc cctccgtgg gcggcagcga aactctgcgc ccgcacgccg gggtgccgcc    240
gagtccggct ttgagtaccc agcaaggtca agcaggcgaa ggaggggggcg ggggttcctg   300
ggcgcgcccc cgtccgcgca cagtcggggc cttggaaggg ggtgtgcgca gccgccgag    360
tcagtcccgc tcgcctgccg cccgcgcccg gtccccgagg gggacgttg cgcgcgttcg    420
gggatcccgg agcgcccggc gccccacgcc ctcccttcgg ctcgctagct gctccttggc   480
gctgctttca gacttgttgc gcctcgatct gggggggcaga aggctggccc gggagacccg   540
gcggctgagg gccgagccgc gaagcccagg gatgcgccag agaggcgcgc ggctccgcgg   600
gtgggcgctg cgctggggg ctcgagcctg gggtttgccg cctccgatcc cagggacggg   660
cgcttgttcc tgccggggtc ccgcgcaggg gcggatagag ggcgattcgt cgcctcggcc   720
```

```
tcaggcagca ctcatccgga tcccgggcta gggaggggggc gcagccaagt tgtggagccc   780
tcggaggccc ttccctctcc cgcaggctcc ggccctctc ggacctcggt ggccgcgtcc   840
gtgaaatggg gacgcgggct ctgctctcgg atcccttcca gcccccgacc ctccgcactt   900
g                                                                      901

SEQ ID NO: 72               moltype = DNA   length = 1561
FEATURE                     Location/Qualifiers
source                      1..1561
                            mol_type = other DNA
                            organism = synthetic construct
SEQUENCE: 72
aaacattatc aggatgtgca accaagcccc catttctcac cttggtaggc acaaaaatcc   60
ttcggaggca tcctgtaaga ggcttgcgag actcttacca agccacccccg gctttaaacg   120
cctctccagc cacctgtgaa ccgcgaagga gccggcttc ccttgccacc   180
agtaccctcg cgggccgagg tcgttctccc ggtcggcttc ccgcctcacc cgaaaaggaa   240
ttagagcatc tacccaagac ggtgactggc agggcagatc aaggtgtcct ggtctcggcc   300
ccagccccgc ggtgcgcccc gcccgcttac cttgaccggg tgcaggtagc catcgccgcg   360
cagggcgccc aacccggcgt ccgccggcgc ctcggcgtcg tcctgcaggc tgcgggtgag   420
atgcgcgatg taggtggtgg ccagcagcag cacgtccagc ttggacagct tggtgtcggg   480
cggcacggac ggcagcgtgc gctgcagctc caggaaagcg tgccgcaggg tctgcacccg   540
gctgcgctcc cgcgccgcat tcgccgccgc cggccgcccg ctcccggaac gcgagccgcc   600
cccagggccc gccggccccg gccccgtccg cccgggacgc gagtcgcgca tggcggcggc   660
caggggcgcg ggctcggcgc tggcgctgag ggggctgccc gctgggcggc cgcggtccat   720
ggcagcttcc cgcgccgcgc gcgctgcaaa ggaccgaagg tgcggtgagg ccggggggcg   780
gtcgggctta acccgagagg cgcagccccc tggttctccc cgtgcgccca ccagcagccc   840
aacggggcta agggcgctct caagcgagct cgttttgccc gggacgcgat ttgcttccgg   900
acgtctgggg agagttgcgg aactccggag ttcttgggct tcctagaagg ataagaagag   960
gcgcagtgcc ggctttgctt ttcaggggca aattaagcaa aaggtctact ctacccggga   1020
agaaagatct cggaagcaca gctcaggatc agcactcgtt cgcgcttggg tgactttatc   1080
caacccggca cgcacgagag gtggccgggc tccttctcgc cgacgccgcg gaaaaccacg   1140
gctcaccagc cgccctcggc ctttcacgcc agggggggatt tctgcccgag gagcggggga   1200
cccttagcct cacctcgggg tacggcaccc gccaccgttc cgagcccgag agctgcgcag   1260
tacgcgtctg acgggcccct cacctttcct ggagcggctg agtggagctc cgctccgtcg   1320
tgagggcggg cgaggggcgt ggagcagggc ctgtgtggcc agggccgcgc tggtcactcc   1380
atcctcgtcc ggccgatgcc caagtcgacg gctgtttcca acctccgctg gctgtgactt   1440
ttatgcgggc gccccgcggc caggcgtgtg tgctccgacc ggctaaggca ggtcgggcgg   1500
aggacctggc ccaccggaga ggctacgccg ggggctgagg cggcttagag ggtcattaat   1560
c                                                                      1561

SEQ ID NO: 73               moltype = DNA   length = 1151
FEATURE                     Location/Qualifiers
source                      1..1151
                            mol_type = other DNA
                            organism = synthetic construct
SEQUENCE: 73
gtagctgcca aggagtagcc aacaagcacc agatttatgt gcactttgaa agaagcacct   60
tcaccattgg cttttttaagc ggcgctgtcg ctagggaggcg cggcagcct   120
cggggagcag cccgggctgt ttgttccgtc accgggggaaa ggaggtacac acagtcgcgc   180
gcgcacggac acacacacac acgcacgcac gcacacacac cggtggcgag ttcgagcccc   240
gcggcccctg tccgccgcg tgcgcccctc gacacagctc gcctcccgcc ccctgattcc   300
tgctgctacc gcccagagga gaaaggaacc tctgcctcga atttccccac tgcgccgggca   360
gctgcggaga gcggcgaggg tgggcgcgag gcggagaacg cgatgaatga gttctccct   420
cgcctcggag ttgtctgagt tggcggcgct gcgcccaggc ttccggctct cagcgcccca   480
cgcgcgcgtg gctccccggg ctgccaccca cgcccgcggc cggggccgag ccagccacgc   540
aggggcagcg aggctccgga gctcctgtcc cggccccagt ccgggtaaaa ggagggttgt   600
ccccagcgga ggcgcacagc cgcgcgttct ccctgcactc tcttcgcggt cccatctgtt   660
ccccatggcg tctcatccgc aaacccggat ccaggcttac ctggagaaga acaagatcgg   720
tcccctgttt gaggtaaggc gctgtggagg agggcagtcc cgttgtcttt aggggaaggg   780
gtgcagtaat gaaaacagaa cactcccaat cccacccctc ccagggaagg agggctagag   840
aaccaacgcg cgggagaggg cgccctggga ttcactggca ttcgctctgt cccggccagg   900
tgtcctggaa cgcggccggg cgggcactta gccagttacc tgaacgcgga caggtcgagct   960
cgggagggcc cagcctcagc ctggcagggg aagtttttggc cctctgactg tcctgcacct   1020
ctcagctaca tgttcaggac ccgggcaggc tgaggcaggc gacgcatacg gatgcacaca   1080
ctcagactgt gttgcacacg cacactttct tttttgaatt cacgctatct tgagtgttcg   1140
tgttggattt t                                                           1151

SEQ ID NO: 74               moltype = DNA   length = 1081
FEATURE                     Location/Qualifiers
source                      1..1081
                            mol_type = other DNA
                            organism = synthetic construct
SEQUENCE: 74
gcaaacagac acggagggtt gattcttctt cagggaaatg gctggccact ccccttgattt   60
gggagaaact aaactggcct tctcgttccc agtcccagaa cctccacccc tttcgaattc   120
ttcccaacgg gctgaccctg cccggcgccc aggagcgccc tgggtatctc ctggctgctc   180
tcccgaatcc ttgcgcgccg cgcccctacc aggttcactg ggtgcacgta gccgttctca   240
tagcggtcct cctgcaacag ctgccgcagg tgagcgatgt aactggaagc cagcggagc   300
gtgtccagct tggagagctt agtgtcgggg ggcacccagg gcaggctggt cttgagcctg   360
gagaaggctt tgctcagcac gcgcatccgg gcacgctcac gggcgttggc cgcgttccgc   420
```

-continued

```
tgcgactgct tgcactctgc ggctgagccc ttggccggga ggggcttctt gccaccaccg    480
cccgcgctac cacctgcgcc gccgccccca gccacacggg gccgcttcct cttgcagcct    540
tccgcgctgc cggctgtgcc cagagcgcag cgctcctcct cgccgtcggg gtcctcctcc    600
tctgccgacg agttgtcact gggcgaggcg tagctgcgct ctacgccgcg gaggggcggc    660
ctcttggagg cggggaccgg gtactcccgc tgcagcccgc gaagctccat ctcctccgga    720
tcactcaccg agcccgtgga catcccgttg tcccccttgc ccacacgcgt cctctttcct    780
cccccctggc cagtctcgct gtctccgcct tccgctccct ggcggaggcg gaggccagag    840
agcgctccaa ggaagactaa aaacccaggc cgggaagcgc ggggtgagaa agcgaggtgg    900
gtggcgagag cgtgagcgcc cctctgctga ccccggggag cgtggactac gagttggcgc    960
ccaagtccag aatccgcgcg caccgcggta agctgcgcct tttgaaaagg ctatctgtac   1020
tccttggaac aaaccacccc gggcaagaa gaggggttg taaaggggc caagaggtgg   1080
g                                                                  1081

SEQ ID NO: 75            moltype = DNA   length = 181
FEATURE                  Location/Qualifiers
source                   1..181
                         mol_type = other DNA
                         organism = synthetic construct
SEQUENCE: 75
aataattaca gtcagtttca cttaagggg agatcagccc ggtgctcttc ggccgccccg     60
ggaggaaaag ggcggggagt gggggcaggt cggccgggca gtccagcttg cccggcccag    120
ggcctgacca ccccggctcc ccatctggct ggtgcatggc gcggggaagg gggcgcgcca    180
g                                                                    181

SEQ ID NO: 76            moltype = DNA   length = 721
FEATURE                  Location/Qualifiers
source                   1..721
                         mol_type = other DNA
                         organism = synthetic construct
SEQUENCE: 76
ttgagaaaaa caatttaaga aaagtaaaaa ggaagtgtcc agagcaggaa gggaattcac     60
aaatgtagcc tccagcggga acagctccct ggctgccgag ctccagcggg aggggagtcg    120
agcgtttct ttgccactta cctagtcccc tgtctacaaa gctggtgatc gtattagccg    180
acttggaaga ctggaaaaag ctggcattga tgcccagctt ctcagccgatg gagtaagtcc    240
tgtagattga cagcatgtac tcgtggggca ccacgcgcgg acccctgcct ggcggctcct    300
gcgcccgggg ctgctgagcc cggggttcgt cctgaggccg cggctgtggt tcctggccct    360
cccggccgc gtcactgtcg cgcggcgccc gctgcatctt gccttccttg cggcttcgca    420
tgcccttggt ggaacccagc tcggcggacg acgaggagga tgagatggaa gcctgctgga    480
aaccgggcaa atcccacaga aaactgatga ggaagacgac cgagacgagg accctgggag    540
tatccatggc gggcaagtgg ctgcgtctcc ccaggaggcg gtggcggcgg cgcaggacgc    600
gcggggcacg gagcggctgg acagcggccg gggcccggct cctcgggcgg actcggagtg    660
cgaggagccg ggtcccagcc acacaaaccc cggccccgcc acgcccctc ccgcccctcg    720
c                                                                    721

SEQ ID NO: 77            moltype = DNA   length = 597
FEATURE                  Location/Qualifiers
source                   1..597
                         mol_type = other DNA
                         organism = synthetic construct
SEQUENCE: 77
cgagcgcccc cgagccccga gcccgagtcc ccgagcctga gccgcaatcg ctgcggtact     60
ctgctccgga ttcgtgtgcg cgggctgcgc cgagcgctgg gcaggaggct tcgttttgcc    120
ctggttgcaa gcagcggctg ggagcagccg gtccctgggg aatatgcggc gcgcgtggat    180
cctgctcacc ttgggcttgg tggcctgcgt gtcggcggag tcggtgagtg ggccaggcgg    240
aggatgcggg cgccgtttag ggtgtttgaa gctacgagag gagcccgcag ggaataggg    300
agcgccacct ggggaacccc cagtccccaa gtatacaccg gagatccgct gggacaaatg    360
cgctcgtccg gtcacccttt cccctcttc ccttcctcag aaaagcgctg ctcgctggcg    420
ttaccccgcg gtccgcggga atggggcac cgagaattgc ggtttggtct agccgcagag    480
gcccctgaag tcactcccaa cttcttcgcc ctcggcgggt cttgctgcgt ggtctgggaa    540
ggacggaggg gaaagggtgg caggaggggg gagcctgggt cgggcccgcg agggaac      597

SEQ ID NO: 78            moltype = DNA   length = 476
FEATURE                  Location/Qualifiers
source                   1..476
                         mol_type = other DNA
                         organism = synthetic construct
SEQUENCE: 78
cggctagggc gaggtaaccg acactacgtg gaatcgcagt aggcgatccc tcaaggggat     60
actggggag gcacggaacg cgtccgaaaa tgctgggacg cggccactg gattcccagt    120
cctgcggcga cccctcctc gttgaggggt ggaggttgca ccgcggggcg tcagggacgg    180
gaggacattt tcataggagt tacacggag tgccgcaagc agggcgaggc ggggtacgtg    240
tgacacggc ctcggcttcg ggtcgcctgg ccgctggggg acagaggctt ccctcccgcc    300
acgctcgccc tctctggccc tggcggggcg cttctgggc cgggaggagt ctcgtctccg    360
gcggagcgcc tgccggcacc cagcttccct ccccgccct ggcggtggga acttgatttc    420
tcctttggt cgcgcttcgg gggctggagc ttgtttcccc acgtcgccca atgagc       476

SEQ ID NO: 79            moltype = DNA   length = 378
FEATURE                  Location/Qualifiers
source                   1..378
```

-continued

```
                          mol_type = other DNA
                          organism = synthetic construct
SEQUENCE: 79
cggcgctcgg cttcgggtcg cctggccgct gggggacaga ggcttccctc ccgccacgct    60
cgccctctct ggccctggcg gggcgcttct ggggccggga ggagtctcgt ctccggcgga   120
gcgcctgccg gcacccagct tccctccccc gccctggcgg tgggaacttg atttctcctt   180
ttggtcgcgc ttcgggggct ggagcttgtt tccccacgtc gcccaatgag cgccctctaa   240
agggaactgc ctccttggcc tcctctcgtc cgcagctgcc tccacctggg cgccaggagc   300
tctgtcgggc caggtggaag cttgagcacc ccagatttcg tctgcagcct cagtgccctc   360
tggggtctca gggagtgc                                                 378

SEQ ID NO: 80           moltype = DNA   length = 301
FEATURE                 Location/Qualifiers
source                  1..301
                        mol_type = other DNA
                        organism = synthetic construct
SEQUENCE: 80
tttccttccc cctttcctg cctatgacat ggtgatgaaa tgtgaagagc tggaaatcac     60
aaagcccacc gaggtggctg cgggtctgcc tccgaagtta tcagtgtaat cgggcctctg   120
tgtatgcctg cacgtgtatt ttcatgattg gaagattagg agcacggatt tgttcctgca   180
agtctcctct tttgttgtca tgagagtgtt atgttaacgc ttgtgataac gataagacag   240
aaactattga aaagggtgca gtggtggtgt gaaggattaa tcctttgctt gcttcacatc   300
t                                                                   301

SEQ ID NO: 81           moltype = DNA   length = 361
FEATURE                 Location/Qualifiers
source                  1..361
                        mol_type = other DNA
                        organism = synthetic construct
SEQUENCE: 81
atgtggaaga acctttaatc agagaagtaa tctgaaaact caccttctca cccatacaga     60
catcaagccc tacagctgcg agcagtgcgg caaagtgttc aggcgaaact gtgatctgcg   120
gcggcacagc ctgactcaca ccccgcggca ggacttctag agaagcccag gatctgtccc   180
gtgccgccgc tgctcccctc cccagacacc tctccacgtc tcctacccag ggggtcgcat   240
ccctagccct tcactgaccc cagctcttcc cttgctgcag ccgcacctgc agctccaggg   300
agttaactct tcttctgggg gactgagaac tgtagaaagc cacacactac tacatccctt   360
c                                                                   361

SEQ ID NO: 82           moltype = DNA   length = 332
FEATURE                 Location/Qualifiers
source                  1..332
                        mol_type = other DNA
                        organism = synthetic construct
SEQUENCE: 82
taccgccctg cgcagccagg ctggctggca ggctgcagcg ggaagcgcct gtgggtcctc     60
ggcgctgact gcagagctgg gtggaggcag cggaaccaaa actgctgtgt cactgcacgc   120
tgcagctgtt gccagggtga ccgggtgagt ttcccacgct tgcccgggcg gcagcgtgcg   180
ggccggcggg tggggcggag gggtgtgcag agaggccagt ggtgtcgtgc cacccgatgc   240
ccgggggtgt ccactcccct ctcctgggtc acgtgaccag ggccctgcc ctgcggtgtt    300
gtggggtgta tgtgtggttc ttgggggggt cc                                 332
```

What is claimed is:

1. A method of detecting methylation statuses of markers, the method comprising:

converting unmethylated cytosines of a plurality of DNA fragments in a sample into uracils to generate a plurality of converted DNA fragments, wherein the plurality of DNA fragments were obtained from a biological sample;

sequencing the plurality of converted DNA fragments to generate a plurality of sequence reads, wherein each sequence read corresponds to a converted DNA fragment; and detecting a methylation status for each of three or more markers identified in the sequence reads, wherein a first of the three or more markers is a methylation locus comprising at least a portion of SEQ ID NO. 1, a second of the three or more markers is a methylation locus comprising at least a portion of SEQ ID NO. 2, and a third of the three or more markers is a methylation locus comprising at least a portion of SEQ ID NO. 3.

2. The method of claim 1, wherein the plurality of DNA fragments (in total) comprise at least 1 ng of DNA.

3. The method of claim 1, wherein the plurality of DNA fragments consist essentially of DNA fragments each of which has a length in a range from 10 bp to 800 bp.

4. The method of claim 1, wherein the plurality of DNA fragments consist essentially of DNA fragments each of which has a length in a range from 1000 bp to 200,000 bp.

5. The method of claim 1, wherein each of the plurality of sequence reads is at least 50 bp.

6. The method of claim 1, wherein the method further comprises detecting a methylation status for a fourth methylation locus comprising at least a portion of SEQ ID NO. 70 and a fifth methylation locus comprising at least a portion of SEQ ID NO. 72.

7. A method of detecting methylation statuses of markers, the method comprising:

converting unmethylated cytosines of a plurality of DNA fragments in a sample into uracils to generate a plurality of converted DNA fragments, wherein the plurality of DNA fragments were obtained from a biological sample;

sequencing the plurality of converted DNA fragments to generate a plurality of sequence reads, wherein each sequence read corresponds to a converted DNA fragment; and detecting a methylation status for each of two or more markers identified in the sequence reads, wherein a first of the two or more markers is a methylation locus comprising at least a portion of SEQ ID NO. 70 and a second of the two or more markers is a methylation locus comprising at least a portion of SEQ ID NO. 72.

8. The method of claim 7, wherein the plurality of DNA fragments (in total) comprise at least 1 ng of DNA.

9. The method of claim 7, wherein the plurality of DNA fragments consist essentially of DNA fragments each of which has a length in a range from 10 bp to 800 bp.

10. The method of claim 7, wherein the plurality of DNA fragments consist essentially of DNA fragments each of which has a length in a range from 1000 bp to 200,000 bp.

11. The method of claim 7, wherein each of the plurality of sequence reads is at least 50 bp.

* * * * *